US012290575B2

(12) United States Patent
Reshetnyak et al.

(10) Patent No.: US 12,290,575 B2
(45) Date of Patent: *May 6, 2025

(54) FLUORESCENT COMPOUND COMPRISING A FLUOROPHORE CONJUGATED TO A pH-TRIGGERED POLYPEPTIDE

(71) Applicants: UNIVERSITY OF RHODE ISLAND BOARD OF TRUSTEES, Kingston, RI (US); YALE UNIVERSITY, New Haven, CT (US)

(72) Inventors: Yana K. Reshetnyak, Saunderstown, RI (US); Oleg A. Andreev, Saunderstown, RI (US); Donald M. Engelman, New Haven, CT (US)

(73) Assignees: University of Rhode Island Board of Trustees, Kingston, RI (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/349,855

(22) Filed: Jul. 10, 2023

(65) Prior Publication Data
US 2024/0075170 A1 Mar. 7, 2024

Related U.S. Application Data

(62) Division of application No. 15/713,324, filed on Sep. 22, 2017, now Pat. No. 11,779,662.

(60) Provisional application No. 62/398,448, filed on Sep. 22, 2016.

(51) Int. Cl.
| *A61K 49/00* | (2006.01) |
| *A61B 5/00* | (2006.01) |
| *A61K 49/04* | (2006.01) |
| *A61K 49/22* | (2006.01) |
| *C07K 14/00* | (2006.01) |
| *C07K 19/00* | (2006.01) |
| *C09B 69/10* | (2006.01) |
| *C09K 11/06* | (2006.01) |
| *G01N 33/58* | (2006.01) |

(52) U.S. Cl.
CPC ........ *A61K 49/0056* (2013.01); *A61B 5/0082* (2013.01); *A61K 49/0034* (2013.01); *A61K 49/04* (2013.01); *A61K 49/221* (2013.01); *A61K 49/227* (2013.01); *C07K 14/001* (2013.01); *C07K 19/00* (2013.01); *C09B 69/107* (2013.01); *C09K 11/06* (2013.01); *G01N 33/582* (2013.01); *A61B 5/0071* (2013.01); *C09K 2211/1466* (2013.01)

(58) Field of Classification Search
None
See application file for complete search history.

(56) References Cited

U.S. PATENT DOCUMENTS

| 8,076,451 | B2 | 12/2011 | Reshetnyak et al. | |
| 8,703,909 | B2 | 4/2014 | Reshetnyak et al. | |
| 8,846,081 | B2 | 9/2014 | Reshetnyak et al. | |
| 9,289,508 | B2 | 3/2016 | Reshetnyak et al. | |
| 9,676,823 | B2 | 6/2017 | Reshetnyak et al. | |
| 9,750,693 | B2 | 9/2017 | Reshetnyak et al. | |
| 9,814,781 | B2 | 11/2017 | Reshetnyak et al. | |
| 10,512,606 | B2 | 12/2019 | Reshetnyak et al. | |
| 11,229,710 | B2 | 1/2022 | Reshetnyak et al. | |
| 11,267,853 | B2 | 3/2022 | Reshetnyak et al. | |
| 11,274,126 | B2 | 3/2022 | Reshetnyak et al. | |
| 11,738,096 | B2* | 8/2023 | Reshetnyak | C09K 11/06 424/9.6 |
| 11,779,662 | B2 | 10/2023 | Reshetnyak et al. | |
| 11,857,509 | B2 | 1/2024 | Reshetnyak et al. | |
| 12,029,793 | B2 | 7/2024 | Reshetnyak et al. | |
| 2008/0233107 | A1 | 9/2008 | Reshetnyak et al. | |
| 2011/0268660 | A1 | 11/2011 | Danikas et al. | |
| 2012/0039990 | A1 | 2/2012 | Reshetnyak et al. | |
| 2012/0142042 | A1 | 6/2012 | Reshetnyak et al. | |
| 2015/0051153 | A1 | 2/2015 | Reshetnyak et al. | |
| 2015/0086617 | A1 | 3/2015 | Reshetnyak et al. | |
| 2015/0165071 | A1 | 6/2015 | Takahashi et al. | |
| 2015/0191508 | A1 | 7/2015 | Reshetnyak et al. | |
| 2016/0213790 | A1 | 7/2016 | Chen et al. | |
| 2016/0222212 | A1 | 8/2016 | Davis | |
| 2016/0256560 | A1 | 9/2016 | Reshetnyak et al. | |
| 2018/0064648 | A1 | 3/2018 | Reshetnyak et al. | |
| 2018/0117183 | A1 | 5/2018 | Reshetnyak et al. | |
| 2018/0221500 | A1 | 8/2018 | Reshetnyak et al. | |

(Continued)

FOREIGN PATENT DOCUMENTS

| WO | WO-2006078816 A2 | 7/2006 |
| WO | WO-2012021790 A1 | 2/2012 |

(Continued)

OTHER PUBLICATIONS

Golijanin et al. ('Targeted imaging of urothelium carcinoma in human bladders by an ICG pHLIP peptide ex vivo' PNAS v113(42) Oct. 18, 2016 pp. 11829-11834) (Year: 2016).*

Pubchem, "Indocyanine green," PubChem CID 5282412, accessed at pubmed.ncbi.nlm.nih.gov, accessed on Dec. 28, 2017, 44 pages.

Adochite, R., et al., "Comparative Study of Tumor Targeting and Biodistribution of pH (Low) Insertion Peptides (pHLIP(®) Peptides) Conjugated with Different Fluorescent Dyes," Molecular Imaging and Biology 18(5):686-696, Elsevier Science, United States (Oct. 2016).

(Continued)

*Primary Examiner* — Ronald T Niebauer
(74) *Attorney, Agent, or Firm* — Sterne, Kessler, Goldstein & Fox P.L.L.C.

(57) ABSTRACT

The present subject matter provides compounds, compositions, and methods for identifying, monitoring, treating, and removing diseased tissue. Compounds, compositions, and methods for identifying, monitoring, and detecting circulating fluids such as blood are also provided.

17 Claims, 39 Drawing Sheets
(28 of 39 Drawing Sheet(s) Filed in Color)
Specification includes a Sequence Listing.

(56) References Cited

U.S. PATENT DOCUMENTS

| | | |
|---|---|---|
| 2018/0369425 A1 | 12/2018 | Reshetnyak et al. |
| 2019/0231904 A1 | 8/2019 | Reshetnyak et al. |
| 2019/0382448 A1 | 12/2019 | Reshetnyak et al. |
| 2020/0237926 A1 | 7/2020 | Reshetnyak et al. |
| 2020/0246420 A1 | 8/2020 | Reshetnyak et al. |
| 2020/0253872 A1 | 8/2020 | Reshetnyak et al. |
| 2020/0262881 A1 | 8/2020 | Reshetnyak et al. |
| 2020/0323882 A1 | 10/2020 | Reshetnyak et al. |
| 2022/0088208 A1 | 3/2022 | Reshetnyak et al. |
| 2022/0281919 A1 | 9/2022 | Reshetnyak et al. |
| 2024/0042063 A1 | 2/2024 | Reshetnyak et al. |
| 2024/0066096 A1 | 2/2024 | Reshetnyak et al. |
| 2024/0148911 A1 | 5/2024 | Reshetnyak et al. |
| 2024/0173258 A1 | 5/2024 | Reshetnyak et al. |
| 2024/0342296 A1 | 10/2024 | Reshetnyak et al. |

FOREIGN PATENT DOCUMENTS

| | | | |
|---|---|---|---|
| WO | WO 2012/047354 | * | 4/2012 |
| WO | WO-2012047354 A2 | | 4/2012 |
| WO | WO-2014013730 A1 | | 1/2014 |
| WO | WO-2017165452 A1 | | 9/2017 |
| WO | WO-2018057912 A1 | | 3/2018 |
| WO | WO-2018227132 A1 | | 12/2018 |
| WO | WO-2020159983 A1 | | 8/2020 |
| WO | WO-2020160009 A1 | | 8/2020 |
| WO | WO-2020160031 A1 | | 8/2020 |
| WO | WO-2020160047 A2 | | 8/2020 |
| WO | WO-2020190733 A1 | | 9/2020 |
| WO | WO-2024040027 A2 | | 2/2024 |

OTHER PUBLICATIONS

Adochite, R., et al., "Targeting Breast Tumors With PH (Low) Insertion Peptides," Molecular Pharmaceutics 11(8):2896-2905, American Chemical Society, United States (Jul. 2014).

Alander, J.T., et al., "A Review of Indocyanine Green Fluorescent Imaging in Surgery," International Journal of Biomedical Imaging Article ID 940585:1-26, Hindawi Publishing Corporation, United States (2012).

Althausen, A.F., et al., "Non-invasive Papillary Carcinoma of the Bladder Associated With Carcinoma in Situ," The Journal of Urology 116(5):575-580, Lippincott Williams & Wilkins, United States (Nov. 1976).

Anastasiadis, A., and Reijke, T.M.D., "Best Practice in the Treatment of Nonmuscle Invasive Bladder Cancer," Therapeutic Advances in Urology 4(1):13-32, Sage Publications, England (Feb. 2012).

Andreev, O.A., et al., "Targeting Diseased Tissues by pHLIP Insertion at Low Cell Surface pH," Frontiers in Physiology 5(97):1-7, Frontiers Research Foundation, Switzerland (Mar. 2014).

Ankersmit, M., et al., "Near Infrared Fluorescence Lymphatic Laparoscopy of the Colon and Mesocolon," Colorectal disease: the Official Journal of the Association of Coloproctology of Great Britain and Ireland 13(Suppl 7):70-73, Blackwell Science Limited, England (Nov. 2011).

Aoki, T., et al., "Image-Guided Liver Mapping Using Fluorescence Navigation System With Indocyanine Green for Anatomical Hepatic Resection," World Journal of Surgery 32(8):1763-1767, Springer International, United States (Aug. 2008).

Azuma, R., et al., "Detection of Skin Perforators by Indocyanine Green Fluorescence Nearly Infrared Angiography," Plastic and Reconstructive Surgery 122(4):1062-1067, Lippincott Williams & Wilkins, United States (Oct. 2008).

Bailey, K.M., et al., "Targeting the Metabolic Microenvironment of Tumors," Advances in Pharmacology 65:63-107, Academic Press, United States (Jan. 2012).

Benson, R.C., and Kues, H.A., "Fluorescence Properties of Indocyanine Green as Related to Angiography," Physics in Medicine and Biology 23(1):159-163, IOP Publishing, England (Jan. 1978).

Bjornsson, O.G., et al., "Physiochemical Studies of Indocyanine Green (Icg): Absorbance/Concentration Relationship, PH Tolerance and Assay Precision in Various Solvents," Experientia 38(12):1441-1442, Birkhäuser Verlag, Switzerland (Dec. 1982).

Bjornsson, O.G., et al., "Physiochemical Studies on Indocyanine Green: Molar Lineic Absorbance, PH Tolerance, Activation Energy and Rate of Decay in Various Solvents," Journal of Clinical Chemistry and Clinical Biochemistry. Zeitschrift für klinische Chemie und klinische Biochemie 21(7):453-458, Walter De Gruyter, Germany (Jul. 1983).

Boni, L., et al., "Clinical Applications of Indocyanine Green (Icg) Enhanced Fluorescence in Laparoscopic Surgery," Surgical Endoscopy 29(7):2046-2055, Springer International, Germany (Jul. 2015).

Burger, M., et al., "Photodynamic Diagnosis of Non-muscle-Invasive Bladder Cancer With Hexaminolevulinate Cystoscopy: A Meta-Analysis of Detection and Recurrence Based on Raw Data," European Urology 64(5):846-854, Elsevier Science, Switzerland (Nov. 2013).

Burggraaf, J., et al., "Detection of Colorectal Polyps in Humans Using an Intravenously Administered Fluorescent Peptide Targeted Against C-Met," Nature Medicine 21(8):955-961, Nature Publishing Company, United States (Aug. 2015).

Cahill, R.A., et al., "Near-Infrared (Nir) Laparoscopy for Intraoperative Lymphatic Road-Mapping and Sentinel Node Identification During Definitive Surgical Resection of Early-Stage Colorectal Neoplasia," Surgical Endoscopy 26(1):197-204, Springer, Germany (Jan. 2012).

Campagnoli, T.R., et al., "Choroidal Melanoma Initially Treated As Hemangioma: Diagnostic and Therapeutic Considerations," Retinal Cases & Brief Reports 10(2):175-182, Wolters Kluwer Health, United States (Apr. 2016).

Carrion-Vazquez, M., et al., "The Mechanical Stability of Ubiquitin Is Linkage Dependent," Nature Structural Biology 10(9):738-743, Nature Pub. Co, United States (Sep. 2003).

Choromokos, E., et al., "Infrared Absorption Angiography," Journal of the Biological Photographic Association 37(2):100-104, Biological Photographic Association, United States (Apr. 1969).

Cruz-Monserrate, Z., et al., "Targeting Pancreatic Ductal Adenocarcinoma Acidic Microenvironment," Scientific Reports 4:1-8, Nature Publishing Group, England (Mar. 2014).

Damaghi, M., et al., "PH Sensing and Regulation in Cancer," Frontiers in Physiology 4:370, 1-11, Frontiers Research Foundation, Switzerland (Dec. 2013).

Daumar, P., et al., "Efficient (18)F-Labeling of Large 37-Amino-Acid Phlip Peptide Analogues and Their Biological Evaluation," Bioconjugate Chemistry 23(8):1557-1566, American Chemical Society, United States (Aug. 2012).

Demoin, D.W., et al., "PET Imaging of Extracellular pH in Tumors with (64)Cu- and (18)F-Labeled pHLIP Peptides: A Structure-Activity Optimization Study," Bioconjugate Chemistry 27(9):2014-2023, American Chemical Society, United States (Sep. 2016).

Desai, N.D., et al., "Improving the Quality of Coronary Bypass Surgery With Intraoperative Angiography: Validation of a New Technique," Journal of the American College of Cardiology 46(8):1521-1525, Elsevier Biomedical, United States (Oct. 2005).

Desmettre, T., et al., "Fluorescence Properties and Metabolic Features of Indocyanine Green (Icg) As Related to Angiography," Survey of Ophthalmology 45(1):15-27, Elsevier Science, United States (Jul. 2000).

Dietz, H., and Matthias, R., "Protein Structure by Mechanical Triangulation," Proceedings of the National Academy of Sciences of the United States of America 103(5):1244-1247, National Academy of Sciences, United States (Jan. 2006).

Eckhardt, B.L., et al., "Genomic Analysis of a Spontaneous Model of Breast Cancer Metastasis to Bone Reveals a Role for the Extracellular Matrix," Molecular Cancer Research 3(1):41275, American Association for Cancer Research, United States (Jan. 2005).

Estrella, V. et al., "Acidity Generated by the Tumor Microenvironment Drives Local Invasion," Cancer Research 73(5):1524-1535, American Association for Cancer Research, United States (Mar. 2013).

(56) References Cited

OTHER PUBLICATIONS

Ferroli, P., et al., "Application of Intraoperative Indocyanine Green Angiography for Cns Tumors: Results on the First 100 Cases," Acta Neurochirurgica. Supplement 109:251-257, Springer-Verlag, Austria (2011).
Fischer, T., et al., "Detection of Rheumatoid Arthritis Using Nonspecific Contrast Enhanced Fluorescence Imaging," Academic Radiology 17(3):375-381, Association Of University Radiologists, United (Mar. 2010).
Flower, R. W., "Injection Technique for Indocyanine Green and Sodium Fluorescein Dye Angiography of the Eye," Investigative Ophthalmology 12(12):881-895, C V Mosby Co, United States (Dec. 1973).
Gatenby, R.A., et al., "Acid-mediated Tumor Invasion: a Multidisciplinary Study," Cancer Research 66(10):5216-5223, American Association for Cancer Research, United States (May 2006).
Gillies, R.J., et al., "Evolutionary Dynamics Unifies Carcinogenesis and Cancer," Nature Reviews. Cancer 12(7):487-493, Nature Pub. Group, England (Jun. 2012).
Gompels, L.L., et al., "In Vivo Optical Imaging in Arthritis—an Enlightening Future?" Rheumatology 49(8):1436-1446, Oxford University Press, England (Aug. 2010).
Griffiths, M., et al., "Indocyanine Green-Based Fluorescent Angiography in Breast Reconstruction," Gland Surgery 5(2):133-149, AME Publishing Company, China (Apr. 2016).
Habazettl, H., et al., "Near-Infrared Spectroscopy and Indocyanine Green Derived Blood Flow Index for Noninvasive Measurement of Muscle Perfusion During Exercise," Journal of Applied Physiology 108(4):962-967, American Physiological Society, United States (Apr. 2010).
Handa, T., et al., "Preliminary Experience for the Evaluation of the Intraoperative Graft Patency With Real Color Charge-Coupled Device Camera System: An Advanced Device for Simultaneous Capturing of Color and Near-Infrared Images During Coronary Artery Bypass Graft," Interactive Cardiovascular and Thoracic Surgery 9(2):150-154, Oxford University Press, England (Aug. 2009).
Ishizawa, T., et al., "Intraoperative Fluorescent Cholangiography Using Indocyanine Green: A Biliary Road Map for Safe Surgery," Journal of the American College of Surgeons 208(1):e1-4, Lippincott Williams & Wilkins, Inc, United States (Jan. 2009).
Jacobs, L., "Positive Margins: The Challenge Continues for Breast Surgeons," Annals of Surgical Oncology 15(5):1271-1272, Springer, United States (May 2008).
Jia, Y., et al., "Quantitative Optical Coherence Tomography Angiography of Vascular Abnormalities in the Living Human Eye," Proceedings of the National Academy of Sciences of the United States of America 112(18):E2395-E2402, National Academy of Sciences, United States (May 2015).
Jocham, D., et al., "Photodynamic Diagnosis in Urology: State-Of-The-Art," European Urology 53(6):1138-1148, Elsevier Science, Switzerland (Jun. 2008).
Kamat, A., et al., "Defining and Treating the Spectrum of Intermediate Risk Nonmuscle Invasive Bladder Cancer," The Journal of Urology 192(2):305-315, Wolters Kluwer, United States (Aug. 2014).
Karabadzhak, A.G., et al., "Phlip-Fire, a Cell Insertion-Triggered Fluorescent Probe for Imaging Tumors Demonstrates Targeted Cargo Delivery in Vivo," ACS Chemical Biology 9(11):2545-2553, American Chemical Society, United States (Nov. 2014).
Kimbrough, C.W., et al., "Targeting Acidity in Pancreatic Adenocarcinoma: Multispectral Optoacoustic Tomography Detects Ph-Low Insertion Peptide Probes in Vivo," Clinical Cancer research: an official journal of the American Association for Cancer Research 21(20):4576-4585, The Association, United States (Oct. 2015).
Kogure, K., and Choromokos, E., "Infrared Absorption Angiography," Journal of Applied Physiology 26(1):154-157, American Physiological Society, United States (Jan. 1969).
Kogure, K., et al., "Infrared Absorption Angiography of the Fundus Circulation," Archives of Ophthalmology 83(2):209-214, American Medical Association, United States (Feb. 1970).
Kohl-Bareis, M., et al., "Noninvasive Monitoring of Cerebral Blood Flow by a Dye Bolus Method: Separation of Brain From Skin and Skull Signals," Journal of Biomedical Optics 7(3):464-470, The International Society for Optical Engineering in cooperation with International Biomedical Optics Society, United States (Jul. 2002).
Korn, J.M., et al., "Indocyanine Green Spy Elite-Assisted Sentinel Lymph Node Biopsy in Cutaneous Melanoma," Plastic and Reconstructive Surgery 133(4):914-922, Lippincott Williams & Wilkins, United States (Apr. 2014).
Kozin, S.V., et al., "The Cell Transmembrane PH Gradient in Tumors Enhances Cytotoxicity of Specific Weak Acid Chemotherapeutics," Cancer Research 61(12):4740-4743, American Association for Cancer Research, United States (Jun. 2001).
Lee, B.T., et al., "Intraoperative Near-Infrared Fluorescence Imaging in Perforator Flap Reconstruction: Current Research and Early Clinical Experience," Journal of Reconstructive Microsurgery 26(1):59-65, Thieme-Stratton, United States (Jan. 2010).
Lee, B.T., et al., "The Flare Intraoperative Near-Infrared Fluorescence Imaging System: A First-In-Human Clinical Trial in Perforator Flap Breast Reconstruction," Plastic and Reconstructive Surgery 126(5):1472-1481, Lippincott Williams & Wilkins, United States (Nov. 2010).
Lerner, S.P., et al., "Fluorescence and White Light Cystoscopy for Detection of Carcinoma in Situ of the Urinary Bladder," Urologic Oncology 30(3):285-289, Elsevier, United States (May 2012).
Leung, T.S., et al., "Theoretical Investigation of Measuring Cerebral Blood Flow in the Adult Human Head Using Bolus Indocyanine Green Injection and Near-Infrared Spectroscopy," Applied Optics 46(10):1604-1614, Optica Publishing Group, United States (Apr. 2007).
Luo, Z., et al., "Optical Molecular Imaging Approach for Rapid Assessment of Response of Individual Cancer Cells to Chemotherapy," Journal of Biomedical Optics 17(10):106006-1-106006-8, SPIE—the International Society for Optical Engineering in cooperation with International Biomedical Optics Society, United States (Oct. 2012).
Luo, Z., et al., "Widefield Optical Imaging of Changes in Uptake of Glucose and Tissue Extracellular PH in Head and Neck Cancer," Cancer Prevention Research 7(10):1035-1044, American Association for Cancer Research, United States (2014).
Macholl, S., et al., "In Vivo PH Imaging With (99M)Tc-Phlip," Molecular Imaging and Biology 14(6):725-734, Springer, United States (Dec. 2012).
Mariotto, A.B., et al., "Projections of the Cost of Cancer Care in the United States: 2010-2020," Journal of the National Cancer Institute 103(2):117-128, Oxford University Press, England (Jan. 2011).
Marshall, M.V, et al., "Near-Infrared Fluorescence Imaging in Humans with Indocyanine Green: A Review and Update," Open Surgical Oncology Journal 2(2):12-25, Bentham Science, United States (May 2010).
Mondal, S.B, et al., "Real-Time Fluorescence Image-Guided Oncologic Surgery," Advances in Cancer Research 124:171-211, Academic Press, United States (Jan. 2014).
Moon, C.P., and Fleming, K.G., "Side-Chain Hydrophobicity Scale Derived From Transmembrane Protein Folding Into Lipid Bilayers," Proceedings of the National Academy of Sciences of the United States of America 108(25):10174-10177, National Academy of Sciences, United States (Jun. 2011).
Murray, J.D, et al., "Fluorescent Intraoperative Tissue Angiography With Indocyanine Green: Evaluation of Nipple-Areola Vascularity During Breast Reduction Surgery," Plastic and Reconstructive Surgery 126(1):33e-34e, Lippincott Williams & Wilkins, United States (Jul. 2010).
Oesterhelt, F., et al., "Unfolding Pathways of Individual Bacteriorhodopsins," Science 288(5463):143-146, American Association for the Advancement of Science, United States (Apr. 2000).
Pasin, E., et al., "Superficial Bladder Cancer: An Update on Etiology, Molecular Development, Classification, and Natural History," Reviews in Urology 10(1):31-43, MedReviews LLC, United States (2008).

(56) References Cited

OTHER PUBLICATIONS

Polom, K., et al., "Current Trends and Emerging Future of Indocyanine Green Usage in Surgery and Oncology: A Literature Review," Cancer 117(21):4812-4822, Wiley, United States (Nov. 2011).

Reshetnyak, Y.K., et al., "Measuring Tumor Aggressiveness and Targeting Metastatic Lesions With Fluorescent Phlip," Molecular Imaging and Biology 13(6):1146-1156, Springer, United States (Dec. 2011).

Rink, M., et al., "Hexyl Aminolevulinate-Guided Fluorescence Cystoscopy in the Diagnosis and Follow-up of Patients With Non-muscle-Invasive Bladder Cancer: A Critical Review of the Current Literature," European Urology 64(4):624-638, Elsevier Science, Switzerland (Oct. 2013).

Roberts, D.W., et al., "Coregistered Fluorescence-Enhanced Tumor Resection of Malignant Glioma: Relationships Between δ-Aminolevulinic Acid-Induced Protoporphyrin Ix Fluorescence, Magnetic Resonance Imaging Enhancement, and Neuropathological Parameters. Clinical Article," Journal of Neurosurgery 114(3):595-603, American Association of Neurological Surgeons, United States (Mar. 2011).

Santos Cortes, J.A., et al., "Photodynamic Diagnosis in Urology: State of the Art," Archivos Españoles de Urología 64(1):18-31, Iniestares, Spain (Jan. 2011).

Schomacker, K.T., et al., "Biodistribution of Indocyanine Green in a Porcine Burn Model: Light and Fluorescence Microscopy," The Journal of Trauma 43(5):813-819, Lippincott Williams & Wilkins, United States (Nov. 1997).

Sela, M., and Zisman, E., "Different Roles of D-Amino Acids in Immune Phenomena," The FASEB Journal: official publication of the Federation of American Societies for Experimental Biology 11(6):449-456, The Federation, United States (May 1997).

Serganova, I., et al., "Metabolic Imaging: A Link Between Lactate Dehydrogenase A, Lactate, and Tumor Phenotype," Clinical Cancer Research: an Official Journal of the American Association for Cancer Research 17(19):6250-6261, The Association, United States (Oct. 2011).

Siegel, R., et al., "Cancer Statistics, 2012," CA: A Cancer Journal for Clinicians 62(1):10-29, American Cancer Society, Inc., United States (2012).

Smith, G., et al., "Prognostic Significance of Biopsy Results of Normal-Looking Mucosa in Cases of Superficial Bladder Cancer," British Journal of Urology 55(6):665-669, Blackwell Science, England (Dec. 1983).

Stummer, W., et al., "Fluorescence-Guided Surgery With 5-Aminolevulinic Acid for Resection of Malignant Glioma: A Randomised Controlled Multicentre Phase III Trial," The Lancet. Oncology 7(5):392-401, Lancet Pub. Group, England (May 2006).

Styczynski, M.P, et al., "BLOSUM62 Miscalculations Improve Search Performance," Nature Biotechnology 26(3):274-275, Nature America Publishing, United States (Mar. 2008).

Tajima, Y., et al., "Sentinel Node Mapping Guided by Indocyanine Green Fluorescence Imaging During Laparoscopic Surgery in Gastric Cancer," Annals of Surgical Oncology 17(7):1787-1793, Springer, United States (Jul. 2010).

Tao, K, et al., "Imagable 4T1 Model for the Study of Late Stage Breast Cancer," BMC Cancer 8(228):1-19, BioMed Central, England (Aug. 2008).

Tobis, S., et al., "Robot-Assisted and Laparoscopic Partial Nephrectomy With Near Infrared Fluorescence Imaging," Journal of Endourology 26(7):797-802, Mary Ann Liebert, United States (Jul. 2012).

UniProt, "UniProtKB- P08100 (OPSD_HUMAN)," UniProt Accession No. P08100, accessed at uniprot.org, accessed on Nov. 7, 2018, 20 pages.

Unno, N., et al., "Indocyanine Green Fluorescence Angiography for Intraoperative Assessment of Blood Flow: A Feasibility Study," European Journal of Vascular and Endovascular Surgery: the Official Journal of the European Society for Vascular Surgery 35(2):205-207, Elsevier, England (Feb. 2008).

Van Der Vorst, J.R., et al., "Near-Infrared Fluorescence Imaging of a Solitary Fibrous Tumor of the Pancreas Using Methylene Blue," World Journal of Gastrointestinal Surgery 4(7):180-184, Baishideng Publishing Group, United States (Jul. 2012).

Verbeek, F.P.R., et al., "Intraoperative Near Infrared Fluorescence Guided Identification of the Ureters Using Low Dose Methylene Blue: A First in Human Experience," The Journal of Urology 190(2):574-579, Wolters Kluwer, United States (Aug. 2013).

Viola-Villegas, N.T., et al., "Understanding the Pharmacological Properties of a Metabolic Pet Tracer in Prostate Cancer," Proceedings of the National Academy of Sciences of the United States of America 111(20):7254-7259, National Academy of Sciences, United States (May 2014).

Weerakkody, D., et al., "Family of pH (Low) Insertion Peptides for Tumor Targeting," Proceedings of the National Academy of Sciences of the United States of America 110(15):5834-5839, National Academy of Sciences, United States (Mar. 2013).

Wimley, W.C., et al., "Solvation Energies of Amino Acid Side Chains and Backbone in a Family of Host-guest Pentapeptides," Biochemistry 35(16):5109-5124, American Chemical Society, United States (Apr. 1996).

Winer, J.H., et al., "Intraoperative Localization of Insulinoma and Normal Pancreas Using Invisible Near-Infrared Fluorescent Light," Annals of Surgical Oncology 17(4):1094-1100, Springer, United States (Apr. 2010).

Woitzik, J., et al., "Intraoperative Control of Extracranial-Intracranial Bypass Patency by Near-Infrared Indocyanine Green Videoangiography," Journal of Neurosurgery 102(4):692-698, American Association of Neurological Surgeons, United States (Apr. 2005).

Wu, D., et al., "Contrast Agents for Photoacoustic and Thermoacoustic Imaging: A Review," International Journal of Molecular Sciences 15(12):23616-23639, MDPI, Switzerland (Dec. 2014).

Yang, J., et al., "Twist, a Master Regulator of Morphogenesis, Plays an Essential Role in Tumor Metastasis," Cell 117(7):927-939, Cell Press, United States (Jun. 2004).

Zelken, J.A., and Tufaro, A,P., et al., "Current Trends and Emerging Future of Indocyanine Green Usage in Surgery and Oncology: An Update," Annals of Surgical Oncology 22(Suppl 3):S1271-S1283, Springer, United States (Dec. 2015).

Zheng, M., et al., "Development of Bioorthogonal Reactions and Their Applications in Bioconjugation," Molecules 20(2):3190-3205, MDPI, Switzerland (Feb. 2015).

Zuk, R.J., et al., "Clinicopathological Importance of Primary Dysplasia of Bladder," Journal of Clinical Pathology 41(12):1277-1280, BMJ Pub. Group, England (Dec. 1988).

Brito, J., et al., "Ex Vivo Fluorescence Imaging of Urothelial Carcinoma in Human Bladders Targeted by Lcg-Phlip," The Journal of Urology, 195(4):e671-e672, Wolters Kluwer, United States (May 2016).

Lee, S., et al., "Peptides and Peptide Hormones for Molecular Imaging and Disease Diagnosis," 110(5):3087-3111, American Chemical Society, United States (May 2010).

Maria, et al., "FDG PET-CT vs CT Scan in the staging of Urothelial Neoplasms," The Journal of Urology 195(4S):e671-e672, Wolters Kluwer, United States (May 2016).

Gencore, "AASEQ1_05052022_112421," SEQ_ID_N0_9_pep_vs_SEQ_ID_N0_15_pep_align, Bioacceleration Ltd., 1 page (May 2022).

Gencore, "AASEQ1_05052022_102505," SEQ_ID_NO_ 4_pep_vs_SEQ_ID_N0_15_pep_align, Bioacceleration Ltd., 1 page (May 2022).

Dojin News, "Near Infrared Fluorescent Dye Labeling Reagent ICG-maleimide," accessed at https://www.dojindo.co.jp/letterj/140/commercial/03.html, 2 pages (1 page of Foreign language & 1 page of English language) (2015).

Isoelectric Point Calculator, "Isoelectric Point Calculator 2.0" Result for (ACEQNPIYWARYADWLFTTPLLLLDLALLVDADET (SEQ ID No. 221) in U.S. Appl. No. 16/334,734) accessed at http://www.ipc2-isoelectric-point.org/, accessed on Oct. 4, 2021, 2 pages.

Fendos, J. and Engelmanb, D., "pHLIP and Acidity as a Universal Biomarker for Cancer," The Yale Journal of Biology and Medicine 85(1):29-35, Yale Journal of Biology and Medicine, United States (Mar. 2012).

(56) References Cited

OTHER PUBLICATIONS

PHLIP Trademark Entry, Registration No. 3944903, accessed at http://tmsearch.uspto.gov/bin/showfield?f=doc&state=4808:x2r8gw. 2.9, accessed on Feb. 4, 2021, 2 pages (Feb. 2021).

Golijanin, J., et al., "Targeted imaging of urothelium carcinoma in human bladders by an ICG pHLIP peptide ex vivo," Proc Natl Acad Sci USA 113(42):11829-11834, National Academy of Sciences, United States (Oct. 2016).

International Search Report and Written Opinion for Application No. PCT/US2017/052984, International Search Authority, United States, mailed on Mar. 5, 2018, 12 pages.

* cited by examiner

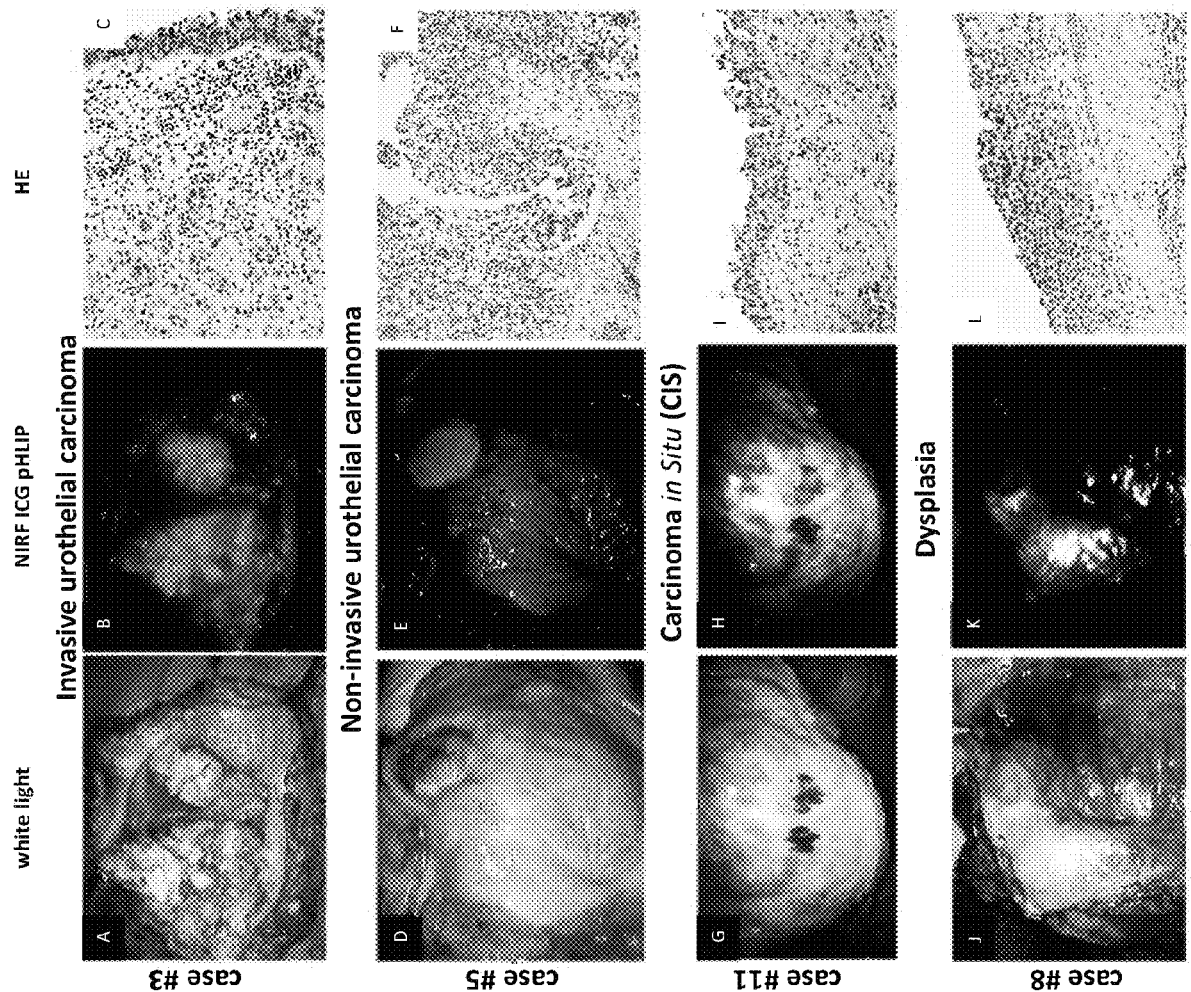
FIGS. 2A-L

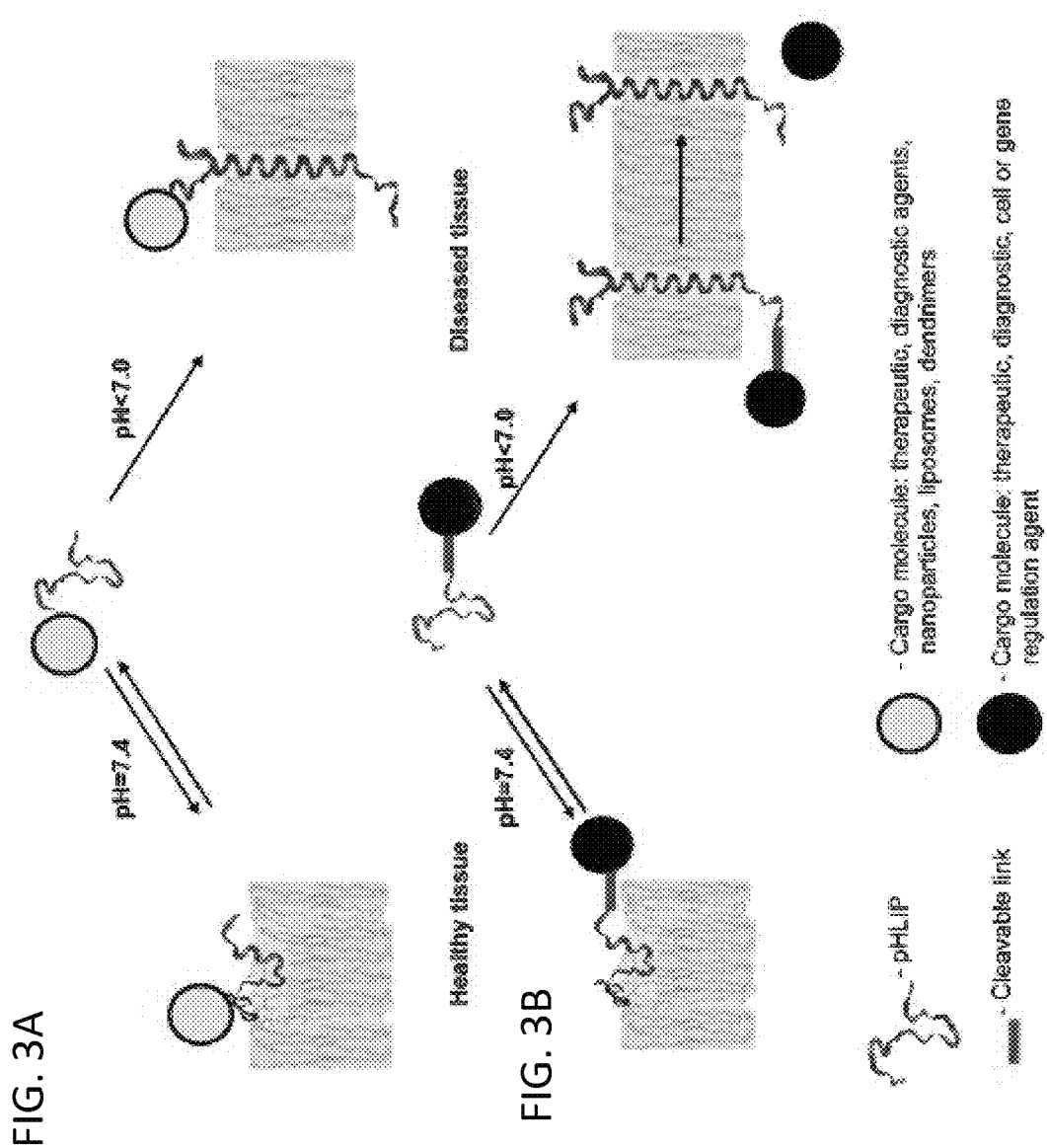

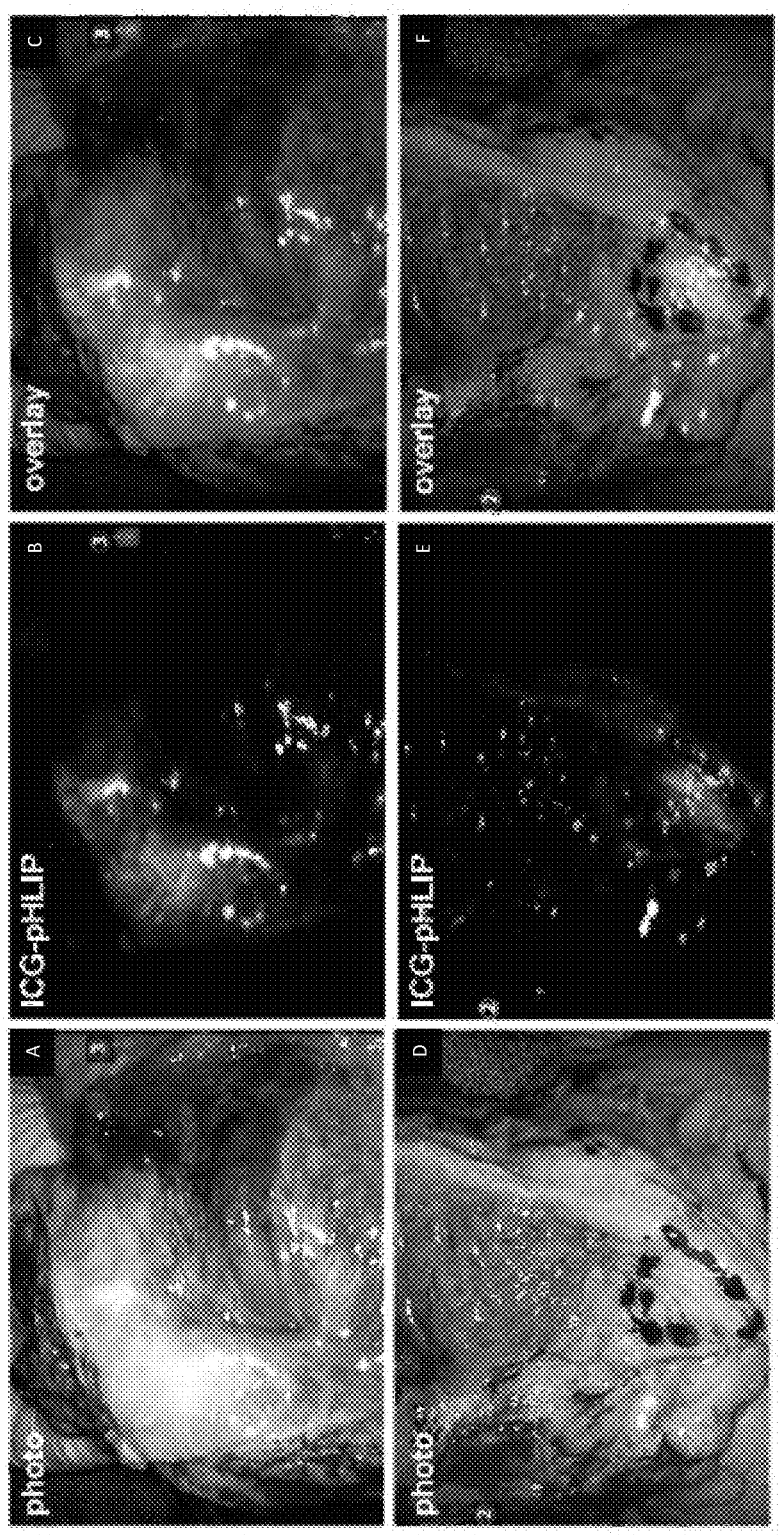
FIGS. 4A-F

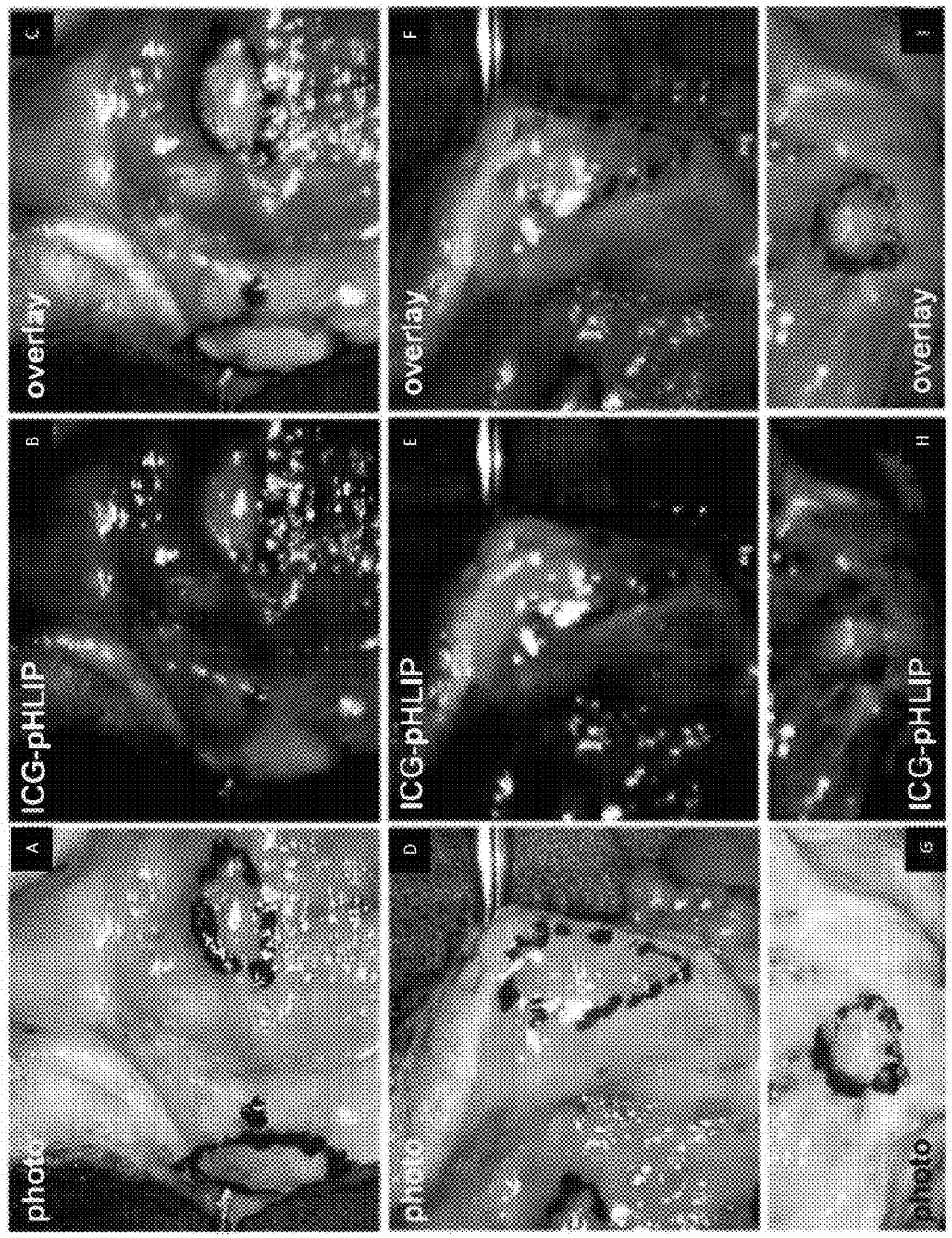
FIGS. 5A-I

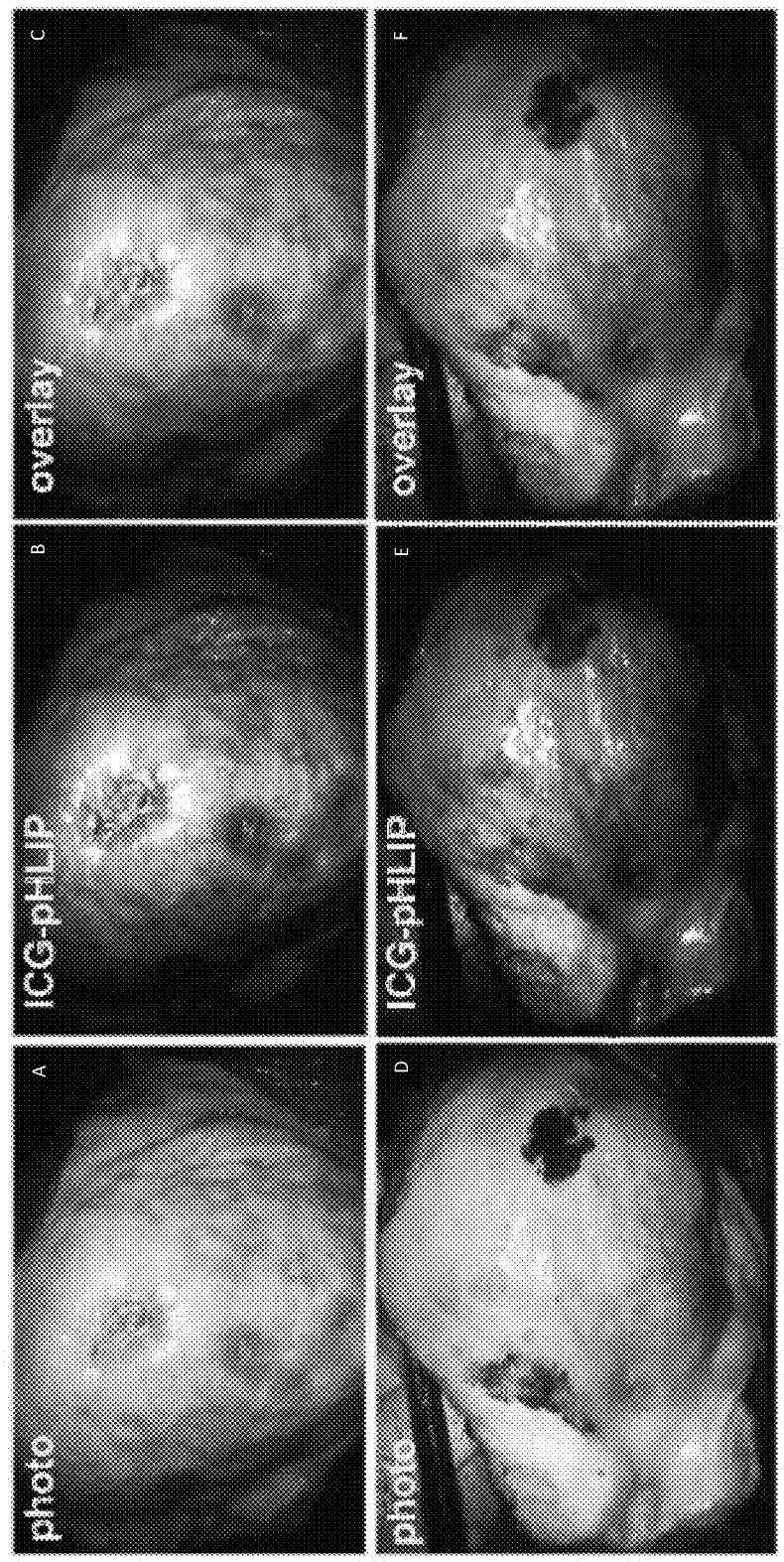
FIGS. 6A-F

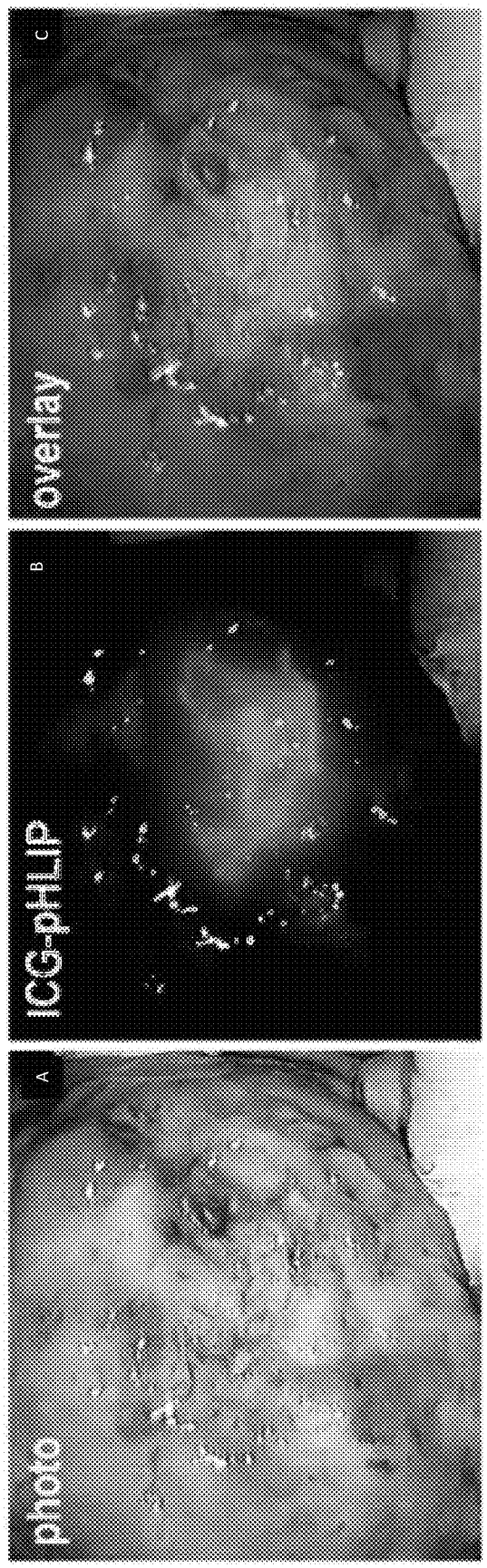
FIGS. 7A-C

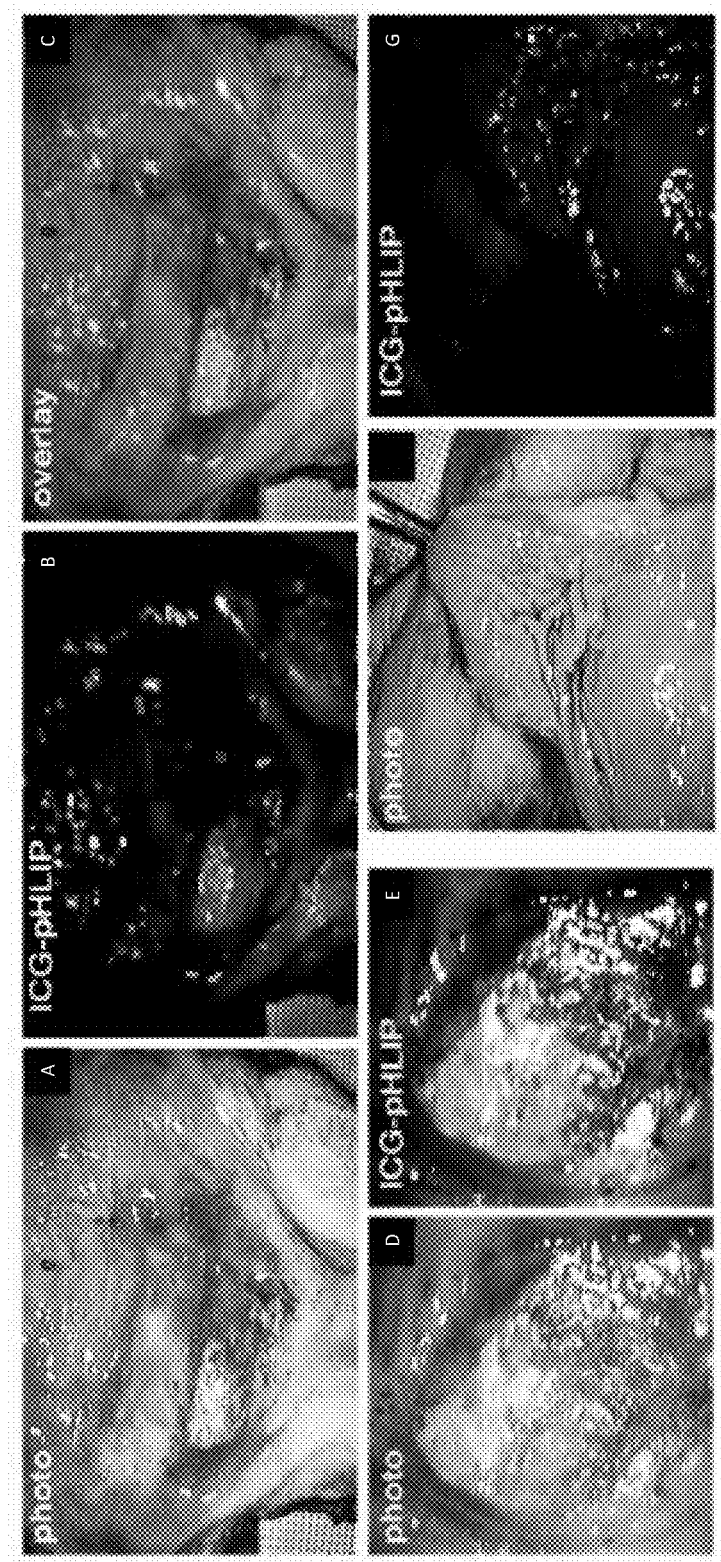
FIGS. 8A-G

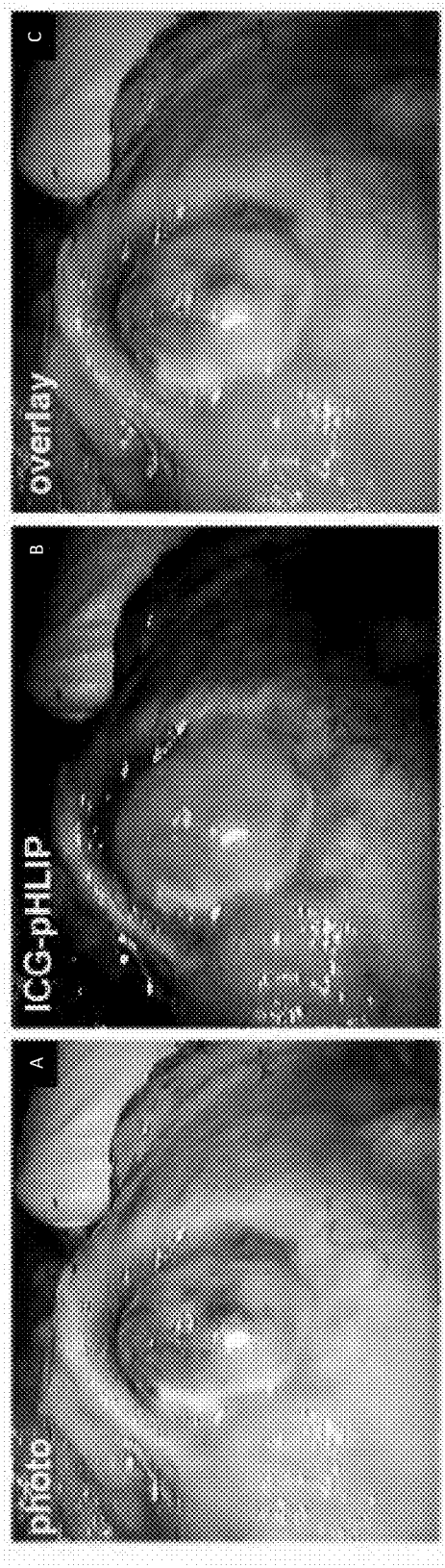
FIGS. 9A-C

Targeting 4T1 murine mammary carcinoma by ICG-pHLIP (40 µM, 100 µL, IV inj., imaging at 16 h)

Highly invasive 4T1 mammary carcinoma model mimics stage IV of human breast cancer FIG. 12  Targeting AY27 rat bladder cancer in nude mice by ICG-pHLIP (40 μM, 100 μL, IV inj., imaging at 16 h)

FIG. 13  Targeting 4T1 tumor by ICG-pHLIP (20, 10 and 5 µM, IV inj., imaging at 16 h)

The fluorescent signal is decreasing with the decrease of the ICG-pHLIP injected dose Targeting 4T1 tumor by 10 µM of ICG-pHLIP IV and IP inj., imaging at 16 h IP and IV routes of administration of ICG-pHLIP result in similar tumor targeting (and distribution in organs)

Targeting 4T1 tumor by 20 μM of ICG-pHLIP and IR800-pHLIP, IV inj., imaging at 16 h The fluorescent signal in tumor detected by the Stryker endoscope is higher for ICG-pHLIP compared to IR800-pHLIP Targeting 4T1 tumor by 20 µM of ICG-pHLIP and IR800-pHLIP, IV inj., imaging at 16 h ➢ The fluorescent signal in tumor detected by the Stryker endoscope is higher for ICG-pHLIP compared to IR800-pHLIP
➢ The ICG-pHLIP is cleared by liver
➢ The IR800-pHLIP is cleared by kidney

FIG. 19

FLUORESCENT COMPOUND COMPRISING A FLUOROPHORE CONJUGATED TO A pH-TRIGGERED POLYPEPTIDE

RELATED APPLICATION

This application is a division of U.S. patent application Ser. No. 15/713,324, filed Sep. 22, 2017. U.S. patent application Ser. No. 15/713,324 claims the benefit of priority under 35 U.S.C. § 119(e) to U.S. Provisional Application No. 62/398,448, filed Sep. 22, 2016, the entire content of which is incorporated herein by reference.

STATEMENT AS TO FEDERALLY SPONSORED RESEARCH

This invention was made with government support under R01 GM073857 awarded by the National Institutes of Health. The government has certain rights in the invention.

INCORPORATION BY REFERENCE OF SEQUENCE LISTING

The contents of the text file named "5095_0060004_Seqlisting_ ST26.xml", which was created on Jul. 5, 2023, and is 999,334 bytes in size, is hereby incorporated by reference in its entirety for all purposed.

FIELD OF THE INVENTION

The present invention relates to cancer therapy and diagnostics, including, e.g., fluorescence-image guided procedures.

BACKGROUND

Bladder cancer is the fifth most common cancer, constituting 4.5% of all new cancer cases in the United States. 76,960 new cases were estimated in 2016 and the death rate currently expected from bladder cancer is 21% (16,390). Approximately 2.4 percent of men and women will be diagnosed with bladder cancer at some point during their lifetime. In 2012, there were an estimated 577,403 individuals living with bladder cancer in the United States. Almost all of these patients require continuous surveillance, and, occasionally, treatments. For all stages combined, the 5-year relative survival rate is 77%. Survival declines to 70% at 10 years and 65% at 15 years after diagnosis. Bladder cancer can be non-muscle or muscle invasive. Half of all bladder cancer patients are diagnosed while the tumor is non-muscle invasive, for which the 5-year survival is 96%. Most (up to 98%) of malignant bladder tumors arise in the epithelium, 90-92% of these bladder cancers are urothelial carcinomas (Siegel et al. (2012) CA Cancer J Clin 62(1):10-29, Pasin et al. (2008) Rev Urol 10(1):31-43). Less common bladder cancers are squamous cell or adenocarcinomas. Approximately 20-25% of patients have muscle invasive disease, and of non-muscle invasive disease patients will progress to muscle invasive disease at 5 years follow up depending on intermediate or high risk of the progression (Anastasiadis & de Reijke (2012) Ther Adv Urol 4(1):13-32, Kamat et al. (2014) J Urol 192(2):305-315).

SUMMARY OF THE INVENTION

The present subject matter provides, inter alia, fluorescent compounds comprising, consisting essentially of, or consisting of a pH-triggered polypeptide (a "pHLIP peptide") and a fluorophore. Such compounds may be referred to herein as "pHLIP®-fluorophore compounds." Methods and compositions comprising such fluorescent compounds are also provided. For example, non-limiting implementations relate to fluorescence-image guided medical procedures, such as fluorescence and optoacoustic imaging.

In various embodiments, the pHLIP® peptide has the sequence: $X_n Y_m$; $Y_m X_n$; $X_n—Y_m X_j$; $Y_m X_n Y_i$; $Y_m X_n Y_i X_j$; $X_n Y_m X_j Y_i$; $Y_m X_n Y_i X_j Y_i$; $X_n Y_m X_j Y_i X_i$; $Y_m X_n Y_i X_j Y_i X_h$; $X_n Y_m X_j Y_i X_h Y_g$; $Y_m X_n Y_i X_j Y_i X_h Y_g$; $X_n Y_m X_j Y_i X_h Y_g X_f$; $(XY)_n$; $(YX)_n$; $(XY)_n Y_m$; $(YX)_n Y_m$; $(XY)_n X_m$; $(YX)_n X_m$; $Y_m(XY)_n$; $Y_m(YX)_n$; $X_n(XY)_m$; $X_n(YX)_m$; $(XY)_n Y_m(XY)_i$; $(YX)_n Y_m(YX)_i$; $(XY)_n X_m(XY)_i$; $(YX)_n X_m(YX)_i$; $Y_m(XY)_n$; $Y_m(YX)_n$; $X_n(XY)_m$; $X_n(YX)_m$, wherein, i) Y is a non-polar amino acid with solvation energy, $\Delta G_x^{cor} > +0.50$, or Gly (see, e.g., Table 1), ii) X is a protonatable amino acid, and iii) n, m, I, j, l, h, g, f are integers from 1 to 8.

In some embodiments, the pHLIP® peptide has the following sequence: $NH_2$-ACDDQNPWRAYLDLLFPTDTLLLDLLWA-COOH (SEQ ID NO: 4), where "$NH_2$—" is the amino-terminal end of the peptide (and is part of the N-terminal alanine) and the "—COOH" is the carboxy-terminal end of the peptide (and is part of the C-terminal alanine). In amino acid sequences disclosed herein (e.g., in text, tables, structures, lists, or otherwise), the "$NH_2$—" and/or the "—COOH" of a peptide may optionally be omitted or not shown.

In certain embodiments, the fluorophore is covalently attached to the cysteine of a pHLIP® peptide having the sequence: $NH_2$-ACDDQNPWRAYLDLLFPTDTLLLD-LLWA-COOH (SEQ ID NO: 4). In various embodiments, the pHLIP®-fluorophore compound has the following structure (SEQ ID NO: 4 is disclosed below):

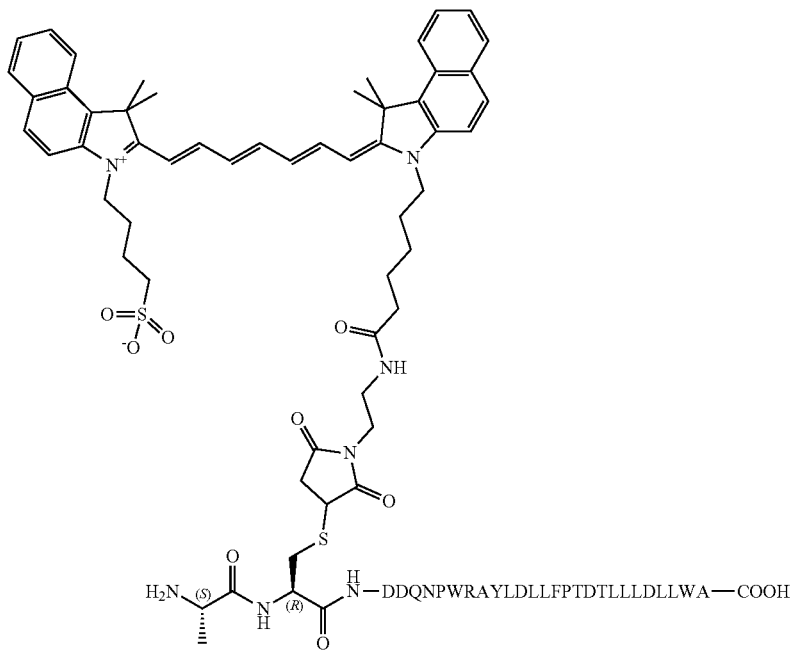

In the sequence above, the pHLIP® peptide sequence is NH$_2$-ACDDQNPWRAYLDLLFPTDTLLLDLLWA-COOH (SEQ ID NO. 4), however the structures of the alanine and the cysteine at the N-terminal end of the peptide are shown.

In some embodiments, the pHLIP® peptide has a net negative charge at a pH of about 7.5 or 7.75 in water.

In certain embodiments, the pHLIP® peptide has an acid dissociation constant at logarithmic scale (pKa) of less than about 4.0, 4.5, 5.0, 5.5, 6.0, 6.5, or 7.

In various embodiments, the pHLIP® peptide comprising at least 1 artificial protonatable amino acid. As used herein, an "artificial" amino acid is an amino acid that is not genetically encoded.

In some embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 genetically coded amino acids.

In certain embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 non-genetically coded amino acids.

In various embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 D-amino acids.

In some embodiments, the pHLIP® peptide comprises at least 8 amino acids, wherein, at least 2, 3, or 4 of the 8 amino acids of said peptide are non-polar, and at least 1, 2, 3, or 4 of the at least 8 amino acids of said pHLIP® peptide are protonatable.

In certain embodiments, the pHLIP® peptide comprises a functional group to which a fluorophore may be attached. For example, the pHLIP® peptide comprised a functional group before it was part of the pHLIP®-fluorophore compound, and the fluorophore was attached covalently to the pHLIP® peptide via a chemical interaction involving the functional group. In some embodiments, the pHLIP® peptide comprises a functional group, and the fluorophore is non-covalently attached (e.g., via non-covalent binding such as an electrostatic interaction) to the functional group. In the context of attachment of a pHLIP® peptide to a fluorophore, a "functional group" is a portion of a compound (such as a pHLIP® peptide) that is used to attach the compound to another compound (such as a pHLIP® peptide to a fluorophore). A "functional group" may optionally be referred to as an "attachment group." In various embodiments, a functional group is chemically reactive. In some embodiments, a functional group on a pHLIP® peptide reacts with a functional group on a fluorophore to leave a covalent bond that connects the pHLIP® peptide to the fluorophore, resulting in a pHLIP®-fluorophore compound. Non-limiting examples of functional groups include amino acid side chains (such as the —SH side chain of cysteine or a —NH$_2$ side chain of lysine); thiols (e.g., moieties comprising, consisting essentially of, or consisting of —SH); esters such as maleimide esters; moieties comprising—she; and moieties that may be involved in click reactions (such as azides, alkynes, strained difluorooctynes, diaryl-strained-cyclooctynes, 1,3-nitrones, cyclooctenes, trans-cycloalkenes, oxanorbornadienes, tetrazines, tetrazoles, activated alkenes, and oxanorbornadienes.

As used herein, the term "fluorophore" includes any compound that emits energy. The energy may be in the form of, e.g., acoustic energy (such as sound waves), heat, or electromagnetic radiation. In various embodiments, the electromagnetic radiation may be visible or non-visible to the human eye. In some embodiments, the electromagnetic radiation is infrared or near-infrared. Non-limiting examples of fluorophores include luminescent compounds, fluorescent compounds, phosphorescent compounds, chemiluminescent compounds, optoacoustic compounds, and quencher compounds (e.g., fluorescent quencher compounds). Fluorophores may comprise, e.g., small molecule compounds (e.g., organic compounds having a molecular weight of less than about 2000, 1000, or 500 daltons), proteins, or chelated metals (e.g., a chelator attached to a metal via covalent or non-covalent coordination bonds, wherein the combination of the chelator and the metal is fluorescent). In some embodiments, a chelated metal is within a "cage" formed by a chelator, and the combination of the chelator and the metal is fluorescent. In certain embodiments, the emission of energy (e.g., electromagnetic radiation such as luminescence, acoustic energy such as sound waves, or heat) does not involve the absorption and then emission of energy. In some embodiments, the emission of energy involves the absorbance and then the emission of energy.

As used herein, a compound that transfers greater than 50% the energy of absorbed light into the heat is called a "quencher." In some embodiments, a quencher transfers all of the energy of absorbed light into heat. In various embodiments, a quencher can emit some amount of light, but most of the absorbed energy (e.g., at least about 55%, 60%, 65%, 70%, 75%, 80%, 85%, 90%, 95%, 96%, 97%, 98%, 99% of the absorbed energy) is transferred into the heat. Non-limiting examples of quenchers include: i) Dabsyl (dimethylaminoazobenzenesulfonic acid); ii) Black Hole Quenchers (which can quench in wide range of practically the entire visible spectrum); and iii) TRDye QC-1 [which can quench in the range for visible to NIR (500-900 nm)]. A main principle of optoacoustic imaging is the following: Absorption of light by a fluorophore or quencher, and the transfer of energy into heat, which leads to thermal expansion and the generation of acoustic waves, which are detected. In general, fluorophores transfer some, e.g., a minimal amount, of energy to heat; however most of the energy of a fluorophore is emitted in a form of light. In certain preferred embodiments relating to luminescent fluorophores (e.g., fluorophores that emit electromagnetic radiation such as light), a fluorophore emits more energy in the form of electromagnetic radiation (e.g., light), and less energy is transferred to heat. In certain preferred embodiments relating to quenchers, a quencher emits less energy in the form of electromagnetic radiation (e.g., light), and more energy is transferred to heat. Therefore, ICG can be used as a fluorophore in fluorescent imaging, as well as in optoacoustic imaging, due its property of transferring some energy to the heat.

In various embodiments, 1, 2, 3, 4, 5 or more fluorophores are attached to the pHLIP® peptide.

In some embodiments, the functional group of the pHLIP® peptide to which a fluorophore may be (or has been) attached comprises an amino acid, azido modified amino acid, or alkynyl modified amino acid. In certain embodiments, the pHLIP® peptide is covalently attached to the fluorophore via an amide bond.

In certain embodiments, the functional group of the pHLIP® peptide comprises (or comprised) a free sulfhydryl (SH), or a primary amine.

In embodiments, the pHLIP® peptide is attached to one or more fluorophores (e.g., a fluorophore, a quencher such as a fluorophore quencher, or a combination comprising a fluorophore-quencher pair) to form a pHLIP®-fluorophore compound that is used as a diagnostic, imaging, ex vivo imaging agent, or as a research tool. In various embodiments, the pHLIP® peptide comprises one or more fluorophores attached to a functional group used as a diagnostic, imaging, ex vivo imaging agent, or as a research tool.

In some embodiments, the fluorophore comprises a fluorescent dye, or a fluorescent quencher, or a combination of both.

In some embodiments, a fluorophore-quencher system used in fluorescence-guided imaging. For non-limiting descriptions of such systems, see, e.g., www.bachem.com/service-support/newsletter/peptide-trends-july-2016/. A non-limiting example of the use of a fluorophore-quencher system is described in Karabadzhak et al. (2014) ACS Chem Biol. 9(11):2545-53, the entire content of which is incorporated herein by reference. In certain embodiments, when the distance between a fluorophore and a quencher increases [e.g., because of a conformational change or due to the breakage of a bond (such as a peptide or other bond) connecting the fluorophore and the quencher], then the intensity of emission of fluorophore increases. In certain embodiments, the efficiency of fluorescence increases when the distance between the fluorophore and the quencher increases, which results in increased of fluorescent intensity.

In some embodiments, a pHLIP® compound comprising a fluorophore or a quencher (e.g., a pHLIP®-quencher) is used for optoacoustic imaging. In various embodiments, optoacoustic imaging comprises a compound or moiety that absorbs light and transfers it to heat (e.g., with a optoacoustic imaging agent), which is measured by ultrasound, as opposed to fluorescence. In embodiments, fluorescence comprises a compound of moiety that absorbs light and emits it in the form of fluorescence or phosphorescence. In some embodiments, a fluorophore (e.g., a fluorophore that emits more energy in the form of light than heat) is used for optoacoustic imaging. In certain embodiments, an ICG-pHLIP® peptide is used for optoacoustic imaging. A non-limiting example of the use of a compound comprising a pHLIP® peptide and a fluorescent dye as a multispectral optoacoustic tomography (MSOT) imaging agent is described in Kimbrough et al. (2015) Clin Cancer Res. 21(20):4576-85, the entire content of which is incorporated herein by reference.

In certain embodiments, the fluorophore comprises a near-infrared (NIR) fluorescent dye, e.g., indocyanine green (ICG), which operates in (e.g., has a peak emission wavelength within) NIR wavelengths. Infrared radiation extends from the nominal red edge of the visible spectrum at 700 nanometers (nm) to 1 mm. NIR radiation comprises a wavelength of 750 nm to 1.4 µm. In some embodiments, the ICG has a peak emission wavelength between 810 nm and 880 nm (e.g., in the context of a pHLIP®-fluorophore compound). In certain embodiments, the ICG has a peak emission wavelength between 810 nm and 860 nm. In various embodiments, the ICG has a peak emission wavelength of about 800, 805, 810, 815, 820, 825, 830, 835, 840, 845, 850, 855, 860, 865, 870, or 880 nm. In some embodiments, a 805 nm laser is used for ICG excitation. In certain embodiments, a 801, 802, 803, 804, 804, 805, 806, 807, 808, 809, 810, 800-805, 804-806, or 802-807 nm laser is used for ICG excitation.

Non-limiting examples of NIR imaging systems (which may be useful in, e.g., clinical and diagnostic applications) include INFRARED 800™, available from Carl Zeiss Meditec AG; Artemis®, available from Quest Medical Imaging BV; HyperEye Medical System®, available from Mizuho Medical Co. Ltd.; Near infrared fluorescence imager PDE® C9830, available from Hamamatsu Photonics K.K.; SPECTROPATH® Image-Guided Surgery System, available from Spectropath Inc.; the following from NOVADAQ Technologies Inc.: SPY Elite® (imaging for open surgery), PINPOINT® (endoscopic fluorescence imaging), LUNA® (Fluorescence Angiography for Wound Care); Firefly® Fluorescence imaging for the da Vinci Si System, available from Intuitive Surgical Inc.; NIR Leica® FL800, available from Leica Microsystems; Fluobeam®, available from Fluoptics Minatec-BHT; KG, Storz Karl Storz-Endoskope® (Near-Infrared/Indocyanine Green), available from Karl Storz GmbH & Co.; and InfraVision™ Imaging System, available from Stryker Corporation.

In various embodiments, the fluorophore comprises an agent that operates at a wavelength (e.g., has a peak emission wavelength within) of from about 670 nm to about 750 nm, e.g., methylene blue.

In certain embodiments, the fluorophore comprises a cyanine dye. In embodiments, a cyanine dye operates at a wavelength (e.g., has a peak emission wavelength within) of 550-620 nm, 590-700 nm, 650-730 nm, 680-770 nm, 750-820 nm, or 770-850 nm. Non-limiting examples of cyanine dyes include Cy2, Cy3, Cy3B, Cy3.5, Cy5, Cy5.5, Cy7, and Cy7.5. In some embodiments, the cyanine dye is Cy3, Cy3.5, Cy5, Cy5.5, Cy7, or Cy7.5. In certain embodiments, the Cy3 has a peak emission wavelength between 550 and 620 nm (e.g., in the context of a pHLIP®-fluorophore compound). In various embodiments, the Cy3.5 has a peak emission wavelength between 590 and 700 nm (e.g., in the context of a pHLIP®-fluorophore compound). In some embodiments, the Cy5 has a peak emission wavelength between 650 and 730 nm (e.g., in the context of a pHLIP®-fluorophore compound). In certain embodiments, the Cy5.5 has a peak emission wavelength between 680 and 770 nm (e.g., in the context of a pHLIP®-fluorophore compound). In various embodiments, the Cy7 has a peak emission wavelength between 750 and 820 nm (e.g., in the context of a pHLIP®-fluorophore compound). In certain embodiments, the Cy7.5 has a peak emission wavelength between 770 and 850 nm (e.g., in the context of a pHLIP®-fluorophore compound).

In some embodiments, the peak emission wavelength of a fluoroophore may vary (e.g., by about 5, 6, 7, 8, 9, or 10%) based on the environment and/or solvent around the fluorophore.

In some embodiments, the fluorophore comprises a fluorescent, or an optoacoustic contrast imaging agent. In certain embodiments, an optoacoustic imaging agent is fluorescent. In various embodiments, an optoacoustic imaging agent is not fluorescent. In certain embodiments, an optoacoustic imaging agent absorbs light, and transfers most of the light's energy (e.g., at least about 55%, 60%, 65%, 70%, 75%, 80%, 85%, 90%, 95%, 96%, 97%, 98%, 99% of the light's energy) into heat. In various embodiments, the heat is detected by ultrasound. In some embodiments, a quencher is be a fluorophore with a very low quantum yield, such that most of the energy absorbed by the quencher is transferred to heat rather than electromagnetic radiation (such as light).

Non-limiting examples of optoacoustic contrast imaging agents include ICG (which can be used for fluorescent imaging as well as for optoacoustic imaging), Alexa Fluor 750, Evans blue, BHQ3 (Black Hole Quencher®-3; commercially available from, e.g., Biosearch Technologies, California, United States), QXL®680 (commercially available from, e.g., Cambridge Bioscience, Cambridge, United Kingdom), IRDye®800CW (commercially available from, e.g., LI-COR, Nebraska, United States), MMPSense™750 FAST (commercially available from, e.g., PerkinElmer Inc., Texas, United States), diketopyrrolopyrrole cyanine, cypate-C18, Au nanoparticles (such as Au nanospheres, Au nanoshells, Au nanorods, Au nanocages, Au nanoclusters, Au nanostars, and Au nanobeacons), nanoparticles comprising a gold core covered with the Raman molecular tag trans-1,2-bis(4-pyridyl)-ethylene, Ag nanoplates, Ag nanosystems, quantum dots, nanodiamonds, polypyrrole nanoparticles, copper sulfide, graphene nanosheets, iron oxide-gold core-shells, Gd2O3, single-walled carbon nanotubules, dye-loaded perfluorocarbon-based nanoparticles, AuMBs, triggered nanodroplets, cobalt nanowontons, nanoroses, goldsilica core shell nanorods, superparamagnetic iron oxide, and methylene blue. Non-limiting examples and descriptions of optoacoustic contrast imaging agents are described in Wu et al. (2014) *Int. J. Mol. Sci.*, 15, 23616-23639 (see, e.g., Table 1), the entire contents of which are incorporated herein by reference.

In various embodiments, a pHLIP®-fluorophore compound provided herein is for use as an agent in preoperative, intraoperative and postoperative settings.

In some embodiments, a pHLIP®-fluorophore compound provided herein is for use as an agent for ex vivo imaging, and ex vivo diagnostics.

In various embodiments, a pHLIP®-fluorophore compound provided herein is used to detect or image diseased tissue. Non-limiting examples of diseased tissue include cancerous tissue, inflamed tissue, ischemic tissue, arthritic tissue, cystic fibrotic tissue, tissue infected with a microorganism, and atherosclerotic tissue.

In some embodiments, a pHLIP®-fluorophore compound provided herein is for use as an agent in fluorescence angiography. Fluorescence angiography is a procedure in which a fluorescent compound (such as a pHLIP®-fluorophore compound disclosed herein) is injected into the bloodstream. The fluorescent compound highlights the blood vessels. In various embodiments, the vessels are in the back of the eye. In some embodiments the vessels are imaged or photographed. In non-limiting examples, fluorescence angiography is used to identify, detect image, or manage an eye disorder. In certain embodiments relating to ophthalmology, fluorescence angiography may be used to look at blood flow in, e.g., the retina and choroid.

In various embodiments, fluorescence angiography provides real-time imaging of blood vessels to follow changes during surgical procedures. Some non-limiting examples include the use of fluorescence in ophthalmology to evaluate the chorioretinal vasculature; in cardiothoracic surgery to assess the effectiveness of a coronary artery bypass; in neurovascular surgery to assess the effect of a superficial temporal artery-middle cerebral artery bypass graft in cerebral revascularization procedure; in hepatobilliary surgery to identify the haptic segment and subsegment for anatomical hepatic resection; in reconstructive surgeries; and in cholecystectomy and colorectal resection. In non-limiting examples of diagnostic applications, fluorescence angiography is used for imaging of hemodynamics in the brain; circulatory features of rheumatoid arthritis; muscle perfusion; burns and to assess various other effects of trauma.

In certain embodiments, a pHLIP®-fluorophore compound provided herein is for visualization of blood circulation in ophthalmology, cardiothoracic surgery, bypass coronary surgery, neurosurgery, hepatobilliary surgery, reconstructive surgery, cholecystectomy, colorectal resection, brain surgery, muscle perfusion, wound and trauma surgery, and laparoscopic surgery.

In various embodiments, a pHLIP®-fluorophore compound provided herein is for visualization of lymph nodes.

In some embodiments, a pHLIP®-fluorophore compound provided herein is for visualization or detection of pre-cancerous tissue or cancerous lesions.

In certain embodiments, a pHLIP®-fluorophore compound provided herein is for visualization or detection of pre-cancerous tissue or cancerous lesions in bladder, upper urinary tract, kidney, prostate, breast, head and neck, oral, pancreatic, lungs, liver, cervical, ovarian, or brain tumors.

In various embodiments, a pHLIP®-fluorophore compound provided herein for real-time assessment of blood flow and tissue perfusion during intraoperative procedures.

In an aspect, provided herein is a composition for parenteral, local, or systemic administration comprising a pHLIP®-fluorophore compound.

In an aspect, included herein is a composition for intravenous, intraarterial, intraperitoneal, intracerebral, intracerebroventricular, intrathecal, intracardiac, intracavernous, intraosseous, intraocular, intravitreal administration of a pHLIP®-fluorophore compound.

In an aspect, provided herein is composition for intramuscular, intradermal, transdermal, transmucosal, intralesional, subcutaneous, topical, epicutaneous, extra-amniotic, intravaginal, intravesical, nasal, or oral administration of a pHLIP®-fluorophore compound.

In an aspect, included herein is a composition for an ex vivo treatment of biopsy specimens, liquid biopsy specimens, surgically removed tissue, surgically removed liquids, or blood comprising a pHLIP®-fluorophore compound.

In an aspect, a subject's blood is contacted with the pHLIP®-fluorophore compound (e.g., in vivo or ex vivo).

In various embodiments, a lower dose of a fluorophore (such as ICG) is effective when the fluorophore is part of a pHLIP® fluorophore composition, e.g., conjugate, compared to the effective dose (e.g., for imaging or detection) of the free fluorophore, e.g., the non-conjugated fluorophore. In some embodiments, administration of a lower effective dose of the fluorophore as part of a pHLIP® fluorophore compound results in lower side effects. In certain embodiments, a fluorophore may make a subject more sensitive to solar radiation after administration such that the subject develops a greater degree of sunburn following exposure to solar radiation compared to a subject to which a fluorophore such as ICG has not been administered. In various embodiments, a fluorophore is delivered as part of a pHLIP® fluorophore compound to subject in a lower dose than would be necessary if the fluorophore was administered in free form, thereby reducing or minimizing phototoxicity (e.g., toxicity to the skin/sunburn) from exposure to solar radiation than if the free form of the fluorophore was administered.

In some embodiments, the pHLIP®-fluorophore compound comprises a pHLIP® and ICG (e.g., an ICG-pHLIP® peptide such as ICG-Var3). In certain embodiments, the pHLIP®-fluorophore compound is administered at a dose of about 0.01-0.5 mg/kg of a subject. In various embodiments, the pHLIP®-fluorophore compound is administered at a dose of about 0.02-0.2 mg/kg of a subject. In some embodiments, the pHLIP®-fluorophore compound is administered at a dose of about 0.01, 0.02, 0.03, 0.04, 0.05, 0.06, 0.07, 0.08, 0.09, 0.1, 0.125, 0.15, 0.175, 0.2, 0.25, or 0.5 mg/kg of a subject. In certain embodiments, the pHLIP®-fluorophore compound is administered at a dose of at least about 0.01, 0.02, 0.03, 0.04, 0.05, 0.06, 0.07, 0.08, 0.09, 0.1, 0.125, 0.15, 0.175, or 0.2 mg/kg, but less than about 0.25, 0.5, 1, 2, 3, 4, or 5 mg/kg. In various embodiments, 1-10 mg of the pHLIP®-fluorophore compound is administered to a subject. In some embodiments, about 0.5 1, 2, 3, 4, 5, 6, 7, 8, 9, 10, or 15 mg of the pHLIP®-fluorophore compound is administered to a subject. In certain embodiments, at least 0.5, 1, 2, or 3 mg, but less than 10 or 1 mg, of the pHLIP®-fluorophore compound is administered to the subject. In various embodiments, about 0.3-3 µmol of the pHLIP®-fluorophore compound is administered to the subject. In some embodiments, about 0.1, 0.5, 1, 1.5, 2, 2.5, 3, 3.5, 4, 4.5, or 5 µmol of the pHLIP®-fluorophore compound is administered to the subject. In certain embodiments, at least about 0.1, 0.5, or 1 µmol, but less than 3, 4, or 5 µmol, of the pHLIP®-fluorophore compound is administered to the subject. In various embodiments, the pHLIP®-fluorophore compound is administered by intravenous injection for about 1, 2, 3, 4, 5, 6, 7, 8, 9, 10, 11, 12, 13, 14, 15, 16, 17, 18, 19, 20, 1-10, 1-15, 5-10, 5-15, 5-20, 10-15, 10-20, or 15-20 minutes.

In certain embodiments, about 0.5 1, 2, 3, 4, 5, 6, 7, 8, 9, 10, or 15 mg of the pHLIP®-fluorophore compound is instilled into an organ or tissue (e.g. a bladder). In certain embodiments, at least 0.5, 1, 2, or 3 mg, but less than 10 or 1 mg, of the pHLIP®-fluorophore compound is instilled into an organ or tissue (e.g. a bladder). In various embodiments, about 0.3-3 µmol of the pHLIP®-fluorophore compound is instilled into an organ or tissue (e.g. a bladder). In some embodiments, about 0.1, 0.5, 1, 1.5, 2, 2.5, 3, 3.5, 4, 4.5, or 5 µmol of the pHLIP®-fluorophore compound is instilled into an organ or tissue (e.g. a bladder). In certain embodiments, at least about 0.1, 0.5, or 1 µmol, but less than 3, 4, or 5 µmol, of the pHLIP®-fluorophore compound is instilled into an organ or tissue (e.g. a bladder). In various embodiments, the pHLIP®-fluorophore compound is instilled into an organ or tissue (e.g. a bladder) for about 1, 2, 3, 4, 5, 6, 7, 8, 9, 10, 11, 12, 13, 14, 15, 16, 17, 18, 19, 20, 1-10, 1-15, 5-10, 5-15, 5-20, 10-15, 10-20, or 15-20 minutes.

In certain embodiments, the pHLIP®-fluorophore compound further comprises polyethylene glycol. In some embodiments, the pHLIP®-fluorophore compound further comprises one or more polyethylene glycol subunits (e.g., 3, 4, 5, 6, 7, 8, 9, 0, 11, 12, 13, 14, 15, 16, 17, 18, 19, 20, 3-10, 10-20, or 3-20 subunits).

Included herein is a method for detecting (e.g., imaging) blood flow in a subject, comprising (a) administering a pHLIP®-fluorophore compound comprising a fluorophore (such as ICG) disclosed herein to the subject; (b) contacting the subject (e.g., an area, cell, tissue, or organ of the subject, such as an area or tissue that may comprise a portion of the administered pHLIP®-fluorophore compound) with electromagnetic radiation comprising an excitation wavelength of the fluorophore; and (c) detecting electromagnetic radiation emitted from the pHLIP®-fluorophore compound in the subject. In embodiments, detection of the radiation indicates the presence (e.g., the location or amount at a location) of blood in the subject. In embodiments, an image of the blood in the subject is produced.

Also provided is a method for detecting (e.g., imaging) a pHLIP®-fluorophore compound in a subject, comprising (a) administering a pHLIP®-fluorophore compound comprising a fluorophore (such as ICG) disclosed herein to the subject; (b) contacting the subject (e.g., an area or tissue of the subject, such as an area, cell, tissue, or organ that may comprise a portion of the administered pHLIP®-fluorophore compound) with electromagnetic radiation comprising an excitation wavelength of the fluorophore; and (c) detecting electromagnetic radiation emitted from the pHLIP®-fluorophore compound in the subject. In embodiments, detection of the radiation indicates the presence (e.g., the location or amount at a location) of a bodily fluid such as blood in the subject. In embodiments, an image of the blood in the subject is produced.

Included herein is a method for optoacoustic detection or imaging of blood flow in a subject, comprising (a) administering a pHLIP®-fluorophore compound, wherein the fluorophore is an optoacoustic imaging agents such as a luminescent fluorophore or a quencher; (b) contacting the subject (e.g., an area, cell, tissue, or organ of the subject, such as an area or tissue that may comprise a portion of the administered pHLIP®-fluorophore compound) with electromagnetic radiation comprising an excitation wavelength of the fluorophore; and (c) detecting energy such as acoustic energy (e.g., sound waves). In embodiments, detection of the energy indicates the presence (e.g., the location or amount at a location) of blood in the subject. In various embodiments, an image of the blood in the subject is produced. In some embodiments, the presence of acoustic energy is detected by ultrasound (e.g., heat is released and creates expansion, generating sound waves, which is detected).

The present subject matter also provides a method for detecting (e.g., imaging) a pHLIP®-fluorophore compound in a subject, wherein the fluorophore is an optoacoustic imaging agents such as a luminescent fluorophore or a quencher, the method comprising (a) administering the pHLIP®-fluorophore compound to the subject; (b) contacting the subject (e.g., an area or tissue of the subject, such as an area, cell, tissue, or organ that may comprise a portion of the administered pHLIP®-fluorophore compound) with electromagnetic radiation comprising an excitation wavelength of the fluorophore; and (c) detecting energy such as acoustic energy (e.g., sound waves). In embodiments, detection of the energy indicates the presence (e.g., the location or amount at a location) of a bodily fluid such as blood in the subject. In embodiments, an image of the blood in the subject is produced. In embodiments, the presence of acoustic energy is detected by ultrasound.

Depending on context, "excitation wavelength" may be used synonymously with "absorption wavelength."

In various embodiments, the method comprises a fluorescence-guided imaging procedure performed during surgery or during a doctor's visit. In some embodiments, the method comprises fluorescence angiography. In certain embodiments, the method comprises the assessment of the perfusion of tissues and organs. In various embodiments, the method comprises the assessment of hepatic function. In some embodiments, the fluorescence-guided imaging procedure comprises targeting, marking, detecting, or visualization of pre-cancerous tissue, cancerous tissue, inflamed tissue, ischemic tissue, arthritic tissue, tissue infected with a microorganism, and/or atherosclerotic tissue. In certain embodiments, the method comprises assessing patency of a coronary artery bypass during cardiothoracic surgery. In some embodiments, the method comprises assessing the effect of a superficial temporal artery-middle cerebral artery bypass graft during or after neurovascular surgery, e.g., in a cerebral revascularization procedure. In certain embodiments, the method comprises identify the haptic segment and subsegment for anatomical hepatic resection during hepatobillary surgery. In some embodiments, the method comprises imaging tissue or blood during a reconstructive surgery. In certain embodiments, the method comprises imaging tissue or blood during cholecystectomy or colorectal resection. In some embodiments, the method comprises intraoperatively identifying brain tumors such as malignant gliomas.

In various embodiments, the method comprises a diagnostic imaging procedure. In some embodiments, the method comprises retinal angiography. In certain embodiments, the method comprises detecting or imaging chorioretinal vasculature.

In some embodiments, the method comprises mapping and visualization of lymph nodes. In certain embodiments, the method comprises targeting and marking (e.g., visualizing or detecting) pre-cancerous tissue, cancerous lesions and/or assessment of tumor margins.

In various embodiments, the pHLIP®-fluorophore compound is administered by parenteral, local, or systemic administration. In certain embodiments, a pHLIP®-fluorophore compound is administered by intravenous, intraarterial, intraperitoneal, intracerebral, intracerebroventricular, intrathecal, intracardiac, intracavernous, intraosseous, intraocular, or intravitreal administration. In various embodiments, pHLIP®-fluorophore compound is administered by intramuscular, intradermal, transdermal, transmucosal, intralesional, subcutaneous, topical, epicutaneous, extra-amniotic, intravaginal, intravesical, nasal, or oral administration.

In an aspect, provided herein is a method for the ex vivo staining of human specimens and ex vivo diagnostics, comprising (a) contacting a biological sample from a subject with a pHLIP®-fluorophore compound comprising a fluorophore (such as ICG) disclosed herein; (b) contacting the biological sample with electromagnetic radiation comprising an excitation wavelength of the fluorophore; and (c) detecting electromagnetic radiation emitted from the pHLIP®-fluorophore compound. In embodiments, the biological sample comprises a biopsy specimen, a liquid biopsy specimen, surgically removed tissue, a surgically removed liquid, or blood.

In some embodiments, the pHLIP® peptide comprises a sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

```
                              (SEQ ID NO: 36)
WARYADWLFTTPLLLLDLALL, (SEQ ID NO: 37)
YARYADWLFTTPLLLLDLALL, (SEQ ID NO: 38)
WARYSDWLFTTPLLLYDLGLL, (SEQ ID NO: 39)
WARYTDWFTTPLLLYDLALLA, (SEQ ID NO: 40)
WARYTDWLFTTPLLLYDLGLL, (SEQ ID NO: 41)
WARYADWLFTTPLLLLDLSLL, (SEQ ID NO: 42)
LLALDLLLLPTTFLWDAYRAW, (SEQ ID NO: 43)
LLALDLLLLPTTFLWDAYRAY, (SEQ ID NO: 44)
LLGLDYLLLPTTFLWDSYRAW, (SEQ ID NO: 45)
ALLALDYLLLPTTFWDTYRAW, (SEQ ID NO: 46)
LLGLDYLLLPTTFLWDTYRAW, (SEQ ID NO: 47)
LLSLDLLLLPTTFLWDAYRAW, (SEQ ID NO: 48)
GLAGLLGLEGLLGLPLGLLEGLWLGL, (SEQ ID NO: 49)
LGLWLGELLGLPLGLLGELGLLGALG, (SEQ ID NO: 50)
WRAYLDLLFPTDTLLLDLLW, (SEQ ID NO: 51)
WLLDLLLTDTPFLLDLYARW,
```

-continued

WARYLEWLFPTETLLLEL, (SEQ ID NO: 52)

WAQYLELLFPTETLLLEW, (SEQ ID NO: 53)

LELLLTETPFLWELYRAW, (SEQ ID NO: 54)

WELLLTETPFLLELYQAW, (SEQ ID NO: 55)

WLFTTPLLLLNGALLVE, (SEQ ID NO: 56)

WLFTTPLLLLPGALLVE, (SEQ ID NO: 57)

WARYADLLFPTTLAW, (SEQ ID NO: 58)

EVLLAGNLLLLPTTFLW, (SEQ ID NO: 59)

EVLLAGPLLLLPTTFLW, (SEQ ID NO: 60)

WALTTPFLLDAYRAW, (SEQ ID NO: 61)

NLEGFFATLGGEIALWSLVVLAIE, (SEQ ID NO: 62)

EGFFATLGGEIALWSDVVLAIE, (SEQ ID NO: 63)

EGFFATLGGEIPLWSDVVLAIE, (SEQ ID NO: 64)

EIALVVLSWLAIEGGLTAFFGELN, (SEQ ID NO: 65)

EIALVVDSWLAIEGGLTAFFGE, (SEQ ID NO: 66)

EIALVVDSWLPIEGGLTAFFGE, (SEQ ID NO: 67)

ILDLVFGLLFAVTSVDFLVQW, (SEQ ID NO: 68)
and

WQVLFDVSTVAFLLGFVLDLI. (SEQ ID NO: 69)

In embodiments, the pHLIP® peptide comprises the amino acid sequence WRAYLDLLFPTDTLLLDLLW (SEQ ID NO: 50) with additional amino acids (e.g., 1, 2, 3, 4, 5, 6, 7, 8, 9, 10 or more amino acids) optionally added to either side.

In certain embodiments, the pHLIP® peptide has the sequence:

WARYADWLFTTPLLLLDLALL, (SEQ ID NO: 70)

YARYADWLFTTPLLLLDLALL, (SEQ ID NO: 71)

WARYSDWLFTTPLLLYDLGLL, (SEQ ID NO: 72)

WARYTDWFTTPLLLYDLALLA, (SEQ ID NO: 73)

WARYTDWLFTTPLLLYDLGLL, (SEQ ID NO: 74)

WARYADWLFTTPLLLLDLSLL, (SEQ ID NO: 75)

LLALDLLLLPTTFLWDAYRAW, (SEQ ID NO: 76)

LLALDLLLLPTTFLWDAYRAY, (SEQ ID NO: 77)

LLGLDYLLLPTTFLWDSYRAW, (SEQ ID NO: 78)

ALLALDYLLLPTTFWDTYRAW, (SEQ ID NO: 79)

LLGLDYLLLPTTFLWDTYRAW, (SEQ ID NO: 80)

LLSLDLLLLPTTFLWDAYRAW, (SEQ ID NO: 81)

GLAGLLGLEGLLGLPLGLLEGLWLGL, (SEQ ID NO: 82)

LGLWLGELLGLPLGLLGELGLLGALG, (SEQ ID NO: 83)

WRAYLDLLFPTDTLLLDLLW, (SEQ ID NO: 84)

WLLDLLLTDTPFLLDLYARW, (SEQ ID NO: 85)

WARYLEWLFPTETLLLEL, (SEQ ID NO: 86)

WAQYLELLFPTETLLLEW, (SEQ ID NO: 87)

LELLLTETPFLWELYRAW, (SEQ ID NO: 88)

WELLLTETPFLLELYQAW, (SEQ ID NO: 89)

WLFTTPLLLLNGALLVE, (SEQ ID NO: 90)

WLFTTPLLLLPGALLVE, (SEQ ID NO: 91)

WARYADLLFPTTLAW, (SEQ ID NO: 92)

EVLLAGNLLLLPTTFLW, (SEQ ID NO: 93)

EVLLAGPLLLLPTTFLW, (SEQ ID NO: 94)

WALTTPFLLDAYRAW, (SEQ ID NO: 95)

NLEGFFATLGGEIALWSLVVLAIE, (SEQ ID NO: 96)

EGFFATLGGEIALWSDVVLAIE, (SEQ ID NO: 97)

EGFFATLGGEIPLWSDVVLAIE, (SEQ ID NO: 98)

EIALVVLSWLAIEGGLTAFFGELN, (SEQ ID NO: 99)

EIALVVDSWLAIEGGLTAFFGE, (SEQ ID NO: 100)

EIALVVDSWLPIEGGLTAFFGE, (SEQ ID NO: 101)

```
ILDLVFGLLFAVTSVDFLVQW,                    (SEQ ID NO: 102)
or

WQVLFDVSTVAFLLGFVLDLI.                    (SEQ ID NO: 103)
```

In various embodiments, the pHLIP® peptide comprises the sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

```
WARYAXWLFTTPLLLLXLALL,                    (SEQ ID NO: 104)

YARYAXWLFTTPLLLLXLALL,                    (SEQ ID NO: 105)

WARYSXWLFTTPLLLYXLGLL,                    (SEQ ID NO: 106)

WARYTXWFTTPLLLYXLALLA,                    (SEQ ID NO: 107)

WARYTXWLFTTPLLLYXLGLL,                    (SEQ ID NO: 108)

WARYAXWLFTTPLLLLXLSLL,                    (SEQ ID NO: 109)

LLALXLLLLPTTFLWXAYRAW,                    (SEQ ID NO: 110)

LLALXLLLLPTTFLWXAYRAY,                    (SEQ ID NO: 111)

LLGLXYLLLPTTFLWXSYRAW,                    (SEQ ID NO: 112)

ALLALXYLLLPTTFWXTYRAW,                    (SEQ ID NO: 113)

LLGLXYLLLPTTFLWXTYRAW,                    (SEQ ID NO: 114)

LLSLXLLLLPTTFLWXAYRAW,                    (SEQ ID NO: 115)

GLAGLLGLXGLLGLPLGLLXGLWLGL,               (SEQ ID NO: 116)

LGLWLGXLLGLPLGLLGXLGLLGALG,               (SEQ ID NO: 117)

WRAYLXLLFPTXTLLLXLLW,                     (SEQ ID NO: 118)

WLLXLLLTXTPFLLXLYARW,                     (SEQ ID NO: 119)

WARYLXWLFPTXTLLLXL,                       (SEQ ID NO: 120)

WAQYLXLLFPTXTLLLXW,                       (SEQ ID NO: 121)

LXLLLTXTPFLWXLYRAW,                       (SEQ ID NO: 122)

WXLLLTXTPFLLXLYQAW,                       (SEQ ID NO: 123)

WLFTTPLLLLNGALLVX,                        (SEQ ID NO: 124)

WLFTTPLLLLPGALLVX,                        (SEQ ID NO: 125)

WARYAXLLFPTTLAW,                          (SEQ ID NO: 126)

XVLLAGNLLLLPTTFLW,                        (SEQ ID NO: 127)

XVLLAGPLLLLPTTFLW,                        (SEQ ID NO: 128)

WALTTPFLLXAYRAW,                          (SEQ ID NO: 129)

NLXGFFATLGGXIALWSLVVLAIX,                 (SEQ ID NO: 130)

XGFFATLGGXIALWSXVVLAIX,                   (SEQ ID NO: 131)

XGFFATLGGXIPLWSXVVLAIX,                   (SEQ ID NO: 132)

XIALVVLSWLAIXGGLTAFFGXLN,                 (SEQ ID NO: 133)

XIALVVXSWLAIXGGLTAFFGX,                   (SEQ ID NO: 134)

XIALVVXSWLPIXGGLTAFFGX,                   (SEQ ID NO: 135)

ILXLVFGLLFAVTSVXFLVQW,                    (SEQ ID NO: 136)
and

WQVLFXVSTVAFLLGFVLXLI,                    (SEQ ID NO: 137)
``` wherein each X is, individually, D, E, Gla, or Aad.

In some embodiments, the pHLIP® peptide comprises the sequence:

```
WARYAXWLFTTPLLLLXLALL,                    (SEQ ID NO: 138)

YARYAXWLFTTPLLLLXLALL,                    (SEQ ID NO: 139)

WARYSXWLFTTPLLLYXLGLL,                    (SEQ ID NO: 140)

WARYTXWFTTPLLLYXLALLA,                    (SEQ ID NO: 141)

WARYTXWLFTTPLLLYXLGLL,                    (SEQ ID NO: 142)

WARYAXWLFTTPLLLLXLSLL,                    (SEQ ID NO: 143)

LLALXLLLLPTTFLWXAYRAW,                    (SEQ ID NO: 144)

LLALXLLLLPTTFLWXAYRAY,                    (SEQ ID NO: 145)

LLGLXYLLLPTTFLWXSYRAW,                    (SEQ ID NO: 146)

ALLALXYLLLPTTFWXTYRAW,                    (SEQ ID NO: 147)

LLGLXYLLLPTTFLWXTYRAW,                    (SEQ ID NO: 148)

LLSLXLLLLPTTFLWXAYRAW,                    (SEQ ID NO: 149)
```

-continued

GLAGLLGLXGLLGLPLGLLXGLWLGL, (SEQ ID NO: 150)

LGLWLGXLLGLPLGLLGXLGLLGALG, (SEQ ID NO: 151)

WRAYLXLLFPTXTLLLXLLW, (SEQ ID NO: 152)

WLLXLLLTXTPFLLXLYARW, (SEQ ID NO: 153)

WARYLXWLFPTXTLLLXL, (SEQ ID NO: 154)

WAQYLXLLFPTXTLLLXW, (SEQ ID NO: 155)

LXLLLTXTPFLWXLYRAW, (SEQ ID NO: 156)

WXLLLTXTPFLLXLYQAW, (SEQ ID NO: 157)

WLFTTPLLLLNGALLVX, (SEQ ID NO: 158)

WLFTTPLLLLPGALLVX, (SEQ ID NO: 159)

WARYAXLLFPTTLAW, (SEQ ID NO: 160)

XVLLAGNLLLLPTTFLW, (SEQ ID NO: 161)

XVLLAGPLLLLPTTFLW, (SEQ ID NO: 162)

WALTTPFLLXAYRAW, (SEQ ID NO: 163)

NLXGFFATLGGXIALWSLVVLAIX, (SEQ ID NO: 164)

XGFFATLGGXIALWSXVVLAIX, (SEQ ID NO: 165)

XGFFATLGGXIPLWSXVVLAIX, (SEQ ID NO: 166)

XIALVVLSWLAIXGGLTAFFGXLN, (SEQ ID NO: 167)

XIALVVXSWLAIXGGLTAFFGX, (SEQ ID NO: 168)

XIALVVXSWLPIXGGLTAFFGX, (SEQ ID NO: 169)

ILXLVFGLLFAVTSVXFLVQW, (SEQ ID NO: 170)

or

WQVLFXVSTVAFLLGFVLXLI, (SEQ ID NO: 171)

wherein each X is, individually, D, E, Gla, or Aad.

In certain embodiments, the pHLIP® peptide comprises the sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

$X_2X_2RX_2X_2X_1X_2X_2X_2X_3X_3X_2X_2X_2X_2X_1X_2X_2X_2$, (SEQ ID NO: 447)

$X_2X_2RX_2X_3X_1X_2X_2X_2X_3X_3X_2X_2X_2X_2X_1X_2GX_2X_2$, (SEQ ID NO: 448)

$X_2X_2RX_2X_3X_1X_2X_2X_3X_3X_2X_2X_2X_2X2X_1X_2X_2X_2X_2$, (SEQ ID NO: 449)

$X_2X_2RX_2X_2X_1X_2X_2X_2X_3X_3X_2X_2X_2X_2X_1X_2X_3X_2X_2$, (SEQ ID NO: 450)

$X_2X_2X_2X_2X_1X_2X_2X_2X_2X_3X_3X_2X_2X_2X_1X_2X_2RX_2X_2$, (SEQ ID NO: 451)

$X_2X_2GX_2X_1X_2X_2X_2X_2X_3X_3X_2X_2X_2X_1X_3X_2RX_2X_2$, (SEQ ID NO: 452)

$X_2X_2X_2X_2X_1X_2X_2X_2X_2X_3X_3X_2X_2X_1X_3X_2RX_2X_2$, (SEQ ID NO: 453)

$X_2X_2X_3X_2X_1X_2X_2X_2X_2X_3X_3X_2X_2X_2X_1X_2X_2RX_2X_2$, (SEQ ID NO: 454)

$GX_2X_2GX_2X_2GX_2X_1GX_2X_2GX_2X_2X_2GX_2X_2X_1GX_2X_2X_2GX_2$, (SEQ ID NO: 455)

$X_2GX_2X_2X_2GX_1X_2X_2GX_2X_2X_2GX_2X_2GX_1X_2GX_2X_2GX_2X_2G$, (SEQ ID NO: 456)

$X_2RX_2X_2X_2X_1X_2X_2X_2X_2X_3X_1X_3X_2X_2X_2X_1X_2X_2X_2$, (SEQ ID NO: 457)

$X_2X_2X_2X_1X_2X_2X_2X_3X_1X_3X_2X_2X_2X_2X_1X_2X_2X_2RX_2$, (SEQ ID NO: 458)

$X_2X_2RX_2X_2X_1X_2X_2X_2X_2X_3X_1X_3X_2X_2X_2XX_2$, (SEQ ID NO: 459)

$X_2X_2QX_2X_2X_1X_2X_2X_2X_2X_3X_1X_3X_2X_2X_2X_1X_2$, (SEQ ID NO: 460)

$X_2X_1X_2X_2X_2X_3X_1X_3X_2X_2X_2X_2X_1X_2X_2RX_2X_2$, (SEQ ID NO: 461)

$X_2X_1X_2X_2X_2X_3X_1X_3X_2X_2X_2X_2X_1X_2X_2QX_2X_2$, (SEQ ID NO: 462)

$X_2X_2X_2X_3X_3X_2X_2X_2X_2X_2NGX_2X_2X_2X_2X_1$, (SEQ ID NO: 463)

$X_2X_2X_2X_3X_3X_2X_2X_2X_2X_2GX_2X_2X_2X_2X_1$, (SEQ ID NO: 464)

$X_2X_2RX_2X_2X_1X_2X_2X_2X_2X_3X_3X_2X_2X_2$, (SEQ ID NO: 465)

$X_1X_2X_2X_2X_2GNX_2X_2X_2X_2X_2X_3X_3X_2X_2X_2$, (SEQ ID NO: 466)

$X_1X_2X_2X_2X_2GX_2X_2X_2X_2X_2X_2X_3X_3X_2X_2X_2$, (SEQ ID NO: 467)

$X_2X_2X_2X_3X_3X_2X_2X_2X_2X_1X_2X_2RX_2X_2$, (SEQ ID NO: 468)

$GNX_2X_1GX_2X_2X_2X_3X_2GGX_1X_2X_2X_2X_2X_3X_2X_2X_2X_2X_2X_1$, (SEQ ID NO: 469)

$X_1GX_2X_2X_2X_3X_2GGX_1X_2X_2X_2X_2X_3X_1X_2X_2X_2X_2X_2X_1$, (SEQ ID NO: 470)

$X_1GX_2X_2X_2X_3X_2GGX_1X_2X_2X_2X_2X_3X_1X_2X_2X_2X_2X_2X_1$, (SEQ ID NO: 471)

$X_1X_2X_2X_2X_2X_2X_2X_3X_2X_2X_2X_2X_1GGX_2X_3X_2X_2X_2GX_1X_2NG$, (SEQ ID NO: 472)

$X_1X_2X_2X_2X_2X_2X_1X_3X_2X_2X_2X_2X_1GGX_2X_3X_2X_2X_2GX_1$, (SEQ ID NO: 473)

-continued (SEQ ID NO: 474)
X₁X₂X₂X₂X₂X₂X₁X₃X₂X₂X₂X₂X₁GGX₂X₃X₂X₂X₂GX₁, (SEQ ID NO: 475)
X₂X₂X₁X₂X₂X₂GX₂X₂X₂X₂X₂X₃X₃X₂X₁X₂X₂X₂QX₂,
and (SEQ ID NO: 476)
X₂QX₂X₂X₂X₁X₂X₃X₃X₂X₂X₂X₂GX₂X₂X₂X₁X₂X₂, wherein each X₁ is, individually, D, E, Gla, or Aad, each X₂ is, individually, A, I, L, M, F, P, W, Y, V, or G and each X₃ is, individually, S, T, or G.

In various embodiments, the pHLIP® peptide comprises the sequence:

(SEQ ID NO: 477)
X₂X₂RX₂X₂X₁X₂X₂X₂X₃X₃X₂X₂X₂X₂X₁X₂X₂X₂X₂, (SEQ ID NO: 478)
X₂X₂RX₂X₃X₁X₂X₂X₂X₃X₃X₂X₂X₂X₂X2X₁X₂GX₂X₂, (SEQ ID NO: 479)
X₂X₂RX₂X₃X₁X₂X₂X₃X₃X₂X₂X₂X₂X₁X₂X₂X₂X₂, (SEQ ID NO: 480)
X₂X₂RX₂X₂X₁X₂X₂X₂X₃X₃X₂X₂X₂X₂X₁X₂X₃X₂, (SEQ ID NO: 481)
X₂X₂X₂X₂X₁X₂X₂X₂X₂X₂X₃X₃X₂X₂X₂X₁X₂X₂RX₂X₂, (SEQ ID NO: 482)
X₂X₂GX₂X₁X₂X₂X₂X₂X₂X₃X₃X₂X₂X₂X₁X₃X₂RX₂X₂, (SEQ ID NO: 483)
X₂X₂X₂X₂X₂X₁X₂X₂X₂X₂X₂X₃X₃X₂X₂X₁X₃X₂RX₂X₂, (SEQ ID NO: 484)
X₂X₂X₃X₂X₁X₂X₂X₂X₂X₂X₃X₃X₂X₂X₂X₁X₂X₂RX₂X₂, (SEQ ID NO: 485)
GX₂X₂GX₂X₂GX₂X₁GX₂X₂GX₂X₂X₂GX₂X₂X₁GX₂X₂X₂GX₂, (SEQ ID NO: 486)
X₂GX₂X₂X₂GX₁X₂X₂GX₂X₂X₂GX₂X₂GX₁X₂GX₂X₂GX₂X₂G, (SEQ ID NO: 487)
X₂RX₂X₂X₂X₁X₂X₂X₂X₂X₃X₁X₃X₂X₂X₂X₁X₂X₂X₂, (SEQ ID NO: 488)
X₂X₂X₂X₁X₂X₂X₂X₃X₁X₃X₂X₂X₂X₂X₁X₂X₂X₂RX₂, (SEQ ID NO: 489)
X₂X₂RX₂X₂X₁X₂X₂X₂X₂X₃X₁X₃X₂X₂X₂XX₂, (SEQ ID NO: 490)
X₂X₂QX₂X₂X₁X₂X₂X₂X₂X₃X₁X₃X₂X₂X₂X₁X₂, (SEQ ID NO: 491)
X₂X₁X₂X₂X₂X₃X₁X₃X₂X₂X₂X₂X₁X₂X₂RX₂X₂, (SEQ ID NO: 492)
X₂X₁X₂X₂X₂X₃X₁X₃X₂X₂X₂X₂X₁X₂X₂QX₂X₂, (SEQ ID NO: 493)
X₂X₂X₂X₃X₃X₂X₂X₂X₂X₂NGX₂X₂X₂X₂X₁, (SEQ ID NO: 494)
X₂X₂X₂X₃X₃X₂X₂X₂X₂X₂GX₂X₂X₂X₂X₁, (SEQ ID NO: 495)
X₂X₂RX₂X₂X₁X₂X₂X₂X₂X₃X₃X₂X₂X₂, (SEQ ID NO: 496)
X₁X₂X₂X₂X₂GNX₂X₂X₂X₂X₃X₃X₂X₂X₂, (SEQ ID NO: 497)
X₁X₂X₂X₂X₂GX₂X₂X₂X₂X₂X₃X₃X₂X₂X₂, (SEQ ID NO: 498)
X₂X₂X₂X₃X₃X₂X₂X₂X₂X₁X₂X₂RX₂X₂, (SEQ ID NO: 499)
GNX₂X₁GX₂X₂X₂X₃X₂GGX₁X₂X₂X₂X₂X₃X₂X₂X₂X₂X₂X₁, (SEQ ID NO: 500)
X₁GX₂X₂X₂X₃X₂GGX₁X₂X₂X₂X₂X₃X₁X₂X₂X₂X₂X₂X₁, (SEQ ID NO: 501)
X₁GX₂X₂X₂X₃X₂GGX₁X₂X₂X₂X₂X₃X₁X₂X₂X₂X₂X₂X₁, (SEQ ID NO: 502)
X₁X₂X₂X₂X₂X₂X₃X₂X₂X₂X₂X₁GGX₂X₃X₂X₂X₂GX₁X₂NG, (SEQ ID NO: 503)
X₁X₂X₂X₂X₂X₂X₁X₃X₂X₂X₂X₂X₁GGX₂X₃X₂X₂X₂GX₁, (SEQ ID NO: 504)
X₁X₂X₂X₂X₂X₂X₁X₃X₂X₂X₂X₂X₁GGX₂X₃X₂X₂X₂GX₁, (SEQ ID NO: 505)
X₂X₂X₁X₂X₂X₂GX₂X₂X₂X₂X₂X₃X₃X₂X₁X₂X₂X₂QX₂,
and (SEQ ID NO: 506)
X₂QX₂X₂X₂X₁X₂X₃X₃X₂X₂X₂X₂X₂GX₂X₂X₂X₁X₂X₂, wherein each X₁ is, individually, D, E, Gla, or Aad, each X₂ is, individually, A, I, L, M, F, P, W, Y, V, or G, and each X₃ is, individually, S, T, or G.

In some embodiments, the pHLIP® peptide comprises a sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

(SEQ ID NO: 172)
AEQNPIYWARYAEWLFTTPLLLLELALLVEAEET, (SEQ ID NO: 173)
ADDQNPWRAYLDLLFPDTTDLLLLDLLWDADET, (SEQ ID NO: 174)
AEEQNPWRAYLELLFPETTELLLLELLWEAEET, (SEQ ID NO: 175)
AEQNPIYWARYAGlaWLFTTPLLLLGlaLALLVDADET, (SEQ ID NO: 176)
AEQNPIYWARYAAadWLFTTPLLLLAadLALLVDADET, (SEQ ID NO: 177)
AEQNPIYWARYAAadWLFTTPLLLLGlaLALLVDADET, (SEQ ID NO: 178)
CEQNPIYWARYADWHFTTPLLLLDLALLVDADE, (SEQ ID NO: 179)
ADNNPWIYARYADLTTFPLLLLDLALLVDFDD, (SEQ ID NO: 180)
ADNNPFIYARYADLTTWPLLLLDLALLVDFDD, (SEQ ID NO: 181)
ADNNPFIYARYADLTTFPLLLLDLALLVDWDD, (SEQ ID NO: 182)
ADNNPFPYARYADLTTWILLLLDLALLVDFDD, (SEQ ID NO: 183)
ADNNPFIYAYRADLTTFPLLLLDLALLVDWDD, (SEQ ID NO: 184)
ADNNPFIYATYADLRTFPLLLLDLALLVDWDD,

-continued

ADDQNPWRAYLDLLFPTDTLLLDLLWDADE, (SEQ ID NO: 185)

ADDQNPWRAYLGlaLLFPTDTLLLDLLW, (SEQ ID NO: 186)

ADDQNPWRAYLDLLFPTGlaTLLLDLLW, (SEQ ID NO: 187)

ADDQNPWRAYLDLLFPTDTLLLGlaLLW, (SEQ ID NO: 188)

ADDQNPWRAYLGlaLLFPTGlaTLLLDLLW, (SEQ ID NO: 189)

ADDQNPWRAYLGlaLLFPTDTLLLGlaLLW, (SEQ ID NO: 190)

ADDQNPWRAYLDLLFPTGlaTLLLGlaLLW, (SEQ ID NO: 191)

ADDQNPWRAYLGlaLLFPTGlaTLLLGlaLLW, (SEQ ID NO: 192)

ADDQNPWRAYLAadLLFPTDTLLLDLLW, (SEQ ID NO: 193)

ADDQNPWRAYLDLLFPTAadTLLLDLLW, (SEQ ID NO: 194)

ADDQNPWRAYLDLLFPTDTLLLAadLLW, (SEQ ID NO: 195)

ADDQNPWRAYLAadLLFPTAadTLLLDLLW, (SEQ ID NO: 196)

ADDQNPWRAYLAadLLFPTDTLLLAadLLW, (SEQ ID NO: 197)

ADDQNPWRAYLDLLFPTAadTLLLAadLLW, (SEQ ID NO: 198)

ADDQNPWRAYLAadLLFPTAadTLLLAadLLW, (SEQ ID NO: 199)

ADDQNPWRAYLGlaLLFPTAadTLLLDLLW, (SEQ ID NO: 200)

ADDQNPWRAYLGlaLLFPTDTLLLAadLLW, (SEQ ID NO: 201)

ADDQNPWRAYLGlaLLFPTGlaTLLLAadLLW, (SEQ ID NO: 202)

ADDQNPWRAYLAadLLFPTGlaTLLLDLLW, (SEQ ID NO: 203)

ADDQNPWRAYLAadLLFPTDTLLLGlaLLW, (SEQ ID NO: 204)

ADDQNPWRAYLGlaLLFPTAadTLLLGlaLLW, (SEQ ID NO: 205)

GEEQNPWLGAYLDLLFPLELLGLLELGLW, (SEQ ID NO: 206)

EQNPIYILDLVFGLLFAVTSVDFLVQWDDAGD, (SEQ ID NO: 207)

NNEGFFATLGGEIALWSDVVLAIE, (SEQ ID NO: 208)
and

DNNEGFFATLGGEIPLWSDVVLAIE. (SEQ ID NO: 209)

In certain embodiments, the pHLIP® peptide comprises the sequence:

AEQNPIYWARYAEWLFTTPLLLLELALLVEAEET, (SEQ ID NO: 210)

ADDQNPWRAYLDLLFPDTTDLLLLDLLWDADET, (SEQ ID NO: 211)

AEEQNPWRAYLELLFPETTELLLLELLWEAEET, (SEQ ID NO: 212)

AEQNPIYWARYAGlaWLFTTPLLLLGlaLALLVDADET, (SEQ ID NO: 213)

AEQNPIYWARYAAadWLFTTPLLLLLAadLALLVDADET, (SEQ ID NO: 214)

AEQNPIYWARYAAadWLFTTPLLLLGlaLALLVDADET, (SEQ ID NO: 215)

CEQNPIYWARYADWHFTTPLLLLDLALLVDADE, (SEQ ID NO: 216)

ADNNPWIYARYADLTTFPLLLLDLALLVDFDD, (SEQ ID NO: 217)

ADNNPFIYARYADLTTWPLLLLDLALLVDFDD, (SEQ ID NO: 218)

ADNNPFIYARYADLTTFPLLLLDLALLVDWDD, (SEQ ID NO: 219)

ADNNPFPYARYADLTTWILLLLDLALLVDFDD, (SEQ ID NO: 220)

ADNNPFIYAYRADLTTFPLLLLDLALLVDWDD, (SEQ ID NO: 221)

ADNNPFIYATYADLRTFPLLLLDLALLVDWDD, (SEQ ID NO: 222)

ADDQNPWRAYLDLLFPTDTLLLDLLWDADE, (SEQ ID NO: 223)

ADDQNPWRAYLGlaLLFPTDTLLLDLLW, (SEQ ID NO: 224)

ADDQNPWRAYLDLLFPTGlaTLLLDLLW, (SEQ ID NO: 225)

ADDQNPWRAYLDLLFPTDTLLLGlaLLW, (SEQ ID NO: 226)

ADDQNPWRAYLGlaLLFPTGlaTLLLDLLW, (SEQ ID NO: 227)

ADDQNPWRAYLGlaLLFPTDTLLLGlaLLW, (SEQ ID NO: 228)

ADDQNPWRAYLDLLFPTGlaTLLLGlaLLW, (SEQ ID NO: 229)

ADDQNPWRAYLGlaLLFPTGlaTLLLGlaLLW, (SEQ ID NO: 230)

ADDQNPWRAYLAadLLFPTDTLLLDLLW, (SEQ ID NO: 231)

ADDQNPWRAYLDLLFPTAadTLLLDLLW, (SEQ ID NO: 232)

ADDQNPWRAYLDLLFPTDTLLLAadLLW, (SEQ ID NO: 233)

ADDQNPWRAYLAadLLFPTAadTLLLDLLW, (SEQ ID NO: 234)

ADDQNPWRAYLAadLLFPTDTLLLAadLLW, (SEQ ID NO: 235)

ADDQNPWRAYLDLLFPTAadTLLLAadLLW, (SEQ ID NO: 236)

ADDQNPWRAYLAadLLFPTAadTLLLAadLLW, (SEQ ID NO: 237)

ADDQNPWRAYLGlaLLFPTAadTLLLDLLW, (SEQ ID NO: 238)

ADDQNPWRAYLGlaLLFPTDTLLLAadLLW, (SEQ ID NO: 239)

ADDQNPWRAYLGlaLLFPTGlaTLLLAadLLW, (SEQ ID NO: 240)

ADDQNPWRAYLAadLLFPTGlaTLLLDLLW, (SEQ ID NO: 241)

ADDQNPWRAYLAadLLFPTDTLLLGlaLLW, (SEQ ID NO: 242)

ADDQNPWRAYLGlaLLFPTAadTLLLGlaLLW, (SEQ ID NO: 243)

GEEQNPWLGAYLDLLFPLELLGLLELGLW, (SEQ ID NO: 244)

EQNPIYILDLVFGLLFAVTSVDFLVQWDDAGD, (SEQ ID NO: 245)

NNEGFFATLGGEIALWSDVVLAIE, (SEQ ID NO: 246)
or

DNNEGFFATLGGEIPLWSDVVLAIE. (SEQ ID NO: 247)

In various embodiments, the pHLIP® peptide comprises the sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

AXQNPIYWARYAXWLFTTPLLLLXLALLVXAXXT (SEQ ID NO: 248)

AXXQNPWRAYLXLLFPXTTXLLLLXLLWXAXXT, (SEQ ID NO: 249)

AXXQNPWRAYLXLLFPXTTXLLLLXLLWXAXXT, (SEQ ID NO: 250)

AXQNPIYWARYAXWLFTTPLLLLXLALLVXAXXT, (SEQ ID NO: 251)

AXQNPIYWARYAXWLFTTPLLLLXLALLVXAXXT, (SEQ ID NO: 252)

AXQNPIYWARYAXWLFTTPLLLLXLALLVXAXXT, (SEQ ID NO: 253)

CXQNPIYWARYAXWHFTTPLLLLXLALLVXAXX, (SEQ ID NO: 254)

AXNNPWIYARYAXLTTFPLLLLXLALLVXFXX, (SEQ ID NO: 255)

AXNNPFIYARYAXLTTWPLLLLXLALLVXFXX, (SEQ ID NO: 256)

AXNNPFIYARYAXLTTFPLLLLXLALLVXWXX, (SEQ ID NO: 257)

AXNNPFPYARYAXLTTWILLLLXLALLVXFXX, (SEQ ID NO: 258)

AXNNPFIYAYRAXLTTFPLLLLXLALLVXWXX, (SEQ ID NO: 259)

AXNNPFIYATYAXLRTFPLLLLXLALLVXWXX, (SEQ ID NO: 260)

AXXQNPWRAYLXLLFPTXTLLLXLLWXAXX, (SEQ ID NO: 261)

AXXQNPWRAYLXLLFPTXTLLLXLLW, (SEQ ID NO: 262)

AXXQNPWRAYLXLLFPTXTLLLXLLW, (SEQ ID NO: 263)

AXXQNPWRAYLXLLFPTXTLLLXLLW, (SEQ ID NO: 264)

AXXQNPWRAYLXLLFPTXTLLLXLLW, (SEQ ID NO: 265)

AXXQNPWRAYLXLLFPTXTLLLXLLW, (SEQ ID NO: 266)

AXXQNPWRAYLXLLFPTXTLLLXLLW, (SEQ ID NO: 267)

AXXQNPWRAYLXLLFPTXTLLLXLLW, (SEQ ID NO: 268)

AXXQNPWRAYLXLLFPTXTLLLXLLW, (SEQ ID NO: 269)

AXXQNPWRAYLXLLFPTXTLLLXLLW, (SEQ ID NO: 270)

AXXQNPWRAYLXLLFPTXTLLLXLLW, (SEQ ID NO: 271)

AXXQNPWRAYLXLLFPTXTLLLXLLW, (SEQ ID NO: 272)

AXXQNPWRAYLXLLFPTXTLLLXLLW, (SEQ ID NO: 273)

AXXQNPWRAYLXLLFPTXTLLLXLLW, (SEQ ID NO: 274)

AXXQNPWRAYLXLLFPTXTLLLXLLW, (SEQ ID NO: 275)

AXXQNPWRAYLXLLFPTXTLLLXLLW, (SEQ ID NO: 276)

AXXQNPWRAYLXLLFPTXTLLLXLLW, (SEQ ID NO: 277)

AXXQNPWRAYLXLLFPTXTLLLXLLW, (SEQ ID NO: 278)

AXXQNPWRAYLXLLFPTXTLLLXLLW, (SEQ ID NO: 279)

AXXQNPWRAYLXLLFPTXTLLLXLLW, (SEQ ID NO: 280)

AXXQNPWRAYLXLLFPTXTLLLXLLW, (SEQ ID NO: 281)

GXXQNPWLGAYLXLLFPLXLLGLLXLGLW, (SEQ ID NO: 282)

XQNPIYILXLVFGLLFAVTSVXFLVQWXXAGX, (SEQ ID NO: 283)

NNXGFFATLGGXIALWSXVVLAIX, (SEQ ID NO: 284)
and

XNNXGFFATLGGXIPLWSXVVLAIX, (SEQ ID NO: 285)

wherein each X is, individually, D, E, Gla, or Aad.

In some embodiments, the pHLIP® peptide comprises the sequence:

```
                                        (SEQ ID NO: 286)
AXQNPIYWARYAXWLFTTPLLLLXLALLVXAXXT, (SEQ ID NO: 287)
AXXQNPWRAYLXLLFPXTTXLLLLXLLWXAXXT, (SEQ ID NO: 288)
AXXQNPWRAYLXLLFPXTTXLLLLXLLWXAXXT, (SEQ ID NO: 289)
AXQNPIYWARYAXWLFTTPLLLLXLALLVXAXXT, (SEQ ID NO: 290)
AXQNPIYWARYAXWLFTTPLLLLXLALLVXAXXT, (SEQ ID NO: 291)
AXQNPIYWARYAXWLFTTPLLLLXLALLVXAXXT, (SEQ ID NO: 292)
CXQNPIYWARYAXWHFTTPLLLLXLALLVXAXX, (SEQ ID NO: 293)
AXNNPWIYARYAXLTTFPLLLLXLALLVXFXX, (SEQ ID NO: 294)
AXNNPFIYARYAXLTTWPLLLLXLALLVXFXX, (SEQ ID NO: 295)
AXNNPFIYARYAXLTTFPLLLLXLALLVXWXX, (SEQ ID NO: 296)
AXNNPFPYARYAXLTTWILLLLXLALLVXFXX, (SEQ ID NO: 297)
AXNNPFIYAYRAXLTTFPLLLLXLALLVXWXX, (SEQ ID NO: 298)
AXNNPFIYATYAXLRTFPLLLLXLALLVXWXX, (SEQ ID NO: 299)
AXXQNPWRAYLXLLFPTXTLLLLXLLWXAXX, (SEQ ID NO: 300)
AXXQNPWRAYLXLLFPTXTLLLLXLLW, (SEQ ID NO: 301)
AXXQNPWRAYLXLLFPTXTLLLLXLLW, (SEQ ID NO: 302)
AXXQNPWRAYLXLLFPTXTLLLLXLLW, (SEQ ID NO: 303)
AXXQNPWRAYLXLLFPTXTLLLLXLLW, (SEQ ID NO: 304)
AXXQNPWRAYLXLLFPTXTLLLLXLLW, (SEQ ID NO: 305)
AXXQNPWRAYLXLLFPTXTLLLLXLLW, (SEQ ID NO: 306)
AXXQNPWRAYLXLLFPTXTLLLLXLLW, (SEQ ID NO: 307)
AXXQNPWRAYLXLLFPTXTLLLLXLLW, (SEQ ID NO: 308)
AXXQNPWRAYLXLLFPTXTLLLLXLLW, (SEQ ID NO: 309)
AXXQNPWRAYLXLLFPTXTLLLLXLLW, (SEQ ID NO: 310)
AXXQNPWRAYLXLLFPTXTLLLLXLLW, (SEQ ID NO: 311)
AXXQNPWRAYLXLLFPTXTLLLLXLLW, (SEQ ID NO: 312)
AXXQNPWRAYLXLLFPTXTLLLLXLLW, (SEQ ID NO: 313)
AXXQNPWRAYLXLLFPTXTLLLLXLLW, (SEQ ID NO: 314)
AXXQNPWRAYLXLLFPTXTLLLLXLLW, (SEQ ID NO: 315)
AXXQNPWRAYLXLLFPTXTLLLLXLLW, (SEQ ID NO: 316)
AXXQNPWRAYLXLLFPTXTLLLLXLLW, (SEQ ID NO: 317)
AXXQNPWRAYLXLLFPTXTLLLLXLLW, (SEQ ID NO: 318)
AXXQNPWRAYLXLLFPTXTLLLLXLLW, (SEQ ID NO: 319)
AXXQNPWRAYLXLLFPTXTLLLLXLLW, (SEQ ID NO: 320)
GXXQNPWLGAYLXLLFPLXLLGLLXLGLW, (SEQ ID NO: 321)
XQNPIYILXLVFGLLFAVTSVXFLVQWXXAGX, (SEQ ID NO: 322)
NNXGFFATLGGXIALWSXVVLAIX,
or
                                        (SEQ ID NO: 323)
XNNXGFFATLGGXIPLWSXVVLAIX,
``` wherein each X is, individually, D, E, Gla, or Aad.

In certain embodiments, the pHLIP® peptide comprises the sequence of at least 8 to 25 consecutive amino acids (e.g., 8, 9, 10, 11, 12, 13, 14, 15, 16, 17, 18, 19, 20, 21, 22, 23, 24, or 25 consecutive amino acids) that is present in any one of the following sequences:

$$X_2X_1QNX_2X_2X_2X_2X_2RX_2X_2X_1X_2X_2X_2X_3X_3X_2X_2X_2X_2X_2X_1X_2X_2X_2X_2X_2\ X_1X_2\ X_1X_1X_3, \quad \text{(SEQ ID NO: 507)}$$

$$X_2X_1X_1QNX_2X_2RX_2X_2X_2X_1X_2X_2X_2X_2X_1X_3X_3X_1X_2X_2X_2X_2X_1X_2X_2X_2X_1X_2X_1X_1X_3, \quad \text{(SEQ ID NO: 508)}$$

$$CX_1QNX_2X_2X_2X_2X_2RX_2X_2X_1X_2HX_2X_3X_3X_2X_2X_2X_2X_2X_1X_2X_2X_2X_2X_2X_1X_2X_1X_1, \quad \text{(SEQ ID NO: 509)}$$

$$X_2X_1NNX_2X_2X_2X_2X_2RX_2X_2X_1X_2X_3X_3X_2X_2X_2X_2X_2X_2X_1X_2X_2X_2X_2X_2X_1X_2X_1X_1, \quad \text{(SEQ ID NO: 510)}$$

$$X_2X_1NNX_2X_2X_2X_2X_2X_2RX_2X_1X_2X_3X_3X_2X_2X_2X_2X_2X_2X_1X_2X_2X_2X_2X_2X_1X_2X_1X_1, \quad \text{(SEQ ID NO: 511)}$$

$$X_2X_1NNX_2X_2X_2X_2X_2X_3X_2X_2X_1X_2RX_3X_2X_2X_2X_2X_2X_2X_1X_2X_2X_2X_2X_2X_1X_2X_1X_1, \quad \text{(SEQ ID NO: 512)}$$

(SEQ ID NO: 513)
$X_2X_1X_1QNX_2X_2RX_2X_2X_2X_1X_2X_2X_2X_2X_3X_1X_3X_2X_2X_2X_1X_2X_2X_2$
$X_1X_2X_1X_1$, (SEQ ID NO: 514)
$X_2X_1X_1QNX_2X_2RX_2X_2X_2X_1X_2X_2X_2X_2X_3X_1X_3X_2X_2X_2X_1X_2X_2X_2$, (SEQ ID NO: 515)
$X_2X_1X_1QNX_2X_2X_2X_2X_2X_2X_1X_2X_2X_2X_2X_1X_2X_2X_2X_2X_1X_2$
$X_2X_2X_2$, (SEQ ID NO: 516)
$X_1QNX_2X_2X_2X_2X_1X_2X_2X_2X_2X_2X_2X_2X_2X_3X_3X_2X_1X_2X_2X_2$
$QX_2X_1X_1X_2X_2$, (SEQ ID NO: 517)
$NNX_1X_2X_2X_2X_2X_3X_2X_2X_2X_1X_2X_2X_2X_2X_3X_1X_2X_2X_2X_2X_2X_1$,
and (SEQ ID NO: 518)
$X_1NNX_1X_2X_2X_2X_2X_2X_3X_2X_2X_2X_1X_2X_2X_2X_2X_3X_1X_2X_2X_2X_2X_2X_1$, wherein each $X_1$ is, individually, D, E, Gla, or Aad, each $X_2$ is, individually, A, I, L, M, F, P, W, Y, V, or G and each $X_3$ is, individually, S, T, or G.

In various embodiments, the pHLIP® peptide comprises the sequence:

(SEQ ID NO: 519)
$X_2X_1QNX_2X_2X_2X_2X_2RX_2X_1X_2X_2X_2X_3X_3X_2X_2X_2X_2X_2X_1X_2X_2$
$X_2X_2X_2X_1X_2$ $X_1X_1X_3$, (SEQ ID NO: 520)
$X_2X_1X_1QNX_2X_2RX_2X_2X_2X_1X_2X_2X_2X_2X_1X_3X_3X_1X_2X_2X_2X_2X_1X_2$
$X_2X_2X_1X_2X_1X_1X_3$, (SEQ ID NO: 521)
$CX_1QNX_2X_2X_2X_2X_2RX_2X_2X_1X_2HX_2X_3X_3X_2X_2X_2X_2X_2X_1X_2X_2X_2$
$X_2X_2X_1X_2X_1X_1$, (SEQ ID NO: 522)
$X_2X_1NNX_2X_2X_2X_2X_2RX_2X_2X_1X_2X_3X_3X_2X_2X_2X_2X_2X_2X_1X_2X_2X_2$
$X_2X_2X_1X_2X_1X_1$, (SEQ ID NO: 523)
$X_2X_1NNX_2X_2X_2X_2X_2X_2RX_2X_1X_2X_3X_3X_2X_2X_2X_2X_2X_2X_2X_1X_2X_2X_2$
$X_2X_2X_1X_2X_1X_1$, (SEQ ID NO: 524)
$X_2X_1NNX_2X_2X_2X_2X_3X_2X_2X_1X_2RX_3X_2X_2X_2X_2X_2X_2X_2X_1X_2X_2X_2$
$X_2X_2X_1X_2X_1X_1$, (SEQ ID NO: 525)
$X_2X_1X_1QNX_2X_2RX_2X_2X_2X_1X_2X_2X_2X_2X_3X_1X_3X_2X_2X_2X_1X_2X_2X_2$
$X_1X_2X_1X_1$, (SEQ ID NO: 526)
$X_2X_1X_1QNX_2X_2RX_2X_2X_2X_1X_2X_2X_2X_2X_3X_1X_3X_2X_2X_2X_1X_2X_2X_2$, (SEQ ID NO: 527)
$X_2X_1X_1QNX_2X_2X_2X_2X_2X_2X_1X_2X_2X_2X_2X_1X_2X_2X_2X_2X_2X_1X_2$
$X_2X_2X_2$, (SEQ ID NO: 528)
$X_1QNX_2X_2X_2X_2X_1X_2X_2X_2X_2X_2X_2X_2X_2X_3X_3X_2X_1X_2X_2X_2Q$
$X_2X_1X_1X_2X_2$, (SEQ ID NO: 529)
$NNX_1X_2X_2X_2X_2X_3X_2X_2X_2X_1X_2X_2X_2X_2X_3X_1X_2X_2X_2X_2X_2X_1$,
and (SEQ ID NO: 530)
$X_1NNX_1X_2X_2X_2X_2X_3X_2X_2X_2X_1X_2X_2X_2X_2X_3X_1X_2X_2X_2X_2X_2X_1$, wherein each $X_1$ is, individually, D, E, Gla, or Aad, each $X_2$ is, individually, A, I, L, M, F, P, W, Y, V, or G and each $X_3$ is, individually, S, T, or G.

In some embodiments, a pHLIP® peptide comprises at least 8 consecutive amino acids, wherein (i) at least 4 of the 8 consecutive amino acids are non-polar amino acids, (ii) at least 1 of the at least 8 consecutive amino acids is protonatable, and (iii) the at least 8 consecutive amino acids comprise 8 consecutive amino acids in a sequence that is identical to a sequence of 8 consecutive amino acids that occurs in a naturally occurring human protein. In certain embodiments, the pHLIP® peptide has higher affinity for a membrane lipid bilayer at pH 5.0, 5.5, 6, 6.0, 6.5, 6.6, 6.7, 6.8, 6.9, or 7.0 compared to the affinity at pH 7.5, 7.6, 7.7, 7.8, 7.9, or 8.0.

In various embodiments, the at least 8 consecutive amino acids comprise a sequence that is at least 85%, 90%, or 95% identical to (e.g., is 100% identical to) (i) a sequence of at least 8 consecutive amino acids that occurs in a naturally occurring human protein; or (ii) the reverse of a sequence of at least 8 consecutive amino acids that occurs in a naturally occurring human protein. In some embodiments, the naturally occurring human protein is a human rhodopsin protein. In certain embodiments, the of 8 consecutive amino acids that occurs in the human rhodopsin protein are within the following sequence: NLEGFFATLGGEIALWSLVVLAIE (SEQ ID NO: 531). The reverse of this sequence is EIALVVLSWLAIEGGLTAFFGELN (SEQ ID NO: 532).

In various embodiments, the sequence of the pHLIP® peptide comprises 8-20 (e.g., 8, 9, 10, 11, 12, 13, 14, 15, 16, 17, 18, 19, 20, 8-15, 8-20, 10-15, 10-20, or 15-20) consecutive amino acids that have a sequence that is at least 85%, 90%, or 95% identical to a sequence of 8-20 (e.g., 8, 9, 10, 11, 12, 13, 14, 15, 16, 17, 18, 19, 20, 8-15, 8-20, 10-15, 10-20, or 15-20) consecutive amino acids that occurs in a human rhodopsin protein, wherein the sequence of the 8-20 (e.g., 8, 9, 10, 11, 12, 13, 14, 15, 16, 17, 18, 19, 20, 8-15, 8-20, 10-15, 10-20, or 15-20) consecutive amino acids of the pHLIP® peptide has 1, 2, or 3 amino acid substitutions compared to the sequence of the 8-20 (e.g., 8, 9, 10, 11, 12, 13, 14, 15, 16, 17, 18, 19, 20, 8-15, 8-20, 10-15, 10-20, or 15-20) consecutive amino acids that occurs in a human rhodopsin protein. In some embodiments, the sequence has a L to D, L to E, A to P, or C to G substitution compared to the 8-20 (e.g., 8, 9, 10, 11, 12, 13, 14, 15, 16, 17, 18, 19, 20, 8-15, 8-20, 10-15, 10-20, or 15-20) consecutive amino acids that occur in the human rhodopsin protein. In certain embodiments, the sequence of the pHLIP® peptide comprises 20 consecutive amino acids that have a sequence that is 85%, 90%, or 95% identical to the reverse of a sequence of 8-20 (e.g., 8, 9, 10, 11, 12, 13, 14, 15, 16, 17, 18, 19, 20, 8-15, 8-20, 10-15, 10-20, or 15-20) consecutive amino acids that occurs in a human rhodopsin protein, wherein the sequence of the 20 consecutive amino acids has 1, 2, or 3 amino acid substitutions compared to the reverse of the sequence of the 8-20 (e.g., 8, 9, 10, 11, 12, 13, 14, 15, 16, 17, 18, 19, 20, 8-15, 8-20, 10-15, 10-20, or 15-20) consecutive amino acids that occurs in a human rhodopsin protein. In some embodiments, the sequence has a L to D, L to E, A to P, or C to G substitution compared to the reverse of the 8-20 (e.g., 8, 9, 10, 11, 12, 13, 14, 15, 16, 17, 18, 19, 20, 8-15, 8-20, 10-15, 10-20, or 15-20) consecutive amino acids that occur in the human rhodopsin protein.

A non-limiting example of a genomic nucleotide sequence that encodes human rhodopsin is available under National Center for Biotechnology Information (NCBI) Reference Sequence No: NC_000003.12, all information available under NCBI Reference Sequence No: NC_000003.12 is incorporated herein by reference. The nucleotide sequence that is available from NCBI Reference Sequence No: NC_000003.12 is as follows:

(SEQ ID NO: 31)
AGAGTCATCCAGCTGGAGCCCTGAGTGGCTGAGCTCAGGCCTTCGCAGCA
TTCTTGGGTGGGAGCAGCCACGGGTCAGCCACAAGGGCCACAGCCATGAA
TGGCACAGAAGGCCCTAACTTCTACGTGCCCTTCTCCAATGCGACGGGTG
TGGTACGCAGCCCCTTCGAGTACCCACAGTACTACCTGGCTGAGCCATGG
CAGTTCTCCATGCTGGCCGCCTACATGTTTCTGCTGATCGTGCTGGGCTT
CCCCATCAACTTCCTCACGCTCTACGTCACCGTCCAGCACAAGAAGCTGC
GCACGCCTCTCAACTACATCCTGCTCAACCTAGCCGTGGCTGACCTCTTC
ATGGTCCTAGGTGGCTTCACCAGCACCCTCTACACCTCTCTGCATGGATA
CTTCGTCTTCGGGCCCACAGGATGCAATTTGGAGGGCTTCTTTGCCACCC
TGGGCGGTATGAGCCGGGTGTGGGTGGGGTGTGCAGGAGCCCGGGAGCAT
GGAGGGGTCTGGGAGAGTCCCGGGCTTGGCGGTGGTGGCTGAGAGGCCTT
CTCCCTTCTCCTGTCCTGTCAATGTTATCCAAAGCCCTCATATATTCAGT
CAACAAACACCATTCATGGTGATAGCCGGGCTGCTGTTTGTGCAGGGCTG
GCACTGAACACTGCCTTGATCTTATTTGGAGCAATATGCGCTTGTCTAAT
TTCACAGCAAGAAAACTGAGCTGAGGCTCAAAGAAGTCAAGCGCCCTGCT
GGGGCGTCACACAGGGACGGGTGCAGAGTTGAGTTGGAAGCCCGCATCTA
TCTCGGGCCATGTTTGCAGCACCAAGCCTCTGTTTCCCTTGGAGCAGCTG
TGCTGAGTCAGACCCAGGCTGGGCACTGAGGGAGAGCTGGGCAAGCCAGA
CCCCTCCTCTCTGGGGGCCCAAGCTCAGGGTGGGAAGTGGATTTTCCATT
CTCCAGTCATTGGGTCTTCCCTGTGCTGGGCAATGGGCTCGGTCCCCTCT
GGCATCCTCTGCCTCCCCTCTCAGCCCCTGTCCTCAGGTGCCCCTCCAGC
CTCCCTGCCGCGTTCCAAGTCTCCTGGTGTTGAGAACCGCAAGCAGCCGC
TCTGAAGCAGTTCCTTTTTGCTTTAGAATAATGTCTTGCATTTAACAGGA
AAACAGATGGGGTGCTGCAGGGATAACAGATCCCACTTAACAGAGAGGAA
AACTGAGGCAGGGAGAGGGGAAGAGACTCATTTAGGGATGTGGCCAGGCA
GCAACAAGAGCCTAGGTCTCCTGGCTGTGATCCAGGAATATCTCTGCTGA
GATGCAGGAGGAGACGCTAGAAGCAGCCATTGCAAAGCTGGGTGACGGGG
AGAGCTTACCGCCAGCCACAAGCGTCTCTCTGCCAGCCTTGCCCTGTCTC
CCCCATGTCCAGGCTGCTGCCTCGGTCCCATTCTCAGGGAATCTCTGGCC
ATTGTTGGGTGTTTGTTGCATTCAATAATCACAGATCACTCAGTTCTGGC
CAGAAGGTGGGTGTGCCACTTACGGGTGGTTGTTCTCTGCAGGGTCAGTC
CCAGTTTACAAATATTGTCCCTTTCACTGTTAGGAATGTCCCAGTTTGGT
TGATTAACTATATGGCCACTCTCCCTATGGAACTTCATGGGGTGGTGAGC

-continued
AGGACAGATGTCTGAATTCCATCATTTCCTTCTTCTTCCTCTGGGCAAAA
CATTGCACATTGCTTCATGGCTCCTAGGAGAGGCCCCCACATGTCCGGGT
TATTTCATTTCCCGAGAAGGGAGAGGGAGGAAGGACTGCCAATTCTGGGT
TTCCACCACCTCTGCATTCCTTCCCAACAAGGAACTCTGCCCCACATTAG
GATGCATTCTTCTGCTAAACACACACACACACACACACACACAACACA
CACACACACACACACACACACACACACACAAAACTCCCTACCGGGTTCCC
AGTTCAATCCTGACCCCCTGATCTGATTCGTGTCCCTTATGGGCCAGAG
CGCTAAGCAAATAACTTCCCCCATTCCCTGGAATTTCTTTGCCCAGCTCT
CCTCAGCGTGTGGTCCCTCTGCCCCTTCCCCCTCCTCCCAGCACCAAGCT
CTCTCCTTCCCCAAGGCCTCCTCAAATCCCTCTCCCACTCCTGGTTGCCT
TCCTAGCTACCCTCTCCCTGTCTAGGGGGAGTGCACCCTCCTTAGGCAG
TGGGGTCTGTGCTGACCGCCTGCTGACTGCCTTGCAGGTGAAATTGCCCT
GTGGTCCTTGGTGGTCCTGGCCATCGAGCGGTACGTGGTGGTGTGTAAGC
CCATGAGCAACTTCCGCTTCGGGGAGAACCATGCCATCATGGGCGTTGCC
TTCACCTGGGTCATGGCGCTGGCCTGCGCCGCACCCCCACTCGCCGGCTG
GTCCAGGTAATGGCACTGAGCAGAAGGGAAGAAGCTCCGGGGGCTCTTTG
TAGGGTCCTCCAGTCAGGACTCAAACCCAGTAGTGTCTGGTTCCAGGCAC
TGACCTTGTATGTCTCCTGGCCCAAATGCCCACTCAGGGTAGGGTGTAG
GGCAGAAGAAGAAACAGACTCTAATGTTGCTACAAGGGCTGGTCCCATCT
CCTGAGCCCCATGTCAAACAGAATCCAAGACATCCCAACCCTTCACCTTG
GCTGTGCCCCTAATCCTCAACTAAGCTAGGCGCAAATTCCAATCCTCTTT
GGTCTAGTACCCCGGGGGCAGCCCCCTCTAACCTTGGGCCTCAGCAGCAG
GGGAGGCCACACCTTCCTAGTGCAGGTGGCCATATTGTGGCCCCTTGGAA
CTGGGTCCCACTCAGCCTCTAGGCGATTGTCTCCTAATGGGGCTGAGATG
AGACACAGTGGGGACAGTGGTTTGGACAATAGGACTGGTGACTCTGGTCC
CCAGAGGCCTCATGTCCCTCTGTCTCCAGAAAATTCCCACTCTCACTTCC
CTTTCCTCCTCAGTCTTGCTAGGGTCCATTTCTTACCCCTTGCTGAATTT
GAGCCCACCCCCTGGACTTTTTCCCCATCTTCTCCAATCTGGCCTAGTTC
TATCCTCTGGAAGCAGAGCCGCTGGACGCTCTGGGTTTCCTGAGGCCCGT
CCACTGTCACCAATATCAGGAACCATTGCCACGTCCTAATGACGTGCGCT
GGAAGCCTCTAGTTTCCAGAAGCTGCACAAAGATCCCTTAGATACTCTGT
GTGTCCATCTTTGGCCTGGAAAATACTCTCACCCTGGGGCTAGGAAGACC
TCGGTTTGTACAAACTTCCTCAAATGCAGAGCCTGAGGGCTCTCCCCACC
TCCTCACCAACCCTCTGCGTGGCATAGCCCTAGCCTCAGCGGGCAGTGGA
TGCTGGGGCTGGGCATGCAGGGAGAGGCTGGGTGGTGTCATCTGGTAACG
CAGCCACCAAACAATGAAGCGACACTGATTCCACAAGGTGCATCTGCATC
CCCATCTGATCCATTCCATCCTGTCACCCAGCCATGCAGACGTTTATGAT
CCCCTTTTCCAGGGAGGGAATGTGAAGCCCAGAAAGGGCCAGCGCTCGG
CAGCCACCTTGGCTGTTCCCAAGTCCCTCACAGGCAGGGTCTCCCTACCT
GCCTGTCCTCAGGTACATCCCCGAGGGCCTGCAGTGCTCGTGTGGAATCG

```
ACTACTACACGCTCAAGCCGGAGGTCAACAACGAGTCTTTTGTCATCTAC
ATGTTCGTGGTCCACTTCACCATCCCCATGATTATCATCTTTTTCTGCTA
TGGGCAGCTCGTCTTCACCGTCAAGGAGGTACGGGCCGGGGGTGGGCGG
CCTCACGGCTCTGAGGGTCCAGCCCCCAGCATGCATCTGCGGCTCCTGCT
CCCTGGAGGAGCCATGGTCTGGACCCGGGTCCCGTGTCCTGCAGGCCGCT
GCCCAGCAGCAGGAGTCAGCCACCACACAGAAGGCAGAGAAGGAGGTCAC
CCGCATGGTCATCATCATGGTCATCGCTTTCCTGATCTGCTGGGTGCCCT
ACGCCAGCGTGGCATTCTACATCTTCACCCACCAGGGCTCCAACTTCGGT
CCCATCTTCATGACCATCCCAGCGTTCTTTGCCAAGAGCGCCGCCATCTA
CAACCCTGTCATCTATATCATGATGAACAAGCAGGTGCCTACTGCGGGTG
GGAGGGCCCCAGTGCCCCAGGCCACAGGCGCTGCCTGCCAAGGACAAGCT
ACTTCCCAGGGCAGGGGAGGGGGCTCCATCAGGGTTACTGGCAGCAGTCT
TGGGTCAGCAGTCCCAATGGGAGTGTGTGAGAAATGCAGATTCCTGGCC
CCACTCAGAACTGCTGAATCTCAGGGTGGGCCCAGGAACCTGCATTTCCA
GCAAGCCCTCCACAGGTGGCTCAGATGCTCACTCAGGTGGGAGAAGCTCC
AGTCAGCTAGTTCTGGAAGCCCAATGTCAAAGTCAGAAGGACCCAAGTCG
GGAATGGGATGGGCCAGTCTCCATAAAGCTGAATAAGGAGCTAAAAGTC
TTATTCTGAGGGGTAAAGGGGTAAAGGGTTCCTCGGAGAGGTACCTCCGA
GGGGTAAACAGTTGGGTAAACAGTCTCTGAAGTCAGCTCTGCCATTTTCT
AGCTGTATGGCCCTGGGCAAGTCAATTTCCTTCTCTGTGCTTTGGTTTCC
TCATCCATAGAAAGGTAGAAAGGGCAAAACACCAAACTCTTGGATTACAA
GAGATAATTTACAGAACACCCTTGGCACACAGAGGGCACCATGAAATGTC
ACGGGTGACACAGCCCCCTTGCTCAGTCCCTGGCATCTCTAGGGGTGA
GGAGCGTCTGCCTAGCAGGTTCCCTCCAGGAAGCTGGATTTGAGTGGATG
GGGCGCTGGAATCGTGAGGGGCAGAAGCAGGCAAAGGGTCGGGCGAACC
TCACTAACGTGCCAGTTCCAAGCACACTGTGGGCAGCCCTGGCCCTGACT
CAAGCCTCTTGCCTTCCAGTTCCGGAACTGCATGCTCACCACCATCTGCT
GCGGCAAGAACCCACTGGGTGACGATGAGGCCTCTGCTACCGTGTCCAAG
ACGGAGACGAGCCAGGTGGCCCCGGCCTAAGACCTGCCTAGGACTCTGTG
GCCGACTATAGGCGTCTCCCATCCCCTACACCTTCCCCCAGCCACAGCCA
TCCCACCAGGAGCAGCGCCTGTGCAGAATGAACGAAGTCACATAGGCTCC
TTAATTTTTTTTTTTTTTAAGAAATAATTAATGAGGCTCCTCACTCAC
CTGGGACAGCCTGAGAAGGGACATCCACCAAGACCTACTGATCTGGAGTC
CCACGTTCCCCAAGGCCAGCGGGATGTGTGCCCCTCCTCCTCCCAACTCA
TCTTTCAGGAACACGAGGATTCTTGCTTTCTGGAAAAGTGTCCCAGCTTA
GGGATAAGTGTCTAGCACAGAATGGGCACACAGTAGGTGCTTAATAAAT
GCTGGATGGATGCAGGAAGGAATGGAGGAATGAATGGGAAGGGAGAACAT
ATCTATCCTCTCAGACCCTCGCAGCAGCAGCAACTCATACTTGGCTAATG
ATATGGAGCAGTTGTTTTTCCCTCCCTGGGCCTCACTTTCTTCTCCTATA
AAATGGAAATCCCAGATCCCTGGTCCTGCCGACACGCAGCTACTGAGAAG
ACCAAAAGAGGTGTGTGTGTGTCTATGTGTGTGTTTCAGCACTTTGTAAA
TAGCAAGAAGCTGTACAGATTCTAGTTAATGTTGTGAATAACATCAATTA
ATGTAACTAGTTAATTACTATGATTATCACCTCCTGATAGTGAACATTTT
GAGATTGGGCATTCAGATGATGGGGTTTCACCCAACCTTGGGGCAGGTTT
TTAAAAATTAGCTAGGCATCAAGGCCAGACCAGGGCTGGGGGTTGGGCTG
TAGGCAGGGACAGTCACAGGAATGCAGAATGCAGTCATCAGACCTGAAAA
AACAACACTGGGGGAGGGGGACGGTGAAGGCCAAGTTCCCAATGAGGGTG
AGATTGGGCCTGGGGTCTCACCCCTAGTGTGGGGCCCCAGGTCCCGTGCC
TCCCCTTCCCAATGTGGCCTATGGAGAGACAGGCCTTTCTCTCAGCCTCT
GGAAGCCACCTGCTCTTTTGCTCTAGCACCTGGGTCCCAGCATCTAGAGC
ATGGAGCCTCTAGAAGCCATGCTCACCCGCCCACATTTAATTAACAGCTG
AGTCCCTGATGTCATCCTTATCTCGAAGAGCTTAGAAACAAAGAGTGGGA
AATTCCACTGGGCCTACCTTCCTTGGGGATGTTCATGGGCCCCAGTTTCC
AGTTTCCCTTGCCAGACAAGCCCATCTTCAGCAGTTGCTAGTCCATTCTC
CATTCTGGAGAATCTGCTCCAAAAAGCTGGCCACATCTCTGAGGTGTCAG
AATTAAGCTGCCTCAGTAACTGCTCCCCCTTCTCCATATAAGCAAAGCCA
GAAGCTCTAGCTTTACCCAGCTCTGCCTGGAGACTAAGGCAAATTGGGCC
ATTAAAAGCTCAGCTCCTATGTTGGTATTAACGGTGGTGGGTTTTGTTGC
TTTCACACTCTATCCACAGGATAGATTGAAACTGCCAGCTTCCACCTGAT
CCCTGACCCTGGGATGGCTGGATTGAGCAATGAGCAGAGCCAAGCAGCAC
AGAGTCCCCTGGGGCTAGAGGTGGAGGAGGCAGTCCTGGGAATGGGAAAA
ACCCCA
```

A non-limiting example of a human rhodopsin amino acid sequence is available under UniProt Accession No: P08100. All information available under UniProt Accession No: P08100 is incorporated herein by reference. An amino acid sequence that is available from UniProt Accession No: P08100 is as follows (the underlined amino acids relate may be used in non-limiting examples of pHLIP®s, and especially as a starting point to design pHLIP® peptides):

(SEQ ID NO: 32)
MNGTEGPNFYVPFSNATGVVRSPFEYPQYYLAEPWQFSMLAAYMFLLIVL

GFPINFLTLYVTVQHKKLRTPLNYILLNLAVADLFMVLGGFTSTLYTSLH

GYFVFGPTGCNLEGFFATLGGEIALWSLVVLAIERYVVVCKPMSNFRFGE

NHAIMGVAFTWVMALACAAPPLAGWSRYIPEGLQCSCGIDYYTLKPEVNN

ESFVIYMFVVHFTIPMIIIFFCYGQLVFTVKEAAAQQQESATTQKAEKEV

TRMVIIMVIAFLICWVPYASVAFYIFTHQGSNFGPIFMTIPAFFAKSAAI

YNPVIYIMMNKQFRNCMLTTICCGKNPLGDDEASATVSKTETSQVAPA

For example, a pHLIP® peptide comprising the sequence DNNEGFFATLGGEIPLWSDVVLAIE (SEQ ID NO: 209) is a useful pHLIP® peptide that comprises 3 substitution mutations (underlined) and one added amino acid (the N-terminal D) compared to NLEGFFATLGGEIALWSLVV-LAIE (SEQ ID NO: 62). See also, e.g., Hum pHLIP® in Table 11, as well as sequences in Tables 5 and 6.

A non-limiting example of a cDNA sequence that encodes human rhodopsin is available under NCBI Reference Sequence No: NM_000539.3, all information available under NCBI Reference Sequence No: NM_000539.3 is incorporated herein by reference. The nucleotide sequence that is available from NCBI Reference Sequence No: NM_000539.3 is as follows:

(SEQ ID NO: 33)
AGAGTCATCCAGCTGGAGCCCTGAGTGGCTGAGCTCAGGCCTTCGCAGCA

TTCTTGGGTGGGAGCAGCCACGGGTCAGCCACAAGGGCCACAGCCATGAA

TGGCACAGAAGGCCCTAACTTCTACGTGCCCTTCTCCAATGCGACGGGTG

TGGTACGCAGCCCCTTCGAGTACCCACAGTACTACCTGGCTGAGCCATGG

CAGTTCTCCATGCTGGCCGCCTACATGTTTCTGCTGATCGTGCTGGGCTT

CCCCATCAACTTCCTCACGCTCTACGTCACCGTCCAGCACAAGAAGCTGC

GCACGCCTCTCAACTACATCCTGCTCAACCTAGCCGTGGCTGACCTCTTC

ATGGTCCTAGGTGGCTTCACCAGCACCCTCTACACCTCTCTGCATGGATA

CTTCGTCTTCGGGCCCACAGGATGCAATTTGGAGGGCTTCTTTGCCACCC

TGGGCGGTGAAATTGCCCTGTGGTCCTTGGTGGTCCTGGCCATCGAGCGG

TACGTGGTGGTGTGTAAGCCCATGAGCAACTTCCGCTTCGGGGAGAACCA

TGCCATCATGGGCGTTGCCTTCACCTGGGTCATGGCGCTGGCCTGCGCCG

CACCCCCACTCGCCGGCTGGTCCAGGTACATCCCCGAGGGCCTGCAGTGC

TCGTGTGGAATCGACTACTACACGCTCAAGCCGGAGGTCAACAACGAGTC

TTTTGTCATCTACATGTTCGTGGTCCACTTCACCATCCCCATGATTATCA

TCTTTTTCTGCTATGGGCAGCTCGTCTTCACCGTCAAGGAGGCCGCTGCC

CAGCAGCAGGAGTCAGCCACCACACAGAAGGCAGAGAAGGAGGTCACCCG

CATGGTCATCATCATGGTCATCGCTTTCCTGATCTGCTGGGTGCCCTACG

CCAGCGTGGCATTCTACATCTTCACCCACCAGGGCTCCAACTTCGGTCCC

ATCTTCATGACCATCCCAGCGTTCTTTGCCAAGAGCGCCGCCATCTACAA

CCCTGTCATCTATATCATGATGAACAAGCAGTTCCGGAACTGCATGCTCA

CCACCATCTGCTGCGGCAAGAACCCACTGGGTGACGATGAGGCCTCTGCT

ACCGTGTCCAAGACGGAGACGAGCCAGGTGGCCCCGGCCTAAGACCTGCC

TAGGACTCTGTGGCCGACTATAGGCGTCTCCCATCCCCTACACCTTCCCC

CAGCCACAGCCATCCCACCAGGAGCAGCGCCTGTGCAGAATGAACGAAGT

CACATAGGCTCCTTAATTTTTTTTTTTTTTAAGAAATAATTAATGAGG

CTCCTCACTCACCTGGGACAGCCTGAGAAGGGACATCCACCAAGACCTAC

TGATCTGGAGTCCCACGTTCCCCAAGGCCAGCGGGATGTGTGCCCCTCCT

CCTCCCAACTCATCTTTCAGGAACACGAGGATTCTTGCTTTCTGGAAAAG

TGTCCCAGCTTAGGGATAAGTGTCTAGCACAGAATGGGGCACACAGTAGG

TGCTTAATAAATGCTGGATGGATGCAGGAAGGAATGGAGGAATGAATGGG

AAGGGAGAACATATCTATCCTCTCAGACCCTCGCAGCAGCAGCAACTCAT

ACTTGGCTAATGATATGGAGCAGTTGTTTTCCCTCCCTGGGCCTCACTT

TCTTCTCCTATAAAATGGAAATCCCAGATCCCTGGTCCTGCCGACACGCA

GCTACTGAGAAGACCAAAAGAGGTGTGTGTGTCTATGTGTGTGTTTCA

GCACTTTGTAAATAGCAAGAAGCTGTACAGATTCTAGTTAATGTTGTGAA

TAACATCAATTAATGTAACTAGTTAATTACTATGATTATCACCTCCTGAT

-continued
AGTGAACATTTTGAGATTGGGCATTCAGATGATGGGGTTTCACCCAACCT

TGGGGCAGGTTTTTAAAAATTAGCTAGGCATCAAGGCCAGACCAGGGCTG

GGGGTTGGGCTGTAGGCAGGGACAGTCACAGGAATGCAGAATGCAGTCAT

CAGACCTGAAAAAACAACACTGGGGGAGGGGGACGGTGAAGGCCAAGTTC

CCAATGAGGGTGAGATTGGGCCTGGGGTCTCACCCCTAGTGTGGGGCCCC

AGGTCCCGTGCCTCCCCTTCCCAATGTGGCCTATGGAGAGACAGGCCTTT

CTCTCAGCCTCTGGAAGCCACCTGCTCTTTTGCTCTAGCACCTGGGTCCC

AGCATCTAGAGCATGGAGCCTCTAGAAGCCATGCTCACCCGCCCACATTT

AATTAACAGCTGAGTCCCTGATGTCATCCTTATCTCGAAGAGCTTAGAAA

CAAAGAGTGGGAAATTCCACTGGGCCTACCTTCCTTGGGGATGTTCATGG

GCCCCAGTTTCCAGTTTCCCTTGCCAGACAAGCCCATCTTCAGCAGTTGC

TAGTCCATTCTCCATTCTGGAGAATCTGCTCCAAAAAGCTGGCCACATCT

CTGAGGTGTCAGAATTAAGCTGCCTCAGTAACTGCTCCCCCTTCTCCATA

TAAGCAAAGCCAGAAGCTCTAGCTTTACCCAGCTCTGCCTGGAGACTAAG

GCAAATTGGGCCATTAAAAGCTCAGCTCCTATGTTGGTATTAACGGTGGT

GGGTTTTGTTGCTTTCACACTCTATCCACAGGATAGATTGAAACTGCCAG

CTTCCACCTGATCCCTGACCCTGGGATGGCTGGATTGAGCAATGAGCAGA

GCCAAGCAGCACAGAGTCCCCTGGGGCTAGAGGTGGAGGAGGCAGTCCTG

GGAATGGGAAAAACCCCA

In some embodiments, the pHLIP® peptide comprises the sequence: $X_nY_m$; $Y_mX_n$; $X_nY_mX_j$; $Y_mX_nY_i$; $Y_mX_nY_iX_j$; $X_nY_mX_jY_i$; $Y_mX_nY_iX_jY_i$; $X_nY_mX_jY_iX_i$; $Y_mX_nY_iX_jY_iX_h$; $X_nY_mX_jY_iX_hY_g$; $Y_mX_nY_iX_jY_iX_hY_g$; $X_nY_mX_jY_iX_hY_gX_f$; $(XY)_n$; $(YX)_n$; $(XY)_nY_m$; $(YX)_nY_m$; $(XY)_nX_m$; $(YX)_nX_m$; $Y_m(XY)_n$; $Y_m(YX)_n$; $X_n(XY)_m$; $X_n(YX)_m$; $(XY)_nY_m(XY)_i$; $(YX)_nY_m(YX)_i$; $(XY)_nX_m(XY)_i$; $(YX)_nX_m(YX)_i$; $Y_m(XY)_n$; $Y_m(YX)_n$; $X_n(XY)_m$; or $X_n(YX)_m$, wherein, (i) each Y is, individually, a non-polar amino acid with solvation energy, $\Delta G_X^{cor} > +0.50$, or Gly; (ii) each X is, individually, a protonatable amino acid, (iii) n, m, i, j, l, h, g, f are each, individually, an integer from 1 to 8.

In certain embodiments, the pHLIP® peptide has a net negative charge at a pH of about 6.5, 6.6, 6.7, 6.8, 6.9, 7.0, 7.1, 7.2, 7.3, 7.4, or 7.5 in water.

In various embodiments, the pHLIP® peptide has an acid dissociation constant on a base 10 logarithmic scale (pKa) of less than about 4.0, 4.5, 5.0, 5.5, 6.0, 6.5, or 7.0. In certain embodiments, the pHLIP® peptide has a pKa of at least about 6.5, 6.6, 6.7, 6.8, 6.9, or 7.0. In some embodiments, the pHLIP® peptide has a pKa between about 6.5 and about 7.0, e.g., about 6.6 and about 7.0, about 6.7 and about 7.0, about 6.8 and about 7.0, or about 6.9 and about 7.0. In certain embodiments, the pHLIP® peptide has a pKa of about 6.5, 6.6, 6.7, 6.8, 6.9, or 7.0.

In some embodiments, the pHLIP® peptide comprises (a) 1 protonatable amino acid which is aspartic acid, glutamic acid, alpha-aminoadipic acid, or gamma-carboxyglutamic acid; or (b) at least 2, 3, or 4 protonatable amino acids, wherein the protonatable amino acids comprise aspartic acid, glutamic acid, alpha-aminoadipic acid, gamma-carboxyglutamic acid, or any combination thereof.

In certain embodiments, the pHLIP® peptide comprises at least 1 non-native protonatable amino acid. In various embodiments, the non-native protonatable amino acid comprises at least 1, 2, 3, or 4 carboxyl groups. In some embodiments, the pHLIP® peptide comprises at least 1, 2, 3, 4, 5, 6, 7, 8, 9, 10, 11, 12, 13, 14, 15, or 16 carboxyl groups. In certain embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 genetically coded amino acids.

In various embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 non-genetically coded amino acids. In some embodiments, the amino acids of the pHLIP® peptide are non-native amino acids. In certain embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 D-amino acids.

In various embodiments, the pHLIP® peptide comprises at least 1 non-genetically coded amino acid, wherein the non-genetically coded amino acid is an aspartic acid derivative, or a glutamic acid derivative.

In some embodiments, the pHLIP® peptide comprises at least 8 consecutive amino acids, wherein, at least 2, 3, or 4 of the at least 8 consecutive amino acids are non-polar, and at least 1, 2, 3, or 4 of the at least 8 consecutive amino acids is protonatable.

In various embodiments, the pHLIP® peptide is directly covalently attached via a bond, or covalently attached via a linker, to a fluorophore.

In some embodiments, a pHLIP® peptide is attached to a fluorophore by a covalent bond, wherein the covalent bond is an ester bond, a disulfide bond, a bond between two selenium atoms, a bond between a sulfur and a selenium atom, or an acid-labile bond. In some embodiments, the pHLIP® peptide is attached to a fluorophore by a covalent bond, wherein the covalent bond is a bond that has been formed by a click chemistry reaction. In certain embodiments, the covalent bond is a bond that has been formed by a reaction between (i) an azide and an alkyne; (ii) an alkyne and a strained difluorooctyne; (iii) a diaryl-strained-cyclooctyne and a 1,3-nitrone; (iv) a cyclooctene, trans-cycloalkene, or oxanorbornadiene and an azide, tetrazine, or tetrazole; (v) an activated alkene or oxanorbornadiene and an azide; (vi) a strained cyclooctene or other activated alkene and a tetrazine; or (vii) a tetrazole that has been activated by ultraviolet light and an alkene. In certain embodiments, the covalent bond is a peptide bond. In various embodiments, the covalent bond is not a peptide bond.

In various embodiments, a pHLIP®-fluorophore compound comprises a pHLIP® peptide that is attached to the linker by a covalent bond. In some embodiments, the covalent bond is a peptide bond. In certain embodiments, the covalent bond is a disulfide bond, a bond between two selenium atoms, or a bond between a sulfur and a selenium atom. In various embodiments, the covalent bond is a bond that has been formed by a click chemistry reaction. In some embodiments, the covalent bond is a bond that has been formed by a reaction between (i) an azide and an alkyne; (ii) an alkyne and a strained difluorooctyne; (iii) a diaryl-strained-cyclooctyne and a 1,3-nitrone; (vi) a cyclooctene, trans-cycloalkene, or oxanorbornadiene and an azide, tetrazine, or tetrazole; (v) an activated alkene or oxanorbornadiene and an azide; (vi) a strained cyclooctene or other activated alkene and a tetrazine; or (vii) a tetrazole that has been activated by ultraviolet light and an alkene. In certain embodiments, the covalent bond is a peptide bond. In various embodiments, the covalent bond is not a peptide bond.

In some embodiments, the linker comprises an artificial polymer or a synthetically produced polymer that has the structure of a polymer that exists in nature. In certain embodiments, the linker comprises a polypeptide, a polylysine, a polyarginine, a polyglutamic acid, a polyaspartic acid, a polycysteine, or a polynucleic acid. In various embodiments, the linker does not comprise an amino acid. In some embodiments, the linker comprises a polysaccharide, a chitosan, or an alginate. In certain embodiments, the linker comprises a poly(ethylene glycol), a poly(lactic acid), a poly(glycolic acid), a poly(lactic-co-glycolic acid), a poly (malic acid), a polyorthoester, a poly(vinylalcohol), a poly (vinylpyrrolidone), a poly(methyl methacrylate), a poly (acrylic acid), a poly(acrylamide), a poly(methacrylic acid), a poly(amidoamine), a polyanhydrides, or a polycyanoacrylate. In various embodiments, the linker comprises poly (ethylene glycol). In certain embodiments, the poly(ethylene glycol) has a molecular weight of 60 to 100000 Daltons, e.g., at least about 60, 100, 200, 300, 400, 500, 600, 700, 800, 900, 1000, 5000, 10000, 15000, 20000, 25000 Daltons, but less than about 100000, 90000, 70000, 60000, 50000, 40000, or 30000 Daltons. In various embodiments, the linker comprises a linear polymer or a branched polymer. In some embodiments, the linker comprises an organic compound structure. In certain embodiments, the organic compound structure has a molecular weight less than about 10, 9, 8, 7, 6, 5, 4, 3, 2, 1, or 0.5 kDa.

In some embodiments, the linker is attached to a fluorophore (e.g., a luminescent fluorophore or a quencher) via a covalent bond. In certain embodiments, the covalent bond is an ester bond, a disulfide bond, a bond between two selenium atoms, a bond between a sulfur and a selenium atom, or an acid-labile bond. In various embodiments, the covalent bond is a bond that has been formed by a click chemistry reaction. In some embodiments, the covalent bond is a bond that has been formed by a reaction between (i) an azide and an alkyne; (ii) an alkyne and a strained difluorooctyne; (iii) a diaryl-strained-cyclooctyne and a 1,3-nitrone; (vi) a cyclooctene, trans-cycloalkene, or oxanorbornadiene and an azide, tetrazine, or tetrazole; (v) an activated alkene or oxanorbornadiene and an azide; (vi) a strained cyclooctene or other activated alkene and a tetrazine; or (vii) a tetrazole that has been activated by ultraviolet light and an alkene. In certain embodiments, the covalent bond is a peptide bond. In various embodiments, the covalent bond is not a peptide bond.

In some embodiments, the fluorophore is a fluorescent dye or a fluorescent protein. Non-limiting examples of fluorophores include fluorescent dyes, phosphorescent dyes, quantum dots, xanthene derivatives, cyanine derivatives, naphthalene derivatives, coumarin derivatives, oxadiaxol derivatives, pyrene derivatives, acridine derivatives, arylmethine derivatives, or tetrapyrrole derivatives. Xanthene derivatives include but are not limited to fluorescein, rhodamine, Oregon green, eosin, Texas red, and Cal Fluor dyes. Cyanine derivatives include but are not limited to cyanine, indocarbocyanine, indocyanine green (ICG), oxacarbocyanine, thiacarbocyanine, merocyanine, and Quasar dyes.

Naphthalene derivatives include but are not limited to dansyl and prodan derivatives. Oxadiazole derivatives include but are not limited to pyridyloxazol, nitrobenzoxadiazole and benzoxadiazole. A non-limiting example of a pyrene derivative is cascade blue. Oxadine derivatives include but are not limited to Nile red, Nile blue, cresyl violet, and oxazine 170. Acridine derivatives include but are not limited to proflavin, acridine orange, and acridine yellow. Arylmethine derivatives include but are not limited to auramine, crystal violet, and malachite green. Tetrapyrrole derivatives include but are not limited to porphin, phtalocyanine, and bilirubin.

In various embodiments, a pHLIP®-fluorophore compound included herein is used as a diagnostic agent, an imaging agent. In some embodiments, a pHLIP®-fluorophore compound provided herein is used as an agent for in vivo imaging or in an in vivo diagnostic method. In certain embodiments, a pHLIP®-fluorophore compound provided herein is used as an agent for ex vivo imaging or in an ex vivo diagnostic method.

Certain implementations comprise a formulation for a parenteral, a local, or a systemic administration comprising a pHLIP®-fluorophore compound as disclosed herein.

Formulations comprising a pHLIP®-fluorophore compound for intravenous, intraarterial, intraperitoneal, intracerebral, intracerebroventricular, intrathecal, intracardiac, intracavernous, intraosseous, intraocular, or intravitreal administration are also provided.

The present subject matter also includes a formulation for intravesical instillation comprising a pHLIP®-fluorophore compound as disclosed herein.

In various embodiments, the fluorophore is covalently attached to the membrane insertion peptide via a linkage such as a thiol linkage or ester linkage or acid-labile linkage. Other types of linkages, chemical bonds, or binding associations are also used. Exemplary linkages or associations are mediated by disulfide, and/or a peptide with a protein binding motif, and/or a protein kinase consensus sequence, and/or a protein phosphatase consensus sequence, and/or a protease-reactive sequence, and/or a peptidase-reactive sequence, and/or a transferase-reactive sequence, and/or a hydrolase-reactive sequence, and/or an isomerase-reactive sequence, and/or a ligase-reactive sequence, and/or an extracellular metalloprotease-reactive sequence, and/or a lysosomal protease-reactive sequence, and/or a beta-lactamase-reactive sequence, and/or an oxidoreductase-reactive sequence, and/or an esterase-reactive sequence, and/or a glycosidase-reactive sequence, and/or a nuclease-reactive sequence.

In certain embodiments, the fluorophore is covalently attached to the membrane insertion peptide via a non-cleavable linkage. In various embodiments, a non-cleavable linkage is a covalent bond that is not cleaved by an enzyme expressed by a mammalian cell, and/or not cleaved by glutathione and/or not cleaved at conditions of low pH. Non-limiting examples of non-cleavable linkages include maleimide linkages, linkages resulting from the reaction of a N-hydroxysuccinimide ester with a primary amine (e.g., a primary amine of a lysine side-chain), linkages resulting from a click reaction, thioether linkages, or linkages resulting from the reaction of a primary amine (—NH$_2$) or thio (—SH) functional group with succinimidyl-4-(N-maleimidomethyl)cyclohexane-1-carboxylate (SMCC). Exemplary non-cleavable linkages include linkages comprising a maleimide alkane linker,

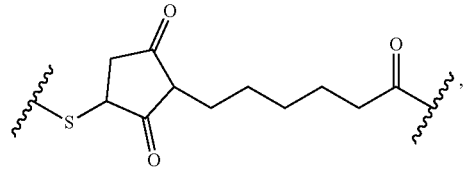 [SMILES: *SC1CC(=O)C(CCCCCC(*)=O)C1=O]

and linkages comprising a maleimide cyclohexane linker,

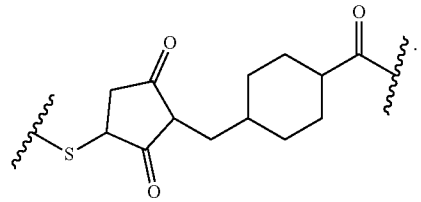 [SMILES: *SC1CC(=O)C(CC2CCC(C(*)=O)CC2)C1=O]

As is described above, the compositions may be used in, e.g., a clinical setting for diagnostic and therapeutic applications in humans as well as animals (e.g., companion animals such as dogs and cats as well as livestock such as horses, cattle, goats, sheep, llamas). Membrane-inserting compounds comprising such moieties may be used in a variety of clinical diagnostic methods, including real-time image-guided therapeutic interventions.

Included herein are compositions that are administered to the body for diagnostic use, e.g., using methods known in the art. For example, the methods are carried out by infusing into a vascular lumen, e.g., intravenously (such as via a jugular vein, peripheral vein or the perivascular space). In some embodiments, the composition is infused into the lungs of a mammal, e.g., as an aerosol or lavage. In various embodiments, the composition is administered by intravesical instillation into a human or animal bladder, oral cavity, intestinal cavity, esophagus, or trachea. In some embodiments, the injection can be into the peritoneal cavity of the mammal, subdermally, or subcutaneously.

Included herein are pharmaceutical compositions comprising a pH-triggered compound and a pharmaceutically acceptable carrier.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, a goat, a chicken, a turkey, or a duck. In certain embodiments, the subject is a human.

The present subject matter provides compounds and compositions for detecting diseased tissue. For example, aspects of the present subject matter relate to the detection of cancerous tissue (e.g., of a tumor or a metastatic lesion) and/or precancerous tissue (e.g., dysplastic tissue). The compound includes a pHLIP® peptide covalently linked to indocyanine green (ICG). The pHLIP® peptide comprises amino acids in the sequence LFPTXTLL (SEQ ID NO: 1), wherein X is a protonatable amino acid. In preferred embodiments, X is a protonatable amino acid other than glutamic acid, such as aspartic acid. Additionally, the pH-triggered peptide has a higher affinity to a membrane lipid bilayer at pH 5.0 compared to at pH 8.0. In various implementations, the ICG is covalently attached to the first or the second amino acid counted from the N-terminus of the pHLIP® peptide.

Aspects of the present disclosure provide pHLIP® peptides linked to an ICG compound. In various implementations, the pHLIP® peptide is directly linked to a ICG by a covalent bond. In some non-limiting examples, the covalent bond is an ester bond, a thioester bond, a disulfide bond, a bond between two selenium atoms, a bond between a sulfur and a selenium atom, or an acid-labile bond.

In some embodiments, the covalent bond between the pHLIP® peptide and the ICG is a bond that has been formed by a click reaction. Non-limiting examples of click reactions include reactions between an azide and an alkyne; an alkyne and a strained difluorooctyne; a diaryl-strained-cyclooctyne and a 1,3-nitrone; a cyclooctene, trans-cycloalkene, or oxanorbornadiene and an azide, tetrazine, or tetrazole; an activated alkene or oxanorbornadiene and an azide; a strained cyclooctene or other activated alkene and a tetrazine; or a tetrazole that has been activated by ultraviolet light and an alkene.

Some implementations provide a pHLIP® peptide that is attached to a linker compound by a covalent bond, wherein the linker compound is attached to the IGC by a covalent bond. In non-limiting examples, the covalent bond between the pHLIP® peptide and the linker compound and/or the covalent bond between the linker compound and the ICG is a disulfide bond, a bond between two selenium atoms, a bond between a sulfur and a selenium atom, or a bond that has been formed by a click reaction.

In various embodiments, the ICG is covalently attached to the pHLIP® peptide via a linkage such as a thiol linkage or thioester linkage or ester linkage or acid-labile linkage. Other types of linkages, chemical bonds, or binding associations may also be used. Exemplary linkages or associations are mediated by disulfide, and/or a peptide with a protein binding motif, and/or a protein kinase consensus sequence, and/or a protein phosphatase consensus sequence, and/or a protease-reactive sequence, and/or a peptidase-reactive sequence, and/or a transferase-reactive sequence, and/or a hydrolase-reactive sequence, and/or an isomerase-reactive sequence, and/or a ligase-reactive sequence, and/or an extracellular metalloprotease-reactive sequence, and/or a lysosomal protease-reactive sequence, and/or a beta-lactamase-reactive sequence, and/or an oxidoreductase-reactive sequence, and/or an esterase-reactive sequence, and/or a glycosidase-reactive sequence, and/or a nuclease-reactive sequence.

In certain embodiments, the fluorophore is covalently attached to the pHLIP® peptide via a non-cleavable linkage. In various embodiments a non-cleavable linkage is a covalent bond that is not cleaved by an enzyme expressed by a mammalian cell, and/or not cleaved by glutathione and/or not cleaved at conditions of low pH. Non-limiting examples of non-cleavable linkages include maleimide linkages [e.g., linkages resulting from the reaction of a maleimide ester with a thiol (e.g., at the thiol of a cysteine side-chain)], N-hydroxysuccinimide (NHS) linkages [e.g., linkages resulting from the reaction of a NHS ester with a primary amine (e.g., at the N-terminus of a polypeptide chain or a primary amine of a lysine side-chain)], linkages resulting from a click reaction, thioester linkages, thioether linkages, or linkages resulting from the reaction of a primary amine (—NH$_2$) or thio (—SH) functional group with succinimidyl-4-(N-maleimidomethyl)cyclohexane-1-carboxylate (SMCC). Exemplary non-cleavable linkages include a maleimide alkane linker, e.g.

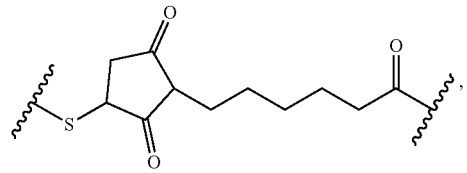 [SMILES: *SC1CC(=O)C(CCCCCC(*)=O)C1=O]

and a maleimide cyclohexane linker, e.g.

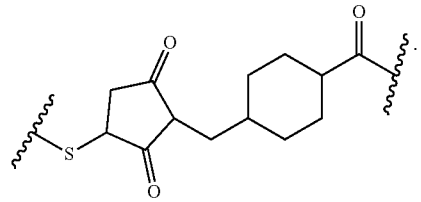 [SMILES: *SC1CC(=O)C(CC2CCC(C(*)=O)CC2)C1=O]

In various embodiments, the pHLIP® peptide comprises amino acids in the sequence ACDDQNPWRAYLDLL-FPTDTLLLDLLWG (SEQ ID NO: 9), and wherein said ICG is covalently attached to the cysteine thereof. In certain embodiments, ICG is covalently bound to the cysteine. In some embodiments, the N-terminus and/or the C-terminus is not bound to any compound. In a non-limiting example, the compound comprises the following structure (SEQ ID NO: 4 is disclosed below):

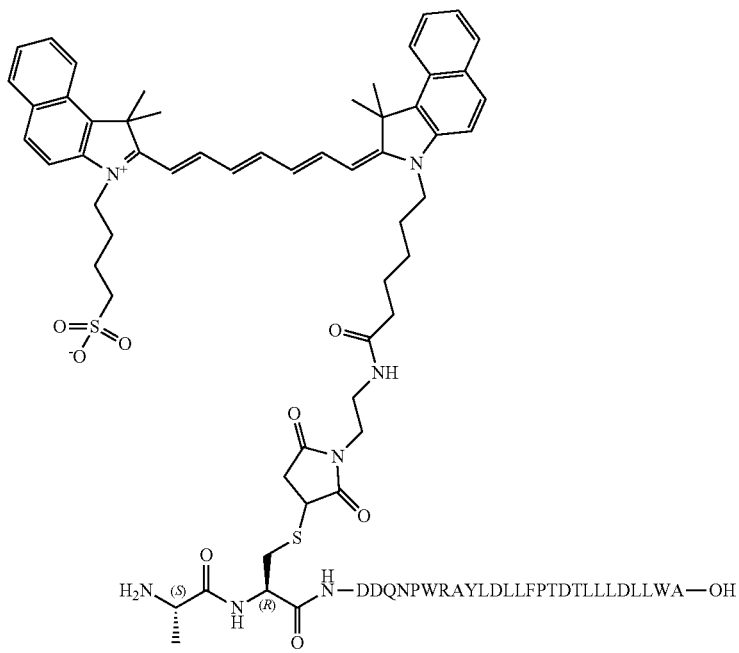

In some embodiments, the pHLIP® peptide comprises amino acids in the sequence ADDQNPWRAYLDLL-FPTDTLLLDLLWG (SEQ ID NO: 2), and the ICG is covalently attached to the N-terminal alanine of the pHLIP® peptide. In a non-limiting example, the compound comprises the following structure (SEQ ID NO: 2 is disclosed below):

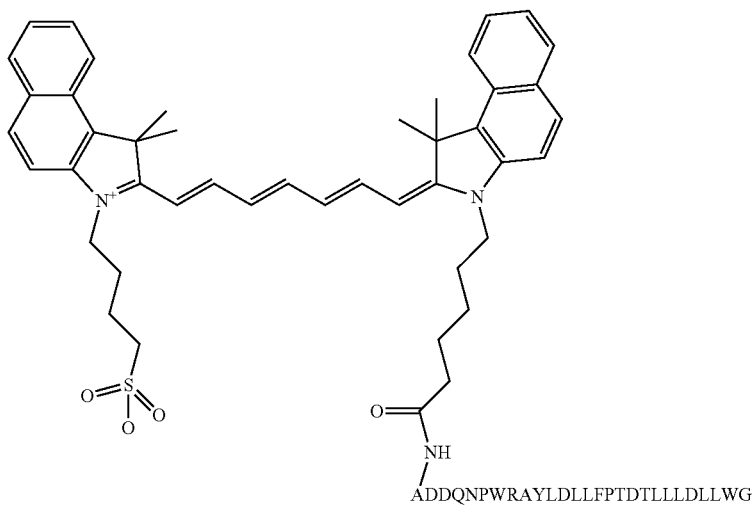

In some embodiments, the pHLIP® peptide comprises amino acids in the sequence AKDDQNPWRAYLDLL-FPTDTLLLDLLWG (SEQ ID NO: 3), and the ICG is covalently attached to the lysine of the pHLIP® peptide. A non-limiting example of such a compound comprises the structure (SEQ ID NO: 3 is disclosed below):

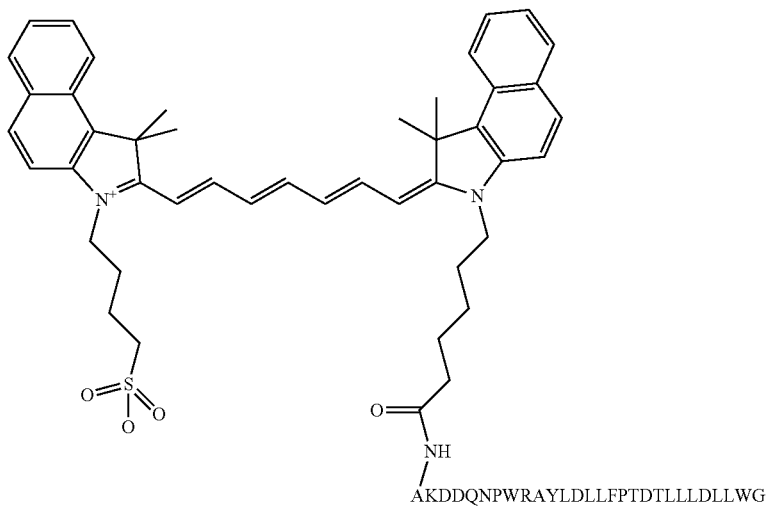
AKDDQNPWRAYLDLLFPTDTLLLDLLWG

In certain embodiments, the pHLIP® peptide comprises amino acids in the sequence ACDDQNPWRAYLDLL-FPTDTLLLDLLWA (SEQ ID NO: 4), and the ICG is covalently attached to the cysteine of the pHLIP® peptide. In a non-limiting example, the compound comprises the structure (SEQ ID NO: 4 is disclosed below):

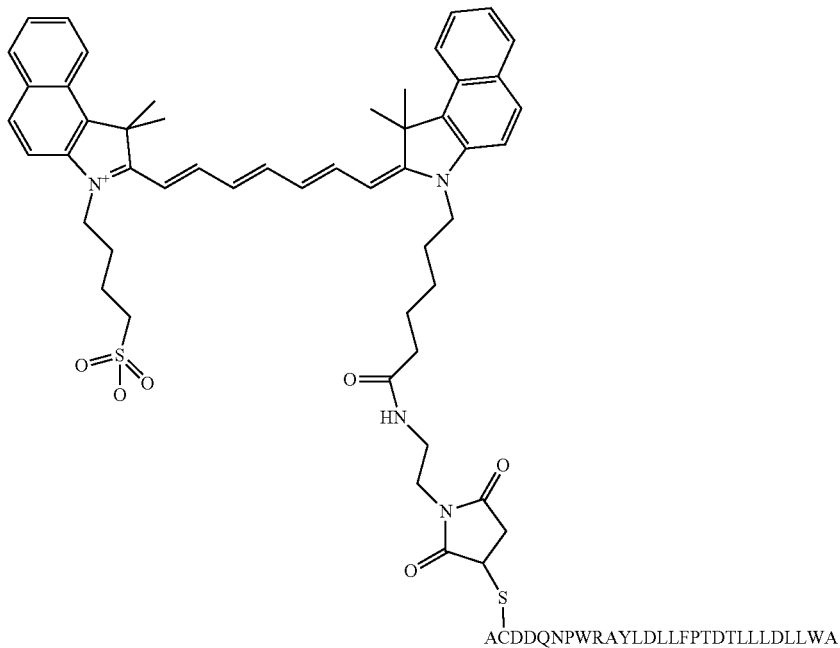
ACDDQNPWRAYLDLLFPTDTLLLDLLWA

In various embodiments, the pHLIP® peptide comprises amino acids in the sequence ACDDQNPWRAYLDLL-FPTDTLLLDLLWA (SEQ ID NO: 4), and wherein said ICG is covalently attached to the cysteine thereof. In certain embodiments, ICG is covalently bound to the cysteine. In some embodiments, the N-terminus and/or the C-terminus is not bound to any compound. In a non-limiting example, the compound comprises the following structure (SEQ ID NO: 4 is disclosed below):

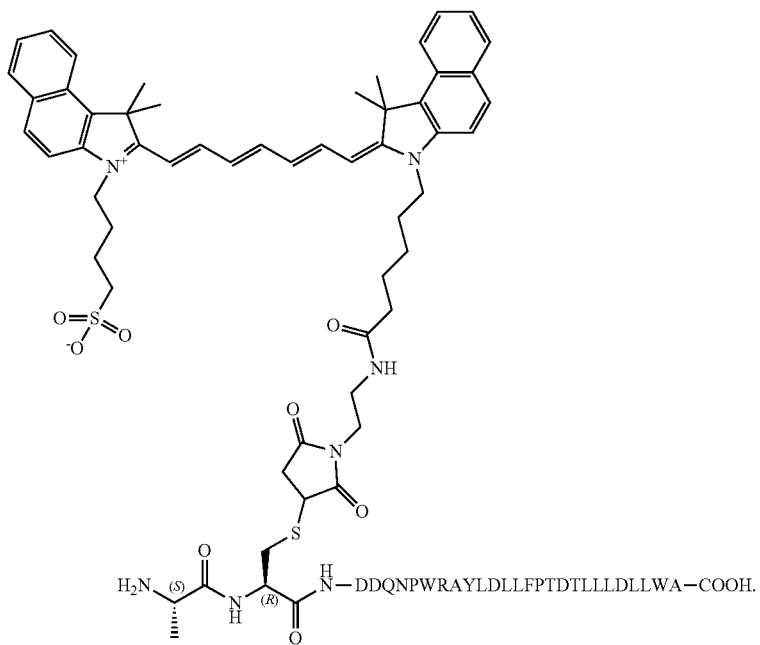
This structure may optionally be drawn as follows (SEQ ID NO: 4 is disclosed below):
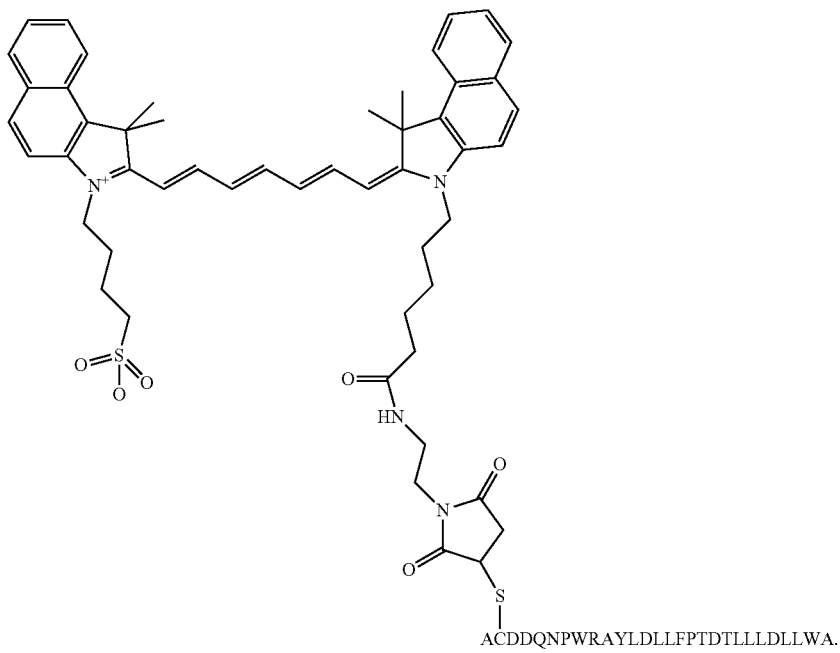
In some embodiments, the pHLIP® peptide comprises amino acids in the sequence ADDQNPWRAYLDLL-FPTDTLLLDLLWA (SEQ ID NO: 5), and the ICG is covalently attached to the N-terminal alanine of the pHLIP® peptide. In a non-limiting example, the compound comprises the following structure:

(SEQ ID NO: 5)

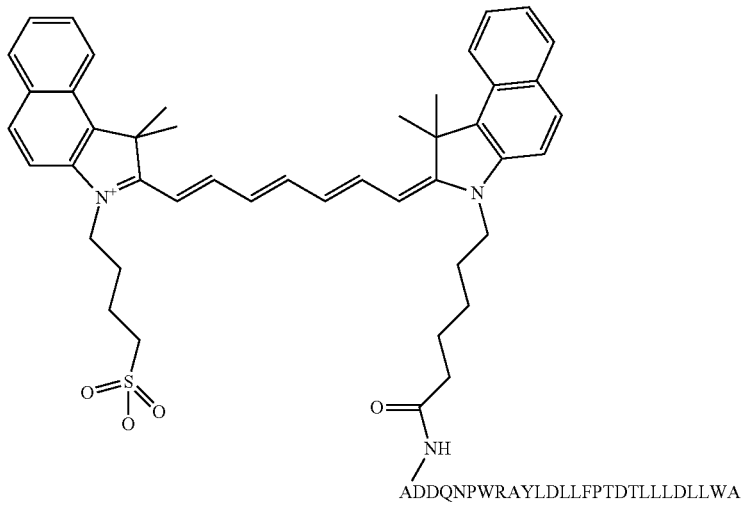

ADDQNPWRAYLDLLFPTDTLLLDLLWA

In some embodiments, the pHLIP® peptide comprises amino acids in the sequence AKDDQNPWRAYLDLL-FPTDTLLLDLLWA (SEQ ID NO: 8), and the ICG is covalently attached to the lysine of the pHLIP® peptide. A non-limiting example of such a compound comprises the structure:

(SEQ ID NO: 8)

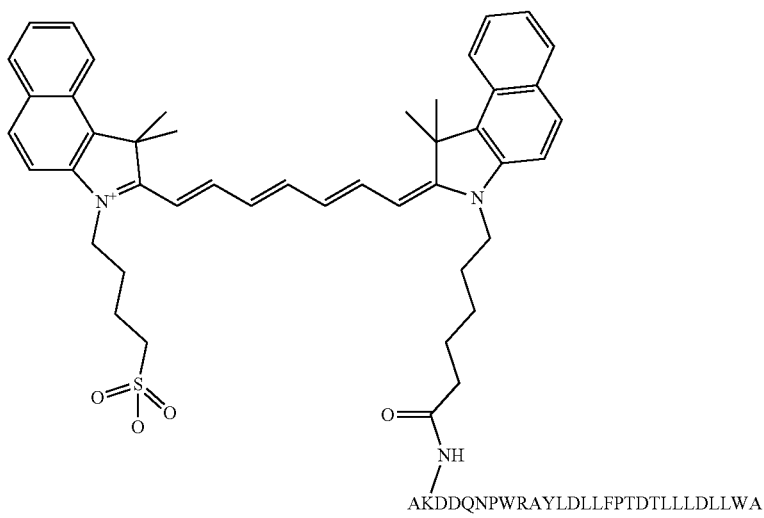

AKDDQNPWRAYLDLLFPTDTLLLDLLWA

Protonatable amino acids include amino acids with acidic side chains (e.g., side chains comprising one or more carboxyl groups). For example, a protonatable amino acid may have a side-chain with a pKa at 25° C. of less than about 7.0, 6.75, 6.5, 6.25, 6, 5.75, 5.5, 5.25, 5.0, 4.75, 4.5, 4.25, 4.0, 3.75, 3.5, 3.25, or 3.0. Non-limiting examples of protonatable amino acids include aspartic acid, glutamic acid, and gamma-carboxyglutamic acid. In various embodiments, the pHLIP® peptide comprises an artificial protonatable amino acid. In some embodiments, the artificial protonatable amino acid comprises at least 1, 2, 3, 4 or 5 carboxyl groups.

Of the standard α-amino acids, all but glycine can exist in either of two optical isomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum. D-amino acids are abundant components of the peptidoglycan cell walls of bacteria, and D-serine acts as a neurotransmitter in the brain. The L and D convention for amino acid configuration refers not to the optical activity of the amino acid itself, but rather to the optical activity of the isomer of glyceraldehyde from which that amino acid can be synthesized (D-glyceraldehyde is dextrorotary; L-glyceraldehyde is levorotary). In some embodiments, all or some of the amino acids in a pHLIP® peptide are D-amino acids. For example, pHLIP® peptide may comprise solely L-amino acids or solely D-amino acids, or a combination of both D-amino acids and L-amino acids.

Various embodiments include a pHLIP® peptide comprising amino acids in the sequence LLFPTDTLLL (SEQ ID NO: 25). In some embodiments, the pHLIP® peptide comprises amino acids in the sequence LDLLFPTDTLLLD (SEQ ID NO: 26). In certain embodiments, the pHLIP® peptide comprises amino acids in the sequence AYLDLL-FPTDTLLLDLL (SEQ ID NO: 27). In various embodiments, the pHLIP® peptide comprises amino acids in the sequence DDQNPWRAYLDLLFPTDTLLLDLLW (SEQ ID NO: 28). In some embodiments, the pHLIP® peptide comprises amino acids in the sequence WRAYLDLL-FPTDTLLLDLLWG (SEQ ID NO: 29) or WRAYLDLL-FPTDTLLLDLLW (SEQ ID NO: 30). Optionally, the pHLIP® peptide comprises 1, 2, 3, 4, 5, 6, 7, 8, 9, 10, 11, 12, 13, 14, 15, 16, 17, 18, 19, 20 or more amino acids at the N-terminus and/or C-terminus of an amino acid sequence disclosed herein.

In various embodiments, the pHLIP® peptide comprises amino acids in the sequence:

ADDQNPWRAYLDLLFPTDTLLLDLLWG, (SEQ ID NO: 2)

AKDDQNPWRAYLDLLFPTDTLLLDLLWG, (SEQ ID NO: 3)

ACDDQNPWRAYLDLLFPTDTLLLDLLWA, (SEQ ID NO: 4)

ADDQNPWRAYLDLLFPTDTLLLDLLWA, (SEQ ID NO: 5)

ADDQNPWRAYLDLLFPTDTLLLDLLWCA, (SEQ ID NO: 6)

ADDQNPWRAYLDLLFPTDTLLLDLLWKA, (SEQ ID NO: 7)

AKDDQNPWRAYLDLLFPTDTLLLDLLWA, (SEQ ID NO: 8)

ACDDQNPWRAYLDLLFPTDTLLLDLLWG, (SEQ ID NO: 9)

ADDQNPWRAYLDLLFPTDTLLLDLLWCG, (SEQ ID NO: 10)

ADDQNPWRAYLDLLFPTDTLLLDLLWKG, (SEQ ID NO: 11)

ACDDQNPWRAYLDLLFPTDTLLLDLLWKG, (SEQ ID NO: 12)

AKDDQNPWRAYLDLLFPTDTLLLDLLWCG, (SEQ ID NO: 13)

ACKDDQNPWRAYLDLLFPTDTLLLDLLWG, (SEQ ID NO: 14)

ACDDQNPWRAYLDLLFPTDTLLLDLLW, (SEQ ID NO: 15)

AKDDQNPWRAYLDLLFPTDTLLLDLLWC, (SEQ ID NO: 16)

ACDDQNPWARYLDWLFPTDTLLLDL, (SEQ ID NO: 17)

CDNNNPWRAYLDLLFPTDTLLLDW, (SEQ ID NO: 18)

ACEEQNPWARYLEWLFPTETLLLEL, (SEQ ID NO: 19)

ACEEQNPWRAYLELLFPTETLLLELLW, (SEQ ID NO: 20)

CEEQQPWAQYLELLFPTETLLLEW, (SEQ ID NO: 21)

CEEQQPWRAYLELLFPTETLLLEW, (SEQ ID NO: 22)

AAEEQNPWARYLEWLFPTETLLLEL, (SEQ ID NO: 23)

or

AKEEQNPWARYLEWLFPTETLLLEL. (SEQ ID NO: 24)

In some embodiments, the amino acid sequence of the pHLIP® peptide is less than 100%, 99%, or 95% identical to the amino acid sequence set forth as SEQ ID NOS: 15, 16, 17, 18, 19, 20, 21, 22, 23, or 24. In some embodiments, the amino acid sequence of the pHLIP® peptide is less than 100%, 99%, or 95% identical to each of the amino acid sequences set forth as SEQ ID NOS: 15, 16, 17, 18, 19, 20, 21, 22, 23, and 24. In certain embodiments, the amino acid sequence of the pHLIP® peptide is 95-100%, 95-99%, or 90-95% identical to one or more of the amino acid sequences set forth as SEQ ID NOS: 15, 16, 17, 18, 19, 20, 21, 22, 23, and 24. In some embodiments, the amino acid sequence of the pHLIP® peptide is identical to SEQ ID NO: 15, 16, 17, 18, 19, 20, 21, 22, 23, or 24.

In certain embodiments, the pHLIP® peptide comprises 20-30 amino acids. For example, the pHLIP® peptide comprises about 20, 21, 22, 23, 24, 25, 26, 27, 28, 29, or 30 amino acids. In some embodiments, at least about 1, 2, 3, 4, 5, 6, 7, 8, 9, or 10, or 1-3, 1-5, or 5-10 N-terminal amino acids of the pHLIP® peptide are outside the cell (i.e., not within the lipid bilayer of the cell membrane) when the pHLIP® peptide is inserted into the cell membrane. In various embodiments, when the compound is inserted into a cell membrane, then the ICG portion thereof is at least about 1, 2, 3, 4, 5, 6, 7, 8, 9, 10, 11, 12, 13, 14, 15, 16, 17, 18, 19, 20, 1-5, 5-10, 5-15, or 10-15 angstroms (Å) from the lipid bilayer of the cell membrane.

Aspects of the present subject matter provide a composition comprising a compound disclosed herein and a pharmaceutically acceptable carrier. In some embodiments, the composition further comprises D-glucose, e.g., about 5-25 mM D-glucose, or about 1, 2, 3, 4, 5, 6, 7, 8, 9, 10, 15, 20, or 25 mM D-glucose. In some embodiments, the composition comprises a buffer, e.g., the composition is buffered such that it comprises pH of about 7.0, 7.1, 7.2, 7.3, 7.4, 7.5, 7.6, 7.8, 7.9, or 8.0. In certain embodiments, the composition comprises phosphate buffered saline (PBS).

Aspects of the present subject matter relate to the detection of oral cavity cancer, e.g., by spraying or administering a composition comprising a compound disclosed herein to the oral cavity. For example, the composition may comprise a mouthwash or a mouth spray.

Also provided is a method for detecting cancer tissue or precancerous tissue in a bodily organ or tissue, comprising (a) contacting the bodily organ or tissue with a compound disclosed herein; (b) contacting the compound with electromagnetic radiation comprising an excitation wavelength of ICG; and (c) detecting electromagnetic radiation emitted from the compound, wherein detection of the radiation indicates the presence of the cancerous tissue or the precancerous tissue. In various embodiments, the level of radiation emitted from a precancerous tissue and/or a cancer tissue is at least 5%, 10%, 15%, 20%, 30%, 40%, 50%, 60%, 70%, 80%, 90%, 2-fold, 3-fold, 4-fold, 5-fold, 6-fold, 7-fold, 8-fold, 9-fold, 10-fold, or 20-fold, 25-fold, or more greater than a level of radiation emitted from normal non-cancerous tissue (e.g., corresponding normal-noncancerous tissue in a corresponding bodily organ or tissue).

The compounds, compositions, and methods provided herein are useful for detecting cancerous or precancerous tissue in many bodily organs and tissues. In some embodiments, the bodily organ is a kidney or a urinary bladder. Non-limiting examples of tissues in which cancerous or precancerous tissue may be detected include bone, joint, ligament, muscle, tendon, salivary gland, tooth, gum, parotid gland, submandibular gland, sublingual gland, pharynx, esophagus, stomach, small intestine (e.g., duodenum, jejunum, and/or ileum), large intestine, liver, gallbladder, pancreas, nasal cavity, pharynx, larynx, trachea, bronchi, lung, diaphragm, kidney, ureter, bladder, urethra, ovary, uterus, fallopian tube, uterus, cervix, vagina, teste, epididymis, vas deferens, seminal vesicle, prostate, bulbourethral gland, pituitary gland, pineal gland, thyroid gland, parathyroid gland, adrenal gland, heart, artery, vein, capillary, lymphatic, lymph node, bone marrow, thymus, spleen, brain, cerebral hemisphere, diencephalon, brainstem, midbrain, pons, medulla oblongata, cerebellum, spinal cord, ventricular, choroid plexus, nerve, eye, ear, olfactory, breast, and skin tissue. In some embodiments, the diseased cancer tissue detected is sarcoma or carcinoma tissue. Non-limiting types of cancer that may be detected using compounds, compositions, and methods disclosed herein include bladder cancer, lung cancer, brain cancer, melanoma, breast cancer, cervical cancer, ovarian cancer, adrenal cancer, esophageal cancer, upper gastrointestinal cancer, anal cancer, bile duct cancer, bladder cancer, bone cancer, Castleman Disease, colon/rectum cancer, endometrial cancer, esophagus cancer, eye cancer, gallbladder cancer, gastrointestinal carcinoid tumors, gastrointestinal stromal tumors (GISTs), gestational trophoblastic disease, Kaposi sarcoma, kidney cancer, laryngeal cancer, hypopharyngeal cancer, liver cancer, malignant mesothelioma, nasal cavity cancer, paranasal sinus cancer, nasopharyngeal cancer, neuroblastoma, oral cavity cancer, oropharyngeal cancer, osteosarcoma, pancreatic cancer, penile cancer, pituitary tumors, prostate cancer, retinoblastoma, rhabdomyosarcoma, salivary gland cancer, sarcoma, small intestine cancer, stomach cancer, testicular cancer, thymus cancer, thyroid cancer, uterine sarcoma, vaginal cancer, vulbar cancer, and Wilms tumors. In various embodiments, the cancer comprises a solid tumor.

In some embodiments, the cancerous or precancerous tissue is in the bladder, the upper urinary tract, a lymph node, a breast, a prostate, a head, a neck, a brain, a pancreas, a lung, a liver, or a kidney.

The compounds, compositions, and methods provided herein are also useful for detecting cancer cells (such as metastatic cancer cells) in tissue such as a lymph node. In some embodiments, the lymph node is in a subject who has cancer. In various embodiments, the lymph node is in a subject with bladder cancer, upper urinary tract cancer, breast cancer, prostate cancer, head and neck cancer, bran cancer, pancreatic cancer, lung cancer, liver cancer, or kidney cancer.

Diseased tissue (e.g., precancerous or cancer tissue) may be detected in tissue samples or biopsies obtained, removed, or provided from a subject. In various embodiments, the tissue comprises a tissue biopsy. Alternatively or in addition, the presence of diseased tissue is detected on a biological surface in vivo or in situ, e.g., the skin surface, the surface of a mucosal membrane, or an internal site (e.g., the internal surface of a bladder, the surface of a colon, the surface of an esophagus, or the surface of a surgical site within the subject). For example, the tissue to be interrogated comprises a lumen, e.g., a duct (such as a kidney duct), a ureter, an intestinal tissue (large or small intestine), an esophagus, or an airway lumen such as a tracheobronchial tube or alveolar tube. In some embodiments, a compound provided herein is used to detect the presence of melanoma tissue. In some embodiments, the bodily organ or tissue is present in a subject.

Optionally, methods disclosed herein may include steps such as washing steps to remove excess unbound or unattached compound, i.e. compound that is not attached to a low pH tissue via insertion of a pHLIP® peptide construct into a cell membrane. For example, an organ sample or tissue biopsy may be washed or perfused before ICG fluorescence is detected (e.g., imaged). In non-limiting examples in which a body cavity or surface has been contacted with a compound (e.g., in liquid or spray form), the cavity or surface may be flushed or washed to remove excess ICG before detection/imaging. In some embodiments, flushing/washing is performed using, e.g., an aqueous solution such as saline or water. In some embodiments, flushing/washing is performed with the carrier that was used to deliver the ICG-pHLIP® peptide.

In some embodiments, contacting a bodily organ, tissue, or fluid (such as blood) with a compound provided herein comprises administering the compound to a subject. For example, the compound is detected in vivo. In certain embodiments, the compound is administered to the subject via intravessical instillation, intravenous injection, intraperitoneal injection, topical administration, mucosal administration, or oral administration. For example, the compound may be administered to a site within the subject (e.g., sprayed, applied onto, delivered as a liquid) via tube that is inserted into the subject. The site may be, e.g., an existing, former, or suspected tumor site, and/or normal tissue that is being assessed for the presence of cancerous or precancerous tissue. In some embodiments, a tube or other device (e.g., a catheter, needle, aspirator, inhaler, endoscope, cystoscope, atomizer, spray nozzle, probe, syringe, pipette, or nebulizer) is used to deliver the compound to, e.g., the esophagus, bladder, or colon. In certain embodiments, fluorescence of the compound is detected (e.g., imaged) using an endoscope or a cystoscope. For example, the endoscope or cystoscope may be configured to (i) emit electromagnetic radiation comprising an excitation wavelength of ICG and/or (ii) detect electromagnetic radiation emitted from the compound (i.e., the ICG component of the compound). In some embodiments, the compound is administered by applying a liquid, powder, or spray comprising the compound to a surface of the subject. In some embodiments, the surface comprises a site within the body of the subject that is accessed and/or exposed via surgery. In some embodiments, the surgery comprises endoscopic surgery or cystoscopic surgery. In certain embodiments, the compound is administered to an oral cavity of the subject.

In various embodiments, electromagnetic radiation emitted from the compound is detected ex vivo. In some embodiments, a tissue sample (e.g., a biopsy or an organ) from a subject is perfused, soaked, sprayed, incubated, and/or injected with a composition comprising a compound herein, followed by washing, and then imaging for ICG fluorescence.

Aspects of the present subject matter relate to methods comprising surgically removing cancerous tissue or precancerous tissue, e.g., cancer tissue or precancerous tissue detected with a compound, composition, or method disclosed herein. For example, the fluorescence of the compounds provided herein may be used to guide surgery such that all cancerous and/or precancerous tissue is removed, i.e., clean (non-cancer containing) margins of the surgical site are achieved.

The present subject matter provides methods for identifying precancerous and cancer/tumor tissue faster than existing pathological methods. For example, tissue removed during surgery can be contacted with ICG-pHLIP® peptides, washed, and then rapidly imaged to determine, e.g., whether all of the tissue removed was precancerous or cancerous and/or whether precancerous or cancerous tissue remains in a subject. Alternatively or in addition, the surgical site may be contacted with a compound (e.g., by local or systemic administration) to determine whether any diseased tissue remains at the site. The methods provided herein do not require, e.g., time consuming immunohistological staining or evaluation by a trained pathologist. The speed (e.g., 30 minutes or less) at which the methods provided herein may be performed enable clinicians to test for the presence or absence of precancerous or cancerous tissue (e.g., within a subject or a sample from the subject) during ongoing surgery, e.g., to determine whether and where surgery should continue (e.g., to remove more tissue).

The development, reoccurrence, and treatment of cancer can also be detected and monitored. For example, a subject who has had cancer surgically removed or treated (e.g., with chemotherapy or radiation) may be tested for cancer using compounds and methods disclosed herein. For example, the inside of a bladder, colon, esophagus, or oral cavity, and/or a mucosal membrane/skin surface may be contacted with a compound provided herein and then detected to determine whether precancerous and/or cancerous tissue is developing or has developed. In instances where, e.g., chemotherapy or radiation therapy efficacy is assessed, the amount of cancer tissue may be monitored. Thus, ICG-pH-triggered compounds provided herein can be used to assist decisions regarding whether cancer treatment should be initiated or continued, and/or whether a different treatment regimen should be attempted (e.g., if a previously administered dose/regimen has not reduced the amount of cancer tissue as desired).

Many different types of subjects with various stages of cancer can be assessed and/or treated using the compounds, compositions, and methods provided herein. However, various embodiments relate to the detection and treatment of cancer before the removal of a large amount of tissue (e.g., an organ such as a bladder or kidney, or, e.g. a portion of an organ such as a colon) is warranted or advisable. In various embodiments, the subject does not comprise invasive or metastatic cancer. In certain embodiments, relating to subjects with urothelial carcinoma, the subject does not comprise high grade urothelial carcinoma. In some embodiments, the subject does not comprise invasive high grade urothelial carcinoma.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

The patent or application file contains at least one drawing executed in color. Copies of this patent or patent application publication with color drawing(s) will be provided by the Office upon request and payment of the necessary fee.

As used herein with respect to the data provided in the drawings and Examples 1-3, the terms "ICG-Var3" "ICG-Var3 peptide" "ICG-Var3 compound" and "ICG-Var3 construct" refer to a pHLIP®-fluorophore compound comprising a pHLIP® peptide with the amino acid sequence NH$_2$-ACDDQNPWRAYLDLLFPTDTLLLDLLWA-COOH (SEQ ID NO: 4) with ICG covalently bound to the cysteine thereof [A-Cys(ICG)-DDQNPWRAYLDLLFPTDTLLLD-LLWA (SEQ ID NO:4)], having the following structure (SEQ ID NO: 4 is disclosed below):

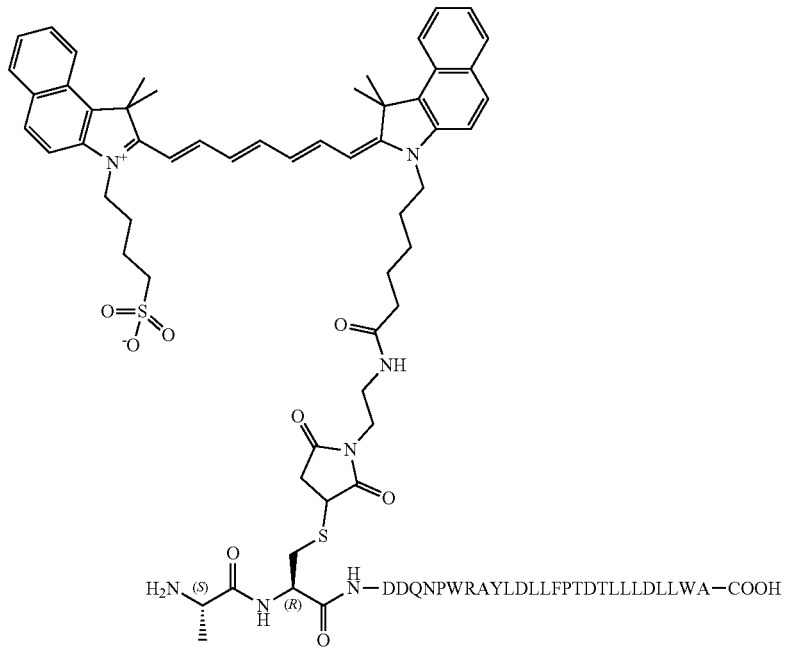

The term "ICG-pHLIP® peptide" is a more general term than "ICG-Var3" and includes any pHLIP®-fluorophore compound comprising ICG and a pHLIP® peptide.

Figure 1A:
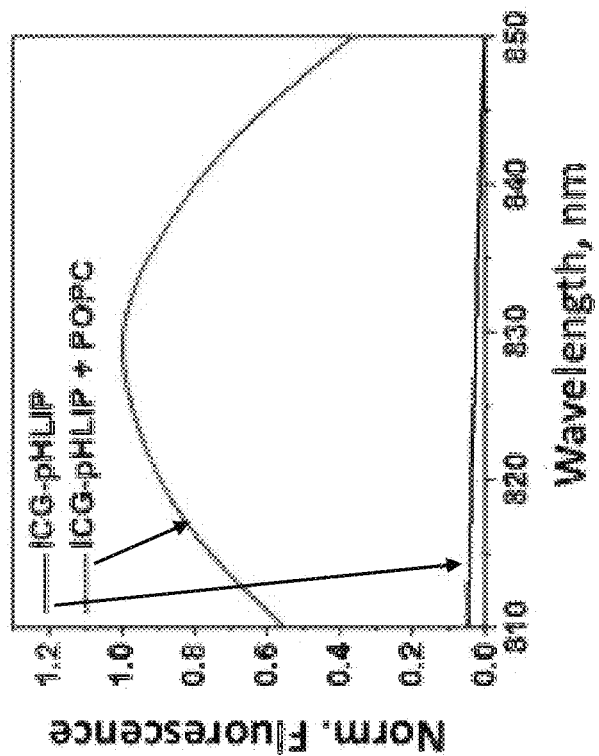
Figure 1B:
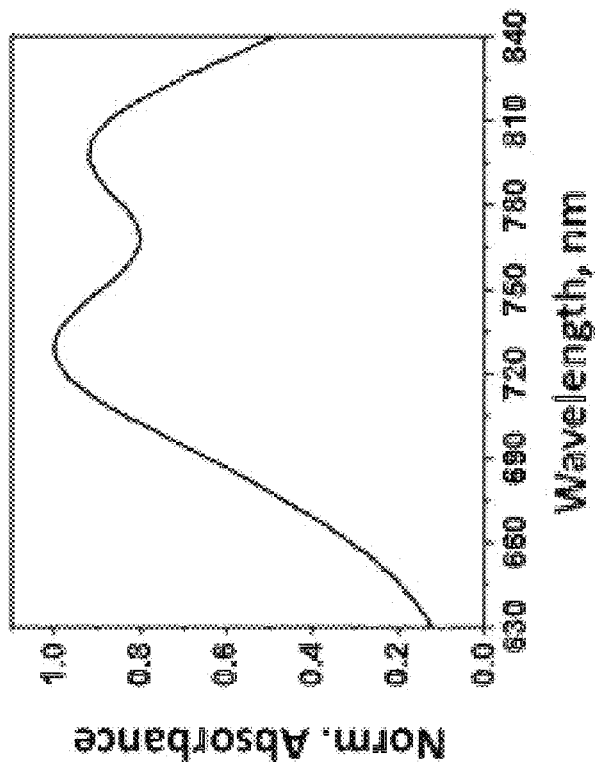

FIGS. 1A-B are graphs showing normalized absorbance (A) and fluorescence (B) spectra of an ICG-Var3 compound measured in phosphate buffered saline (PBS) pH 7.4 containing 10 mM D-glucose. The fluorescence (with an excitation wavelength of 790 nm) of ICG-Var3 compound is increased about 25 fold in the presence of 1-palmitoyl-2-oleoyl-sn-glycero-3-phosphocholine (POPC) liposomes compared to the emission in buffer.

FIGS. 2A-L are images showing representative white light (A, D, G, J), NIR fluorescence (B, E, H, K) ex vivo imaging of bladder specimens and hemolysin and eosin (HE) stained tumor sections (C, F, I, L) are shown, demonstrating targeting of invasive high grade urothelial carcinoma (A, B, C), non-invasive high grade urothelial carcinoma (D, E, F), carcinoma in situ (G, H, I) and dysplasia (J, K, L) by ICG-Var3 imaging agent. The diagnosis was confirmed by pathological analysis. The fluorescent lesions were marked in case #11 to identify locations for pathology analysis.

FIGS. 3A-B are cartoons showing non-limiting examples of (A) pHLIP® tethering of a cargo molecule to the surface of a cell in diseased tissue and (B) pHLIP® delivery of cargo into a cell in diseased tissue.

FIGS. 4A-F are a series of images showing the targeting of cancerous lesions in bladder tissue with a ICG-Var3 compound; white light (A, D), NIR fluorescence (B, E) and overlay of white light and fluorescent images (C, F) are shown.

FIGS. 5A-I are a series of images showing the targeting of cancerous lesions in bladder tissue with a ICG-Var3 compound; white light (A, D, G), NIR fluorescence (B, E, H) and overlay of white light and fluorescent images (C, F, G) are shown.

FIGS. 6A-F are a series of images showing the targeting of cancerous lesions in bladder tissue with a ICG-Var3 compound; white light (A, D), NIR fluorescence (B, E) and overlay of white light and fluorescent images (C, F) are shown.

FIGS. 7A-C are a series of images showing the targeting of cancerous lesions in bladder tissue with a ICG-Var3 compound; white light (A), NIR fluorescence (B) and overlay of white light and fluorescent images (C) are shown.

FIGS. 8A-G are a series of images showing the targeting of cancerous lesions in bladder tissue with a ICG-Var3 compound; white light (A, D, F), NIR fluorescence (B, E, G) and overlay of white light and fluorescent images (C) are shown. The on the figure F and G the case of normal tissue is shown not targeted by ICG-Var3 compound.

FIGS. 9A-C are a series of images showing the targeting of cancerous lesions in bladder tissue with a ICG-Var3 compound; white light (A), NIR fluorescence (B) and overlay of white light and fluorescent images (C) are shown.

Figure 10:
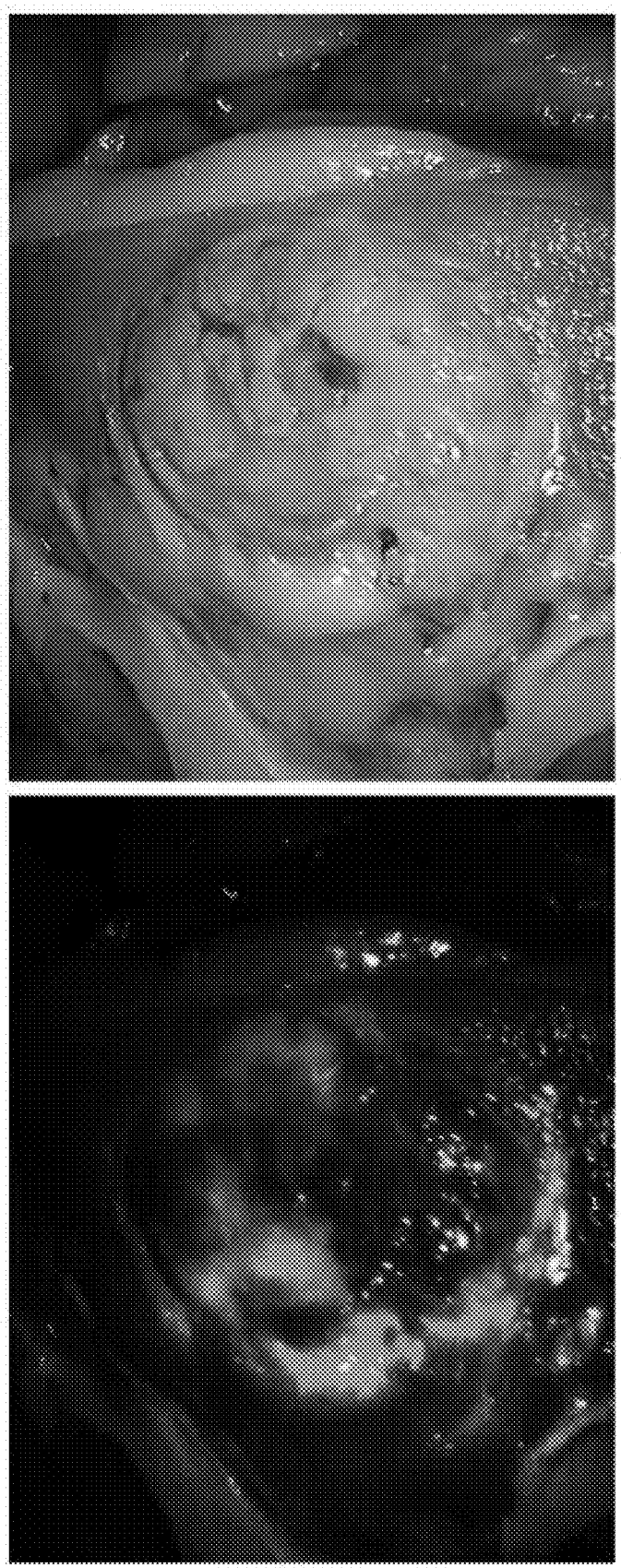

FIG. 10 is a set of images showing the targeting of cancerous lesions in kidney tissue with a ICG-Var3 compound, on the left NIR fluorescence image of kidney is shown and on the right the white light image is shown. Kidney collected after radical nephrectomy was perfused with ICG-Var3 compound for 30 min through the artery to mimic IV administration of the compound, followed by washing with saline and ex vivo imaging.

Figure 11:

FIG. 11 is an image showing the targeting of 4T1 murine mammary carcinoma with an ICG-Var3 compound. The ICG-Var3 compound was administered by intravenous (IV) injection (40 μM, 100 μL) and imaged 16 hours (h) after injection. The highly invasive 4T1 mammary carcinoma model mimics stage IV of human breast cancer.

Figure 12:

FIG. 12 is an image showing the targeting of AY27 rat bladder cancer in nude mice with an ICG-Var3 compound. The ICG-Var3 compound was administered by IV injection (40 μM, 100 μL) and imaged 16 h after injection.

Figure 13:
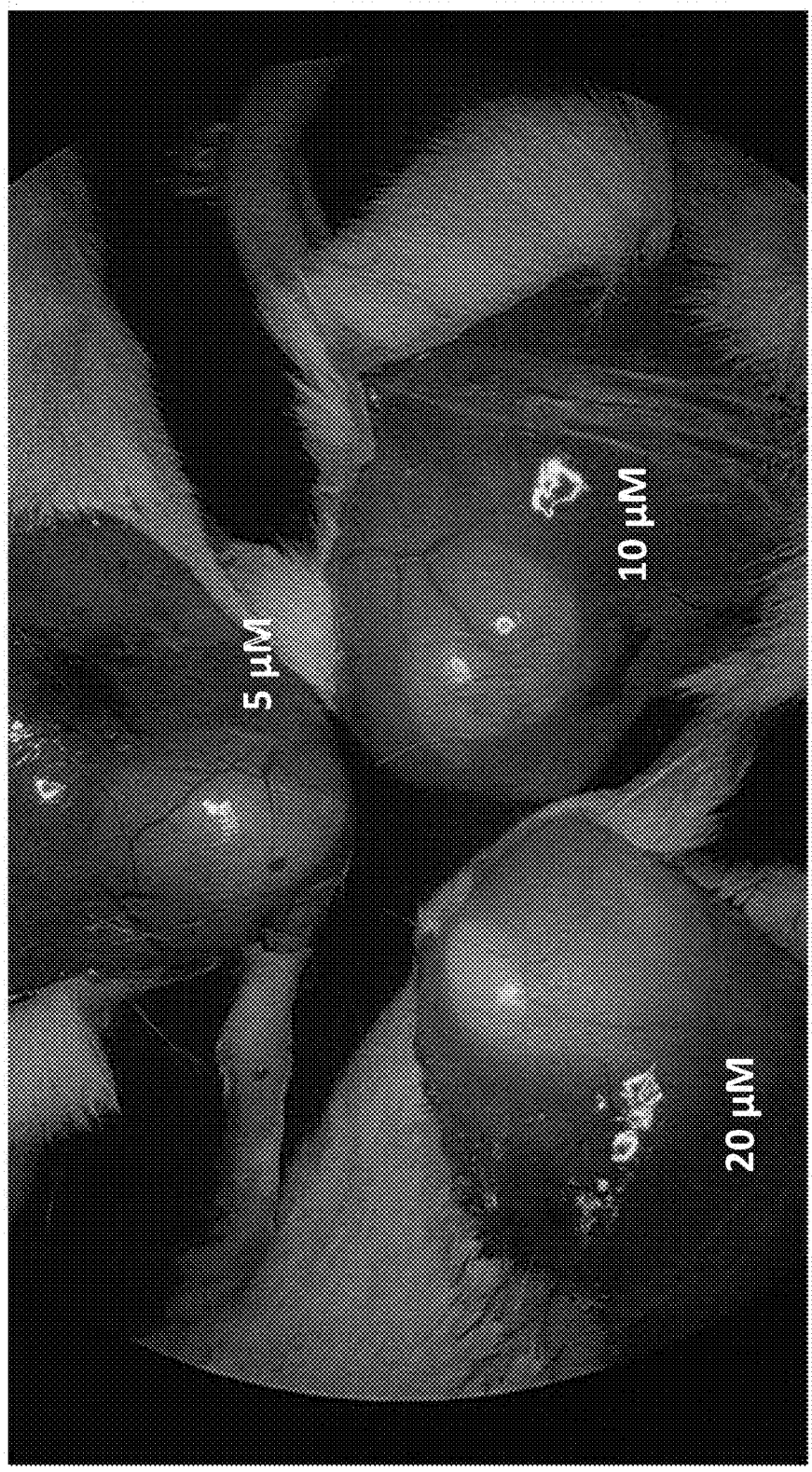

FIG. 13 is an image showing the targeting of 4T1 tumors with an ICG-Var3 compound. The ICG-Var3 compound was administered by IV injection (20, 10 and 5 μM, as indicated) and imaged 16 h after injection. The fluorescent signal decreased with the decrease of the injected ICG-Var3 compound dose.

Figure 14:
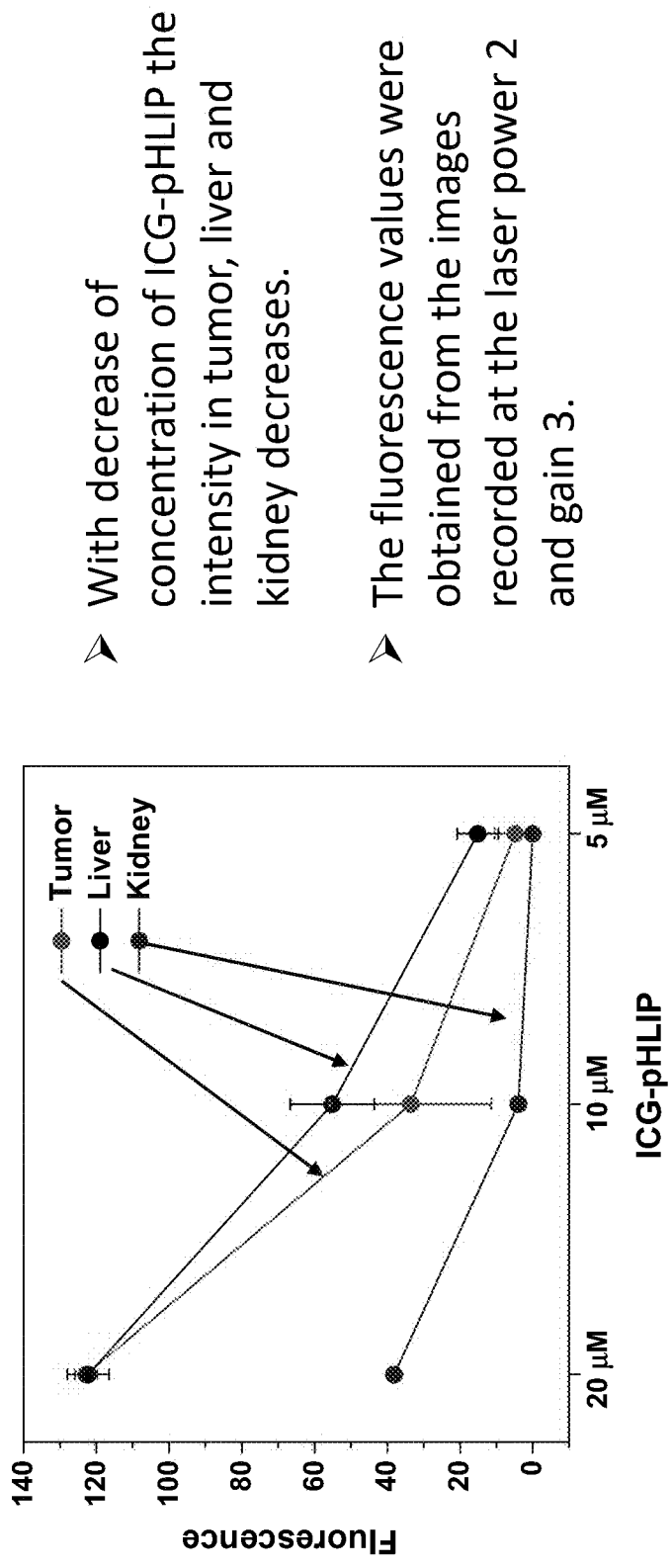

FIG. 14 is a graph showing the targeting of 4T1 tumors with an ICG-Var3 compound (at 20, 10 and 5 μM concentrations, intravenous injection, imaged at 16 h). With decrease of concentration of ICG-Var3 compound, the fluorescence intensity in tumor, liver and kidney decreases. The fluorescence values were obtained from the images recorded using a standard endoscopic light source/imaging system at the laser power 2 and gain 3.

Figure 15:
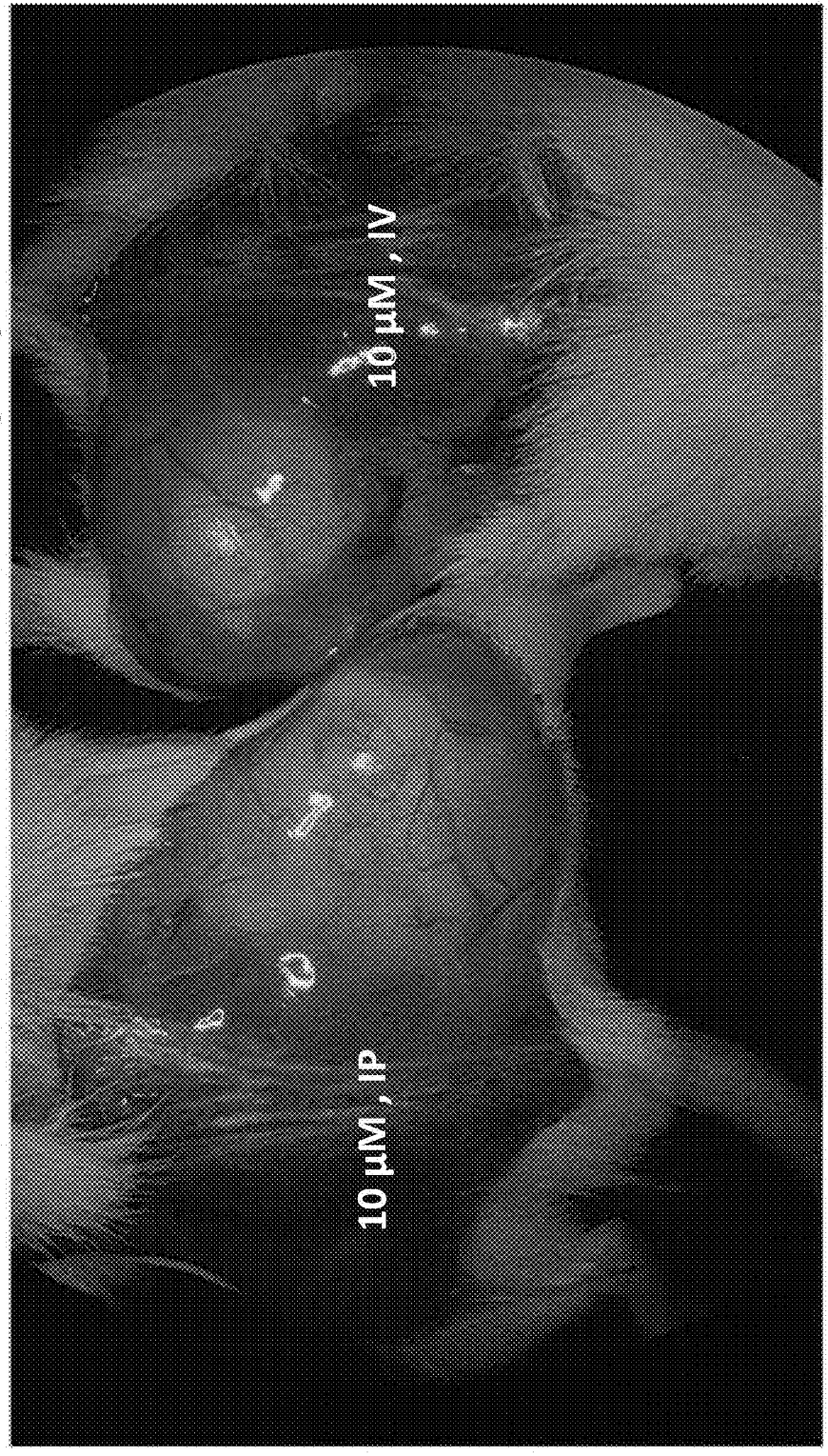

FIG. 15 is an image showing the targeting of 4T1 tumors with 10 μM of ICG-Var3 compound with IV and intraperitoneal (IP) injection. Imaging was performed 16 h after injection.

Figure 16:

FIG. 16 is an image showing targeting of 4T1 tumors with 20 μM of ICG-Var3 compound compared to 20 μM of IR800-pHLIP® compound. The compounds were administered by IV injection and imaging was performed 16 h after injection. The fluorescent signal in tumor detected with an endoscope (e.g., a standard endoscopic light source/imaging system) is higher for the ICG-Var3 compound compared to the IR800-pHLIP® compound.

Figure 17:
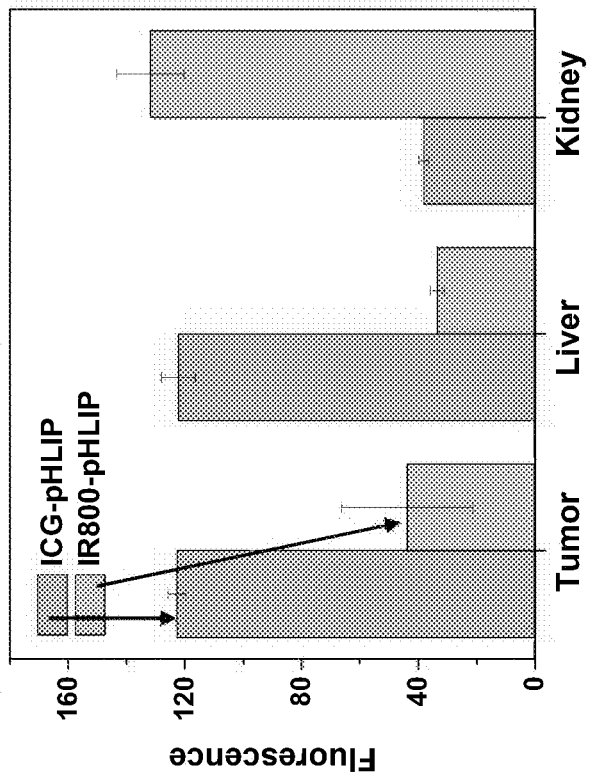

FIG. 17 is a chart comparing the targeting of 4T1 tumors with 20 μM of ICG-Var3 compound versus 20 μM of IR800-pHLIP® compound. The compounds were administered by IV injection and imaging was performed 16 h after injection. The fluorescent signal in a tumor detected by the endoscope was higher for the ICG-Var3 compound compared to the IR800-pHLIP® compound. The ICG-Var3 compound was cleared by the liver and the IR800-pHLIP® compound was cleared by the kidney.

Figure 18:
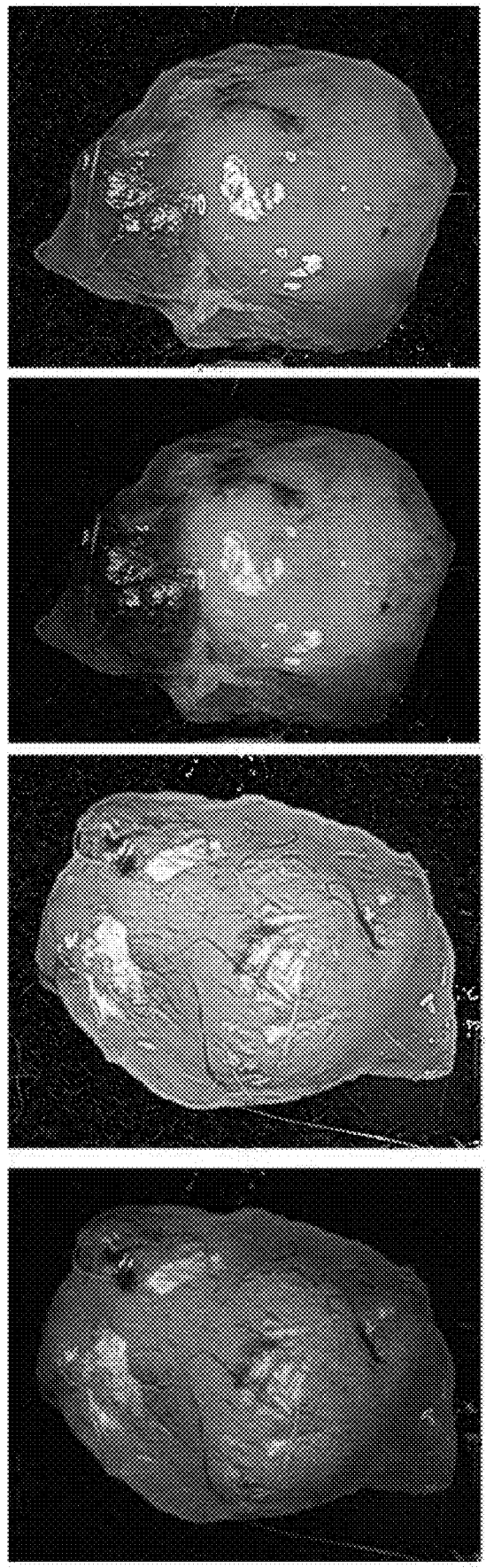

FIG. 18 is a set of images showing the visualization of tumor margins with a ICG-Var3 compound. The tumor margins are defined very well by the ICG-Var3 compound. Additionally, muscle tissue is not targeted by the ICG-Var3 compound.

Figure 19:
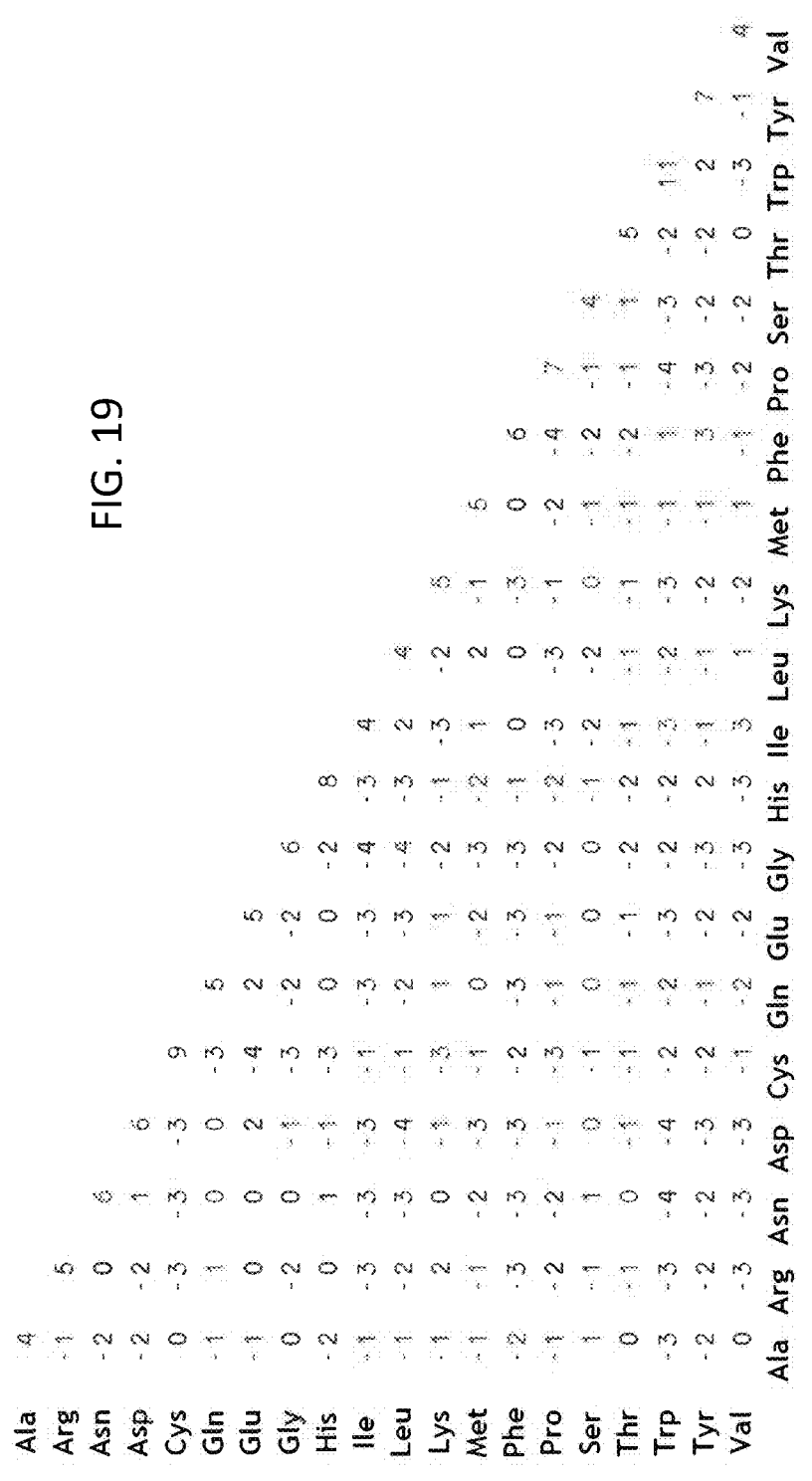

FIG. 19 shows the BLOSUM62 matrix.

Figure 20:
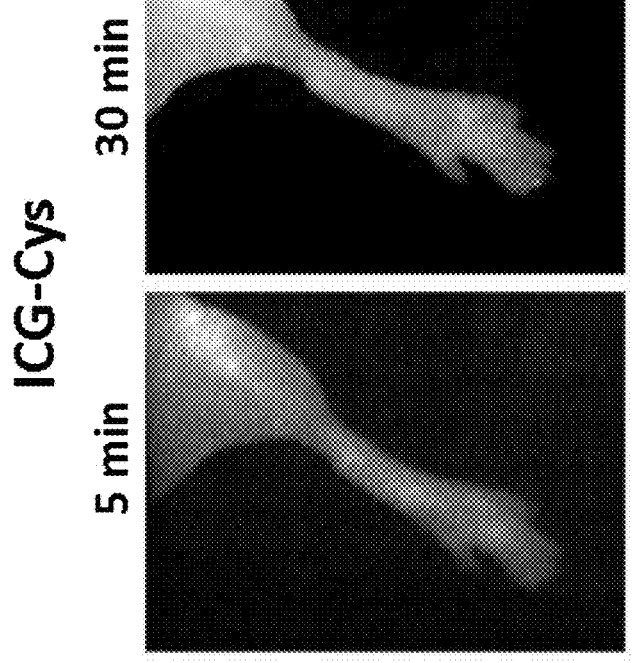

FIG. 20 is a set of NIR fluorescent pictures of mouse leg obtained at 5 and 30 min after IV administration of ICG-Cys (ICG maleimide was conjugated with Cys residue).

Figure 21:
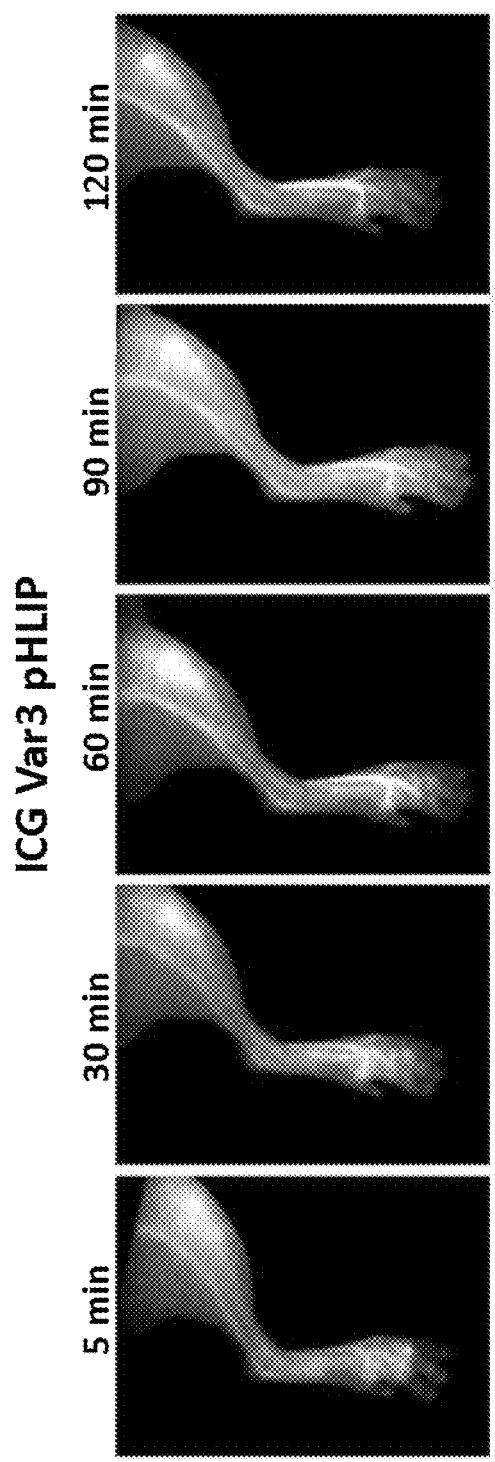

FIG. 21 is a set of NIR fluorescent pictures of a mouse leg obtained at 5, 30, 60, 90 and 120 min after IV administration of ICG-Var3 pHLIP® (ICG-Var3 pHLIP® is an ICG-Var3 compound with a Var3 pHLIP® peptide; see Table 11 for pHLIP® peptide amino acid sequence).

Figure 22:
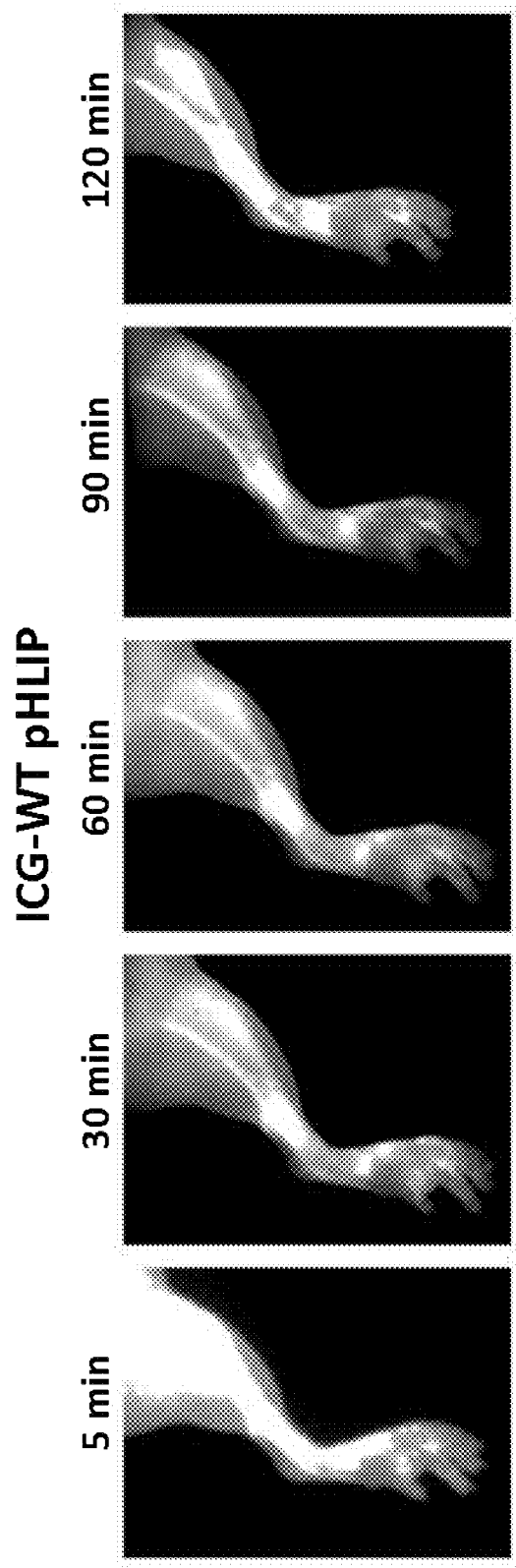

FIG. 22 is a set of NIR fluorescent pictures of a mouse leg obtained at 5, 30, 60, 90 and 120 min after IV administration of ICG-WT pHLIP® (ICG-WT pHLIP® is an ICG-Var3 compound with a WT pHLIP® peptide; see Table 11 for pHLIP® peptide amino acid sequence).

Figure 23:
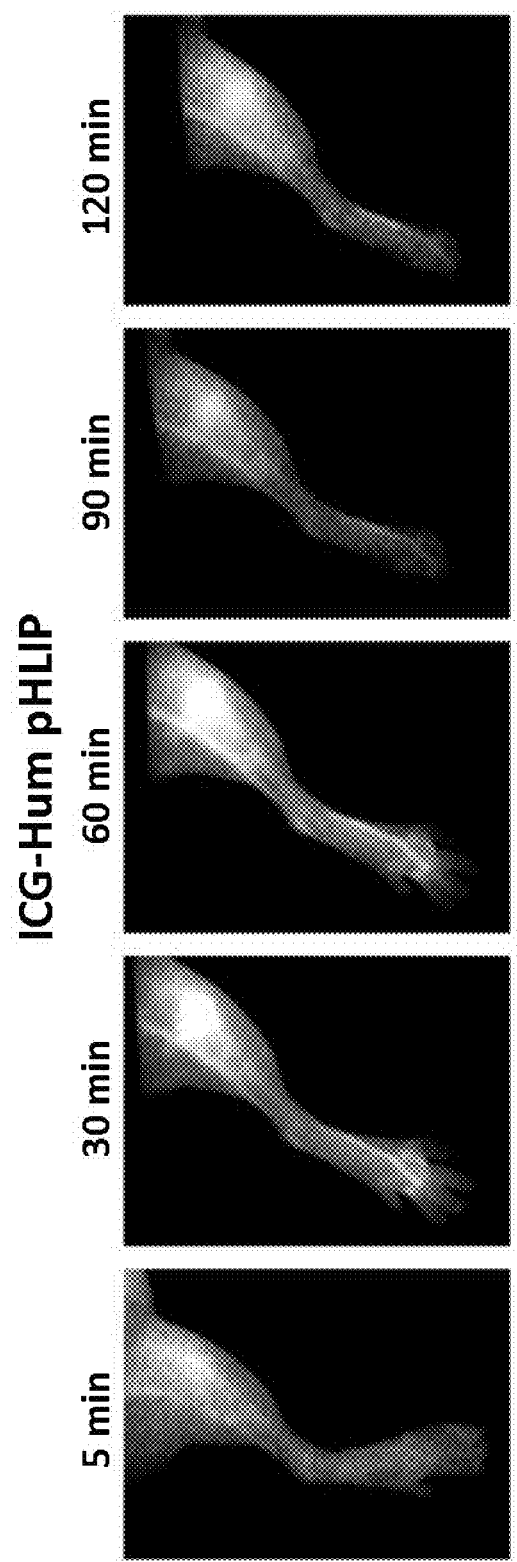

FIG. 23 is a set of NIR fluorescent pictures of a mouse leg obtained at 5, 30, 60, 90 and 120 min after IV administration of ICG-Hum pHLIP® (ICG-Hum pHLIP® is an ICG-Var3 compound with a Hum pHLIP® peptide; see Table 11 for pHLIP® peptide amino acid sequence).

Figure 24:
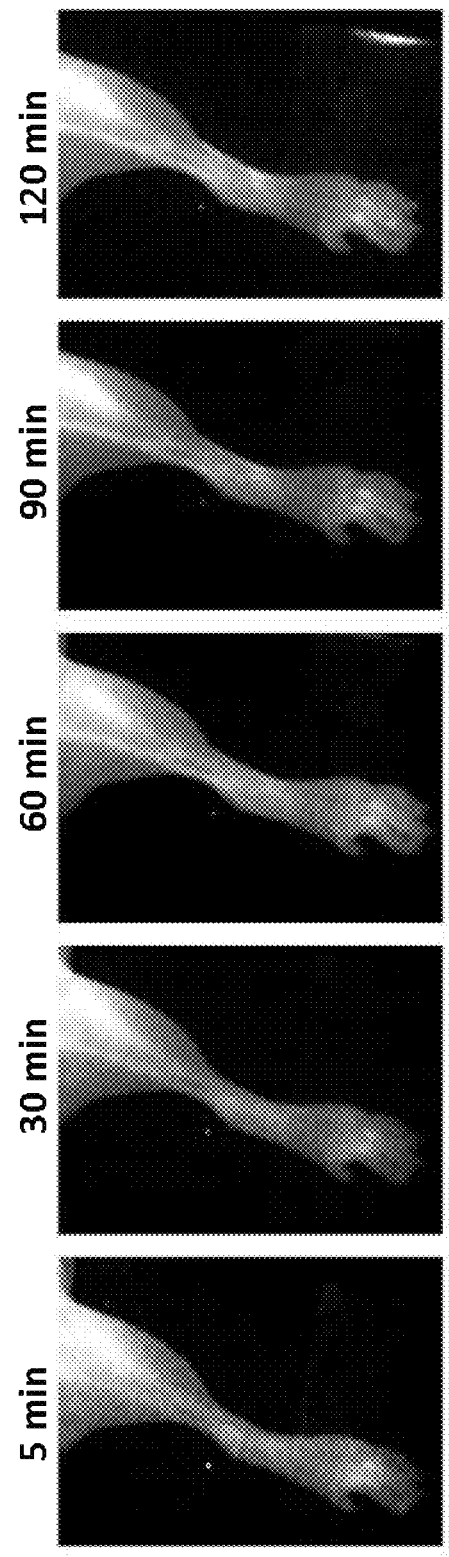

FIG. 24 is a set of NIR fluorescent pictures of a mouse leg obtained at 5, 30, 60, 90 and 120 min after IV administration of ICG-NpHLIP® (ICG-NpHLIP® is an ICG-Var3 compound with a NpHLIP® peptide; see Table 11 for pHLIP® peptide sequence).

Figure 25:

FIG. 25 is a set of NIR fluorescent pictures of a mouse ear obtained at 5 and 30 min after IV administration of ICG-Cys (ICG maleimide was conjugated with Cys residue).

Figure 26:
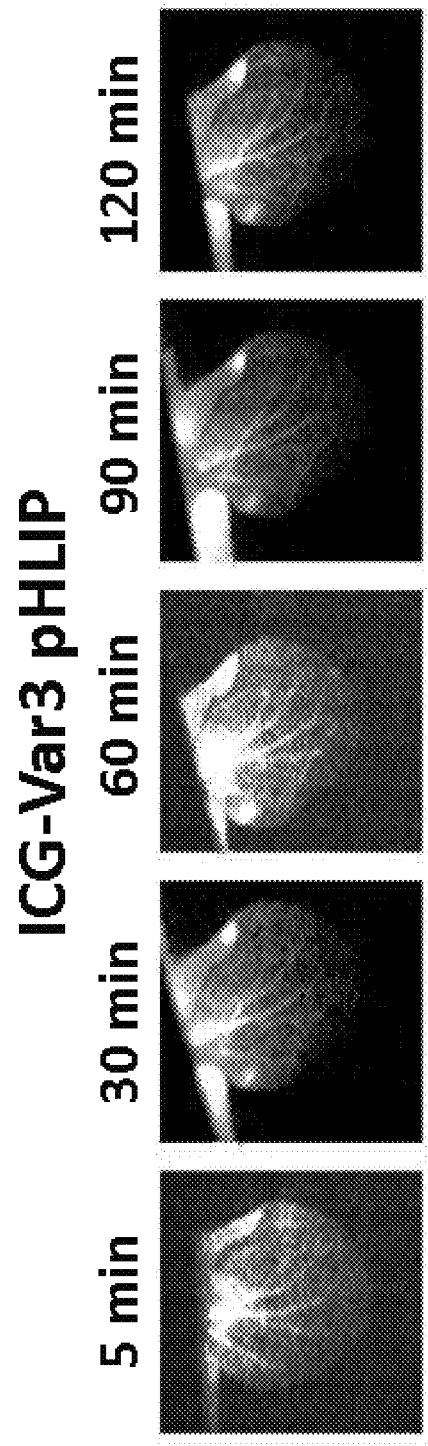

FIG. 26 is a set of NIR fluorescent pictures of a mouse ear obtained at 5, 30, 60, 90 and 120 min after IV administration of ICG-Var3 pHLIP®.

Figure 27:
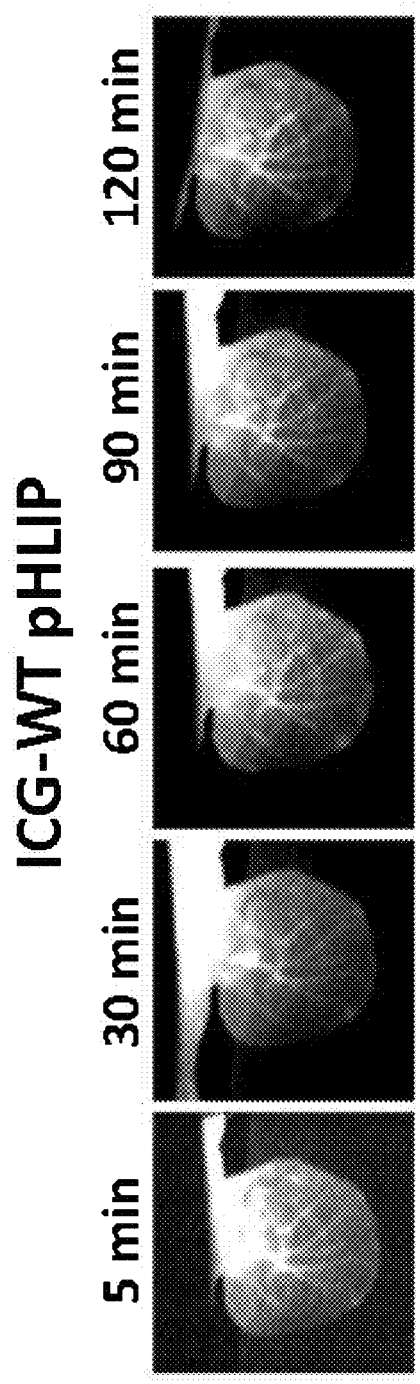

FIG. 27 is a set of NIR fluorescent pictures of a mouse ear obtained at 5, 30, 60, 90 and 120 min after IV administration of ICG-WT pHLIP®.

Figure 28:
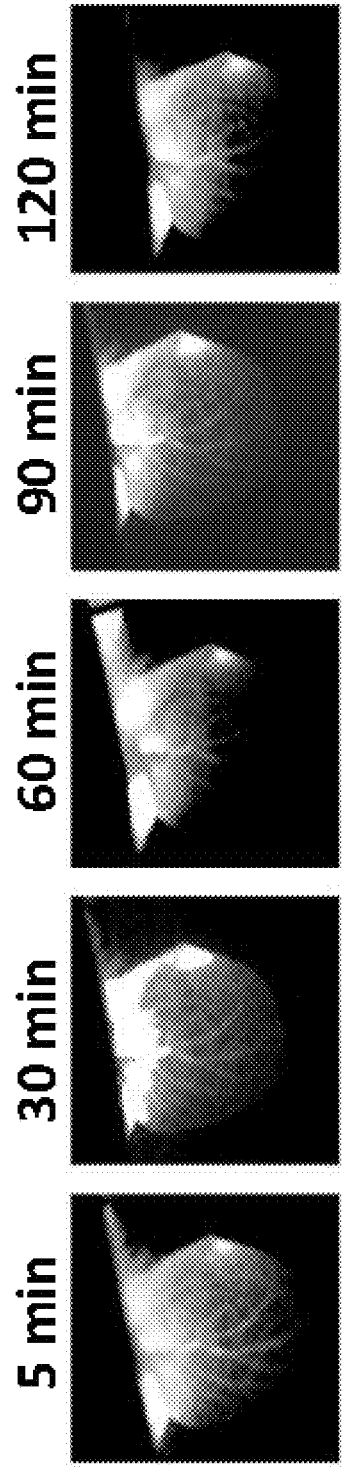

FIG. 28 is a set of NIR fluorescent pictures of a mouse ear obtained at 5, 30, 60, 90 and 120 min after IV administration of ICG-Hum pHLIP®.

Figure 29:
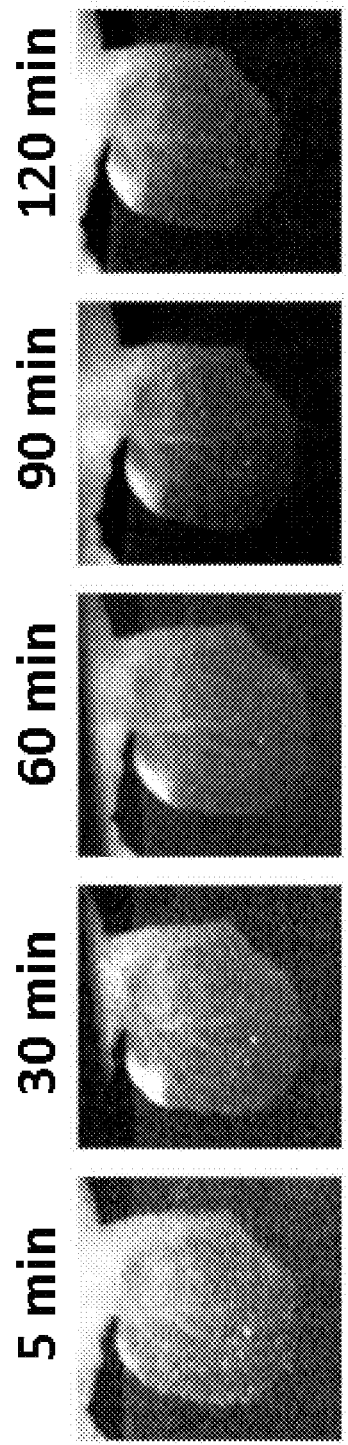

FIG. 29 is a set of NIR fluorescent pictures of a mouse ear obtained at 5, 30, 60, 90 and 120 min after IV administration of ICG-NpHLIP®.

Figure 30:
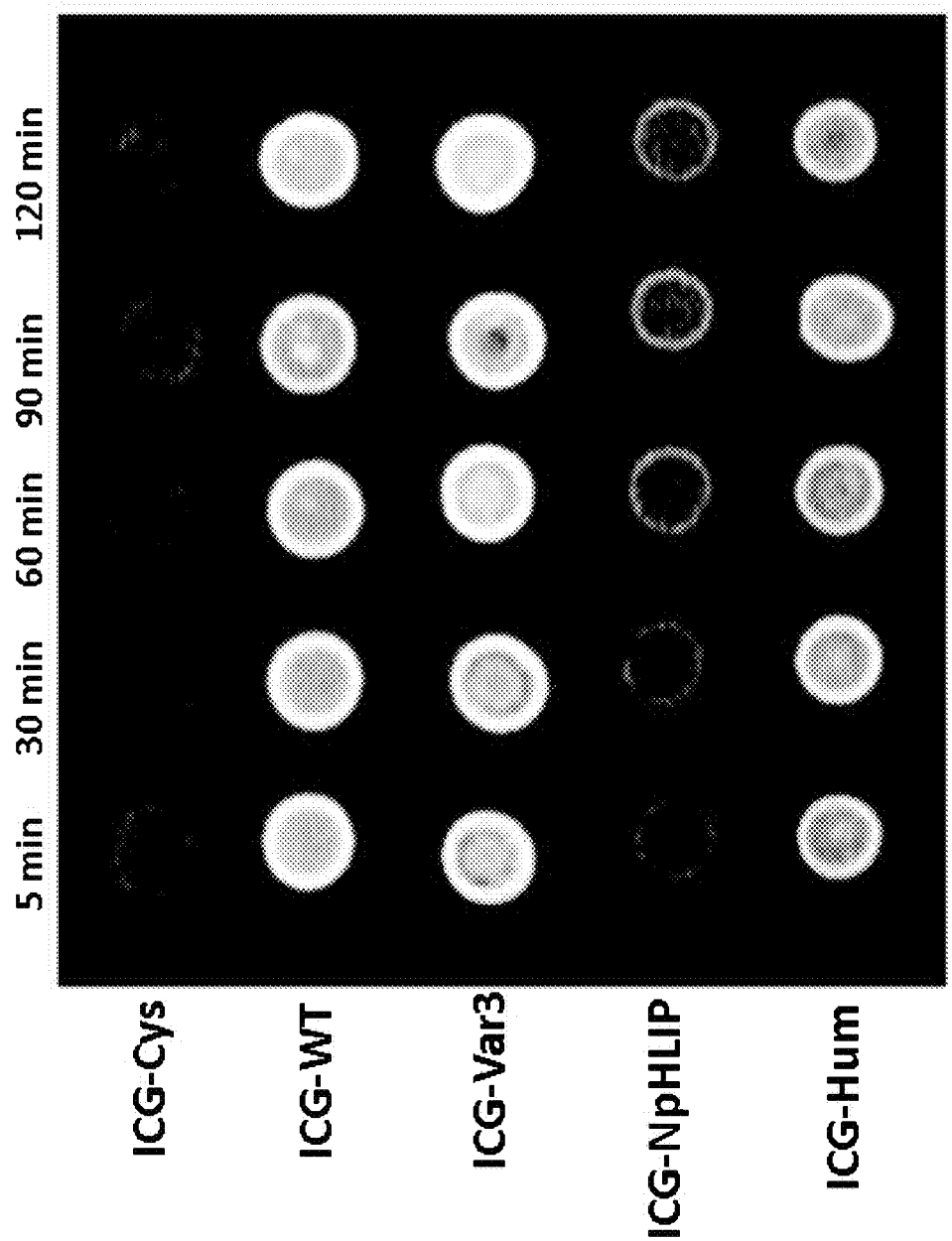

FIG. 30 is a set of NIR fluorescent pictures of a mouse blood collected at 5, 30, 60, 90 and 120 min after IV administration of ICG-Cys, ICG-WT pHLIP®, ICG-Var3 pHLIP®, ICG-NpHLIP® and ICG-Hum pHLIP®.

Figure 31:
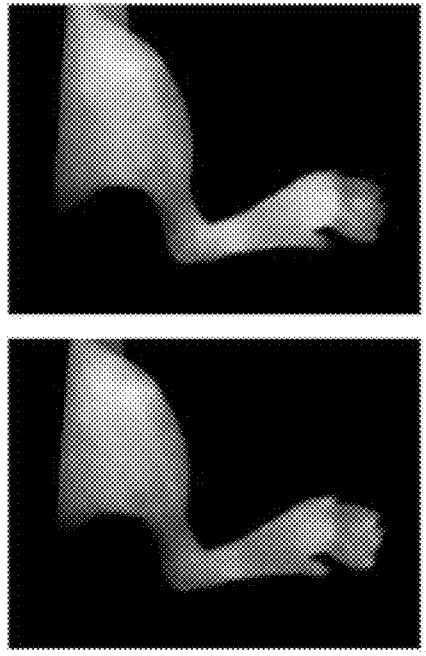

FIG. 31 is a set of NIR fluorescent pictures of a mouse leg obtained at 5 and 30 min after IV administration of IR800-Cys (IR800 maleimide was conjugated with Cys residue).

Figure 32:
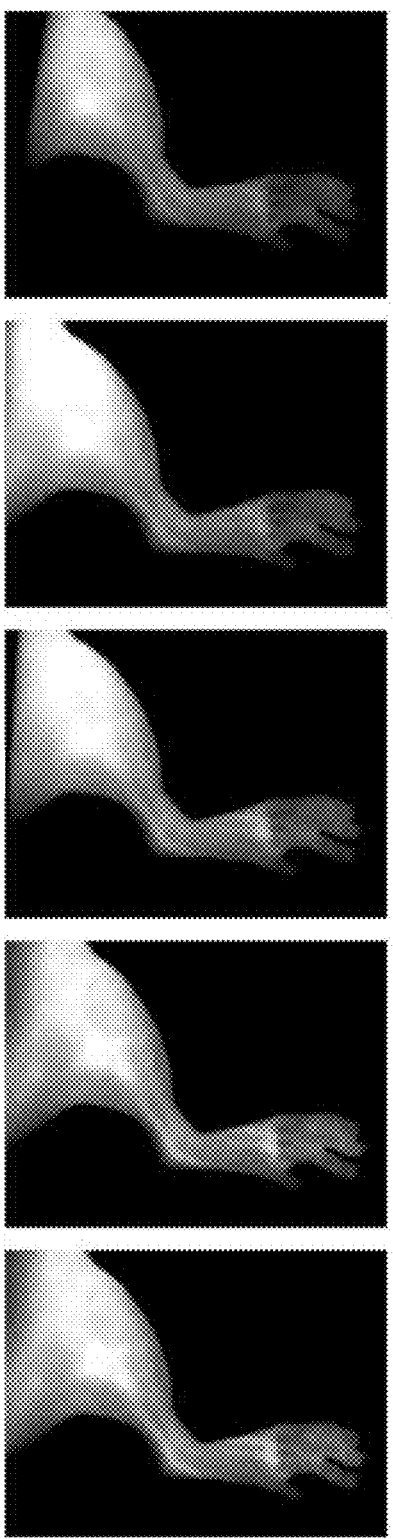

FIG. 32 is a set of NIR fluorescent pictures of a mouse leg obtained at 5, 30, 60, 90 and 120 min after IV administration of IR800-Var3 pHLIP® (see Table 11 for pHLIP® peptide amino acid sequence).

Figure 33:
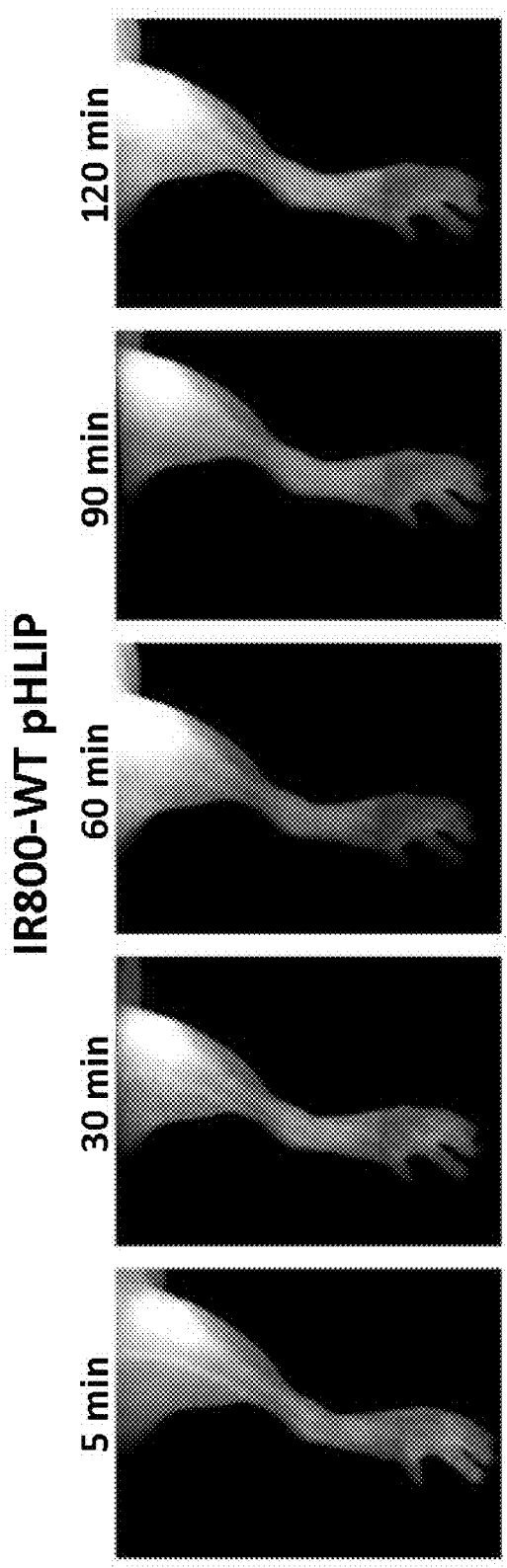

FIG. 33 is a set of NIR fluorescent pictures of a mouse leg obtained at 5, 30, 60, 90 and 120 min after IV administration of IR800-WT pHLIP® (see Table 11 for pHLIP® peptide amino acid sequence).

Figure 34:
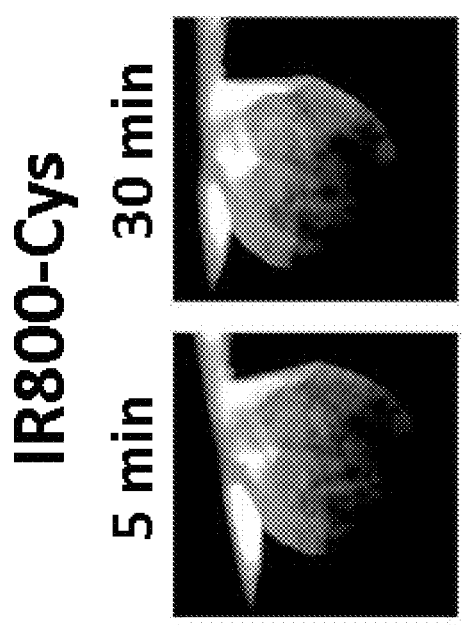

FIG. 34 is a set of NIR fluorescent pictures of a mouse ear obtained at 5 and 30 min after IV administration of IR800-Cys (IR800 maleimide was conjugated with Cys residue).

Figure 35:
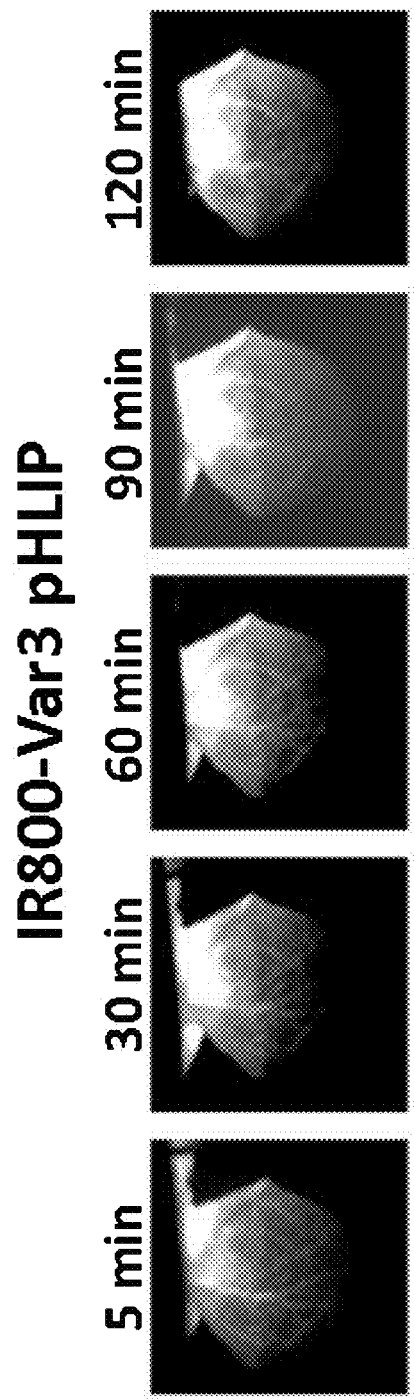

FIG. 35 is a set of NIR fluorescent pictures of a mouse ear obtained at 5, 30, 60, 90 and 120 min after IV administration of IR800-Var3 pHLIP® (see Table 11 for pHLIP® peptide amino acid sequence).

Figure 36:
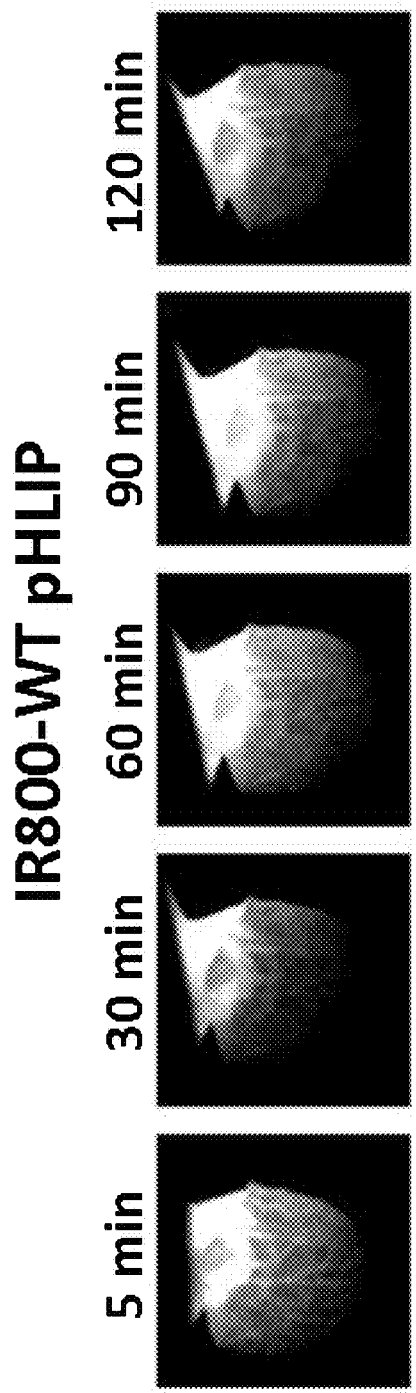

FIG. 36 is a set of NIR fluorescent pictures of a mouse ear obtained at 5, 30, 60, 90 and 120 min after IV administration of IR800-WT pHLIP® (see Table 11 for pHLIP® peptide amino acid sequence).

Figure 37:
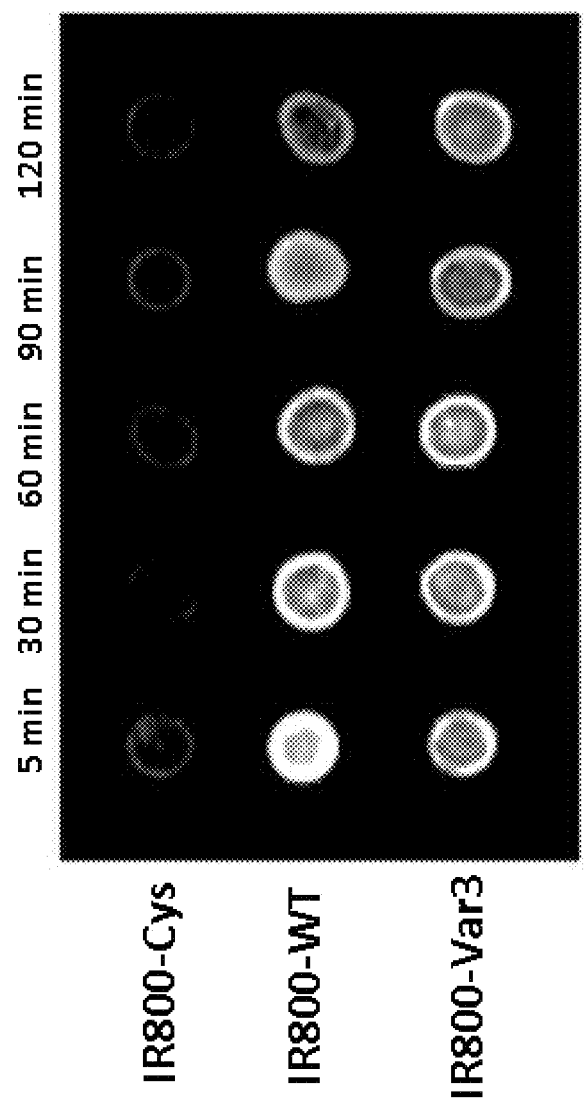

FIG. 37 is a set of NIR fluorescent pictures of a mouse blood collected at 5, 30, 60, 90 and 120 min after IV administration of IR800-Cys, IR800-WT pHLIP® and IR800-Var3 pHLIP® (see Table 11 for pHLIP® peptide amino acid sequences).

Figure 38A:
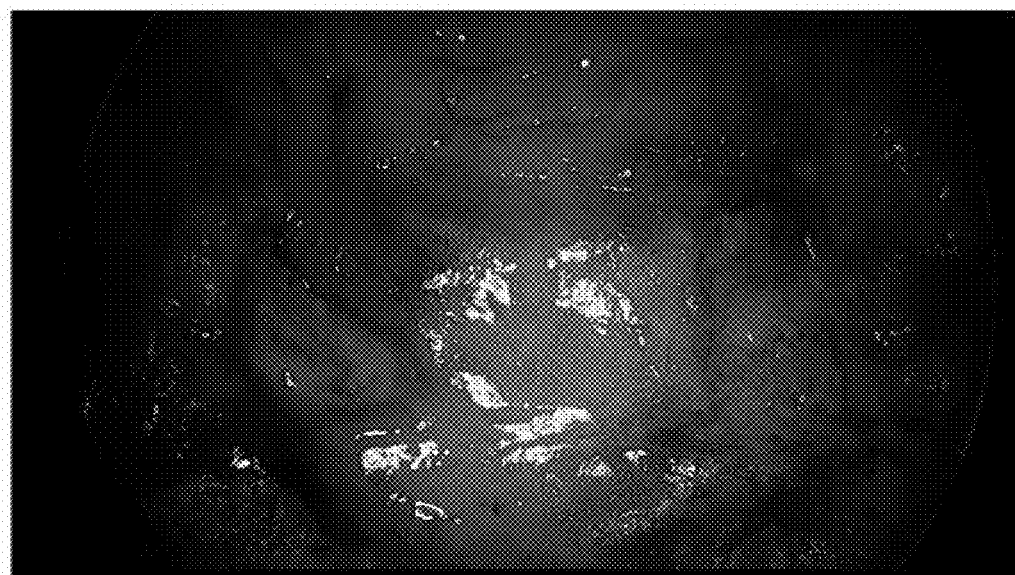
Figure 38B:
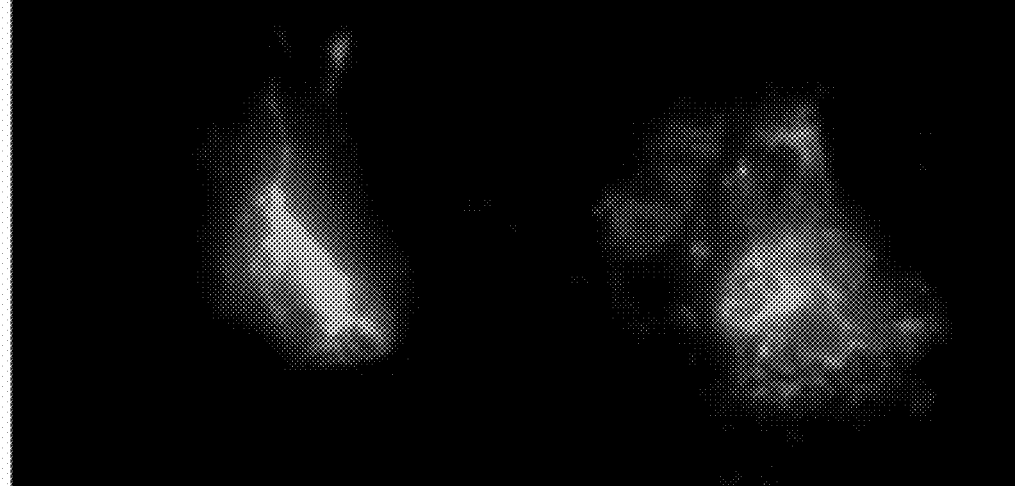
Figure 38C:
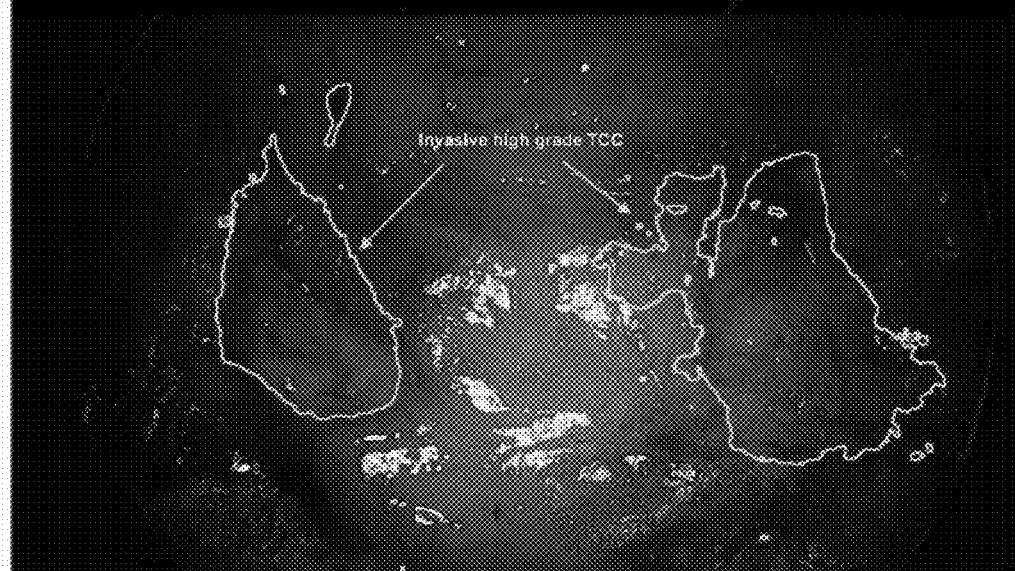

FIGS. 38A-C are a series of images showing the targeting of cancerous lesions in human bladder tissue with ICG-Var3 compound (A) color image of bladder, (B) fluorescent image of bladder), (C) color image of bladder with contour identifying tumor margins are shown [outline/contour shows invasive high grade transitional cell cancer (TCC)]. Diagnosis was confirmed by pathological investigation. 4 µM of 80 mL (1.34 mg) of ICG-Var3 was instilled in PBS with glucose into human bladder obtained after cystectomy surgery for 15 min followed by washing with saline, cutting and imaging with NIR endoscope (see Table 11 for pHLIP® peptide amino acid sequences). Standard pathological analysis (hemolysin and eosin staining) was performed on fluorescent and non-fluorescent tissue samples.

Figure 39A:
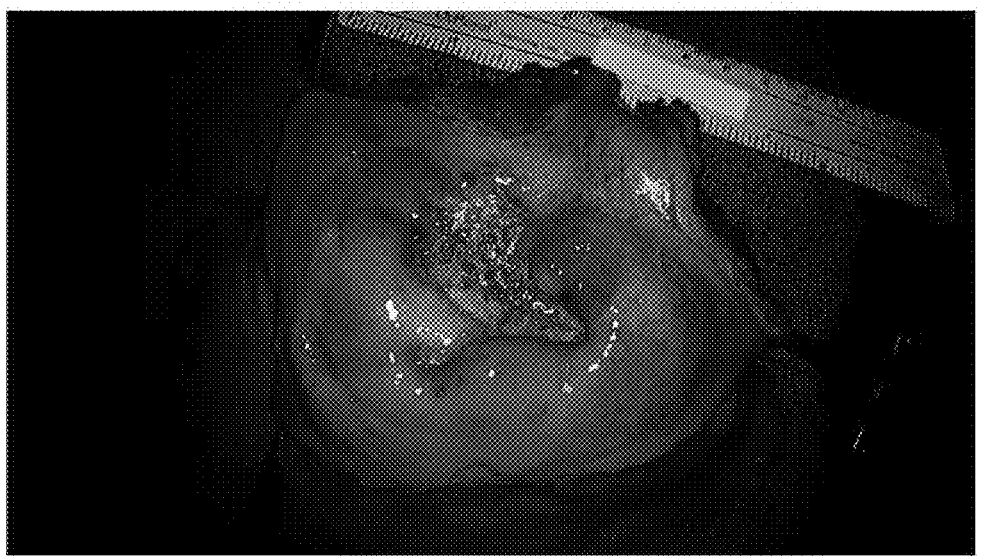
Figure 39B:
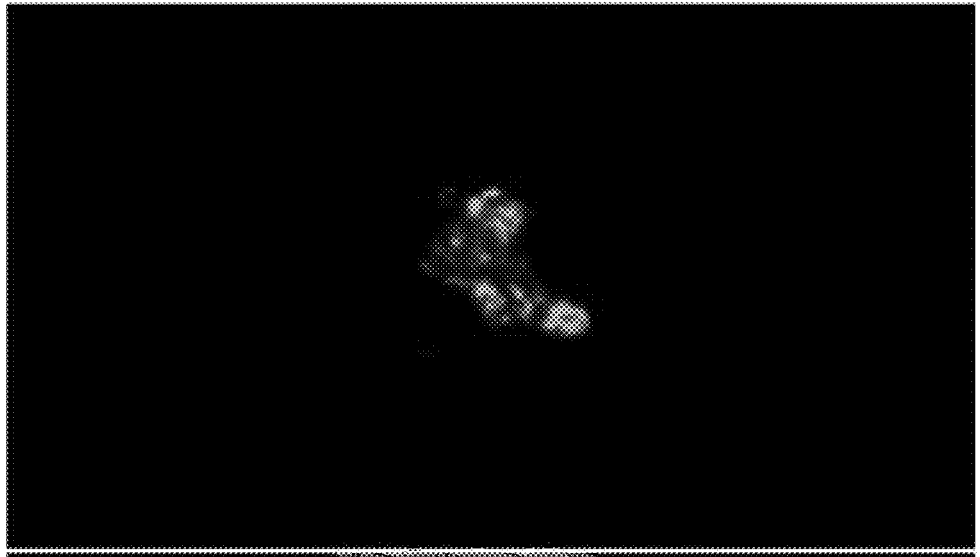
Figure 39C:
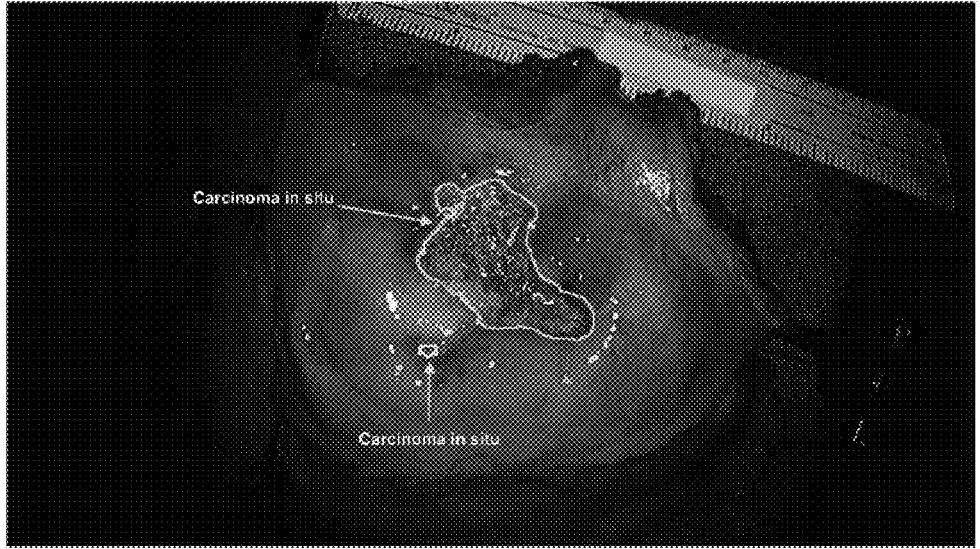

FIGS. 39A-C are a series of images showing the targeting of cancerous lesions in human bladder tissue with ICG-Var3 compound (A) color image of bladder, (B) fluorescent image of bladder), (C) color image of bladder with contour identifying tumor margins are shown (outline/contour shows carcinoma in situ). Diagnosis was confirmed by pathological investigation. 4 µM of 80 mL (1.34 mg) of ICG-Var3 was instilled in PBS with glucose into human bladder obtained after cystectomy surgery for 15 min followed by washing with saline, cutting and imaging with NIR endoscope (see Table 11 for pHLIP® peptide amino acid sequences). Standard pathological analysis (hemolysin and eosin staining) was performed on fluorescent and non-fluorescent tissue samples.

Figure 40A:
Figure 40B:
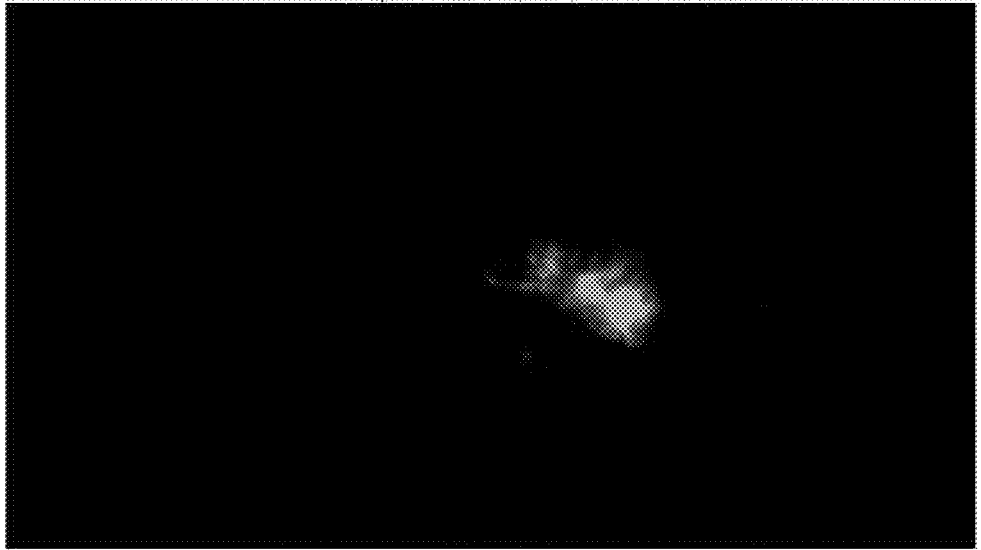
Figure 40C:
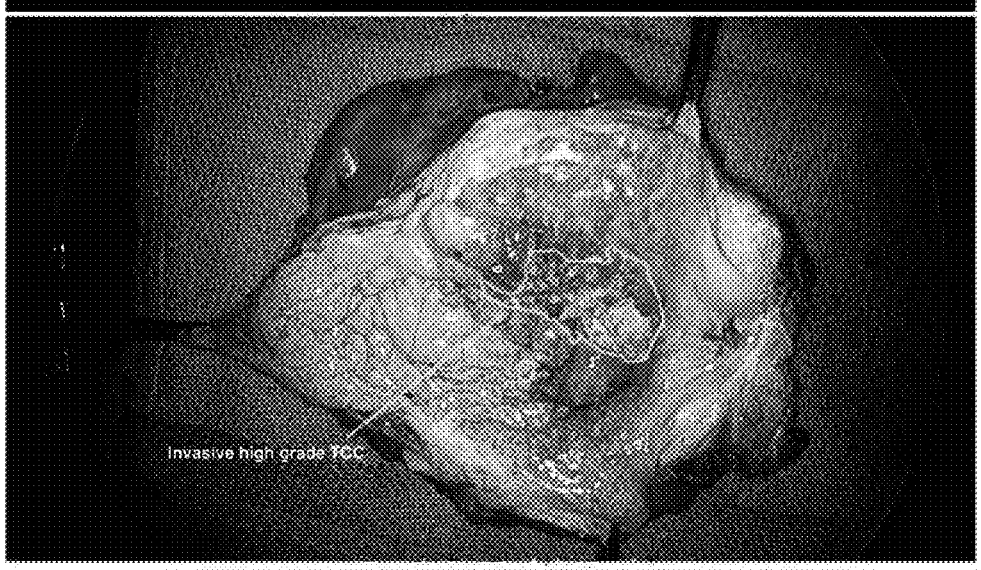
Figure 41B:
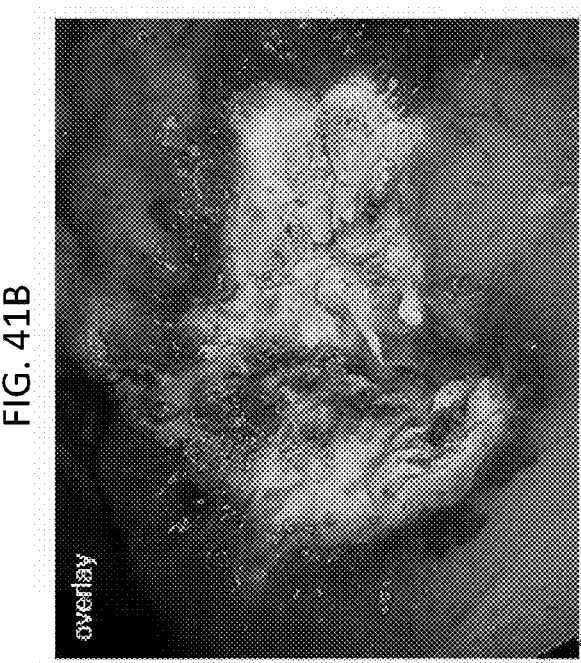
Figure 41D:
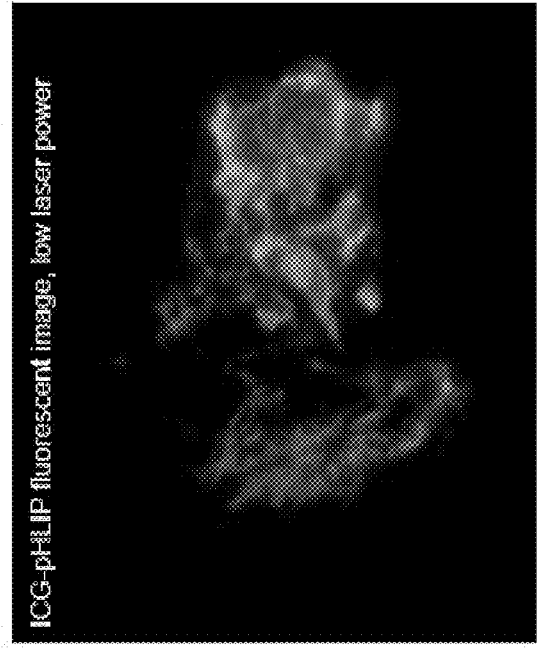
Figure 41A:
Figure 41C:
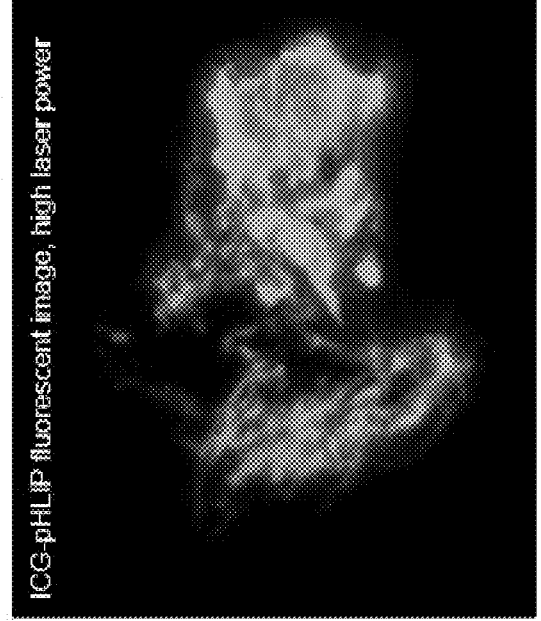

FIGS. 40A-C are a series of images showing the targeting of cancerous lesions in human bladder tissue with ICG-Var3 compound (A) color image of bladder, (B) fluorescent image of bladder), (C) color image of bladder with contour identifying tumor margins are shown. Diagnosis was confirmed by pathological investigation (outline/contour shows invasive high grade TCC). 4 µM of 80 mL (1.34 mg) of ICG-Var3 was instilled in PBS with glucose into human bladder obtained after cystectomy surgery for 15 min followed by washing with saline, cutting and imaging with NIR endoscope (see Table 11 for pHLIP® peptide amino acid sequences). Standard pathological analysis (hemolysin and eosin staining) was performed on fluorescent and non-fluorescent tissue samples.

FIGS. 41A-D are a series of images showing the targeting of cancerous lesions in human bladder tissue with ICG-Var3 compound (4 µM of 80 mL or 1.34 mg) (A) color image of bladder, (B) overlay of color and fluorescent images of bladder), (C and D) fluorescent images of bladder obtained with different excitation laser power are shown.

Figures 42A, 42B:
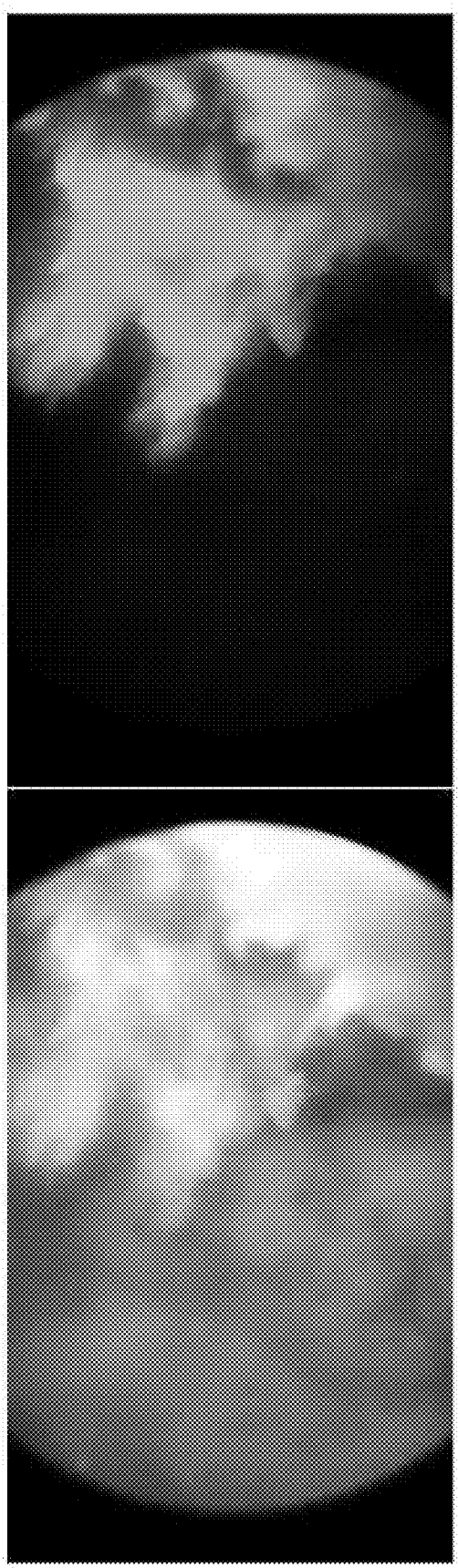

FIGS. 42A and B are series of images showing the targeting of cancerous lesions in human bladder tissue with ICG-Var3 compound (A) color image of bladder, (B) fluorescent image obtained in bladder full with saline, the way as cystoscopy is done. 4 µM of 80 mL (1.34 mg) of ICG-Var3 was instilled in PBS with glucose into human bladder obtained after cystectomy surgery for 15 min followed by washing with saline and imaging bladder full with saline using 5 mm tip of NIR endoscope (see Table 11 for pHLIP® peptide amino acid sequences).

Figure 43A:
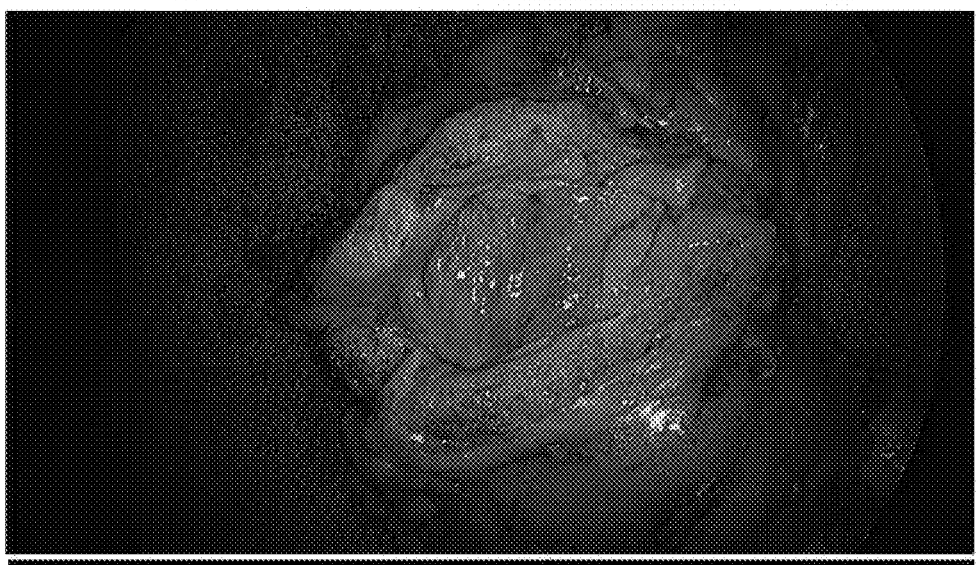
Figure 43B:
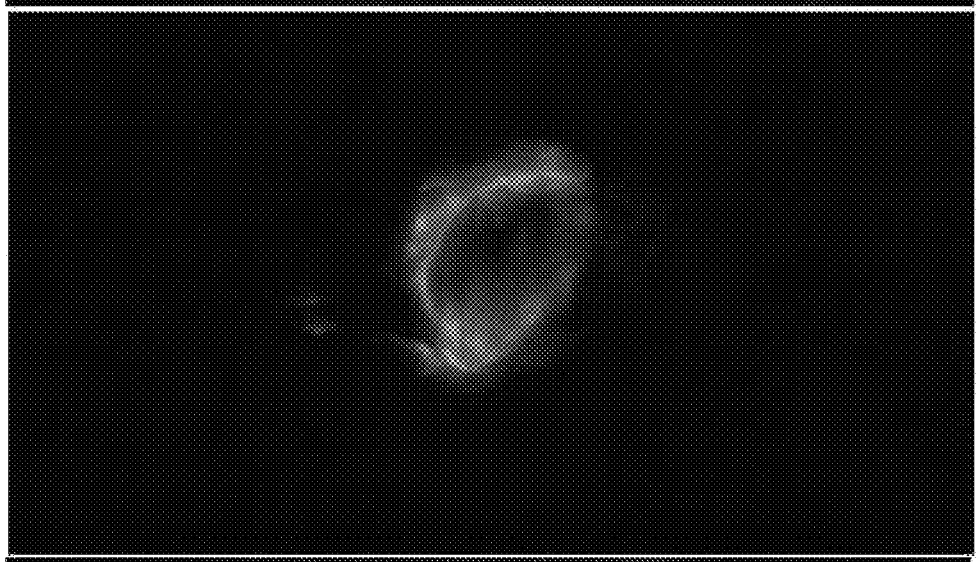
Figure 43C:
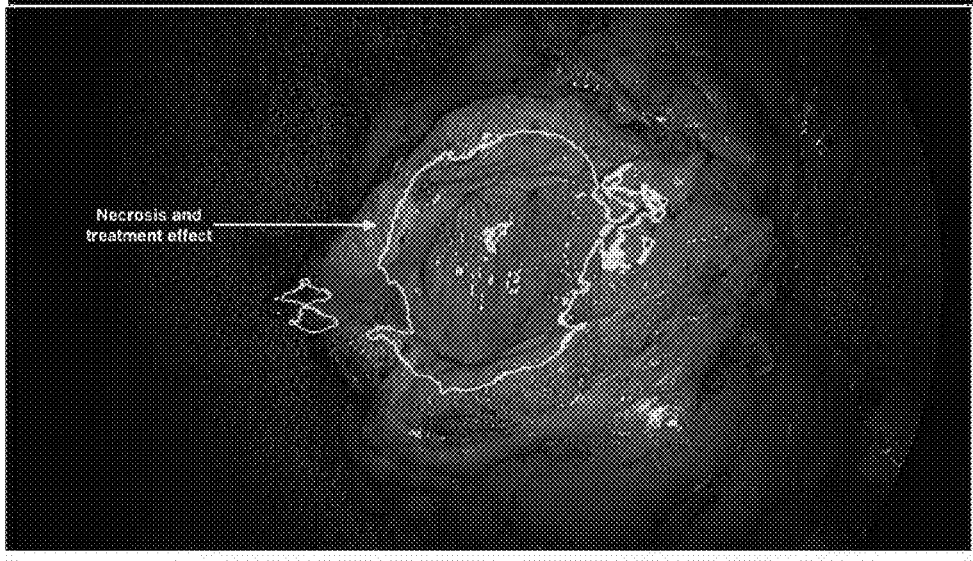

FIGS. 43A-C are a series of images showing the targeting of cancerous lesions in human bladder tissue with IR800-pHLIP® compound (A) color image of bladder, (B) fluorescent image of bladder), (C) color image of bladder with contour identifying tumor margins are shown (outline/contour shows necrosis and treatment effect). Diagnosis was confirmed by pathological investigation. 4 µM of 80 mL (1.34 mg) of IR800-Var3 was instilled in PBS with glucose into human bladder obtained after cystectomy surgery for 15 min followed by washing with saline, cutting and imaging with NIR endoscope (see Table 11 for pHLIP® peptide amino acid sequences). Standard pathological analysis (hemolysin and eosin staining) was performed on fluorescent and non-fluorescent tissue samples.

Figure 44A:
Figure 44B:
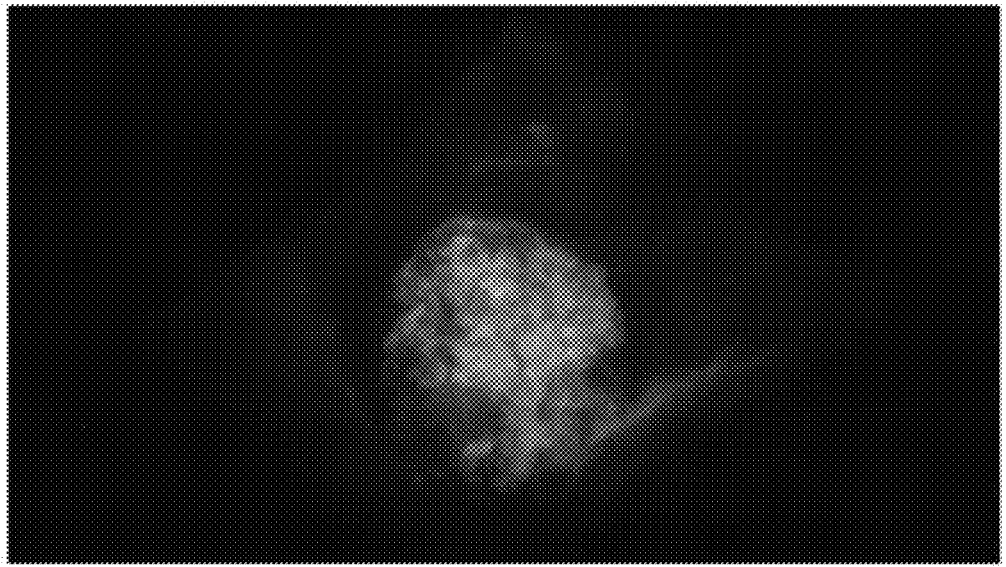
Figure 44C:
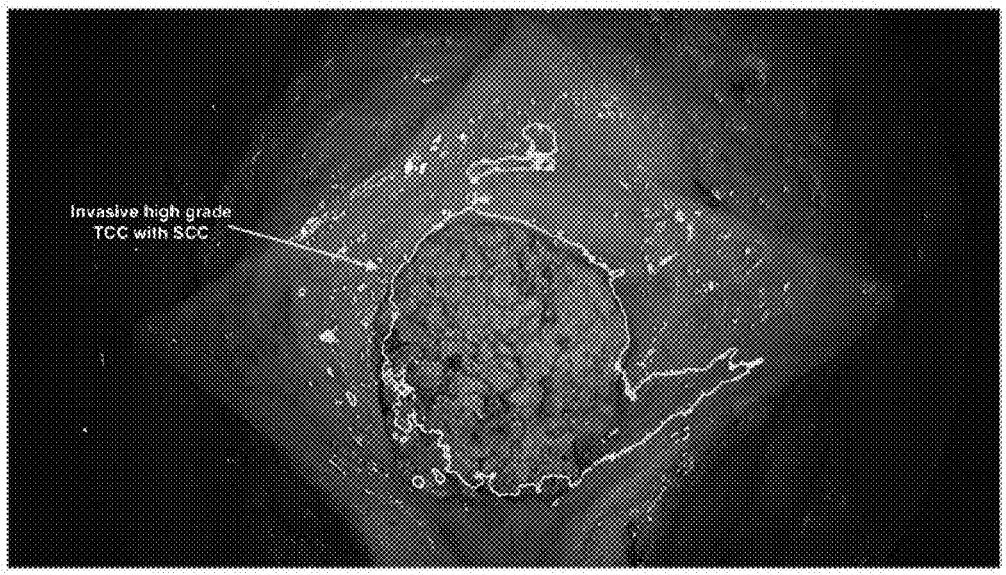

FIGS. 44A-C are a series of images showing the targeting of cancerous lesions in human bladder tissue with IR800-pHLIP® compound (A) color image of bladder, (B) fluorescent image of bladder), (C) color image of bladder with contour identifying tumor margins are shown [outline/contour shows high grade TCC with squamous cell carcinoma (SCC)]. Diagnosis was confirmed by pathological investigation. 4 µM of 80 mL (1.34 mg) of IR800-Var3 was instilled in PBS with glucose into human bladder obtained after cystectomy surgery for 15 min followed by washing with saline, cutting and imaging with NIR endoscope (see Table 11 for pHLIP® peptide amino acid sequences). Standard pathological analysis (hemolysin and eosin staining) was performed on fluorescent and non-fluorescent tissue samples.

Figure 45:
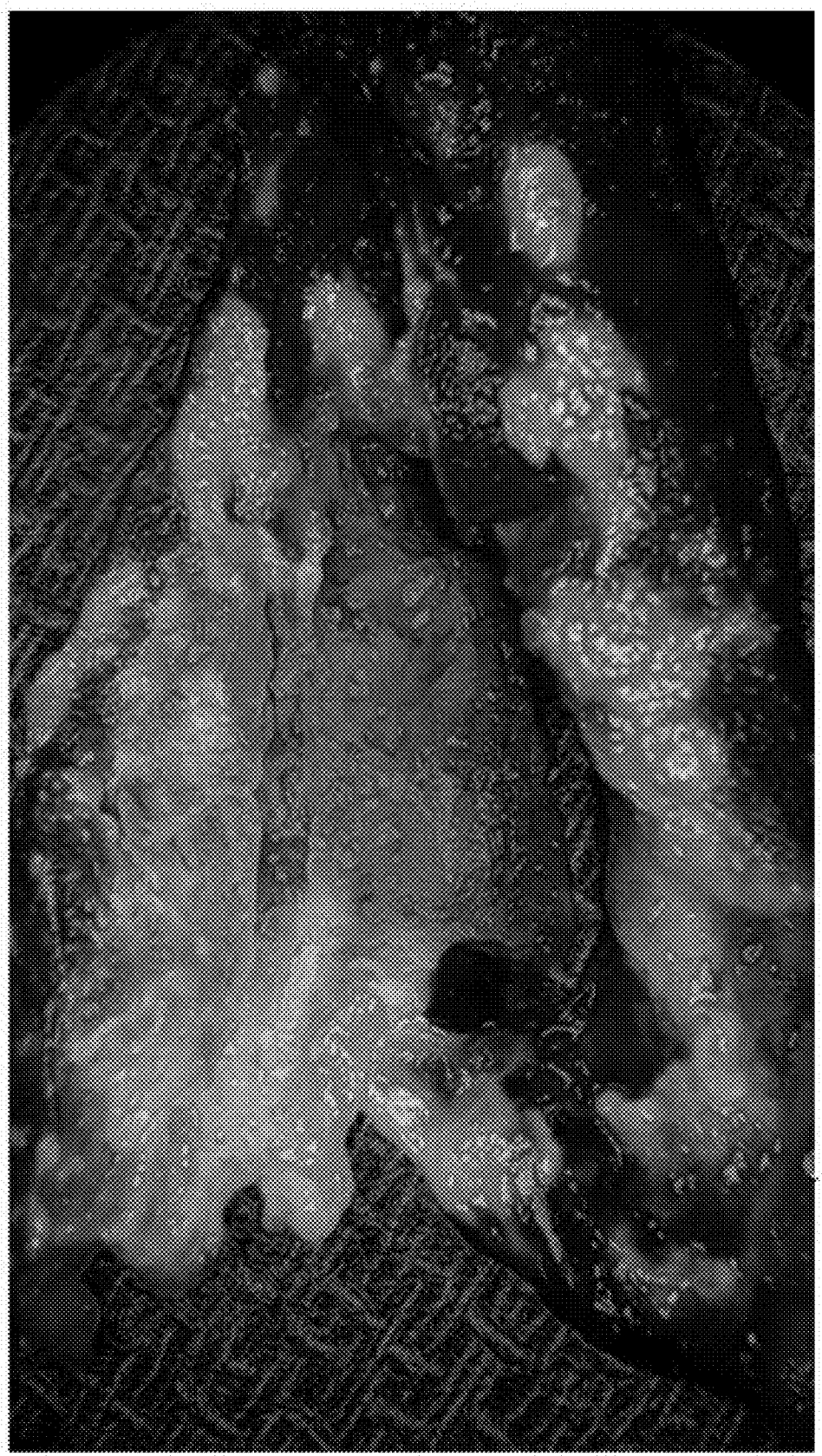

FIG. 45 is an overlay of color and fluorescent images showing the targeting of cancerous lesions in upper urinary tract with ICG-Var3 compound (4 µM of 80 mL or 1.34 mg) (see Table 11 for pHLIP® peptide amino acid sequences).

Figure 46:
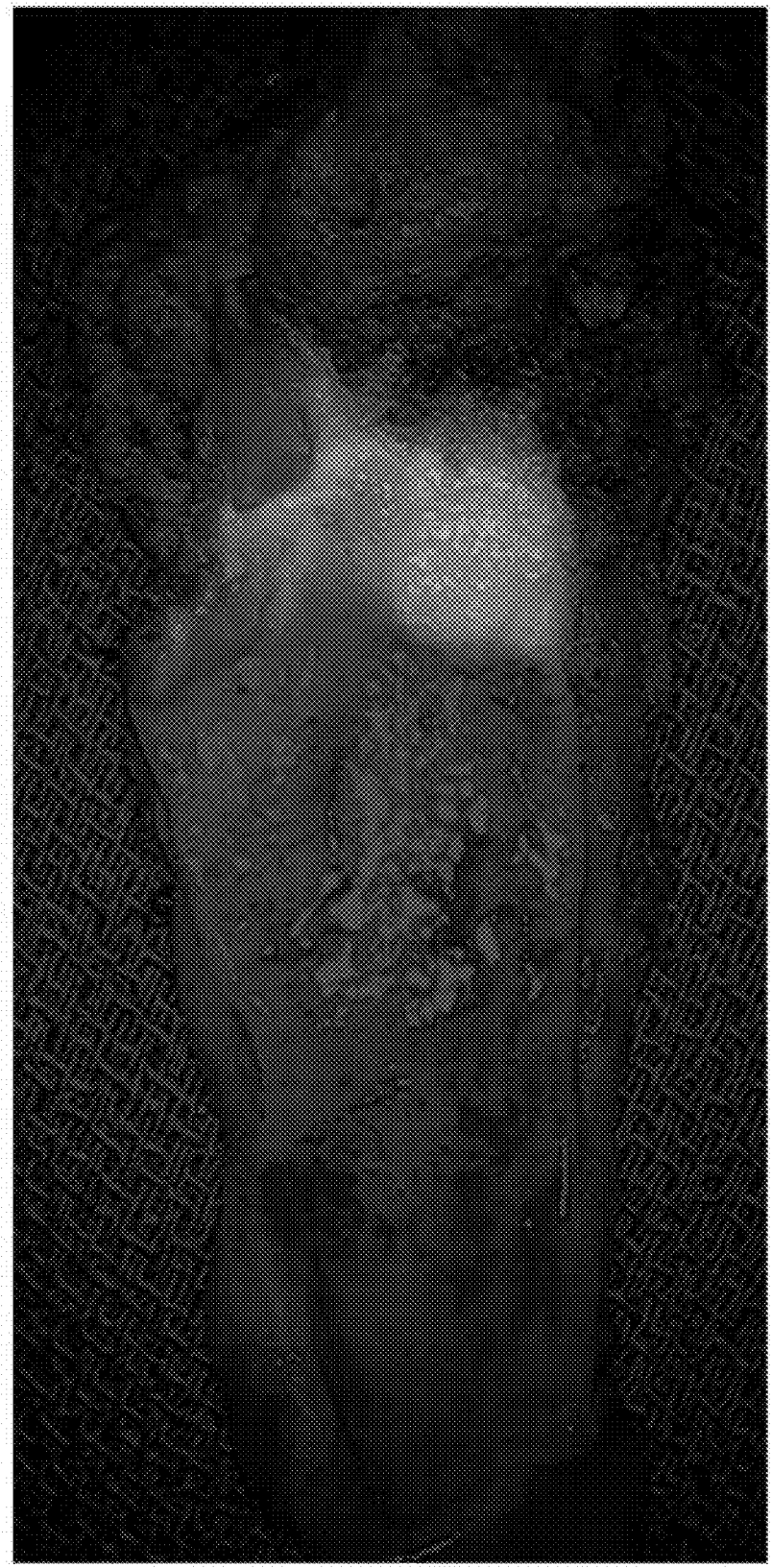

FIG. 46 is an overlay of color and fluorescent images showing the targeting of cancerous lesions in upper urinary tract with ICG-Var3 compound (4 µM of 80 mL or 1.34 mg) (see Table 11 for pHLIP® peptide amino acid sequences).

Figure 47A:
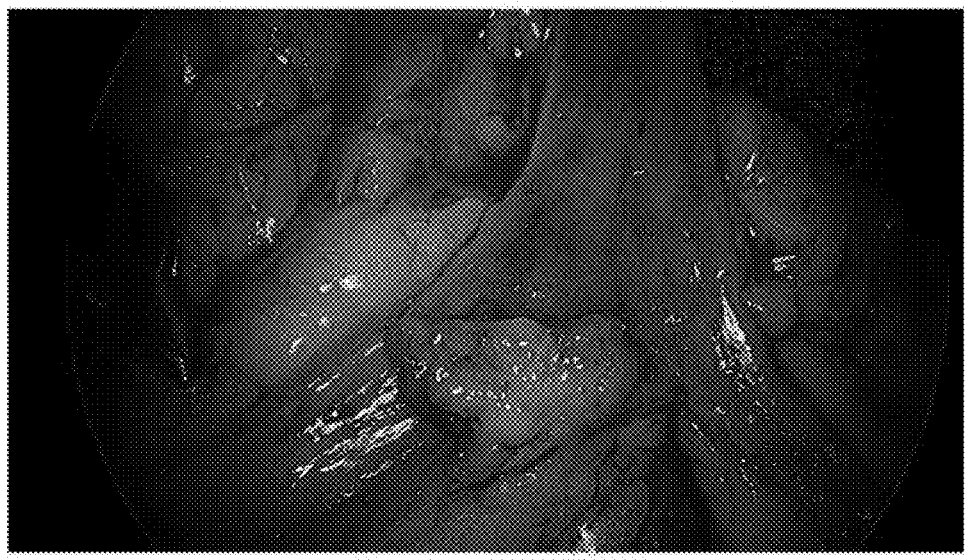
Figure 47B:
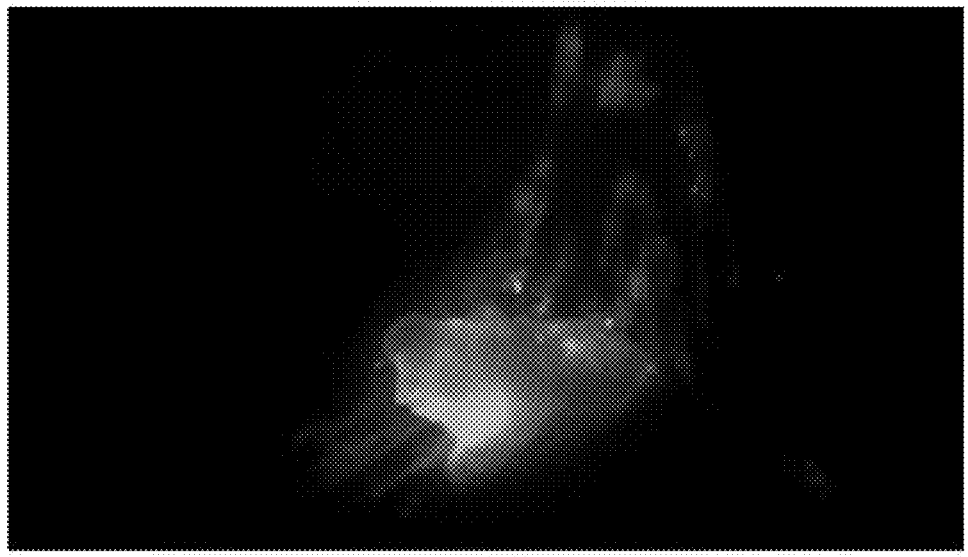
Figure 47C:

FIGS. 47A-C is a series of images showing the targeting of cancerous lesions in human upper urinary tract tissue with ICG-Var3 compound (4 µM of 80 mL or 1.34 mg) (A) color image, (B) fluorescent image, (C) color image with contour identifying tumor margins are shown (outline/contour shows invasive high grade TCC). Diagnosis was confirmed by pathological investigation.

DETAILED DESCRIPTION

Fluorescence imaging has applications in medicine for many image-guided procedures. A long-standing example is fluorescence angiography for the assessment of blood flow and tissue perfusion in preoperative, intraoperative, and postoperative settings. Fluorescence angiography can provide real-time imaging of blood vessels to follow changes during surgical procedures. Some examples include the use of fluorescence in ophthalmology to evaluate the chorioretinal vasculature); cardiothoracic surgery to assess the patency of the coronary artery bypass (Desai et al. 2005 J Am Coll Cardiol 46(8): 1521-1525; Unno et al. 2008 Eur J Vasc Endovasc Surg 35(2): 205-207; Handa et al. 2009 Interact Cardiovasc Thorac Surg 9(2): 150-154); in neurovascular surgery to assess the effect of a superficial temporal artery-middle cerebral artery bypass graft in cerebral revascularization procedure (Woitzik et al. 2005 J Neurosurg 102(4): 692-698); in hepatobilliary surgery to identify the haptic segment and subsegment for anatomical hepatic resection (Aoki et al. 2008 World J Surg 32(8): 1763-1767; Ishizawa et al. 2009 J Am Coll Surg 208(1): el-4); in reconstructive surgeries (Azuma et al. 2008 Plast Reconstr Surg 122(4): 1062-1067; Lee et al. 2010 Plast Reconstr Surg 126(5): 1472-1481; Lee et al. 2010 J Reconstr Microsurg 26(1): 59-65; Murray et al. 2010 Plast Reconstr Surg 126(1): 33e-34e); and in cholecystectomy and colorectal resection (Boni et al. 2015 Surg Endosc 29(7): 2046-2055). In diagnostic applications, fluorescence angiography is used for imaging of hemodynamics in the brain (Kohl-Bareis et al. 2002 J Biomed Opt 7(3): 464-470; Leung et al. 2007 Appl Opt 46(10): 1604-1614); circulatory features of rheumatoid arthritis (Fischer et al. 2010 Acad Radiol 17(3): 375-381; Gompels et al. 2010 Rheumatology (Oxford) 49(8): 1436-1446); muscle perfusion (Habazettl et al. 2010 J Appl Physiol (1985) 108(4): 962-967); burns (Griffiths et al. 2016 Gland Surg 5(2): 133-149) to assess various other effects of trauma (Schomacker et al. 1997 J Trauma 43(5): 813-819). Further, fluorescence image-guided procedures are employed for mapping and visualization of lymph nodes, targeting and marking (e.g., visualizing or detecting) cancerous lesions and assessment of tumor margins by in vivo and ex vivo imaging (Jacobs 2008 Ann Surg Oncol 15(5): 1271-1272; Ankersmit et al. 2011 Colorectal Dis 13 Suppl 7: 70-73; Ferroli et al. 2011 Acta Neurochir Suppl 109: 251-257; Cahill et al. 2012 Surg Endosc 26(1): 197-204; Mondal et al. 2014 Adv Cancer Res 124: 171-211; Burggraaf et al. 2015 Nat Med 21(8): 955-961).

A number of U.S. Food and Drug Administration (FDA) approved fluorescent dyes have been used in the clinic: fluorescein, which emits light at 500-600 nm wavelengths visible by naked eye, is traditionally used in retinal angiography, and NIR fluorescent dyes including ICG and IR800 (a proprietary Li-COR Biosciences fluorescent dye). NIR dyes work in the so-called tissue optical window, from 650-1350 nm, where light has its greatest tissue penetration. Penetrating NIR light is selected for excitation (750-805 nm) and fluorescence is observed at longer emission wavelengths within the window, allowing deepest tissue imaging.

ICG is the most widely used NIR fluorescent dye (Desai et al. 2005 J Am Coll Cardiol 46(8): 1521-1525; Woitzik et al. 2005 J Neurosurg 102(4): 692-698; Unno et al. 2008 Eur J Vasc Endovasc Surg 35(2): 205-207; Marshall et al. 2010 Open Surg Oncol J 2(2): 12-25; Polom et al. 2011 Cancer 117(21): 4812-4822; Alander et al. 2012 Int J Biomed Imaging 2012: 940585; Zelken and Tufaro 2015 Ann Surg Oncol 22 Suppl 3: S1271-1283; Griffith et al. 2016 Gland Surg 5(2): 133-149). ICG was developed for photography by the Kodak Research Laboratories in 1955 and was already approved for clinical use in 1956 (Bjornsson et al. 1982 Experientia 38(12): 1441-1442; Bjornsson et al. 1983 J Clin Chem Clin Biochem 21(7): 453-458). ICG angiography was the first clinical application of ICG (Choromokos et al. 1969 J Biol Photogr Assoc 37(2): 100-104; Kogure and Choromokos 1969 J Appl Physiol 26(1): 154-157; Kogure et al. 1970 Arch Ophthalmol 83(2): 209-214). From the early 1970's ICG was used in ophthalmology for imaging retinal blood vessels, retinal angiography (Flower 1973 Invest Ophthalmol 12(12): 881-895).

Following intravenous injection, ICG is rapidly bound to plasma proteins, with minimal leakage into the interstitium. The half-life time is 2.5 min (Benson and Kues 1978 Phys Med Biol 23(1): 159-163; Desmettre et al. 2000 Surv Ophthalmol 45(1): 15-27). There are no known metabolites. ICG is rapidly extracted by the liver without modifications and nearly exclusively excreted by the liver appearing unconjugated in the bile about 8 min after injection, depending on liver vascularization and function (Alander et al. 2012 Int J Biomed Imaging 2012: 940585). When injected outside blood vessels, ICG binds to proteins and is found in the lymph, reaching the nearest draining lymph node usually within 15 min, and after 1-2 h, it binds to the regional lymph nodes, deposited into macrophages (Tajima et al. 2010 Ann Surg Oncol 17(7): 1787-1793; Korn et al. 2014 Plast Reconstr Surg 133(4): 914-922). The intravenous injection dose of ICG typically varies in the range of 0.5 mg/ml/kg to 2.0 mg/ml/kg of body weight. No significant toxic effects have been observed in humans with the high dose of 5 mg/kg of body weight (Alander et al. 2012 Int J Biomed Imaging 2012: 940585), and chronic toxicity must be modest given the many years of unremarkable clinical experience.

In addition to FDA approved fluorescein and NIR dyes, there are few other FDA approved fluorescent molecules used in specific applications, such as methylene blue (Winer et al. 2010 Ann Surg Oncol 17(4): 1094-1100; van der Vorst et al. 2012 World J Gastrointest Surg 4(7): 180-184; Verbeek et al. 2013 J Urol 190(2): 574-579), and 5-aminolevulinic acid (5-ALA) and its derivatives. 5-ALA and hexaminolevulinate hydrochloride, called Cysview in the United States, are heme precursors that induce production and intracellular accumulation of the fluorescent protoporphyrin, PpIX. 5-ALA is applied in the field of neurosurgery, mostly to intraoperatively identify brain tumors such as malignant gliomas (Stummer et al. 2006 Lancet Oncol 7(5): 392-401; Roberts et al. 2011 J Neurosurg 114(3): 595-603). Cysview is used for fluorescent visualization of cancerous lesions in the bladder using blue light cystoscopy, where 100 mg of Cysview agent dissolved in 50 ml (400 µmol) is applied topically, by intravesical instillation, for about 1 hour. It has been shown that blue light cystoscopy improves visualization of cancerous lesions and recurrence-free survival in patients compared to white light cystoscopy (Jocham et al. 2008 Eur Urol 53(6): 1138-1148; Santos Cortes et al. 2011 Arch Esp Urol 64(1): 18-31; Lerner et al. 2012 Urol Oncol 30(3): 285-289; Burger et al. 2013 Eur Urol 64(5): 846-854; Rink et al. 2013 Eur Urol 64(4): 624-638).

Provided herein, inter alia, are pHLIP®-fluorophore compounds comprising a membrane insertion peptide and a fluorophore (e.g., ICG), i.e., wherein the fluorophore is covalently attached to the membrane insertion peptide. pHLIP®-fluorophore compounds comprising ICG may alternatively be referred to as "ICG-pHLIP® peptides." In various embodiments, a pHLIP®-fluorophore compound inserts into circulating cells and/or cells that line a body lumen (such as a blood vessel, artery, vein, capillary, urinary tract, urethra, renal tube, airway, or alveoli). In some embodiments, a pHLIP®-fluorophore compound has increased fluorescence intensity upon insertion into a cell membrane. Non-limiting aspects of the present subject matter relate to the use of membrane insertion peptides that insert into cell membranes at neutral pH (e.g., pH 7.0) or the pH of a bodily fluid such as blood (e.g., normal blood having a pH between 7.35 and 7.45).

Included herein are ICG-pHLIP® peptides, i.e., compounds comprising ICG and a pHLIP® peptide, wherein the ICG is covalently attached to the pHLIP® peptide. Aspects of the present subject matter relate to the unexpected properties of ICG-pHLIP® peptide compounds. Surprisingly, (i) ICG-pHLIP® peptides selectively target and mark diseased (e.g., tumor) tissue, and (ii) have increased fluorescence intensity upon insertion into cell membranes.

In some embodiments, the fluorophore is ICG. Though free ICG (i.e., ICG that is not conjugated to another molecule) may have an affinity for the hydrophobic lipid bilayer of cell membranes, it is rapidly cleared when injected into the blood of a subject. Thus, high and/or repeated doses of free ICG are needed for diagnostic imaging techniques. However, when conjugated to a membrane insertion peptide, ICG persists much longer in circulation. In various embodiments, the amount of ICG that is administered as part of a pHLIP®-fluorophore compound is 10%, 20%, 30%, 40%, 50%, 60%, 70%, 80%, 90% less than would be administered if the ICG was administered as free ICG (in terms of moles of free ICG). In some embodiments, ICG that is part of a pHLIP®-fluorophore compound is detectable in the blood for at least 25%, 50%, 75%, 100%, 200%, 300%, 400%, 500%, 600%, 700%, 800%, 900%, or 1000% longer than free ICG, when administered in the same amount (in terms of moles of free ICG) under corresponding conditions.

Without being bound by any scientific theory, membrane-inserting compounds comprising ICG reduce the rate at which ICG that is removed from circulation (e.g., by the kidneys and/or liver) by tethering the ICG to the cell membranes of circulating cells such as red blood cells and/or cells that line circulatory system. The tethering of ICG to the cell membranes is non-covalent and reversible. Moreover, as discussed below, the fluorescence of ICG increases when it is in close proximity to a lipid bilayer (such as a cell membrane), enabling more fluorescence to be achieved with less ICG. Thus, lower doses of membrane insertion peptide-conjugated ICG can be used (e.g., for diagnostic approaches) compared to the doses of free ICG that are typically used.

The membrane-inserting compounds provided herein may also provide higher signal-to-noise than free ICG. With respect to embodiments relating to blood and the cardiovasculature, membrane insertion peptides that insert into cell membranes at or near neutral pH may be used. Thus, pH-triggered compounds that may insert at a minimally acidic, neutral, or slightly basic pH, and which may not be suitable for detecting acidic tissues, are useful in various embodiments disclosed herein. In some embodiments, a membrane-inserting compound comprising ICG has at least about 5, 10, 20, 25, 50, or 100 times the half-life of free ICG (e.g., in blood).

The disadvantages of using ICG alone for diagnostic methods includes rapid binding to proteins (such as albumins) and circulating phospholipids in blood, low tissue permeability, and the inability to target cancerous tissue. However, ICG-pHLIP® peptides readily penetrate cancerous tissue to specifically and effectively label tumor tissue for, e.g., surgical removal. Surprisingly, the presence of ICG in an ICG-pHLIP® peptide construct does not disrupt the ability of pHLIP® peptides to accumulate in tumor tissue and specifically insert into the membranes of tumor cells.

When an ICG-pHLIP® peptide is inserted into a cell (e.g., a cell in a tumor or acidic tissue, or a circulating cell such as a red blood cell), the ICG component thereof is held at a distance from the surface of the cell membrane (i.e., outside the lipid bilayer of the cell membrane), where fluorescence of the ICG may be used to detect the cancer cell in contrast to ICG alone, which associates directly with the membrane. Since the ICG component is attached to the pHLIP® peptide component of the ICG-pHLIP® peptide, the ICG component is not free interact with the cell membrane directly or surrounding molecules as it otherwise would. Thus, both the location and the orientation of the ICG with respect to, e.g., the cell membrane, are artificial and indirect. Surprisingly, the ICG component of an ICG-pHLIP® peptide exhibits dramatically increased fluorescence when tethered to the surface of a cancer cell (e.g., in a tumor or metastatic lesion). For example, the fluorescence intensity increases by at least about 10%, 11%, 12%1, 3%, 14%, 15%, 6%1, 7%1, 8%1, 19%, 20%, 21%, 22%, 23%, 24%, 25%, 50%, 75%, 100%, 2-fold, 10-fold, 12-fold, 15-fold, 20-fold, 25-fold, or more is achieved compared to untethered ICG. In certain embodiments, the increased fluorescence of an ICG-pHLIP® peptides upon binding to cell membranes increases the tumor/background signal significantly.

Though ICG may have an affinity for the hydrophobic lipid bilayer of cell membranes, this affinity is not pH specific. Surprisingly, the non-specific affinity of ICG for cell membranes (e.g., along vessels and in normal tissues) does not prevent pHLIP® peptides from infiltrating and specifically and selectively tagging precancerous and cancerous tissue.

The connection between ICG and the cell membrane, being via its attachment to a pH-triggered peptide, is both unnatural and indirect. In various embodiments, the pH-triggered peptide may separate ICG from the cell membrane, e.g. via a stretch of amino acids.

For example, the non-limiting ICG-pHLIP® peptides used in Example 1 (ICG-Var3 compounds) comprise pHLIP® peptides with N-terminal amino acids that separate ICG from the cell membrane.

The separation may comprise a polypeptide tether of, e.g., 1, 2, 3, 4, 5, 6, 7, 8, 9, 10 or more amino acids. SEQ ID NO: 3 comprises about seven N-terminal amino acids separate ICG from the cell membrane by about 11 Å. The underlined portion of the following sequence corresponds to the potential transmembrane portion, and the italicized amino acids indicate the seven N-terminal amino acids:

(SEQ ID NO: 3)
A*KDDQNP*WRAYLDLLFPTDTLLLDLLWG

Assuming a random coil configuration of the seven N-terminal amino acids outside of the lipid bilayer, and taking the contour length per residue to be is 4.3 Å (Dietz, H. Rief, M. *Proc Natl Acad Sci USA* 2006, 103, 1244-1247; Carrion-Vazquez et al., *Nat Struct Biol* 2003, 10, 738-743; Oesterhelt et al., *Science* 2000, 288, 143-146), then the average end-to-end length of the coil can be estimated to be 11 Å. Thus, when ICG is attached to amino acids in the sequence of SEQ ID NO: 3, then the ICG is at the end of a flexible linker of amino acids that is about 11 Å long. Surprisingly, the fluorescence of ICG conjugated to the N-terminus of a pHLIP® peptide was found to increase about 25-fold upon insertion into a cell membrane.

Separation of ICG from the cell membrane is not required, however. In some embodiments, the pHLIP® peptide does not separate ICG from the cell membrane. In certain embodiments, the N-terminal amino acid sequence of the pHLIP® peptide has a length or structure such that the conjugated ICG is less than about 10 Å, 9 Å, 8 Å, 7 Å, 6 Å, 5 Å, 4 Å, 3 Å, 2 Å, 1 Å, 1-5 Å, 1-10 Å, or 5-10 Å from the cell membrane, or is in contact with the cell membrane. Alternatively, the N-terminal amino acid sequence of the pHLIP® peptide has a length or structure such that the conjugated ICG is at least about 1 Å, 2 Å, 3 Å, 4 Å, 5 Å, 6 Å, 7 Å, 8 Å, 9 Å, 10 Å, 11 Å, 12 Å, 13 Å, 14 Å, 15 Å, or 20 Å from the cell membrane. Increased fluorescence upon the indirect association of ICG with a cell membrane (regardless of the distance of IGC from the cell membrane) is surprising.

Bladder cancer is the fifth most common cancer. Timely diagnosis and appropriate early management protocols are of paramount significance for improving patient outcomes. Aspects of the present subject matter relate to the non-limiting data presented herein, which were generated in the first study to show efficient pH dependent near infrared imaging of bladder malignant tumors without targeting of normal tissue. The data presented herein show that conjugates comprising ICG and pHLIP® peptides (which are pHLIP® peptides) bind to and identify cancerous and pre-cancerous tissues. The pH Low Insertion Peptide (pHLIP®-peptide) conjugated with a near infrared fluorescent dye (ICG) (a ICG-pHLIP® peptide such as ICG-Var3) construct is suitable for use as a predictive clinical marker, specifically staining human bladder tumors after intravesical administration ex vivo. The targeting allows delivery of various imaging probes, which may offer early diagnosis and improve the outcomes of endoscopic and radical surgical resection of urothelial carcinomas. In addition, delivery of therapeutic molecules to cancer tissue by pHLIP® peptides such as pHLIP® might open an opportunity for novel targeted treatment of bladder cancers.

An important medical objective is the identification of early stage lesions, such as pre-cancerous tissue or carcinoma in situ, since it is expected that diagnosis at this stage will decrease the frequency of treatments, increasing patient health and reducing expense. Each type and stage of bladder cancer requires a different type of treatment. High recurrence frequency, procedural costs, and the requirement for prolonged active monitoring, make bladder cancer one of the most expensive cancers in the United States, placing a heavy economic burden on the healthcare system from lifetime endoscopic follow ups and treatments. Patients suffer from high morbidity and the complications associated with chemotherapy, radiation and radical surgery (Mariotto et al. (2011) J Natl Cancer Inst 103(2):117-128). Therefore, as noted, timely diagnosis of the tumor and appropriate management protocols are of great significance for decreasing treatment cost and improving a patient's life style. Advances in the early detection of bladder cancer lesions are likely to increase the chances of timely successful treatment, the prevention of recurrences, and bladder function preservation.

Cancers, including urothelial carcinoma, are associated with multiple alterations in the genome, including changes in epigenetic regulation, point mutations, gene deletions, duplications and chromosomal rearrangements. These changes are heterogeneous, leading to heterogeneity of the overexpression of particular biomarkers at the surfaces of cancer cells within a tumor and between tumors. Heterogeneity significantly limits success in the use of cell surface biomarkers for the targeted delivery of therapeutics. On other hand, multiple studies have revealed that neoplastic cells produce an acidic environment due to increased metabolic activity (Damaghi et al. (2013) Front Physiol 4:370). Adaptations to the highly acidic microenvironment are critical steps in the transition from an avascular pre-invasive tumor to a malignant invasive carcinoma (Gillies et al. (2012) Nat Rev Cancer 12(7):487-493; Estrella et al. (2013) Cancer Res 73(5):1524-1535; Gatenby et al. (2006) Cancer Res 66(10):5216-5223). Thus, acidity may provide a universal biomarker for tumor targeting that is not subject to the selection of resistant cell lines (Bailey et al. (2012) Adv Pharmacol 65:63-107). pHLIP® peptides (such as pHLIP® peptides) are a class of membrane-binding peptides that specifically target acidic cells in vitro and in vivo (Andreev et al. (2014) Front Physiol 5:97) by inserting across cellular membranes when the extracellular pH is low (Weerakkody et al. (2013) Proc Natl Acad Sci USA 110(15):5834-5839). pHLIP® peptides (such as pHLIP® peptides) conjugated with fluorescent dyes have been used to differentiate normal from neoplastic tissue in various animal tumor models ((Weerakkody et al. (2013) Proc Natl Acad Sci USA 110 (15):5834-5839; Reshetnyak et al. (2011) Mol Imaging Biol 13(6):1146-1156; Adochite et al. (2014) Mol Pharm 11(8): 2896-2905; Cruz-Monserrate et al. (2014) Sci Rep 4:4410), and in human biopsy head and neck samples (Luo et al. (2014) Cancer Prev Res (Phila) 7(10):1035-1044; Luo et al. (2012) J Biomed Opt 17(10):106006).

In various implementations, an ICG-pHLIP® peptide (such as ICG-Var3 or an ICG-pHLIP®) targets low extracellular pH allowing visualization of malignant lesions in human bladder carcinoma ex vivo. In the non-limiting examples below, cystectomy specimens obtained after radical surgery were immediately irrigated with non-buffered saline and instilled with a solution of the ICG-Var3 construct, incubated, and rinsed. Bladders were subsequently opened and imaged, the fluorescent spots were marked, and a standard pathological analysis was carried out to establish the correlation between ICG-Var3 imaging and white light pathological assessment. Accurate targeting of bladder lesions was achieved with a sensitivity of 97%. Specificity is 100%, but reduced to 80%, if targeting of necrotic tissue from previous transurethral resections or chemotherapy are considered as false positives. ICG-Var3 imaging agent marked high grade urothelial carcinomas, both muscle invasive and non-muscle invasive. Carcinoma in situ (CIS) was accurately diagnosed in 11 cases, whereas only 4 cases were seen using white light, so imaging with the ICG-Var3 compound offers improved early diagnosis of bladder cancers, and may also enable new treatment alternatives.

The ICG-Var3 compound is a promising tool for the early detection of urothelial carcinoma, regardless of subtype, with high sensitivity and specificity. The detection might be used for monitoring the state of disease and/or for marking lesions for surgical removal.

Monitoring and/or diagnosing cancer in a subject can be performed for a variety of cancers, e.g., by assessing whether ICG-pHLIP® peptides specifically bind to a tissue being tested for a neoplasm. In some embodiments, the tissue is in a subject and the compound is applied directly to the tissues or injected systemically (or, e.g., subcutaneously or intraperitoneally). In non-limiting examples, tubes such as catheters are used to deliver compounds disclosed herein to bladder, esophagus, stomach, and colon tissues. The compounds may be administered in, e.g., spray, mist, droplet, liquid, or powder form. In some embodiments, a compound is administered orally and then detected with, e.g., an endoscope or a cystoscope. Mouthwashes and sprays comprising a compound of the present subject matter may be used to detect cancers or precancerous lesions in the oral cavity. The compounds disclosed herein may also be applied directly to a cervix to detect, e.g., cervical cancer tissue. With respect to, e.g., skin cancers, the compounds may be applied to the skin surface. In certain embodiments, the tissue is a sample such as a biopsy and/or an organ or a portion thereof that has been surgically removed.

ICG-pHLIP® peptides such as the ICG-Var3 imaging agent improve diagnosis and resection of cancerous lesions in the bladder. The methods, compounds, compositions, systems, and kits provided herein, will reduce recurrence rates, improve patient outcomes, and lower the cost of medical care for bladder cancer. In addition, success with targeted imaging leads to pHLIP® peptide (such as pHLIP®) delivery of therapeutic molecules to bladder tumor cells, creating an opportunity for targeted treatment of bladder cancers. In various embodiments, an ICG-pHLIP® peptide construct (such as the ICG-Var3construct) is a generally applicable imaging agent, since it targets a general property of the tumor microenvironment, tumor acidity. Targeting of primary tumors and metastatic lesions by fluorescent pHLIP® peptides has been shown in more than 15 varieties of human, murine and rat tumors, including lymphoma, melanoma, pancreatic, breast and prostate transgenic mouse models and human tissue (bladder, kidney, breast and head/neck stained ex vivo). ICG, which is known to have poor tissue penetration and to bind to proteins in blood, has not been attempted. Surprisingly, conjugates comprising ICG and a pHLIP® peptide (e.g., a pHLIP® peptide) are able to specifically target cancer tissues. Moreover, conjugates comprising ICG and pHLIP® peptides have unexpected properties, especially compared to conjugates comprising other fluorophores. For example, ICG fluorescence is enhanced about 25 times when a pHLIP® peptide tethers it to a membrane. This facilitates not only the detection of tumors, but also the identification of boundaries between cancerous and non-cancerous tissue. Increased fluorescence intensity upon tethering to cell membranes has not been observed with other dyes/fluorophores that have been attached to pHLIP® peptides, and allows an enhanced tumor/normal tissue fluorescence ratio.

The data presented in the non-limiting Examples herein show that ICG-Var3 and ICG-WT (ACEQNPIYWARYADWLFTTPLLLLDLALLVDADEGT) (SEQ ID NO: 444) are useful for fluorescence angiography in numerous clinical procedures. The advantages compared to free ICG are significant. In various embodiments, the imaging time is extended from 2-5 min, used now for free ICG to 2-3 hours, with ICG-Var3 (or ICG-WT). Currently, during some procedures free ICG is injected 10 or more times.

In some embodiments, an ICG-pHLIP® (such as ICG-Var3) is injected just once and can be imaged throughout a procedure without creating any disturbance of clinical flow (which occurs, e.g., when free ICG is reinjected). Thus, the flow or sequence of steps or actions in a clinical procedure is disrupted less with an ICG-pHLIP® than with free ICG. ICG-pHLIP®s have significant advantages and provides improvements compared to the use of free-ICG in fluorescence angiography and other of clinical procedures.

Three non-limiting examples of potential ICG-pHLIP® (such as ICG-Var3) use are as follows:

1. Fluorescent Angiography after intravenous administration of an ICG-pHLIP® (such as ICG-Var3): Imaging is performed within 5 min up to 2-3 hours after intravenous injection of an ICG-pHLIP® for visualization of blood vessels and blood perfusion. ICG-Var3 can be used in numerous clinical procedures.
2. Targeting (e.g., identification for subsequent surgical resection) of acidic diseased tissue after intravenous administration of an ICG-pHLIP® (such ICG-Var3): Imaging is performed at later time points, such as >4 hours or next day after intravenous injection of an ICG-pHLIP® for visualization of targeting of acidic diseased tissue, such as precancerous lesions, tumors, cancer cells in lymph nodes, ischemic myocardium, atherosclerotic plaques, site of infection and others. In embodiments, there is more time to blood clearance and clearance of adjacent non-diseased tissue from an ICG-pHLIP® to observe the best contrast (e.g., at an optimal time point) between diseased and non-diseased tissue.
3. Targeting (e.g., identification for subsequent surgical resection) of acidic diseased tissue after topical administration of an ICG-pHLIP® (such as ICG-Var3): Imaging will be performed after topical administration of an ICG-pHLIP®, such as instillation into a urinary bladder to detect bladder cancer, rinsing of mouth to detect oral cancer, spray on skin to detect skin cancer, spray on the cervix to detect cervical cancer, spray into the colon to detect colon cancer, and spray or inhalation into lung airway passages to detect lung cancer. The agent can also be used for non-cancerous applications, such as visualization of wounds or site of infections (which tissues are also acidic). For example, the agents are used in visualization of infection sites related to implanting of various devices, e.g., orthopedic, prosthetic, patches for slow drug release, implants, and cardiovascular devices such as stents in the body. In certain embodiments comprising the topical application of an ICG-pHLIP®, imaging is performed with 10-60 min after topical application of an ICG-pHLIP®.

pH-Triggered Polypeptides

A pH-triggered polypeptide (pHLIP® peptides, also known as "pH-triggered pH (Low) Insertion Peptides") is a water-soluble membrane peptide that interacts weakly with a cell membrane at neutral pH, without insertion into the lipid bilayer, but inserts into the cell membrane and forms a stable transmembrane alpha-helix at acidic pH (e.g., at a pH of less than about 7.0, 6.75, 6.5, 6.25, 6, 5.75, 5.5, 5.25, 5.0, 4.75, 4.5, 4.25, 4.0, 3.75, 3.5, 3.25, or 3.0).

In some embodiments, the pHLIP® peptide comprises at least 1, 2, 3, 4, 5, 6, 7, 8, 9, 11, 12, 13, 14, 15, 16, 17, 18, 19, 20, 21, 22, 23, 24, 25, 26, 27, 28, 29, or 30 genetically coded amino acids. Alternatively or in addition the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 non-genetically coded amino acids. In some embodiments, the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 D-amino acids.

In certain embodiments, the pHLIP® peptide comprised a functional group to which the fluorophore was attached. In various embodiments, the functional group of the pHLIP® peptide comprised an amino acid, azido modified amino acid, or alkynyl modified amino acid. In some embodiments, the functional group of the pHLIP® peptide comprised a free sulfhydryl (SH), or a primary amine. In certain embodiments, one or more fluorophores were attached to the functional group.

In various embodiments, a pHLIP® peptide (e.g. a pHLIP® peptide that is within a compound that comprises the pHLIP® peptide and a fluorophore) has a net neutral charge at a low pH and a net negative charge at a neutral or high pH. In some embodiments, a pHLIP® peptide has a net neutral charge at a pH of less than about 7, 6.9, 6.8, 6.7, 6.6, 6.5, 6.0, 5.5, 5.0, 4.5, or 4.0 and a net negative charge at a pH of about 7, 7.1, 7.2, 7.3, 7.4, 7.5, or 7.75 in water, e.g., distilled water. In certain embodiments, a pHLIP® peptide has a net neutral charge at a pH of less than about 7 and a net negative charge at a pH of about 7 in water. In some embodiments, a pHLIP® peptide has a net neutral charge at a pH of less than about 6.9 and a net negative charge at a pH of about 7 in water. In some embodiments, a pHLIP® peptide has a net neutral charge at a pH of less than about 6.8 and a net negative charge at a pH of about 7 in water. In some embodiments, a pHLIP® peptide has a net neutral charge at a pH of less than about 6.7 and a net negative charge at a pH of about 7 in water. In some embodiments, a pHLIP® peptide has a net neutral charge at a pH of less than about 6.6 and a net negative charge at a pH of about 7 in water. In some embodiments, a pHLIP® peptide has a net neutral charge at a pH of less than about 6.5 and a net negative charge at a pH of about 7 in water. In various embodiments, a pHLIP® peptide has a net neutral charge at a pH of less than about 6.0 and a net negative charge at a pH of about 7. In some embodiments, a pHLIP® peptide has a net neutral charge at a pH of less than about 5.5 and a net negative charge at a pH of about 7 in water. In certain embodiments, a pHLIP® peptide has a net neutral charge at a pH of less than about 5.0 and a net negative charge at a pH of about 7 in water. In various embodiments, a pHLIP® peptide has a net neutral charge at a pH of less than about 4.5 and a net negative charge at a pH of about 7 in water. In some embodiments, a pHLIP® peptide has a net neutral charge at a pH of less than about 4.0 and a net negative charge at a pH of about 7 in water.

In some embodiments, a pHLIP® peptide (e.g., a pHLIP® peptide that is within a compound that comprises the pHLIP® peptide and a fluorophore) has a net negative charge at a pH of about 7, 7.25, 7.5, or 7.75 in water. Alternatively or in addition, the pHLIP® peptide may have an acid dissociation constant at logarithmic scale (pKa) of less than about 4.0, 4.5, 5.0, 5.5, 6.0, 6.5, 6.6, 6.7, 6.8, 6.9, or 7.

In various embodiments, a protonatable amino acid is an amino acid with a pKa of less than about 4.0, 4.5, 5.0, 5.5, 6.0, 6.5, or 7. In certain embodiments, a protonatable amino acid is an amino acid with a pKa of less than about 6.5. In some embodiments, a protonatable amino acid is an amino acid with a pKa of less than about 5.5. In certain embodiments, a protonatable amino acid is an amino acid with a pKa of less than about 4.5. In various embodiments, a protonatable amino acid is an amino acid with a pKa of less than about 4.0. In some embodiments, a protonatable amino acid comprises a carboxyl group.

pHLIP®-fluorophore compounds may comprise pHLIP® peptides of various sizes. For example, a pHLIP® peptide may have 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50 or more amino acids; 8 to 15 amino acids; 8 to 50 amino acids; 8 to 40 amino acids; 8 to 30 amino acids; 8 to 20 amino acids; 8 to 10 amino acids; less than about 20 amino acids; less than 9, 10, 11, 12, 13, 14, or 15 amino acids; 10 amino acids; 9 amino acids, or 8 amino acids. In some embodiments, less than 1, 2, 3, 4, or 5 of the amino acids in the pHLIP® peptide have a net positive charge at a pH of 7, 7.25, 7.5, or 7.75 in water. In certain embodiments, the pHLIP® peptide comprises 0 amino acids having a net positive charge at a pH of about 7, 7.25, 7.5, or 7.75 in water.

In certain embodiments, pHLIP® peptide has about 1, 2, 3, 4, 5, 6, 7, 8, 9, 10 or more aromatic amino acids. For example, the aromatic amino acids may be one or more of a tryptophan, a tyrosine, a phenylalanine, and an artificial aromatic amino acid.

In various embodiments, pHLIP® peptides of the present subject matter have at least 1 protonatable amino acid. For example, a pHLIP® peptide may comprise 1 protonatable amino acid which is aspartic acid, glutamic acid, or gamma-carboxyglutamic acid; or at least 2, 3, 4, 5, 6, 7, 8, 9, 10 or more protonatable amino acids, wherein the protonatable amino acids comprise one or more of aspartic acid, glutamic acid, and gamma-carboxyglutamic acid. In some embodiments, the protonatable amino acid is an artificial amino acid. In a non-limiting example, a pHLIP® peptide has at least 2, 3, 4, 5, 6, 7, 8, 9, 10 or more protonatable amino acids, wherein the protonatable amino acids comprise aspartic acid, glutamic acid, gamma-carboxyglutamic acid, or any combination thereof.

The present subject matter provides pHLIP® peptides having artificial amino acids, such as at least 1 artificial protonatable amino acid. In various embodiments, the artificial protonatable amino acid comprises at least 1, 2, 3, 4 or 5 carboxyl groups and/or the pHLIP® peptide may have at least 1, 2, 3, 4, 5, 6, 7, 8, 9, 10, 11, 12, 13, 14, or 15 carboxyl groups. In some embodiments, a pHLIP® peptide has at least 1, 2, 3, 4, 5, 6, 7, 8, 9, 10, 11, 12, 13, 14, 15, 16, 17, 18, 19, or 20 artificial amino acids. In a non-limiting example, every amino acid of the pHLIP® peptide is an artificial amino acid. In certain embodiments, a pHLIP® peptide may include at least 1, 2, 3, 4, 5, 6, 7, 8, 9, 10, 11, 12, 13, 14, 15, 16, 17, 18, 19, or 20 D-amino acids.

Various implementations of the present subject matter relate to pHLIP® peptides having at least one artificial amino acid which is a cysteine derivative, an aspartic acid derivative, a glutamic acid derivative, a phenylalanine derivative, a tyrosine derivative, or a tryptophan derivative. For example, a pHLIP® peptide may contain a cysteine derivative selected from the group consisting of D-Ethionine, Seleno-L-cystine, S-(2-Thiazolyl)-L-cysteine, and S-(4-Tolyl)-L-cysteine; an aspartic acid derivative which is a N-phenyl(benzyl)amino derivative of aspartic acid; a glutamic acid derivative selected from the group consisting of γ-Carboxy-DL-glutamic acid, 4-Fluoro-DL-glutamic acid, and (4S)-4-(4-Trifluoromethyl-benzyl)-L-glutamic acid; a phenylalanine derivative selected from the group consisting of (S)—N-acetyl-4-bromophenylalanine, N-Acetyl-2-fluoro-DL-phenylalanine, N-Acetyl-4-fluoro-DL-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, 4-(Hydroxymethyl)-D-phenylalanine, N-(3-Indolylacetyl)-L-phenylalanine, p-Iodo-D-phenylalanine, α-Methyl-DL-phenylalanine, 4-Nitro-DL-phenylalanine, and 4-(Trifluoromethyl)-D-phenylalanine; a tyrosine derivative selected from the group consisting of α-Methyl-DL-tyrosine, 3-Chloro-L-tyrosine, 3-Nitro-L-tyrosine, and DL-o-Tyrosine; and/or a tryptophan derivative selected from the group consisting of 5-Fluoro-L-tryptophan, 5-Fluoro-DL-tryptophan, 5-Hydroxy-L-tryptophan, 5-Methoxy-DL-tryptophan, or 5-Methyl-DL-tryptophan.

In various embodiments, a pHLIP® peptide has at least 8 consecutive amino acids, wherein, at least 2, 3, 4, 5, or 6 of the 8 consecutive amino acids of the pHLIP® peptide are non-polar, and at least 1 or 2 of the at least 8 consecutive amino acids of the pHLIP® peptide is protonatable. For example, the pHLIP® peptide may have 8-10 consecutive amino acids, including at least 2, 3, 4, 5, or 6 of the 8-10 consecutive amino acids that are non-polar, and at least 1 or 2 amino acids that are protonatable.

Aspects of the present disclosure provide a pHLIP® peptide that is linked to a fluorophore. In various implementations, the pHLIP® peptide is directly linked to a linker moiety and/or a fluorophore by a covalent bond. In some non-limiting examples, the covalent bond is an ester bond, a disulfide bond, a bond between two selenium atoms, a bond between a sulfur and a selenium atom, or an acid-labile bond.

In some embodiments, the covalent bond between the pHLIP® peptide a linker moiety and/or a fluorophore is a bond that has been formed by a click reaction. Non-limiting examples of click reactions include reactions between an azide and an alkyne; an alkyne and a strained difluorooctyne; a diaryl-strained-cyclooctyne and a 1,3-nitrone; a cyclooctene, trans-cycloalkene, or oxanorbornadiene and an azide, tetrazine, or tetrazole; an activated alkene or oxanorbornadiene and an azide; a strained cyclooctene or other activated alkene and a tetrazine; or a tetrazole that has been activated by ultraviolet light and an alkene.

Some implementations provide a pHLIP® peptide that is attached to a linker compound by a covalent bond, wherein the linker compound is attached to the fluorophore or by a covalent bond. In non-limiting examples, the covalent bond between a pHLIP® peptide and a linker compound and/or the covalent bond between a linker compound and a fluorophore is a disulfide bond, a bond between two selenium atoms, a bond between a sulfur and a selenium atom, or a bond that has been formed by a click reaction.

In various embodiments, the fluorophore has a weight of (a) at least about 0.5, 1, 1.5, 2, 2.5, 5, 6, 7, 8, 9, or 10 kilodaltons (kDa); or (b) less than about 0.5, 1, 1.5, 2, 2.5, 5, 6, 7, 8, 9, or 10 kDa. In a non-limiting example, a pHLIP® peptide is linked to a fluorophore having a weight of at least about 15 kDa. The fluorophore may be, e.g., polar or nonpolar.

In various non-limiting examples, the fluorophore comprises a fluorescent dye or a fluorescent protein.

In various embodiments, pHLIP®-fluorophore compound (or a pHLIP® peptide within a pHLIP®-fluorophore compound) has a higher affinity for a membrane lipid bilayer at low pH compared to that at normal pH. For example, the affinity is at least 5 times higher at pH 5.0 than at pH 8.0. In some embodiments, the affinity is at least 10 times higher at pH 5.0 than at pH 8.0. In some embodiments, the binding/association/partitioning of a pH triggered compound with a membrane lipid bilayer is stronger at low pH (e.g., pH<6.5 or 7.0) compared to a higher pH (e.g., pH≥6.5 or 7.0).

In some embodiments, a non-polar amino acid or amino acids comprise alanine, valine, isoleucine, leucine, methionine, phenylalanine, tyrosine, or tryptophan. In some embodiments, a polar amino acid or amino acids comprise serine, threonine, asparagine, or glutamine. In some embodiments, the non-polar amino acid is an artificial amino acid such as 1-methyl-tryptophan.

In various embodiments, a non-polar amino acid is defined as one having a side-chain solvation energy ≥0.5 kcal/mol. The values of solvation energy ($\Delta G_x^{corr}$) for the 20 common natural amino acids are known, e.g., as determined by Wimley W C, Creamer T P & White S H (1996) Biochemistry 35, 5109-5124 (hereinafter Wimley et al. 1996) or by Moon and Fleming, (2011) Proc. Nat. Acad. Sci. USA 101:10174-10177, the entire content of which is incorporated herein by reference. The table below provides exemplary side chain solvation energies for naturally occurring amino acids.

TABLE 1

Solvation Free Energies of the Side Chains (X) of the 20 Natural Amino Acids in AcWL-X-LL (SEQ ID NO: 534). Non-polar residues are shown in bold and defined as residues with $\Delta G_X^{cor} > +0.50$.

| Residue | Charge | $\Delta G_X^{cor}$ |
|---|---|---|
| Ala | 0 | +0.65 |
| Arg | +1 | −0.66 |
| Asn | 0 | +0.30 |
| Asp | −1 | −2.49 |
| Cys | 0 | +1.17 |
| Gln | 0 | +0.38 |
| Glu | −1 | −2.48 |
| GLY* | 0 | 0 |
| His | +1 | −1.18 |
| Ile | 0 | +2.27 |
| Leu | 0 | +2.40 |
| Lys | +1 | −1.65 |
| Met | 0 | +1.82 |
| Phe | 0 | +2.86 |
| Pro | 0 | +1.01 |
| Ser | 0 | +0.69 |
| Thr | 0 | +0.90 |
| Trp | 0 | +3.24 |
| Tyr | 0 | +1.86 |
| Val | 0 | +1.61 |

Residue solvation free energies of the 20 natural amino acids relative to glycine calculated from the data in Table 1 of Wimley et al. 1996, page 5116. Free energies were corrected for the occlusion of neighboring residue areas and for the anomalous properties of glycine. Residue solvation free energies calculated with mole-fraction units. Residue solvation free energies for the X residue in the context of a AcWL-X-LL peptide (SEQ ID NO: 534) calculated from the free energies in Table 1 or Wimley et al. 1996, page 5116 using the virtual glycine (GLY*) as the reference (see text of Wimley et al. 1996) (SEQ ID NOS: 534, 535, 534 and 535 are disclosed below, respectively, in order of appearance).

$$\Delta G_X^{cor} = \Delta G_{WLXLL} - \Delta G_{WLG*LL} + \Delta \sigma_{np} \Delta A_{host},$$

$$A_{host}(X) = A_{Tnp}(\text{WLXLL}) - A_{Xnp}(\text{WLXLL})$$

These "corrected" values account for X-dependent changes in the nonpolar ASA of the host peptide. Values for Arg and Lys were calculated from experimental free energies measured at pH 1 where the ionic interaction between the side chain and carboxyl group does not occur. $\Delta G_x^{cor}$ is the best estimate of the solvation energy of residues occluded by neighboring residues of moderate size.

Genetically coded amino acids and exemplary non-genetically coded amino acids are listed below in Table 2.

In some embodiments, a pHLIP® peptide comprises one or more cysteine residues. The cysteine residue(s) serves as a point of conjugation of cargo, e.g., using thiol linkage. Other means of linking cargo to a pHLIP® peptide include esters and/or acid-labile linkages. Non cleavable covalent chemical linkages may also be made to secure a fluorophore permanently to a membrane insertion peptide (such as a pHLIP® peptide).

Membrane-inserting compounds provided herein are useful for diagnostic and imaging, or as research reagents/tools (e.g., to evaluate vascular or renal tissue structure or function). Various implementations of the present subject matter relate to a diagnostic conjugate comprising a pH triggered compound and a pharmaceutically acceptable detectable marker linked thereto. Exemplary detectable markers include imaging agents, dyes, nanoparticles, or other detectable labels. In various embodiments, the membrane-inserting compound itself is non-toxic, especially when an effective amount of the membrane-inserting compound is used.

Acting as a monomer, a pHLIP® peptide inserts across a cell membrane without forming a pore. The pHLIP® peptide-nanotechnology platform can be used for, e.g. pH-selective targeting of therapeutic or imaging agents to solid tumors, where they are tethered to the surfaces of tumor cells, and/or pH-selective targeting of tumor cells with cytoplasmic delivery of cargo molecules attached to the pHLIP® peptide's C-terminus via a cleavable bond. In a non-limiting example, a cargo molecule attached to the pHLIP® peptide's C-terminus via an S—S bond that is cleaved in the cytoplasm. Among the successfully injected molecules are the organic dyes, phalloidin (a polar, cyclic peptide of more than 1 kDa), and 12-mer and 18-mer peptide nucleic acids (PNAs). If a cargo molecule is attached to the pHLIP® peptide's N-terminus via a non-cleavable bond, a pHLIP® peptide can tether the cargo molecule to the surface of a cell in acidic tissue. The pH-selective insertion and folding of pHLIP® peptides into membranes has been used to target acidic tissue in vivo, including tumors and sites of inflammation. The pathway of pHLIP® peptide entry into the membrane and the translocation of molecules into cells is not mediated by endocytosis, but by interactions with cell receptors or by formation of pores in the cell membrane. In some embodiments, pHLIP® peptide insertion is associated with the protonation of a residue such as an Asp residue, which leads to an increase in pHLIP® peptide hydrophobicity that immediately (within seconds) triggers the insertion of the peptide into a cell membrane. The insertion is accompanied by the release of energy, which may be used to move cell-impermeable cargo molecules through the lipid bilayer of membrane into the cell.

Peptide interactions with proteins, especially plasma proteins, and membranes influence the pharmacokinetics of the peptide at neutral pH. pHLIP® peptides demonstrate prolonged circulation in the blood, which is consistent with their ability to bind weakly to membrane surfaces at neutral and high pH, preventing the rapid clearance by the kidney expected for a small peptide.

Aspects of the present subject matter relate to "Variant 3" or "Var3" pHLIP® peptides. Var3 pHLIP® peptides include a stretch of amino acids in the sequence LFPTXTLL (SEQ ID NO: 533), wherein X is aspartic acid. Non-limiting examples of Var3 pHLIP® peptide sequences include ADDQNPWRAYLDLLFPTDTLLLDLLWG (SEQ ID NO: 2), AKDDQNPWRAYLDLLFPTDTLLLDLLWG (SEQ ID NO: 3), ACDDQNPWRAYLDLLFPTDTLLLDLLWA (SEQ ID NO: 4), ADDQNPWRAYLDLLFPTDTLLLDLLWA (SEQ ID NO: 5), ADDQNPWRAYLDLLFPTDTLLLDLLWCA (SEQ ID NO: 6), ADDQNPWRAYLDLLFPTDTLLLDLLWKA (SEQ ID NO: 7), AKDDQNPWRAYLDLLFPTDTLLLDLLWA (SEQ ID NO: 8), ACDDQNPWRAYLDLLFPTDTLLLDLLWG (SEQ ID NO: 9), ADDQNPWRAYLDLLFPTDTLLLDLLWCG (SEQ ID NO: 10), ADDQNPWRAYLDLLFPTDTLLLDLLWKG (SEQ ID NO: 11), ACDDQNPWRAYLDLLFPTDTLLLDLLWKG (SEQ ID NO: 12), AKDDQNPWRAYLDLLFPTDTLLLDLLWCG (SEQ ID NO: 13), and ACKDDQNPWRAYLDLLFPTDTLLLDLLWG (SEQ ID NO: 14).

Variants of the pHLIP® peptides exemplified or otherwise disclosed herein may be designed using substitution techniques that are well understood in the art. Neither the pHLIP® peptides exemplified herein nor the variants discussed below limit the full scope of the subject matter disclosed herein.

Non-Limiting Variants of Non-Limiting Exemplified Peptides

Membrane-inserting compounds provided herein may include a membrane insertion peptide (such as pHLIP® peptide or a peptide that is not pH-triggered), e.g. any one of the non-limiting examples pHLIP® peptides provided herein or a variant thereof. Variants of the membrane insertion peptides exemplified or otherwise disclosed herein may be designed using substitution techniques that are well understood in the art. Neither the membrane insertion peptides exemplified herein nor the variants discussed below limit the full scope of the subject matter disclosed herein. Non-limiting examples of variants of the specific membrane insertion disclosed herein include peptides having the reverse amino acid sequence of the specific membrane insertion peptides disclosed. For example, a disclosure of a membrane insertion peptide comprising the sequence WARYADWL (SEQ ID NO: 34) also provides the disclosure of a membrane insertion peptide comprising the sequence LWDAYRAW (SEQ ID NO: 35).

Aspects of the present subject matter relate to membrane insertion peptides that result from 1, 2, 3, 4, 5, 6, 7, 8, 9, 10 or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a residue in a pH-triggered peptide sequence (e.g., corresponding to a location relative to a SEQ ID NO disclosed herein) may be replaced with another amino acid residue from the same side chain family. In certain embodiments, conservative amino acid substitutions may be made using a natural amino acid or a non-natural amino acid.

TABLE 2

Genetically coded and exemplary non-genetically coded amino acids including L-isomes, D-isomers, alpha-isomers, beta-isomers, glycol-, and methyl-modifications.

| No. | Abbrev | Name |
|---|---|---|
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Sec | Selenocysteine |
| 22 | Sem | Selenomethionine |
| 23 | Pyl | Pyrrolysine |
| 24 | Aad | Alpha-aminoadipic acid |
| 25 | Acpa | Amino-caprylic acid |
| 26 | Aecys | Aminoethyl cysteine |
| 27 | Afa | Aminophenyl acetate |
| 28 | Gaba | Gamma-aminobutyric acid |
| 29 | Aiba | Aminoisobutyric acid |
| 30 | Aile | Alloisoleucine |
| 31 | Alg | Allylglycine |
| 32 | Aba | Amino-butyric acid |
| 33 | Aphe | Amino-phenylalanine |
| 34 | Brphe | Bromo-phenylalanine |
| 35 | Cha | Cyclo-hexylalanine |
| 36 | Cit | Citrulline |
| 37 | Clala | Chloroalanine |
| 38 | Cle | Cycloleucine |
| 39 | Clphe | Fenclonine (or chlorophenylalanine) |
| 40 | Cya | Cysteic acid |
| 41 | Dab | Diaminobutyric acid |
| 42 | Dap | Diaminopropionic acid |
| 43 | Dap | Diaminopimelic acid |
| 44 | Dhp | Dehydro-proline |
| 45 | Dhphe | DOPA (or 3,4-dihydroxyphenylalanine) |
| 46 | Fphe | Fluorophenylalanine |
| 47 | Gaa | Glucosaminic acid |
| 48 | Gla | Gamma-carboxyglutamic acid |
| 49 | Hag | Homoarginine |
| 50 | Hlys | Hydroxylysine |
| 51 | Hnvl | Hydroxynorvaline |
| 52 | Hog | Homoglutamine |
| 53 | Hoph | Homophenylalanine |
| 54 | Has | Homoserine |
| 55 | Hse | Homocysteine |
| 56 | Hpr | Hydroxyproline |
| 57 | Iphe | Iodo-phenylalanine |
| 58 | Ise | Isoserine |
| 59 | Mle | Methyl-leucine |
| 60 | Msmet | Methionine-methylsulfonium chloride |
| 61 | Nala | Naphthyl-alanine |
| 62 | Nle | Norleucine (or 2-aminohexanoic acid) |
| 63 | Nmala | N-methyl-alanine |
| 64 | Nva | Norvaline (or 2-aminopentanoic acid) |
| 65 | Obser | O-benzyl-serine |
| 66 | Obtyr | O-benzyl-tyrosine |
| 67 | Oetyr | O-ethyl-tyrosine |
| 68 | Omser | O-methyl-serine |
| 69 | Omthr | O-methy-threonine |
| 70 | Omtyr | O-methyl-tyrosine |
| 71 | Orn | Ornithine |
| 72 | Pen | Penicillamine |
| 73 | Pga | Pyroglutamic acid |
| 74 | Pip | Pipecolic acid |

TABLE 2-continued

Genetically coded and exemplary non-genetically coded amino acids including L-isomes, D-isomers, alpha-isomers, beta-isomers, glycol-, and methyl-modifications.

| No. | Abbrev | Name |
|---|---|---|
| 75 | Sar | Sarcosine |
| 76 | Tfa | Trifluoro-alanine |
| 77 | Thphe | Hydroxy-Dopa |
| 78 | Vig | Vinylglycine |
| 79 | Aaspa | Amino-aminoethylsulfanylpropanoic acid |
| 80 | Ahdna | Amino-hydroxy-dioxanonanolic acid |
| 81 | Ahoha | Amino-hydroxy-oxahexanoic acid |
| 82 | Ahsopa | Amino-hydroxyethylsulfanylpropanoic acid |
| 83 | Tyr(Me) | Methoxyphenyl-methylpropanyl oxycarbonylamino propanoic acid |
| 84 | MTrp | Methyl-tryptophan |
| 85 | pTyr | Phosphorylated Tyr |
| 86 | pSer | Phosphorylated Ser |
| 87 | pThr | Phosphorylated Thr |
| 88 | BLys | BiotinLys |
| 89 | Hyp | Hydroproline |
| 90 | Phg | Phenylglycine |
| 91 | Cha | Cyclohexyl-alanine |
| 92 | Chg | Cyclohexylglycine |
| 93 | Nal | Naphthylalanine |
| 94 | Pal | Pyridyl-alanine |
| 95 | Pra | Propargylglycine |
| 96 | Gly(allyl) | Pentenoic acid |
| 97 | Pen | Penicillamine |
| 98 | MetO | Methionine sulfoxide |
| 99 | Pca | Pyroglutamic acid |
| 100 | Ac-Lys | Acetylation of Lys |

TABLE 3

Non-limiting examples of protonatable residues and their substitutions including L-isomes, D-isomers, alpha-isomers, and beta-isomers.

| Original Residue | Exemplary amino acids substitution |
|---|---|
| Asp (D) | Glu (E); Gla (Gla); Aad (Aad) |
| Glu (E) | Asp (D); Gla (Gla); Aad (Aad) |

TABLE 4

Examples of genetically coded amino acid substitutions

| Original Residue | Substitution |
|---|---|
| Ala (A) | Gly; Ile; Leu; Met; Phe; Pro; Trp; Tyr; Val |
| Arg (R) | Lys |
| Asn (N) | Gln; His |
| Asp (D) | Glu |
| Cys (C) | Ser; Met |
| Gln (Q) | Asn; His |
| Glu (E) | Asp |
| Gly (G) | Ala; Ile; Leu; Met; Phe; Pro; Trp; Tyr; Val |
| His (H) | Asn; Gln |
| Ile (I) | Ala; Gly; Leu; Met; Phe; Pro; Trp; Tyr; Val |
| Leu (L) | Ala; Gly; Ile; Met; Phe; Pro; Trp; Tyr; Val |
| Lys (K) | Arg |
| Met (M) | Ala; Gly; Leu; Ile; Phe; Pro; Trp; Tyr; Val |
| Phe (F) | Ala; Gly; Leu; Ile; Met; Pro; Trp; Tyr; Val |
| Pro (P) | Ala; Gly; Leu; Ile; Met; Phe; Trp; Tyr; Val |
| Ser (S) | Thr |
| Thr (T) | Ser |
| Trp (W) | Ala; Gly; Leu; Ile; Met; Pro; Phe; Tyr; Val |
| Tyr (Y) | Ala; Gly; Leu; Ile; Met; Pro; Phe; Trp; Val |
| Val (V) | Ala; Gly; Leu; Ile; Met; Pro; Phe; Trp; Tyr |

TABLE 5

Non-limiting examples of putative membrane-inserting sequences belonging to different groups of pHLIP ® peptides. Each protonatable residue (shown in underline) could be replaced by its substitution from Table 3. Each non-polar residue could be replaced by its genetically coded amino acid substitution from Table 4, and/or non-genetically coded amino acid substitutions from Table 2.

| Groups | Sequences |
|---|---|
| Var3 | WRAYLDLLFPTDTLLLDLLW (SEQ ID NO: 325) |
| Var3 Reverse | WLLDLLLTDTPFLLDLYARW (SEQ ID NO: 326) |
| WT | WARYADWLFTTPLLLLDLALLVDADE (SEQ ID NO: 327) |
| WT Reverse | EDADVLLALDLLLLPTTFLWDAYRAW (SEQ ID NO: 328) |
| ATRAM | GLAGLLGLEGLLGLPLGLLEGLWLGL (SEQ ID NO: 329) |
| Var7 | WARYLEWLFPTETLLLEL (SEQ ID NO: 330)<br>WAQYLELLFPTETLLLEW (SEQ ID NO: 331) |
| Single D/E | WLFTTPLLLLNGALLVE (SEQ ID NO: 332)<br>WLFTTPLLLLPGALLVE (SEQ ID NO: 333)<br>WARYADLLFPTTLAW (SEQ ID NO: 334) |
| pHLIP ®-Rho | GNLEGFFATLGGEIALWSLVVLAIE (SEQ ID NO: 335)<br>EGFFATLGGEIALWSDVVLAIE (SEQ ID NO: 336)<br>EGFFATLGGEIPLWSDVVLAIE (SEQ ID NO: 337) |
| pHLIP ®-Rho Reverse | EIALVVLSWLAIEGGLTAFFGELNG (SEQ ID NO: 338)<br>EIALVVDSWLAIEGGLTAFFGE (SEQ ID NO: 339)<br>EIALVVDSWLPIEGGLTAFFGE (SEQ ID NO: 340) |
| pHLIP ®-CA9 | ILDLVFGLLFAVTSVDFLVQW (SEQ ID NO: 341) |
| pHLIP ®-CA9 Reverse | WQVLFDVSTVAFLLGFVLDLI (SEQ ID NO: 342) |

TABLE 6

Non-limiting examples of pHLIP sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| Seq ID | Name | Sequence |
|---|---|---|
| SEQ ID NO: 343 | WT-2D | AEQNPIYWARYADWLFTTPLLLLDLALLVDADET |
| SEQ ID NO: 344 | WT-6E | AEQNPIYWARYAEWLFTTPLLLLELALLVEAEET |
| SEQ ID NO: 345 | WT-3D | ADDQNPWRAYLDLLFPDTTDLLLLDLLWDADET |
| SEQ ID NO: 346 | WT-9E | AEEQNPWRAYLELLFPETTELLLLELLWEAEET |
| SEQ ID NO: 347 | WT-GlaD | AEQNPIYWARYAGlaWLFTTPLLLLDLALLVDADET |
| SEQ ID NO: 348 | WT-DGla | AEQNPIYWARYADWLFTTPLLLLGlaLALLVDADET |
| SEQ ID NO: 349 | WT-2Gla | AEQNPIYWARYAGlaWLFTTPLLLLGlaLALLVDADET |
| SEQ ID NO: 350 | WT-AadD | AEQNPIYWARYAAadWLFTTPLLLLDLALLVDADET |
| SEQ ID NO: 351 | WT-DAad | AEQNPIYWARYADWLFTTPLLLLAadLALLVDADET |
| SEQ ID NO: 352 | WT-2Aad | AEQNPIYWARYAAadWLFTTPLLLLAadLALLVDADET |
| SEQ ID NO: 353 | WT-GlaAad | AEQNPIYWARYAGlaWLFTTPLLLLAadLALLVDADET |
| SEQ ID NO: 354 | WT-AadGla | AEQNPIYWARYAAadWLFTTPLLLLGlaLALLVDADET |
| SEQ ID NO: 355 | WT-1 | GGEQNPIYWARYADWLFTTPLLLLDLALLVDADEGTG |

TABLE 6-continued

Non-limiting examples of pHLIP sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| Seq ID | Name | Sequence |
|---|---|---|
| SEQ ID NO: 356 | WT-2 | GGEQNPIYWARYADWLFTTPLLLLDLALLVDADEGT |
| SEQ ID NO: 357 | WT-3 | AAEQNPIYWARYADWLFTTPLLLLDLALLVDADEGTG |
| SEQ ID NO: 358 | WT-4 | AEQNPIYWARYADWLFTTPLLLLDLALLVDADEGT |
| SEQ ID NO: 359 | WT-2N | AEQNPIYWARYANWLFTTPLLLLNLALLVDADEGTG |
| SEQ ID NO: 360 | WT-2K | AEQNPIYWARYAKWLFTTPLLLLKLALLVDADEGTG |
| SEQ ID NO: 361 | WT-2DNNQ | GGEQNPIYWARYADWLFTTPLLLLDLALLVNANQGT |
| SEQ ID NO: 362 | WT-D25A | AAEQNPIYWARYADWLFTTPLLLLALALLVDADEGT |
| SEQ ID NO: 363 | WT-D14A | AAEQNPIYWARYAAWLFTTPLLLLDLALLVDADEGT |
| SEQ ID NO: 364 | WT-P20A | AAEQNPIYWARYADWLFTTALLLLDLALLVDADEGT |
| SEQ ID NO: 365 | WT-D25E | AAEQNPIYWARYADWLFTTPLLLLELALLVDADEGT |
| SEQ ID NO: 366 | WT-D14E | AAEQNPIYWARYAEWLFTTPLLLLDLALLVDADEGT |
| SEQ ID NO: 367 | WT-3D-2 | AAEQNPIIYWARYADWLFTDLPLLLLDLLALLVDADEGT |
| SEQ ID NO: 368 | WT-R11Q | GEQNPIYWAQYADWLFTTPLLLLDLALLVDADEGCG |
| SEQ ID NO: 369 | WT-D25Up | GGEQNPIYWARYADWLFTTPLLLDLLALLVDADEGCG |
| SEQ ID NO: 370 | WT-D25Down | GGEQNPIYWARYADWLFTTPLLLLLDALLVDADEGCG |
| SEQ ID NO: 371 | WT-D14Up | GGEQNPIYWARYDAWLFTTPLLLLDLALLVDADEGTG |
| SEQ ID NO: 372 | WT-D14Down | GGEQNPIYWARYAWDLFTTPLLLLDLALLVDADEGCG |
| SEQ ID NO: 373 | WT-P20G | AAEQNPIYWARYADWLFTTGLLLLDLALLVDADEGT |
| SEQ ID NO: 374 | WT-DH | DDDEDNPIYWARYADWLFTTPLLLLHGALLVDADCT |
| SEQ ID NO: 375 | WT-2H | DDDEDNPIYWARYAHWLFTTPLLLLHGALLVDADECT |
| SEQ ID NO: 376 | WT-L16H | CEQNPIYWARYADWHFTTPLLLLDLALLVDADEGT |
| SEQ ID NO: 377 | WT-1Wa | AEQNPIYWARYADFLFTTPLLLLDLALLVDADET |
| SEQ ID NO: 378 | WT-1Wb | AEQNPIYFARYADWLFTTPLLLLDLALLVDADEGT |
| SEQ ID NO: 379 | WT-1Wc | AEQNPIYFARYADFLFTTPLLLLDLALLWDADET |
| SEQ ID NO: 380 | WT-W6 | ADNNPWIYARYADLTTFPLLLLDLALLVDFDD |
| SEQ ID NO: 381 | WT-W17 | ADNNPFIYARYADLTTWPLLLLDLALLVDFDD |
| SEQ ID NO: 382 | WT-W30 | ADNNPFIYARYADLTTFPLLLLDLALLVDWDD |
| SEQ ID NO: 383 | WT-W17-P7 | ADNNPFPYARYADLTTVVILLLLDLALLVDFDD |
| SEQ ID NO: 384 | WT-W39-R11 | ADNNPFIYAYRADLTTFPLLLLDLALLVDWDD |
| SEQ ID NO: 385 | WT-W30-R15 | ADNNPFIYATYADLRTFPLLLLDLALLVDWDD |
| SEQ ID NO: 386 | WT-Rev | Ac-TEDADVLLALDLLLLPTTFLWDAYRAWYPNQEA-Am |
| SEQ ID NO: 387 | Var1-3D | AEDQNPYWARYADWLFTTPLLLLDLALLVDG |
| SEQ ID NO: 388 | Var1-1D2E | AEDQNPYWARYADWLFTTPLLLLELALLVEG |
| SEQ ID NO: 389 | Var2-3D | AEDQNPYWRAYADLFTPLTLLDLLALWDG |
| SEQ ID NO: 390 | Var3-3D | ADDQNPWRAYLDLLFPTDTLLLDLLWG |
| SEQ ID NO: 391 | Var3-WT | ADDQNPWRAYLDLLFPTDTLLLDLLWDADEG |

TABLE 6-continued

Non-limiting examples of pHLIP sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| Seq ID | Name | Sequence |
|---|---|---|
| SEQ ID NO: 392 | Var3-Gla2D | ADDQNPWRAYLGlaLLFPTDTLLLDLLWG |
| SEQ ID NO: 393 | Var3-DGlaD | ADDQNPWRAYLDLLFPTGlaTLLLDLLWG |
| SEQ ID NO: 394 | Var3-2DGla | ADDQNPWRAYLDLLFPTDTLLLGlaLLWG |
| SEQ ID NO: 395 | Var3-2GlaD | ADDQNPWRAYLGlaLLFPTGlaTLLLDLLWG |
| SEQ ID NO: 396 | Var3-GlaDGla | ADDQNPWRAYLGlaLLFPTDTLLLGlaLLWG |
| SEQ ID NO: 397 | Var3-D2Gla | ADDQNPWRAYLDLLFPTGlaTLLLGlaLLWG |
| SEQ ID NO: 398 | Var3-3Gla | ADDQNPWRAYLGlaLLFPTGlaTLLLGlaLLWG |
| SEQ ID NO: 399 | Var3-Aad2D | ADDQNPWRAYLAadLLFPTDTLLLDLLWG |
| SEQ ID NO: 400 | Var3-DAadD | ADDQNPWRAYLDLLFPTAadTLLLDLLWG |
| SEQ ID NO: 401 | Var3-2DAad | ADDQNPWRAYLDLLFPTDTLLLAadLLWG |
| SEQ ID NO: 402 | Var3-2AadD | ADDQNPWRAYLAadLLFPTAadTLLLDLLWG |
| SEQ ID NO: 403 | Var3-AadDAad | ADDQNPWRAYLAadLLFPTDTLLLAadLLWG |
| SEQ ID NO: 408 | Var3-D2Aad | ADDQNPWRAYLDLLFPTAadTLLLAadLLWG |
| SEQ ID NO: 409 | Var3-3Aad | ADDQNPWRAYLAadLLFPTAadTLLLAadLLWG |
| SEQ ID NO: 410 | Var3-GlaAadD | ADDQNPWRAYLGlaLLFPTAadTLLLDLLWG |
| SEQ ID NO: 411 | Var3-GlaDAad | ADDQNPWRAYLGlaLLFPTDTLLLAadLLWG |
| SEQ ID NO: 412 | Var3-2GlaAad | ADDQNPWRAYLGlaLLFPTGlaTLLLAadLLWG |
| SEQ ID NO: 413 | Var3-AadGlaD | ADDQNPWRAYLAadLLFPTGlaTLLLDLLWG |
| SEQ ID NO: 414 | Var3-AadDGla | ADDQNPWRAYLAadLLFPTDTLLLGlaLLWG |
| SEQ ID NO: 415 | Var3-GlaAadGla | ADDQNPWRAYLGlaLLFPTAadTLLLGlaLLWG |
| SEQ ID NO: 416 | Var3-GLL | GEEQNPWLGAYLDLLFPLELLGLLELGLWG |
| SEQ ID NO: 417 | Var3-M | ADDDDDDPWQAYLDLLFPTDTLLLDLLW |
| SEQ ID NO: 418 | Var4-3E | AEEQNPWRAYLELLFPTETLLLELLW |
| SEQ ID NO: 419 | Var5-3Da | ADDQNPWARYLDWLFPTDTLLLDL |
| SEQ ID NO: 420 | Var6-3Db | DNNNPWRAYLDLLFPTDTLLLDW |
| SEQ ID NO: 421 | Var7-3E | AEEQNPWARYLEWLFPTETLLLEL |
| SEQ ID NO: 422 | Var7-M | DDDDDDPWQAYLDLLFPTDTLALDLW |
| SEQ ID NO: 423 | Var8-3E | EEQQPWAQYLELLFPTETLLLEW |
| SEQ ID NO: 424 | Var9-3E | EEQQPWRAYLELLFPTETLLLEW |
| SEQ ID NO: 425 | Var10-2D | AEDQNPWARYADWLFPTTLLLLD |
| SEQ ID NO: 426 | Var11-2E | AEEQNPWARYAEWLFPTTLLLLE |
| SEQ ID NO: 427 | Var12-1D | AEDQNPWARYADLLFPTTLAW |
| SEQ ID NO: 428 | Var13-1E | AEEQNPWARYAELLFPTTLAW |
| SEQ ID NO: 429 | Var15-2N | DDDDDNPNYWARYANWLFTTPLLLLNGALLVEAEET |
| SEQ ID NO: 430 | Var16-2P | DDDDDNPNYWARYAPWLFTTPLLLLPGALLVEAEET |
| SEQ ID NO: 431 | Var17 | AEQNPIYFARYADFLFTTPLLLLDLALLWDADET |

TABLE 6-continued

Non-limiting examples of pHLIP sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| Seq ID | Name | Sequence |
|---|---|---|
| SEQ ID NO: 432 | Var18 | AEQNPIYWARYADFLFTTPLLLLDLALLVDADET |
| SEQ ID NO: 433 | Var19a | AEQNPIYWARYADWLFTTPL |
| SEQ ID NO: 434 | Var20 | AEQNPIYFARYADLLFPTTLAW |
| SEQ ID NO: 435 | Var21 | AEQNPIYWARYADLLFPTTLAF |
| SEQ ID NO: 436 | Var22 | AEQNPIYWARYADLLFPTTLAW |
| SEQ ID NO: 437 | Var23 | AEQNPIYFARYADWLFTTPL |
| SEQ ID NO: 438 | Var24 | EDQNPWARYADLLFPTTLAW |
| SEQ ID NO: 439 | ATRAM | GLAGLAGLLGLEGLLGLPLGLLEGLWLGLELEGNA |
| SEQ ID NO: 440 | pHLIP-CA9 | EQNPIYILDLVFGLLFAVTSVDFLVQWDDAGD |
| SEQ ID NO: 441 | pHLIP-Rho | GNLEGFFATLGGEIALWSLVVLAIE |
| SEQ ID NO: 442 | pHLIP-RhoM1 | GNNEGFFATLGGEIALWSDVVLAIEG |
| SEQ ID NO: 443 | pHLIP-RhoM2 | GDNNEGFFATLGGEIPLWSDVVLAIEG |

In the table above, "Am" means C-terminal amidation, which is a protected C-terminus, i.e., there is no free COOH group at the C-terminus and there is no charge at the C-terminus. "Ac" means N-terminal acylation, which is a protected N-terminus, i.e., there is no free NH$_2$ group at the N-terminus and there is no charge at the N-terminus.

TABLE 7

Non-limiting examples of linkers and components thereof

| ID | Name |
|---|---|
| 1 | Peptide bond, (—CO—NH—) |
| 2 | Polypeptide |
| 3 | Polylysine |
| 4 | Polyarginine |
| 5 | Polyglutamic acid |
| 6 | Polyaspartic acid |
| 7 | Polycysteine |
| 8 | Collagen |
| 9 | Fibrinogen |
| 10 | Avidin |
| 11 | Streptavidin |
| 12 | Albumin |
| 13 | Antibody |
| 14 | Protein with 1 or more Lys, Arg, Cys, Asp, Glu |
| 15 | (continuation of 14) |
| 16 | Polynucleotide |
| 17 | Polysaccharide |
| 18 | Alginate |
| 19 | Chitosan |
| 20 | Poly(ethylene glycol) (PEG) |
| 21 | Poly(lactic acid) (PLA) |
| 22 | Poly(glycolic acid) (PGA) |
| 23 | Poly(lactic-co-glycolic acid) (PLGA) |
| 24 | Poly(malic acid) (PMA) |
| 25 | Polyorthoesters (POE) |
| 26 | Poly(vinylalcohol) (PVOH, PVA, or PVAl) |
| 27 | (continuation of 26) |
| 28 | Poly(vinylpyrrolidone) (PVP) |
| 29 | Poly(methyl methacrylate) (PMMA) |
| 30 | Poly(acrylic acid) (PAA) |
| 31 | Poly(acrylamide) (PAM) |
| 32 | Poly(methacrylic acid) (PMAA) |
| 33 | Poly(amidoamine) (PAMAM) |
| 34 | Polyanhydrides |
| 35 | Polycyanoacrylate |
| 36 | Particle |
| 37 | Metallic particle |
| 38 | Polymeric particle |
| 39 | Virus-like particle |
| 40 | Nanoparticle |
| 41 | Metallic nanoparticle |
| 42 | Lipid-based nanoparticle |
| 43 | Surfactant-based nanoparticle |
| 44 | Polymeric nanoparticle |
| 45 | Peptide-based nanoparticle |

Substitutions with natural amino acids may alternatively or additionally be characterized using a BLOcks SUbstitution Matrix (a BLOSUM matrix). An example of a BLOSUM matrix is the BLOSUM62 matrix, which is described in Styczynski et al. (2008) "BLOSUM62 miscalculations improve search performance" Nat Biotech 26 (3): 274-275, the entire content of which is incorporated herein by reference. The BLOSUM62 matrix is shown in FIG. 19.

Substitutions scoring at least 4 on the BLOSUM62 matrix are referred to herein as "Class I substitutions"; substitutions scoring 3 on the BLOSUM62 matrix are referred to herein as "Class II substitutions"; substitutions scoring 2 or 1 on the BLOSUM62 matrix are referred to herein as "Class III substitutions"; substitutions scoring 0 or −1 on the BLOSUM62 matrix are referred to herein as "Class IV substitutions"; substitutions scoring −2, −3, or −4 on the BLOSUM62 matrix are referred to herein as "Class V substitutions."

Various embodiments of the subject application include membrane insertion peptides (e.g., pHLIP® peptides) that have 1, 2, 3, 4, 5, 6, 7, 8, 9, 10 or more Class I, II, III, IV, or V substitutions compared to a membrane insertion peptides exemplified herein, or any 1, 2, 3, 4, 6, 7, 8, 9, 10 or more of any combination of Class I, II, III, IV, and/or V substitutions compared to a membrane insertion peptide exemplified herein.

Aspects of the present subject matter also relate to membrane insertion peptides having 1, 2, 3, 4, 5, or more amino acid insertions or deletions compared to membrane insertion peptides exemplified herein.

D-Amino Acids

Of the standard α-amino acids, all but glycine can exist in either of two optical isomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum. D amino acids are abundant components of the peptidoglycan cell walls of bacteria, and D-serine acts as a neurotransmitter in the brain. The L and D convention for amino acid configuration refers not to the optical activity of the amino acid itself, but rather to the optical activity of the isomer of glyceraldehyde from which that amino acid can be synthesized (D-glyceraldehyde is dextrorotary; L-glyceraldehyde is levorotary).

Membrane insertion peptides either fully or partially built of D-amino acids possess advantages over L-membrane insertion peptides. For example, D-membrane insertion peptides are biodegraded slower than their levorotary counterparts leading to enhanced activity and longer biological half-lives (Sela and Zisman, 1997 FASEB J, 11: 449-456, incorporated herein by reference). Thus, D-membrane insertion peptides may be used in the methods disclosed herein. Included herein are membrane insertion peptides that comprise solely L-amino acids or solely D-amino acids, or a combination of both D-amino acids and L-amino acids.

Indocyanine Green

The non-invasive near-infrared (NIR) fluorescence imaging dye ICG is approved by the United States Food and Drug administration (FDA) for ophthalmologic angiography to determine cardiac output and liver blood flow and function. This dye is also used in cancer patients for the detection of solid tumors, localization of lymphnodes, and for angiography during reconstructive surgery, visualization of retinal and choroidal vasculature, and photodynamic therapy. In cancer diagnostics and therapeutics, ICG could be used as both an imaging dye and a hyperthermia agent.

ICG is a tricarbocyanine-type dye with NIR-absorbing properties (peak absorption around 800 nm) and little absorption in the visible range thus exhibit low autofluorescence, tissue absorbance, and scatter at NIR wavelengths (700-900 nm).

Unconjugated ICG may comprise the following structure:

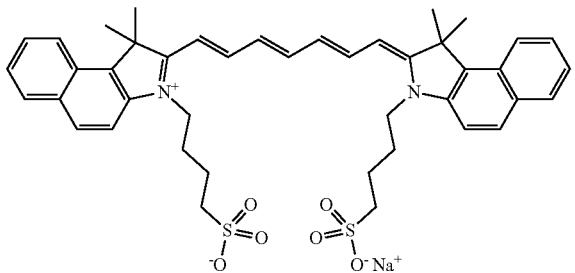

A CAS Registry Number for ICG is 3599-32-4.

ICG may be modified to, e.g., facilitate attachment the attachment thereof to peptides, such as pHLIP®s disclosed herein. Non-limiting examples of commercially available (e.g., from Intrace Medical SA, Lausanne, Switzerland) modified ICG compounds include ICG N-succinimidyl ester (ICG-NHS ester), ICG-CBT, ICG-maleimide, ICG-azide, ICG-alkyne, and ICG-PEG-NHS ester.

The succinimidyl esters (NETS) of the ICG dye offer the opportunity to develop optimal conjugates. Succinimidyl ester active groups provide an efficient and convenient way to selectively link ICG dyes to primary amines (R—$NH_2$) on various substrates (antibodies, peptides, proteins, nucleic-acid, small molecule drugs, etc.). Succinimidyl esters have very low reactivity with aromatic amines, alcohols, and phenols, including tyrosine and histidine. An example of ICG-NHS ester comprises the following features:

Excitation Class: Near infrared, NIR

Excitation/Emission maximum (nm): 790/830

Molecular Weight: 828.04 g·$mol^{-1}$

Formula: $C_{49}H_{53}N_3O_7S$
Structure:

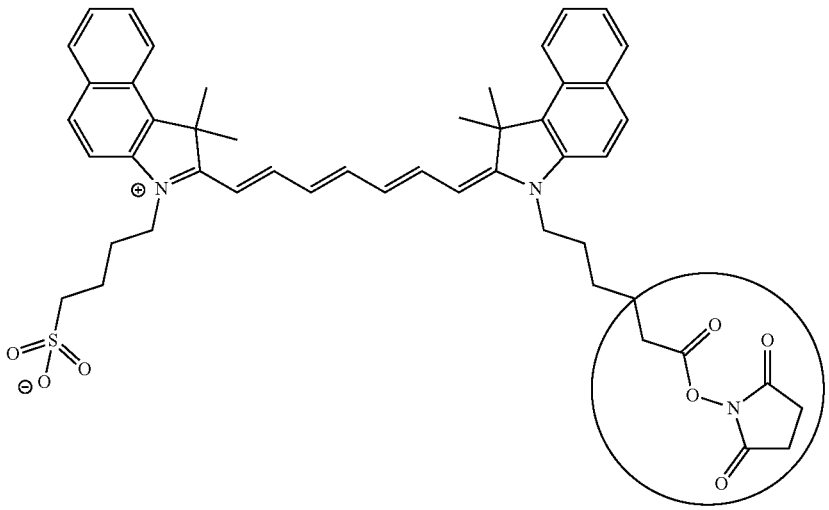 [SMILES: CC1(C)C(/C=C/C=C/C=C/C=C2/N(CCCCCC(=O)ON3C(=O)CCC3=O)c3ccc4ccccc4c3C2(C)C)=[N+](CCCCS(=O)(=O)[O-])c2ccc3ccccc3c21]

The circled portion of the structure above indicates the linker moiety.

A maleimide active group provides an efficient and convenient way to selectively link ICG dye to sulfhydryl groups (free thiol, R—SH) on various substrates (antibodies, peptides, proteins, oligonucleotides, small molecule drugs, etc.) at neutral (physiological) pH without any activation. Maleimides have very low reactivity with amines, alcohols, and phenols (such as tyrosine and histidine) and do not react with histidine and methionine, providing a very high labeling selectivity. An example of ICG-maleimide comprises the following features:

Excitation Class: Near infrared, NIR
Excitation/Emission maximum (nm): 790/830
Molecular Weight: 853.09 g·mol$^{-1}$
Formula: $C_{51}H_{56}N_4O_6S$
Structure:

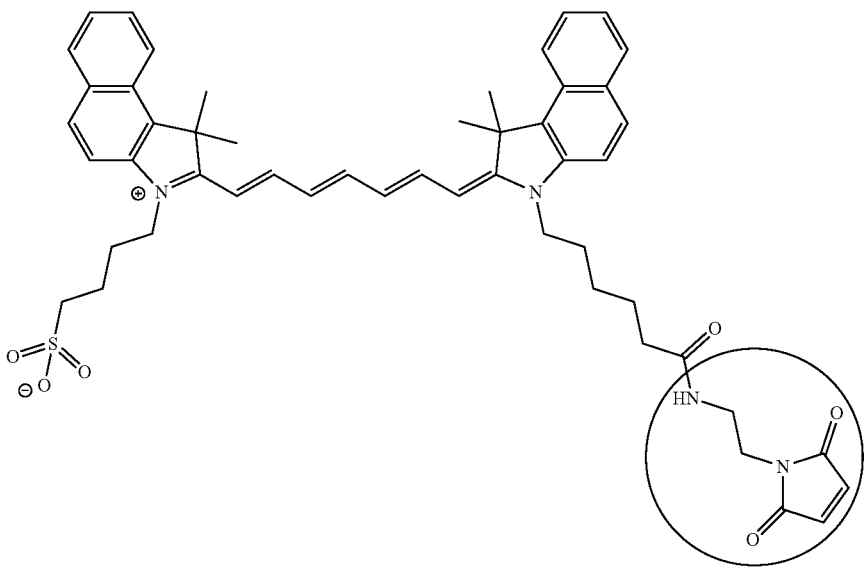 [SMILES: CC1(C)C(/C=C/C=C/C=C/C=C2/N(CCCCCC(=O)NCCN3C(=O)C=CC3=O)c3ccc4ccccc4c3C2(C)C)=[N+](CCCCS(=O)(=O)[O-])c2ccc3ccccc3c21]

The circled portion of the structure above indicates the linker moiety.

The 2-cyanobenzothiazole labeling procedure is based on the biocompatible click-reaction between 2-cyanobenzothiazole moiety and any 1, 2- or 1, 3-aminothiols (e.g. free or N-terminal cysteine). This click reaction is 3 orders of magnitude faster than commonly used Staudinger ligation and can provide useful conjugates. Cyanobenzothiazole (CBT) active groups provide an efficient and convenient way to site-selectively link ICG dyes to 1,2- or 1,3-aminothiols on various substrates (antibodies, peptides, proteins, nucleic-acid, small molecule drugs, etc.) without any additional activation. The labeling reaction with aminothiols is selective over reaction with simple thiols. The CBT click chemistry can be used together with all other biocompatible click reactions (like azide, alkyne, triphenylphosphine, tetrazine etc.), as it is very selective. In addition in ICG-CBT labeling procedure no side product is formed as here is no leaving group (unlike NHS esters). An example of an ICG-CBT comprises the following features:
Excitation Class: Near infrared, NIR
Excitation/Emission maximum (nm): 790/830
Molecular Weight: 931.38 g·mol$^{-1}$
Formula: $C_{55}H_{57}N_5O_5S_2$
Structure:

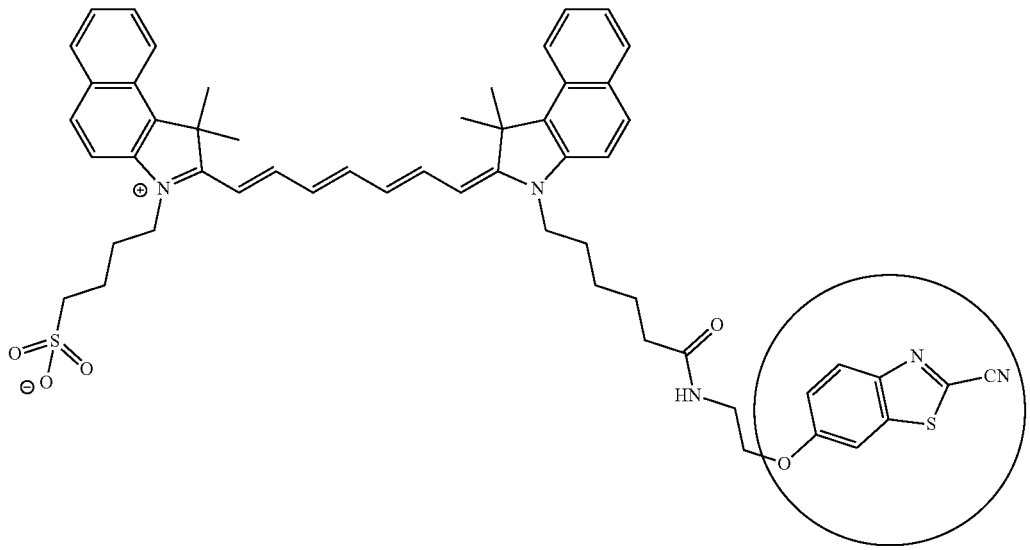 [SMILES: CC1(C)C(/C=C/C=C/C=C/C=C2/N(CCCCCC(=O)NCCOc3ccc4nc(C#N)sc4c3)c3ccc4ccccc4c3C2(C)C)=[N+](CCCCS(=O)(=O)[O-])c2ccc3ccccc3c21]

The circled portion of the structure above indicates the linker moiety.

ICG-azide can be used to label alkyne-tagged biomolecules (like proteins, lipids, nucleic acids, sugars) chemoselectively via click-chemistry. An example of ICG-azide comprises the following features:
Excitation Class: Near infrared, NIR
Excitation/Emission maximum (nm): 790/830
Molecular Weight: 931.21 g·mol$^{-1}$
Formula: $C_{53}H_{66}N_6O_7S$ The circled portion of the structure above indicates the linker moiety.

ICG-alkyne can be used to label azide-tagged molecules via Cu(II)-catalyzed click reaction. The reaction is chemoselective and biocompatible. An example of ICG-alkyne comprises the following features:
Excitation Class: Near infrared, NIR
Excitation/Emission maximum (nm): 790/830

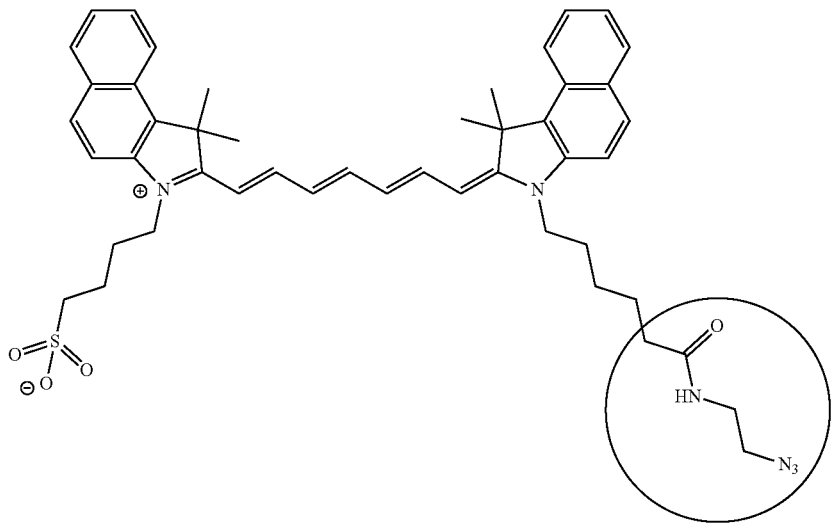 [SMILES: CC1(C)C(/C=C/C=C/C=C/C=C2/N(CCCCCC(=O)NCCN=[N+]=[N-])c3ccc4ccccc4c3C2(C)C)=[N+](CCCCS(=O)(=O)[O-])c2ccc3ccccc3c21]

Solubility: DMSO, DMF, Acetonitrile, Methanol
Molecular Weight: 767.38 g·mol$^{-1}$
Formula: $C_{48}H_{53}N_3O_4S$

Cyanine Fluorophores

Cyanine fluorophores may optionally be referred to herein as "cyanine dyes." Cyanine dyes are molecules containing polymethine bridge between two nitrogen atoms with a delocalized charge:

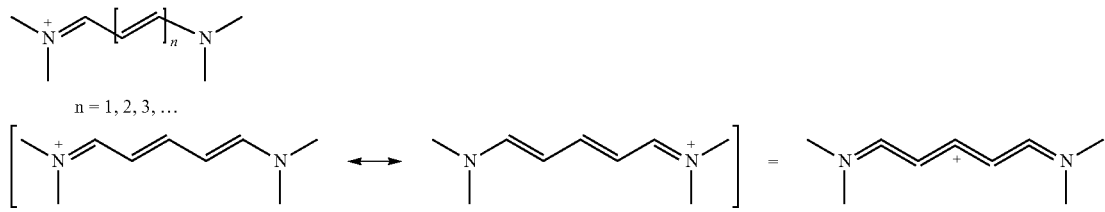

Due to their structure, cyanines have outstandingly high extinction coefficients often exceeding 100,000 Lmol$^{-1}$ cm$^{-1}$. Different substituents allow to control properties of the chromophore, such as absorbance wavelength, photostability, and fluorescence. For example, absorbance and fluorescence wavelength can be controlled by a choice of polymethine bridge length: longer cyanines possess higher absorbance and emission wavelengths up to near infrared region. Non-limiting examples of cyanine dyes include non-sulfonated cyanines, and sulfonated cyanines.

Available non-sulfonated dyes include, e.g., Cy3, Cy3.5, Cy5, Cy5.5, Cy7, and Cy7.5. Cy® stands for 'cyanine', and the first digit identifies the number of carbon atoms between the indolenine groups. Cy2 which is an oxazole derivative rather than indolenin, is an exception from this rule. The suffix 0.5 is added for benzo-fused cyanines. In certain embodiments, variation of the structures allows to change fluorescence properties of the molecules, and to cover most important part of visible and NIR spectrum with several fluorophores.

The structures of Cy3, Cy3.5, Cy5, Cy5.5, Cy7, and Cy7.5 are as follows:

Cy3

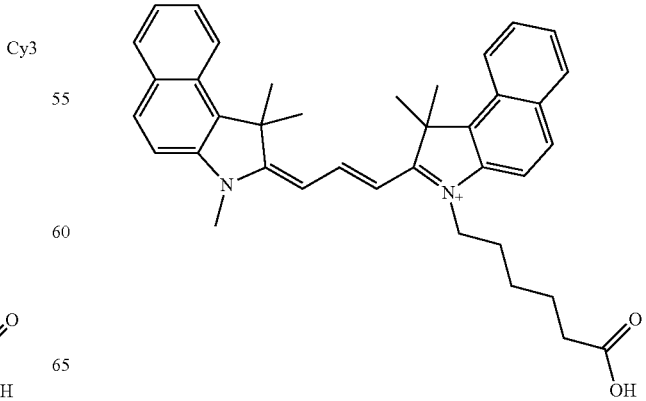

-continued

Cy5

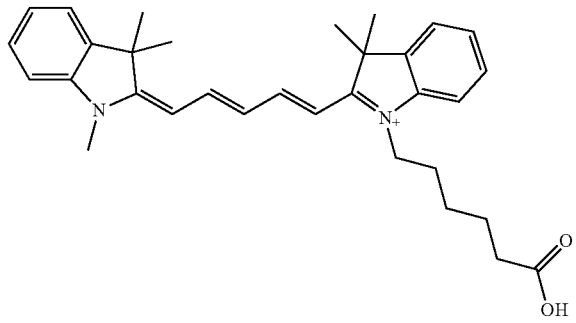

Cy7

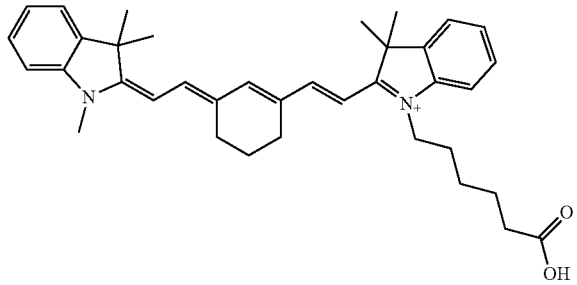

Cy3.5

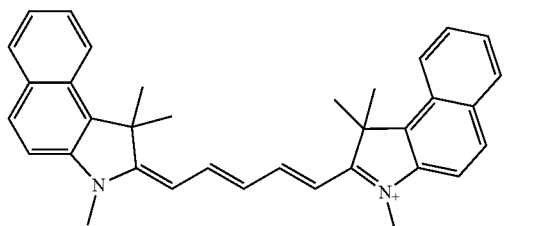
Cy5.5

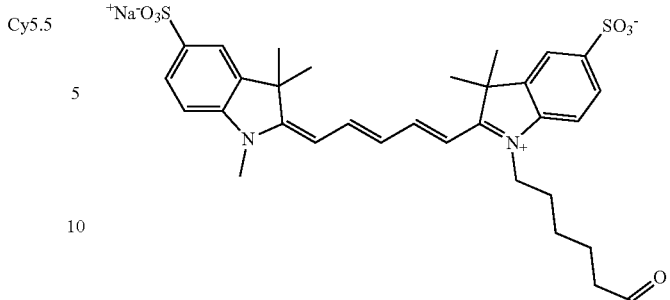
sulfo-Cy5

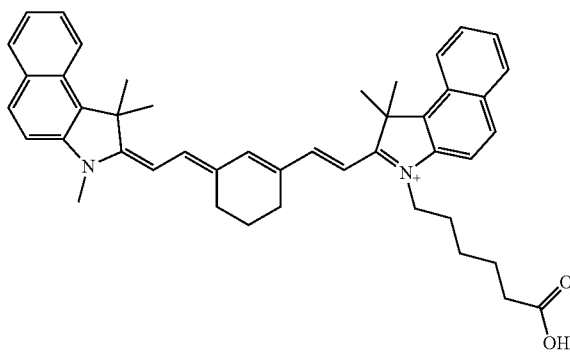
Cy7.5

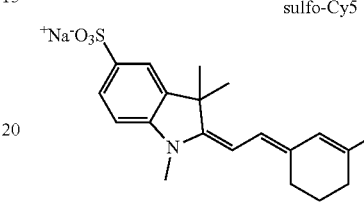
sulfo-Cy7

IR800
The structure of IR800 maleimide is as follows:

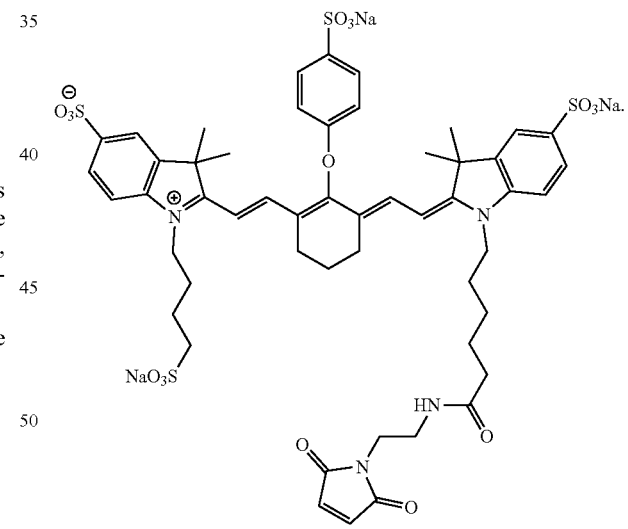

Sulfonated cyanines include additional sulfo-groups which, in some embodiments, facilitate dissolution of dye molecules in aqueous phase. In various embodiments, charged sulfonate groups decrease aggregation of dye molecules and heavily labeled conjugates.

Non-limiting examples of sulfonated cyanines include sulfo-Cy3, sulfo-Cy5, and sulfo-Cy7.

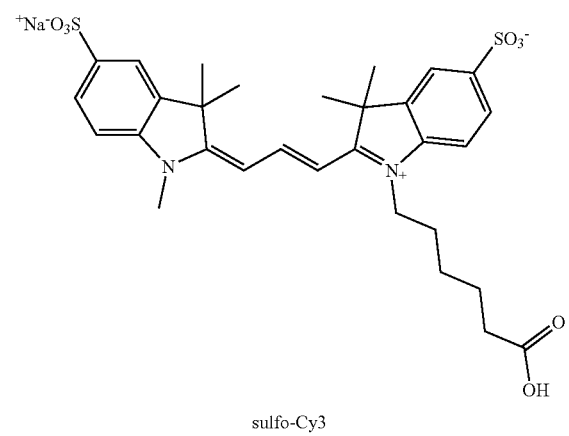
sulfo-Cy3

IR800 is also known as IRDye® 800CW Infrared Dye, and is available from LI-COR Biosciences (Nebraska, United States).

Click Reactions

Compounds described herein (e.g., pHLIP® peptides and compounds comprising multiple pHLIP® peptides) can include a covalent bond between the compound and a cargo compound, between a linker and a cargo compound, between a pHLIP® peptide and a linker, and between two pHLIP® peptides. In embodiments, a covalent bond has been formed by a bio-orthogonal reaction such as a cycloaddition reaction (e.g., a "click" reaction). Exemplary bio-orthogonal reactions suitable for the preparation for such compounds are described in, e.g., Zheng et al., "Development of Bioorthogonal Reactions and Their Applications in Bioconjugation," *Molecules*, 2015, 20, 3190-3205. The diversity and commercial availability of peptide precursors are attractive for constructing the multifunctional entities described herein. Described herein are exemplary, non-limiting click reactions suitable for, e.g., the preparation of pH-triggered peptide compounds that include a covalent bond between the peptide and a cargo compound.

Huisgen Cycloadditions

A category of click reactions includes Huisgen 1,3-dipolar additions of acetylenes to azides. See, e.g., Scheme 1.

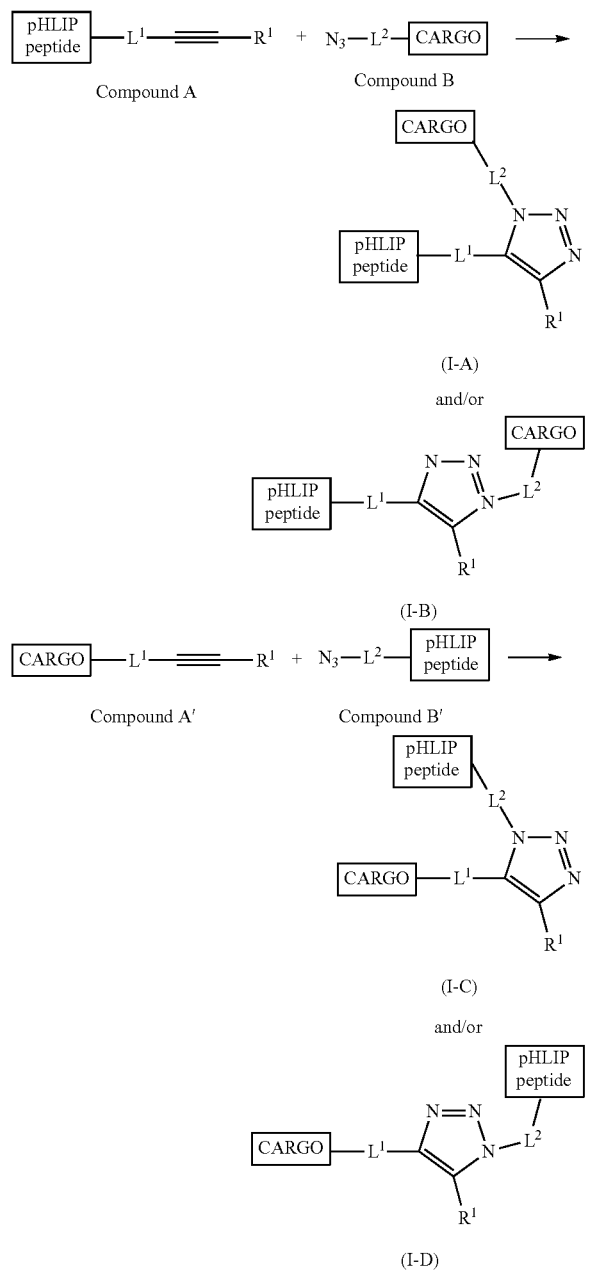

In embodiments, CARGO corresponds to any cargo compound (such as a fluorophore) described herein.

In embodiments, $L^1$ is independently a bond, $-NR^A-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ combines with $R^1$ to form a substituted or unsubstituted 8-membered cycloalkynylene ring, or $L^1$ comprises one or more amino acids as described herein.

In embodiments, $R^1$ is hydrogen, substituted or unsubstituted alkyl, or $R^1$ combines with $L^1$ to form a substituted or unsubstituted 8-membered cycloalkynylene ring, or $L^1$ comprises one or more amino acids as described herein.

In embodiments, $L^1$ combines with $R^1$ to form a substituted or unsubstituted 8-membered cycloalkynylene ring. In embodiments, the 8-membered cycloalkynylene ring is unsubstituted. In embodiments, the 8-membered cycloalkynylene ring comprises two fluoro substitutents (e.g., α to the alkynyl).

In embodiments, $L^2$ is independently a bond, $-NR^B-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

In embodiments, each $R^A$ and $R^B$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the Huisgen cycloaddition is that described in Scheme 2 and Scheme 3.

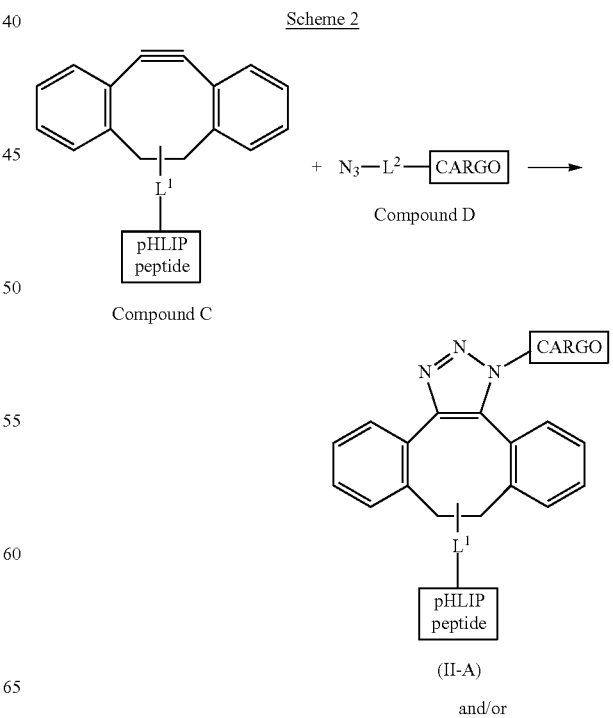

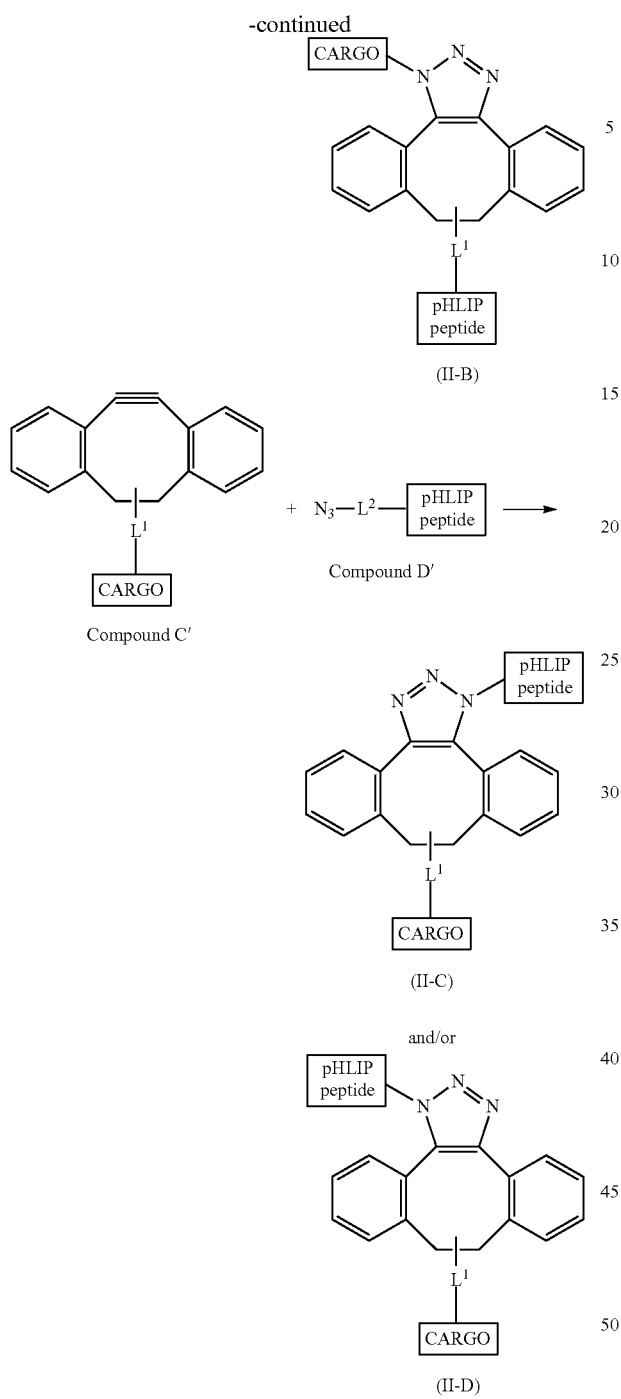
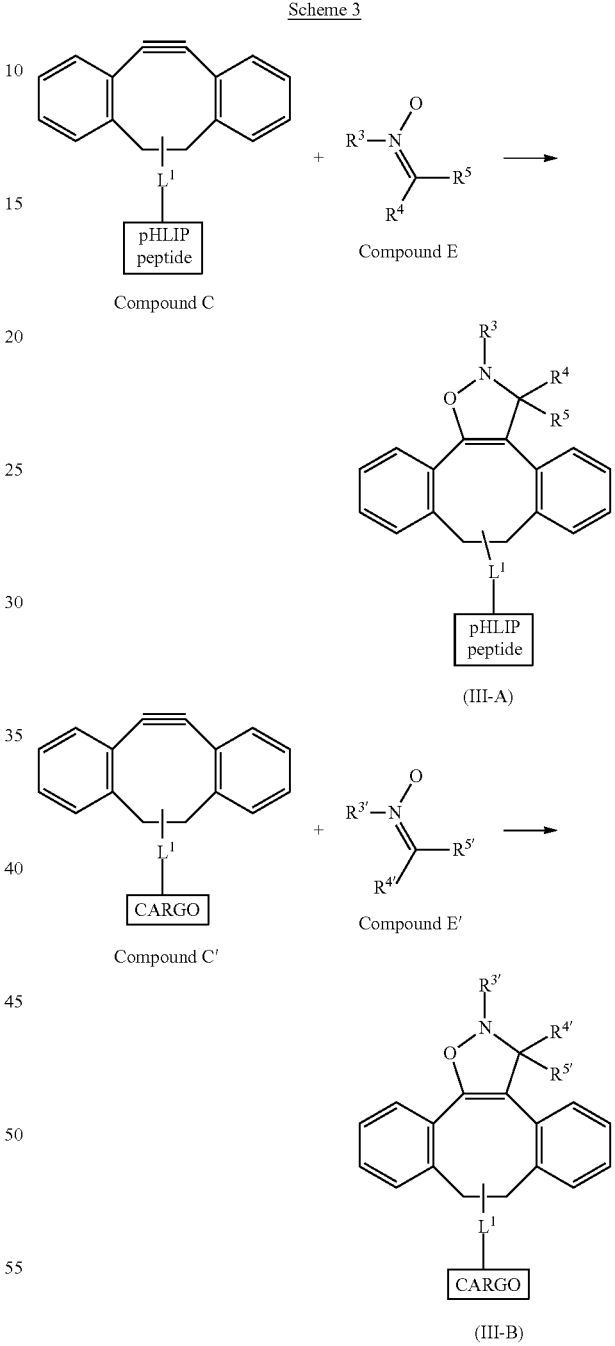

nylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

In embodiments, CARGO corresponds to any cargo compound (such as a fluorophore) described herein.

In embodiments, $L^1$ is independently a bond, —$NR^A$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, —$NR^B$—, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, one of $R^3$, $R^4$, and $R^5$ is a cargo compound, and the other two variables are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, one of $R^{3'}$, $R^{4'}$, and $R^{5'}$ is a pH-triggered peptide compound, the other two variables are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Cycloadditions with Alkenes

In embodiments, certain activated alkenes (e.g., a strained alkene such as cis- or trans-cyclooctene or oxanorbornadiene), which may be represented as compound F or compound F', can undergo cycloaddition reactions with, e.g., an azide (Scheme 4), a tetrazine (Scheme 5), or a tetrazole (Scheme 6).

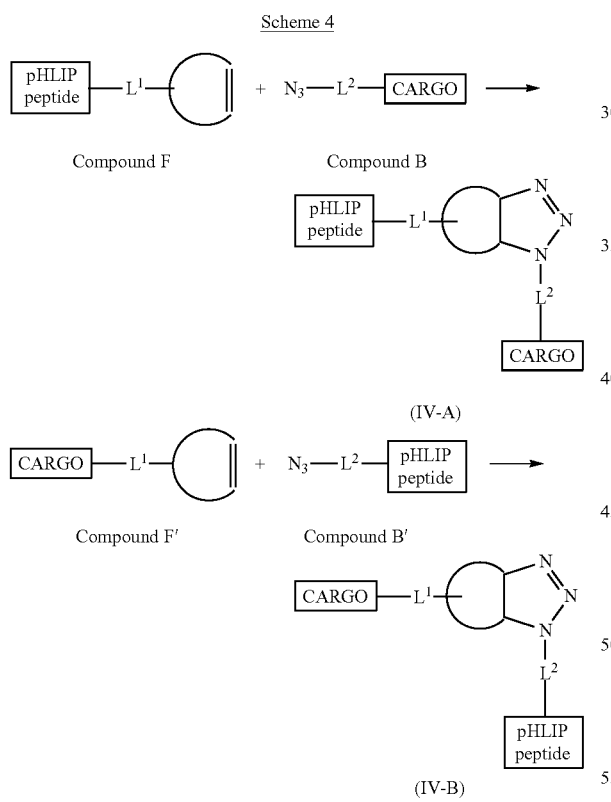

In embodiments, CARGO corresponds to any cargo compound (such as a fluorophore) described herein.

In embodiments, $L^1$ is independently a bond, $-NR^A-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, $-NR^B-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

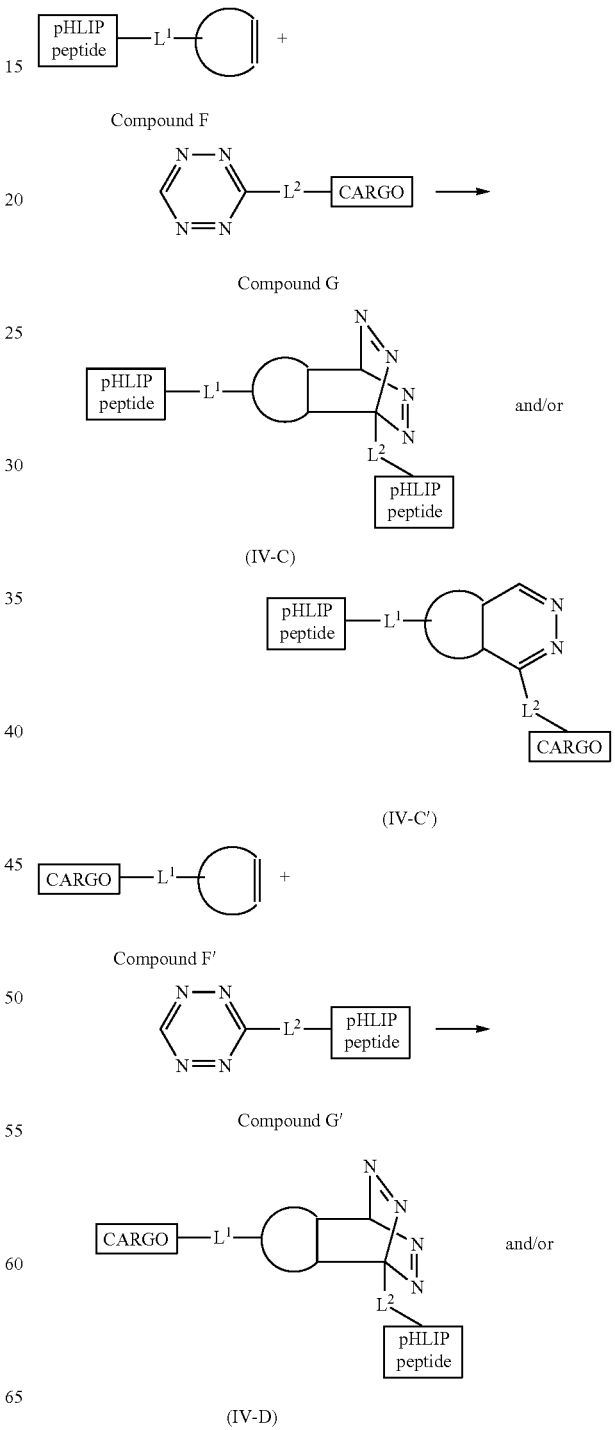

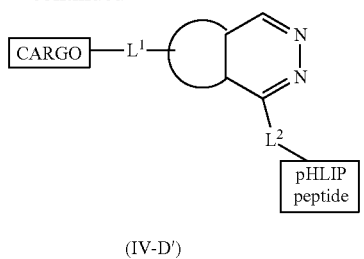

(IV-D')

In embodiments, CARGO corresponds to any cargo compound (such as a fluorophore) described herein.

In embodiments, $L^1$ is independently a bond, $-NR^A-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, $-NR^B-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

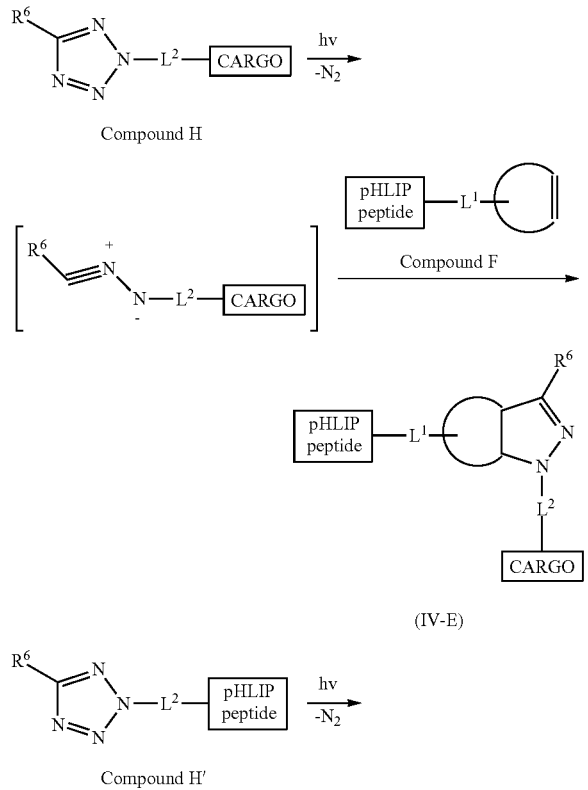

Scheme 6

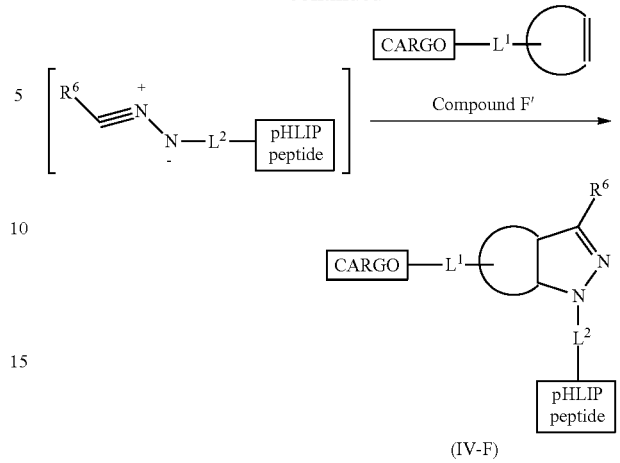

(IV-F)

In embodiments, CARGO corresponds to any cargo compound (such as a fluorophore) described herein.

In embodiments, $L^1$ is independently a bond, $-NR^A-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^1$ comprises one or more amino acids as described herein.

In embodiments, $L^2$ is independently a bond, $-NR^B-$, O, S, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or $L^2$ comprises one or more amino acids as described herein.

In embodiments, $R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the invention features any of the compounds described herein (e.g., any of Compounds A, A', B, B'; C, C', D, D', E, E', F, F', G, G'H, or H'; a compound according to any one of formulas (I-A), (I-B), (I-C), (I-D), (II-A), (II-B), (II-C), (II-D), (III-A), (III-B), (IV-A), (IV-B), (IV-C), (IV-C'), (IV-D), (IV-E), or (IV-F); a compound according to Formula (A) such as any one of Formulas (A4)-(A20); or a compound according to any of SEQ ID NOS: 1-4); or a pharmaceutically acceptable salt thereof.

In embodiments, the invention features a composition (e.g., a pharmaceutical composition) comprising any of the compounds described herein (e.g., any of Compounds A, A', B, B'; C, C', D, D', E, E', F, F', G, G'H, or H'; a compound according to any one of formulas (I-A), (I-B), (I-C), (I-D), (II-A), (II-B), (II-C), (II-D), (III-A), (III-B), (IV-A), (IV-B), (IV-C), (IV-C'), (IV-D), (IV-E), or (IV-F); a compound according to Formula (A) such as any one of Formulas (A4)-(A20); or a compound according to any of SEQ ID NOS: 1-4); or a pharmaceutically acceptable salt thereof.

The term "alkyl," by itself or as part of another substituent, means, unless otherwise stated, a non-cyclic straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom (e.g. selected from the group consisting of N, P, S, Se and Si, and wherein the nitrogen, selenium, and sulfur atoms may optionally be oxidized, and the nitrogen heteroatom may optionally be quaternized). The heteroatom(s) O, N, P, S, Se, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. selected from N, O, and S, wherein the nitrogen and sulfur atoms are optionally oxidized, and the nitrogen atom(s) are optionally quaternized). Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O) NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

As used herein, the terms "heteroatom" or "ring heteroatom" are meant to include oxygen (O), nitrogen (N), sulfur (S), phosphorus (P), and silicon (Si).

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

General Definitions

Unless specifically defined otherwise, all technical and scientific terms used herein shall be taken to have the same meaning as commonly understood by one of ordinary skill in the art (e.g., in medicine, cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" compound, nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure compound" is meant a compound that has been separated from the components that naturally accompany it. Typically, a compound is substantially pure when it is at least 60%, 70%, 80%, 90%, 95%, or even 99%, by weight, free from the proteins and naturally-occurring organic molecules with which the compound is naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Typically and depending on context, the terms "subject," "patient," "individual," and the like as used herein can be generally interchanged. That is, an individual described as a "patient" does not necessarily have a given disease, but may be merely seeking medical advice.

The term "subject" as used herein includes any animal including a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. In some embodiments, the subject is a mammal. In certain embodiments, the subject is a human.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic or imaging compound refers to the quantity of the compound that is sufficient to yield a desired result (e.g., therapeutic outcome or imaging signal strength) without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Various embodiments of the invention relate to pHLIP®-fluorophore compounds comprising a pHLIP® that is attached to a "cargo" such as a "fluorophore." Depending on context, the cargo may be referred to by a name or characteristic of an unconjugated form of the cargo regardless of whether the cargo is conjugated to a pHLIP® peptide. For example, a fluorophore known as "Fluorophore X" when in an unconjugated form may also be referred to herein as "Fluorophore X" when in a form that is bound to a pHLIP® peptide.

Examples and embodiments are provided below to facilitate a more complete understanding of the invention. The following examples and embodiments illustrate the exemplary modes of making and practicing the invention. However, the scope of the invention is not limited to specific examples and embodiments disclosed, which are for purposes of illustration only, since alternative methods can be utilized to obtain similar results.

EMBODIMENTS

Embodiments include the following embodiments P1 to P35.

Embodiment P1. A compound comprising (a) a pH-triggered polypeptide comprising amino acids in the sequence LFPTXTLL (SEQ ID NO: 1), wherein X is a protonatable amino acid, wherein the pH-triggered polypeptide has a higher affinity to a membrane lipid bilayer at pH 5.0 compared to at pH 8.0; and (b) indocyanine green (ICG),
wherein said ICG is covalently attached to the first or the second amino acid counted from the N-terminus of the pH-triggered polypeptide.

Embodiment P2. The compound of embodiment P1, wherein said pH-triggered polypeptide comprises amino acids in the sequence ADDQNPWRAYLDLL-FPTDTLLLDLLWG (SEQ ID NO: 2), and wherein said ICG is covalently attached to the N-terminal alanine thereof.

Embodiment P3. The compound of embodiment P2, comprising the following structure (SEQ ID NO: 2 is disclosed below):

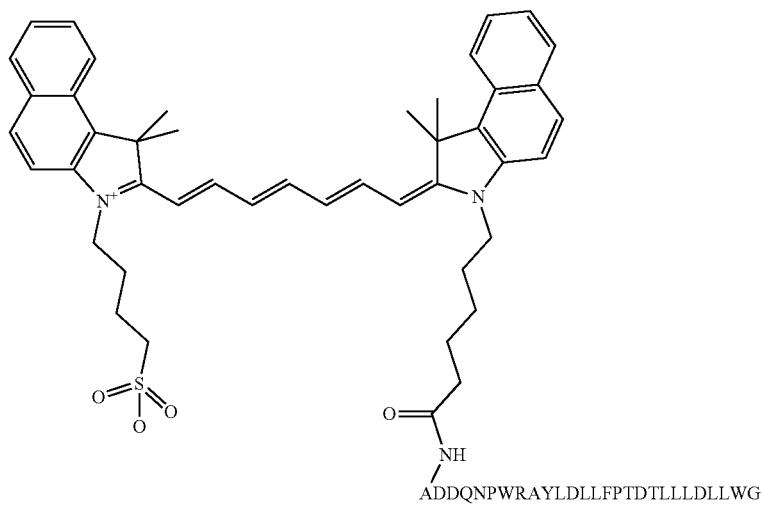

Embodiment P4. The compound of embodiment P1, wherein said pH-triggered polypeptide comprises amino acids in the sequence AKDDQNPWRAYLDLL-FPTDTLLLDLLWG (SEQ ID NO: 3), and wherein said ICG is covalently attached to the lysine thereof.

Embodiment P5. The compound of embodiment P4, comprising the following structure (SEQ ID NO: 3 is disclosed below):

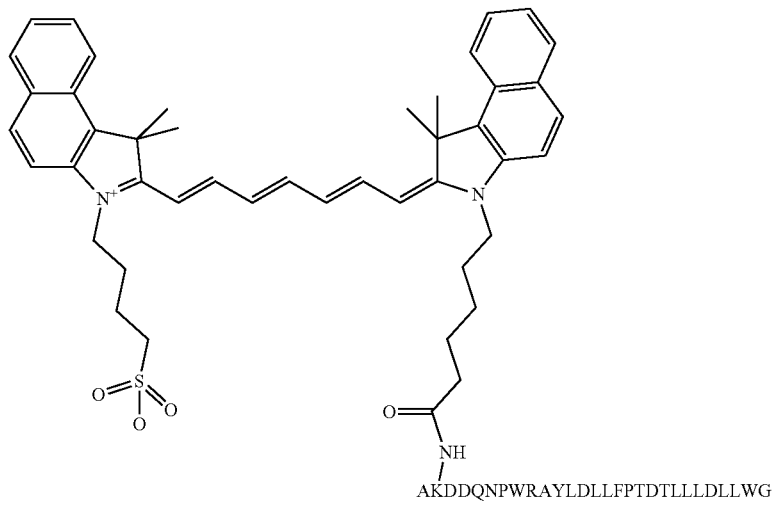

Embodiment P6. The compound of embodiment P1, wherein said pH-triggered polypeptide comprises amino acids in the sequence ACDDQNPWRAYLDLL-FPTDTLLLDLLWA (SEQ ID NO: 4), and wherein said ICG is covalently attached to the cysteine thereof.

Embodiment P7. The compound of embodiment P6, comprising the following structure (SEQ ID NO: 4 is disclosed below):

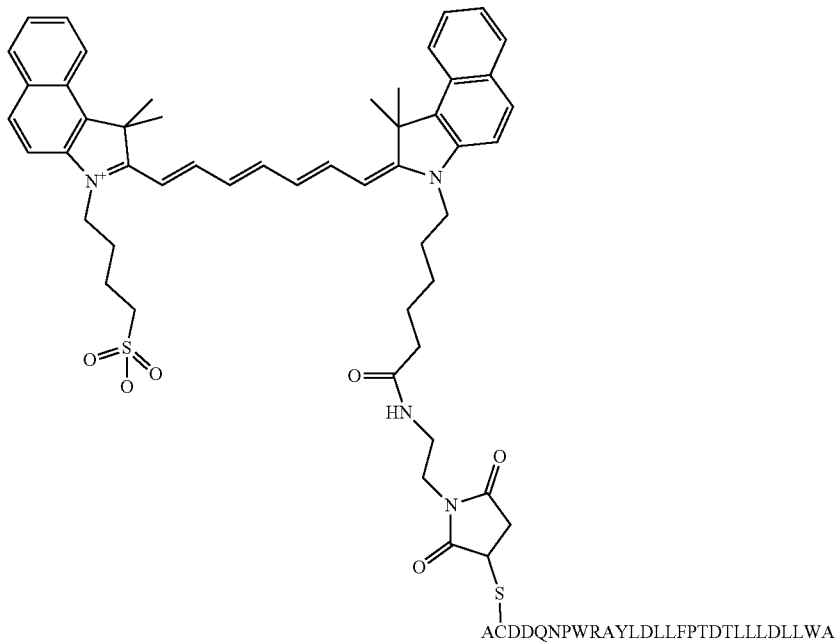

Embodiment P8. The compound of embodiment P1, wherein the pH-triggered polypeptide comprises an artificial protonatable amino acid.

Embodiment P9. The compound of embodiment P8, wherein the artificial protonatable amino acid comprises at least 1, 2, 3, 4 or 5 carboxyl groups.

Embodiment P10. The compound of any one of embodiments P1, P8, or P9, wherein the protonatable amino acid comprises aspartic acid or gamma-carboxyglutamic acid.

Embodiment P11. The compound of embodiment any one of embodiments P1-P10, wherein said pH-triggered polypeptide comprises amino acids in the sequence LLFPTDTLLL (SEQ ID NO: 25).

Embodiment P12. The compound of embodiment 11, wherein said pH-triggered polypeptide comprises amino acids in the sequence LDLLFPTDTLLLD (SEQ ID NO: 26).

Embodiment P13. The compound of embodiment 12, wherein said pH-triggered polypeptide comprises amino acids in the sequence AYLDLLFPTDTLLLDLL (SEQ ID NO: 27).

Embodiment P14. The compound of embodiment 13, wherein said pH-triggered polypeptide comprises amino acids in the sequence DDQNPWRAYLDLLFPTDTLLLD-LLW (SEQ ID NO: 28).

Embodiment P15. The compound of embodiment 14, wherein said pH-triggered polypeptide comprises amino acids in the sequence:

ADDQNPWRAYLDLLFPTDTLLLDLLWG, (SEQ ID NO: 2)

AKDDQNPWRAYLDLLFPTDTLLLDLLWG, (SEQ ID NO: 3)

ACDDQNPWRAYLDLLFPTDTLLLDLLWA, (SEQ ID NO: 4)

-continued

ADDQNPWRAYLDLLFPTDTLLLDLLWA, (SEQ ID NO: 5)

ADDQNPWRAYLDLLFPTDTLLLDLLWCA, (SEQ ID NO: 6)

ADDQNPWRAYLDLLFPTDTLLLDLLWKA, (SEQ ID NO: 7)

AKDDQNPWRAYLDLLFPTDTLLLDLLWA, (SEQ ID NO: 8)

ACDDQNPWRAYLDLLFPTDTLLLDLLWG, (SEQ ID NO: 9)

ADDQNPWRAYLDLLFPTDTLLLDLLWCG, (SEQ ID NO: 10)

ADDQNPWRAYLDLLFPTDTLLLDLLWKG, (SEQ ID NO: 11)

ACDDQNPWRAYLDLLFPTDTLLLDLLWKG, (SEQ ID NO: 12)

AKDDQNPWRAYLDLLFPTDTLLLDLLWCG, (SEQ ID NO: 13)
or

ACKDDQNPWRAYLDLLFPTDTLLLDLLWG. (SEQ ID NO: 14)

Embodiment P16. The compound of any one of embodiments P1 or P8-P11, wherein the amino acid sequence of said pH-triggered polypeptide is less than 100%, 99%, or 95% identical to each of the amino acid sequences set forth as SEQ ID NOS: 15-24.

Embodiment P17. The compound of any one of embodiments P1-P16, wherein said pH-triggered polypeptide comprises 20-30 amino acids.

Embodiment P18. A composition comprising the compound of any one of embodiments P1-P17 and a pharmaceutically acceptable carrier.

Embodiment P19. The composition of embodiment 18, further comprising D-glucose.

Embodiment P20. The composition of embodiment P18 or P19, wherein said composition comprises a mouthwash.

Embodiment P21. A method for detecting cancer tissue or precancerous tissue in a bodily organ or tissue, comprising
(a) contacting the bodily organ or tissue with the compound of any one of embodiments P1-P17;
(b) contacting said compound with electromagnetic radiation comprising an excitation wavelength of ICG; and
(c) detecting electromagnetic radiation emitted from said compound, wherein detection of said radiation indicates the presence of said cancerous tissue or said precancerous tissue.

Embodiment P22. The method of embodiment P21, wherein the level of radiation emitted from precancerous tissue or cancer tissue is at least 20% greater than a level of radiation emitted from normal non-cancerous tissue.

Embodiment P23. The method of embodiment P21 or P22, wherein said bodily organ comprises a kidney or a urinary bladder.

Embodiment P24. The method of any one of embodiments P21-P23, further comprising surgically removing said cancerous tissue or said precancerous tissue.

Embodiment P25. The method of embodiment 21, wherein said tissue has been obtained, removed, or provided from a subject.

Embodiment P26. The method of embodiment P21 or P25, wherein said tissue comprises a tissue biopsy.

Embodiment P27. The method of any one of embodiments P21-P24, wherein said bodily organ or tissue is present in a subject.

Embodiment P28. The method of any one of embodiments P21-P24, wherein contacting the bodily organ or tissue with the compound of any one of embodiments P1-P17 comprises administering the compound to a subject.

Embodiment P29. The method of embodiment P28, wherein the compound is administered to the subject via intravesical instillation, intravenous injection, intraperitoneal injection, topical administration, mucosal administration, or oral administration.

Embodiment P30. The method of embodiment P28 or P29, wherein said compound is administered by applying a liquid, powder, or spray comprising said compound to a surface of said subject.

Embodiment P31. The method of embodiment P30, wherein said surface comprises a site within the body of said subject that is accessed via surgery.

Embodiment P32. The method of embodiment P28 or P29, wherein said compound is administered to an oral cavity of said subject.

Embodiment P33. The method of any one of embodiments P21-P32, wherein electromagnetic radiation emitted from said compound is detected in vivo.

Embodiment P34. The method of any one of embodiments P21-P32, wherein electromagnetic radiation emitted from said compound is detected ex vivo.

Embodiment P35. A method for removing cancer tissue or precancerous tissue from a bodily organ or tissue, comprising surgically removing a cancer cell or a precancerous cell detected according to the method of any one of embodiments P21-P24 or P27-P34.

Further embodiments include the following embodiments 1 to 55.

Embodiment 1. A pHLIP®-fluorophore compound comprising
(a) a pH-triggered polypeptide (pHLIP® peptide); and
(b) a fluorophore, wherein the fluorophore is a near-infrared (NIR) fluorophore, a cyanine fluorophore, or an optoacoustic contrast imaging agent.

Embodiment 2. The compound of embodiment 1, having the structure (SEQ ID NO: 4 is disclosed below):

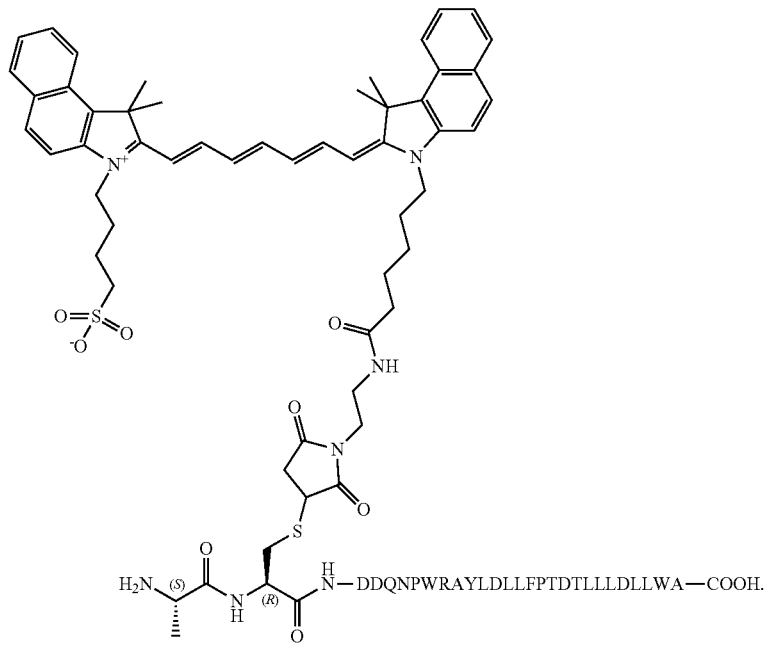

Embodiment 3. The compound of embodiment 1 or 2, wherein the pHLIP peptide comprises amino acids in the sequence LFPTXTLL (SEQ ID NO: 1), wherein X is a protonatable amino acid, and wherein the fluorophore comprises a NIR fluorophore.

Embodiment 4. The compound of any one of embodiments 1-3, wherein X is D.

Embodiment 5. The compound of any one of any one of embodiments 1-4, wherein the fluorophore comprises indocyanine green (ICG).

Embodiment 6. The compound of any one of embodiments 1-5, wherein the pHLIP® peptide comprises the sequence: $X_nY_m$; $Y_mX_n$; $X_nY_mX_j$; $Y_mX_nY_i$; $Y_mX_nY_iX_j$; $X_nY_mX_jY_i$; $Y_mX_nY_iX_jY_i$; $X_nY_mX_jY_iX_h$; $Y_mX_nY_iX_jY_iX_h$; $X_nY_mX_jY_iX_hY_g$; $Y_mX_nY_iX_jY_iX_hY_g$; $X_nY_mX_jY_iX_hY_gX_f$; $(XY)_n$; $(YX)_n$; $(XY)_nY_m$; $(YX)_nY_m$; $(XY)_nX_m$; $(YX)_nX_m$; $Y_m(XY)_n$; $Y_m(YX)_n$; $X_n(XY)_m$; $X_n(YX)_m$; $(XY)_nY_m(XY)_i$; $(YX)_nY_m(YX)_i$; $(XY)_nX_m(XY)_i$; $(YX)_nX_m(YX)_i$; $Y_m(XY)_n$; $Y_m(YX)_n$; $X_n(XY)_m$; $X_n(YX)_m$, wherein, i) Y is a non-polar amino acid with solvation energy, $\Delta G_X^{cor} > +0.50$, or Gly, ii) X is a protonatable amino acid, and iii) n, m, I, j, l, h, g, f are integers from 1 to 8.

Embodiment 7. The compound of any one of embodiments 1-6, wherein the pHLIP® peptide has a net negative charge at a pH of about 7.5 or 7.75 in water.

Embodiment 8. The compound of any one of embodiments 1-7, wherein the pHLIP® peptide has an acid dissociation constant at logarithmic scale (pKa) of less than about 4.0, 4.5, 5.5, 6.0, 6.5, or 7.

Embodiment 9. The compound of any one of embodiments 1-8, wherein the pHLIP® peptide comprises at least 1 artificial protonatable amino acid.

Embodiment 10. The compound of any one of embodiments 1-9, wherein the pHLIP® peptide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 40 genetically coded amino acids.

Embodiment 11. The compound of any one of embodiments 1 or 3-10, wherein the pHLIP® peptide comprises at least 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, or 40 non-genetically coded amino acids.

Embodiment 12. The compound of any one of embodiments 1 or 3-11, wherein the pHLIP® peptide comprises at least 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, or 40 D-amino acids.

Embodiment 13. The compound of any one of embodiments 1-12, wherein the pHLIP® peptide comprises at least 8 amino acids, wherein, at least 2, 3, or 4 of the 8 amino acids of the pHLIP® peptide are non-polar, and at least 1, 2, 3, or 4 of the at least 8 amino acids of the pHLIP® peptide are protonatable.

Embodiment 14. The compound of any one of embodiments 1, 3, 4, or 6-13, wherein the fluorophore a cyanine fluorophore.

Embodiment 15. The compound of any one of embodiments 1-14, wherein the fluorophore is a NIR fluorophore.

Embodiment 16. The compound of any one of embodiments 1-15, wherein the fluorophore comprises an optoacoustic contrast imaging agent.

Embodiment 17. The compound of any one of embodiments 1-16, comprising (a) a pHLIP® peptide comprising amino acids in the sequence LFPTXTLL (SEQ ID NO: 1), wherein X is a protonatable amino acid, wherein the pHLIP® peptide has a higher affinity to a membrane lipid bilayer at pH 5.0 compared to at pH 8.0; and (b) indocyanine green (ICG), wherein said ICG is covalently attached to the first or the second amino acid counted from the N-terminus of the pHLIP® peptide.

Embodiment 18. The compound of embodiment 17, wherein X is D.

Embodiment 19. The compound of embodiment 17 or 18, wherein said pHLIP® peptide comprises amino acids in the sequence ACDDQNPWRAYLDLLFPTDTLLLDLLWA (SEQ ID NO: 4) or ACDDQNPWRAYLDLLFPTDTLLLD-LLWG (SEQ ID NO: 9), and wherein said ICG is covalently attached to the cysteine thereof.

Embodiment 20. The compound of embodiment 19, comprising the following structure (SEQ ID NO: 9 is disclosed below):

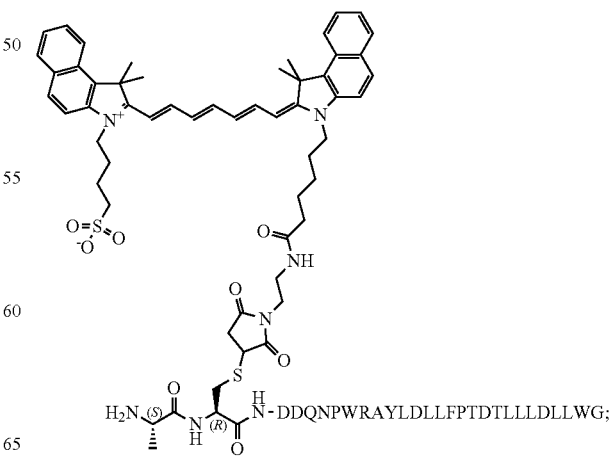

(SEQ ID NO: 4 is disclosed below) or

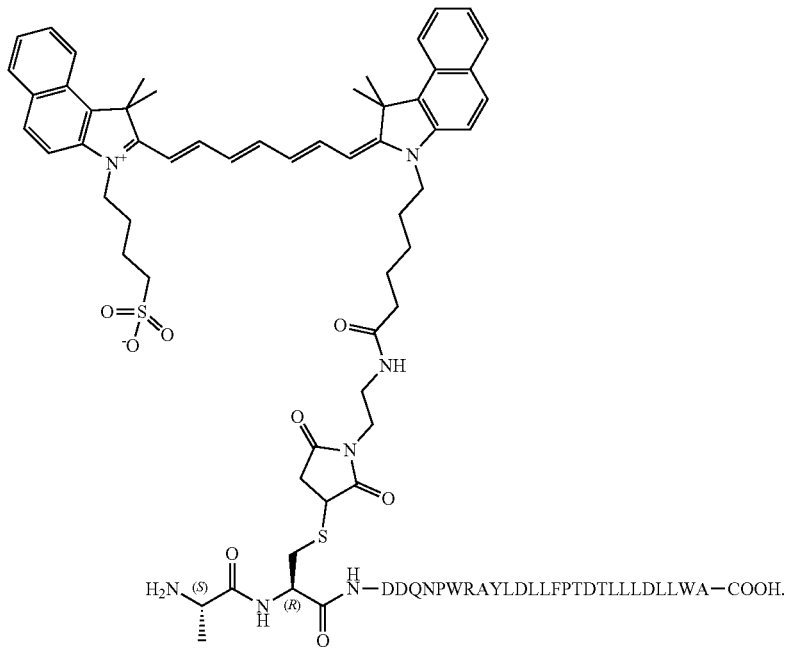

Embodiment 21. The compound of embodiment 17 or 18, wherein said pHLIP® peptide comprises amino acids in the sequence ADDQNPWRAYLDLLFPTDTLLLDLLWA (SEQ ID NO: 5) or ADDQNPWRAYLDLLFPTDTLLLD-LLWG (SEQ ID NO: 2), and wherein said ICG is covalently attached to the N-terminal alanine thereof.

Embodiment 22. The compound of embodiment 21, comprising the following structure (SEQ ID NO: 2 is disclosed below):

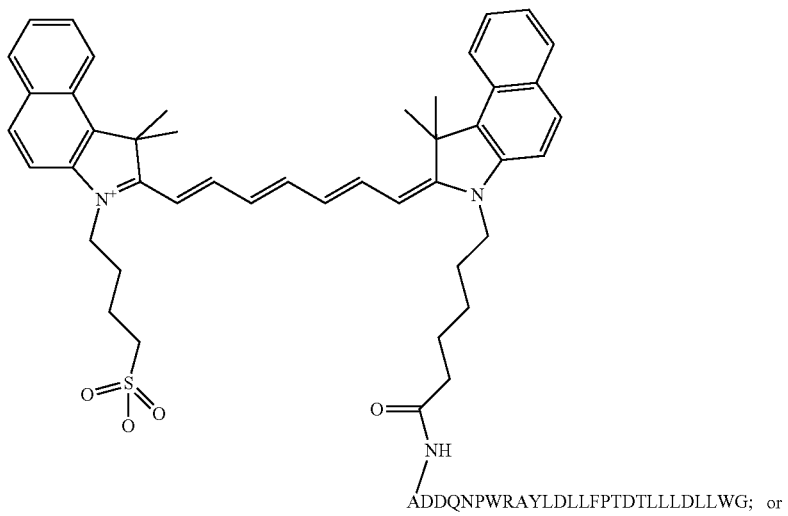

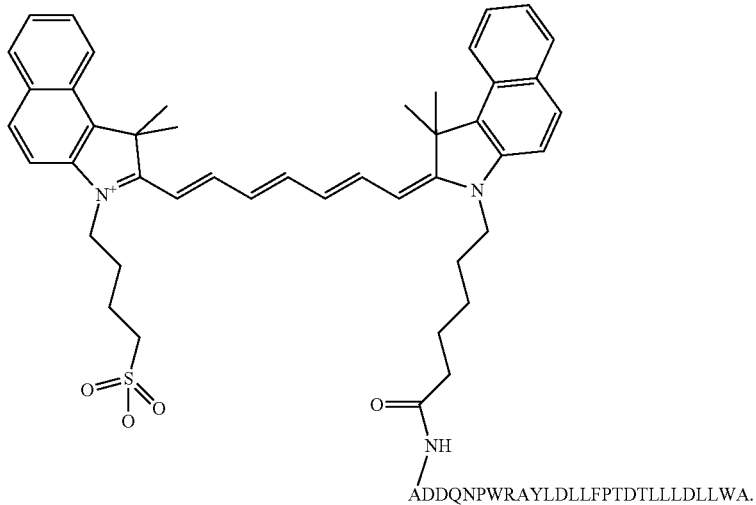

(SEQ ID NO: 5)
ADDQNPWRAYLDLLFPTDTLLLDLLWA.

Embodiment 23. The compound of embodiment 17 or 18, wherein said pHLIP® peptide comprises amino acids in the sequence AKDDQNPWRAYLDLLFPTDTLLLDLLWA (SEQ ID NO: 8) or AKDDQNPWRAYLDLLFPTDTLLLD-LLWG (SEQ ID NO: 3), and wherein said ICG is covalently attached to the lysine thereof.

Embodiment 24. The compound of embodiment 23, comprising the following structure (SEQ ID NO: 3 is disclosed below):

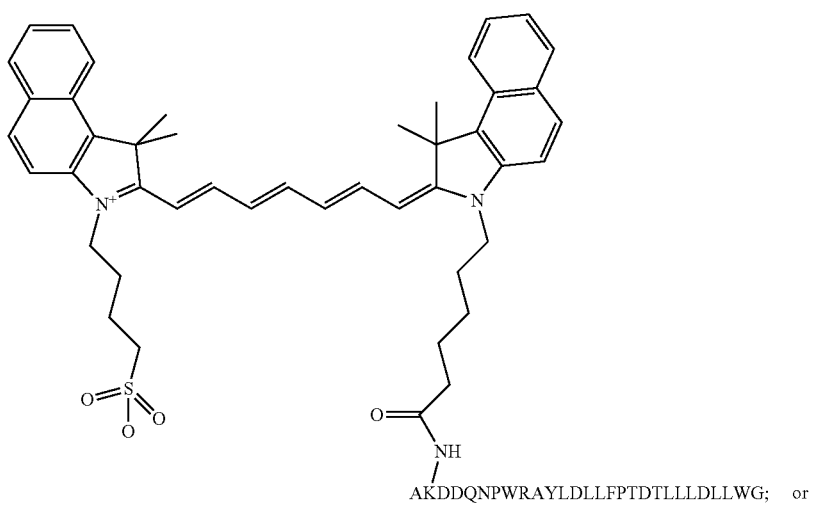

AKDDQNPWRAYLDLLFPTDTLLLDLLWG; or (SEQ ID NO: 8)

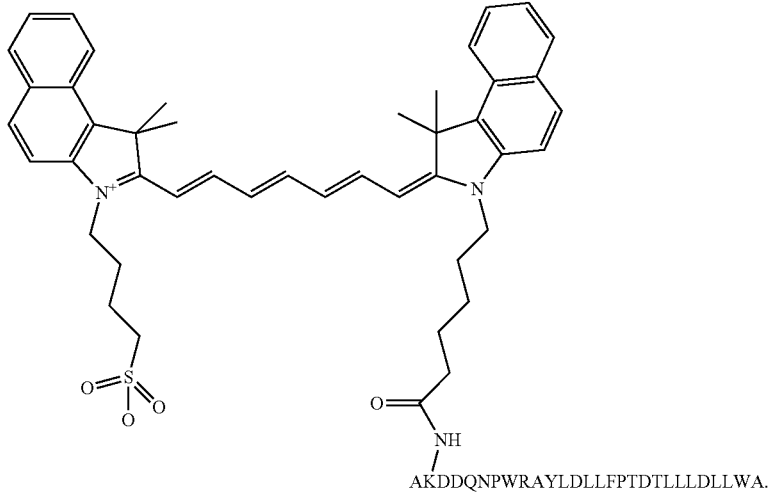

AKDDQNPWRAYLDLLFPTDTLLLDLLWA.

Embodiment 25. The compound of embodiment 17 or 18, wherein said pHLIP® peptide comprises amino acids in the sequence ACDDQNPWRAYLDLLFPTDTLLLDLLWA (SEQ ID NO: 4), and wherein said ICG is covalently attached to the cysteine thereof.

Embodiment 26. The compound of embodiment 25, comprising the following structure (SEQ ID NO: 4 is disclosed below):

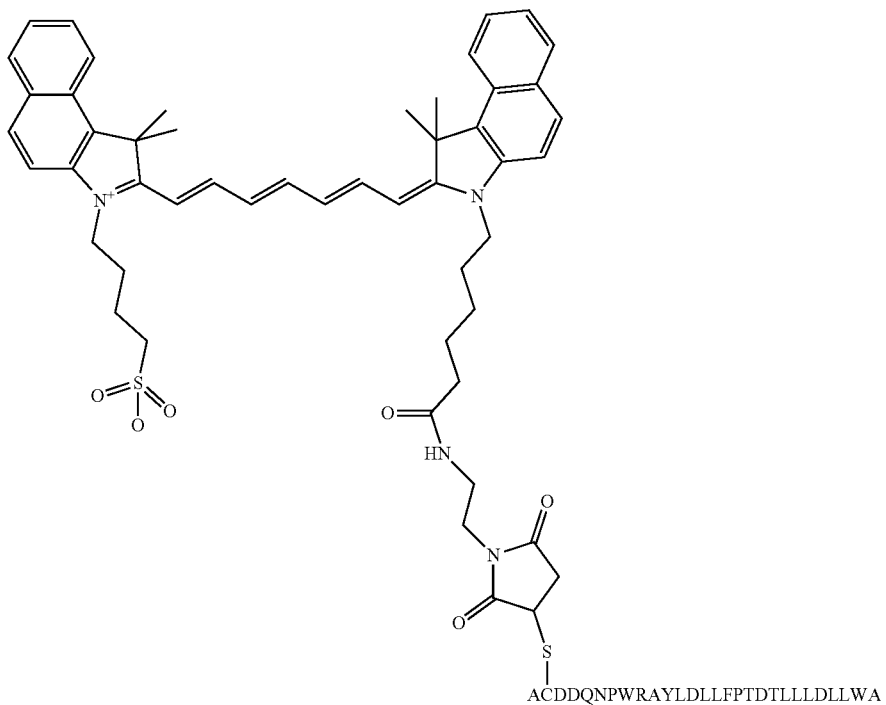

ACDDQNPWRAYLDLLFPTDTLLLDLLWA

Embodiment 27. The compound of embodiment 17 or 18, wherein the pHLIP® peptide comprises an artificial protonatable amino acid.

Embodiment 28. The compound of embodiment 27, wherein the artificial protonatable amino acid comprises at least 1, 2, 3, 4 or 5 carboxyl groups.

Embodiment 29. The compound of embodiment 17, wherein the protonatable amino acid comprises aspartic acid or gamma-carboxyglutamic acid.

Embodiment 30. The compound of any one of embodiments 17-29, wherein said pHLIP® peptide comprises amino acids in the sequence LLFPTDTLLL (SEQ ID NO: 25).

Embodiment 31. The compound of embodiment 30, wherein said pHLIP® peptide comprises amino acids in the sequence LDLLFPTDTLLLD (SEQ ID NO: 26).

Embodiment 32. The compound of embodiment 31, wherein said pHLIP® peptide comprises amino acids in the sequence AYLDLLFPTDTLLLDLL (SEQ ID NO: 27).

Embodiment 33. The compound of embodiment 32, wherein said pHLIP® peptide comprises amino acids in the sequence DDQNPWRAYLDLLFPTDTLLLDLLW (SEQ ID NO: 28).

Embodiment 34. The compound of embodiment 33, wherein said pHLIP® peptide comprises amino acids in the sequence:

```
                                      (SEQ ID NO: 4)
ACDDQNPWRAYLDLLFPTDTLLLDLLWA, (SEQ ID NO: 2)
ADDQNPWRAYLDLLFPTDTLLLDLLWG, (SEQ ID NO: 3)
AKDDQNPWRAYLDLLFPTDTLLLDLLWG, (SEQ ID NO: 5)
ADDQNPWRAYLDLLFPTDTLLLDLLWA, (SEQ ID NO: 6)
ADDQNPWRAYLDLLFPTDTLLLDLLWCA, (SEQ ID NO: 7)
ADDQNPWRAYLDLLFPTDTLLLDLLWKA, (SEQ ID NO: 8)
AKDDQNPWRAYLDLLFPTDTLLLDLLWA, (SEQ ID NO: 9)
ACDDQNPWRAYLDLLFPTDTLLLDLLWG, (SEQ ID NO: 10)
ADDQNPWRAYLDLLFPTDTLLLDLLWCG, (SEQ ID NO: 11)
ADDQNPWRAYLDLLFPTDTLLLDLLWKG, (SEQ ID NO: 12)
ACDDQNPWRAYLDLLFPTDTLLLDLLWKG, (SEQ ID NO: 13)
AKDDQNPWRAYLDLLFPTDTLLLDLLWCG,
or
                                      (SEQ ID NO: 14)
ACKDDQNPWRAYLDLLFPTDTLLLDLLWG.
```

Embodiment 35. The compound of any one of embodiments 17-34, wherein the amino acid sequence of said pHLIP® peptide is less than 100%, 99%, or 95% identical to each of the amino acid sequences set forth as SEQ ID NOS: 15-24.

Embodiment 36. The compound of any one of embodiments 17-35, wherein said pHLIP® peptide comprises 20-30 amino acids.

Embodiment 37. A composition comprising the compound of any one of embodiments 1-36 and a pharmaceutically acceptable carrier.

Embodiment 38. The composition of embodiment 37, further comprising D-glucose.

Embodiment 39. The composition of embodiment 37 or 38, wherein said composition comprises a mouthwash.

Embodiment 40. A method for detecting diseased or damaged tissue in subject, comprising
(a) administering the compound of any one of embodiments 1-36 to the subject;
(b) contacting the subject with electromagnetic radiation comprising an excitation wavelength of the fluorophore; and
(c) detecting electromagnetic radiation emitted from the compound, wherein detection of the radiation indicates the presence of the diseased tissue.

Embodiment 41. The method of embodiment 40, wherein the diseased or damaged tissue is cancer tissue, precancerous tissue, inflamed tissue, ischemic tissue, arthritic tissue, cystic fibrotic tissue, tissue infected with a microorganism, or atherosclerotic tissue.

Embodiment 42. The method of embodiment 41 or 41, wherein the diseased tissue is cancer tissue, and the cancer tissue is in the bladder, the upper urinary tract, a kidney, the prostate, a breast, the head, the neck, the oral cavity, the pancreas, a lung, the liver, the cervix, an ovary, or the brain of the subject.

Embodiment 43. The method of any one of embodiments 40-42, wherein the level of radiation emitted from precancerous tissue or cancer tissue is at least 20% greater than a level of radiation emitted from normal non-cancerous tissue.

Embodiment 44. The method of any one of embodiments 40-43, wherein said bodily organ comprises a kidney or a urinary bladder.

Embodiment 45. A method for detecting movement of a bodily fluid in subject, comprising
(a) administering the compound of any one of embodiments 1-36 to the subject;
(b) contacting the subject with electromagnetic radiation comprising an excitation wavelength of the fluorophore; and
(c) detecting electromagnetic radiation emitted from the compound, wherein detection of the radiation indicates the presence of the bodily fluid.

Embodiment 46. The method of embodiment 45, wherein the bodily fluid comprises blood.

Embodiment 47. The method of embodiment 46, wherein the blood is in circulation, within a bodily lumen, within a vessel lumen, within a capillary lumen, within a vein lumen, within an artery lumen, or within a solid tissue.

Embodiment 48. The method of embodiment 45, wherein the bodily fluid comprises lymph.

Embodiment 49. The method of any one of embodiments 40-48, wherein the compound is administered to the subject via intravesical instillation, intravenous administration, intraperitoneal administration, topical administration, mucosal administration, oral administration, intraarterial administration, intracerebral administration, intracerebroventricular administration, intrathecal administration, intracardiac administration, intracavernous administration, intraosseous administration, intraocular administration, intravitreal administration, intramuscular administration, intradermal administration, transdermal administration, transmucosal administration, intralesional administration, subcutaneous administration, epicutaneous administration, extra-amniotic administration, intravaginal administration, intravesical administration, or nasal administration.

Embodiment 50. The method of any one of embodiments 40-49, wherein said compound is administered by applying a liquid, powder, or spray comprising said compound to a surface of said subject.

Embodiment 51. The method of embodiment 50, wherein said surface comprises a site within the body of said subject that is accessed via surgery.

Embodiment 52. The method of any one of embodiments 40-51, wherein electromagnetic radiation emitted from said compound is detected in vivo.

Embodiment 53. The method of any one of embodiments 40-51, wherein electromagnetic radiation emitted from said compound is detected ex vivo.

Embodiment 54. The method of any one of embodiments 40-53, further comprising surgically removing a cancer or a precancerous cell or tissue identified by step (c).

Embodiment 55. The method of any one of embodiments 40-54, wherein the method comprises fluorescence angiography.

Embodiment 56. The method of any one of embodiments 40-55, which is performed during an ophthalmologic procedure, cardiothoracic surgery, bypass coronary surgery, neurosurgery, hepatobilliary surgery, reconstructive surgery, cholecystectomy, colorectal resection, brain surgery, muscle perfusion, wound or trauma surgery, or laparoscopic surgery.

Embodiment 57. A method for detecting a fluorophore in a biological sample ex vivo,
(a) contacting a biological sample from a subject with the compound of any one of embodiments 1-36;
(b) contacting the biological sample with electromagnetic radiation comprising an excitation wavelength of the fluorophore; and
(c) detecting electromagnetic radiation emitted from the fluorophore.

Embodiment 58. The method of embodiment 57, wherein the biological sample comprises a tissue biopsy specimen, a liquid biopsy specimen, surgically removed tissue, a surgically removed liquid, or blood.

EXAMPLES

Example 1: Targeted Imaging of Urothelium Carcinoma in Human Bladders by an ICG-pHLIP® Peptide (ICG-Var3) Ex Vivo Bladder cancer is the fifth most common in incidence and one of the most expensive cancers to treat. Early detection greatly improves the chances of survival and bladder preservation.

This report is the first study using an ICG-Var3 conjugate for the diagnosis of urothelial carcinoma and precancerous lesions in fresh human radical cystectomy samples ex vivo, and points the way toward a wide range of diagnostic and therapeutic alternatives.

A pHLIP® peptide labeled with a near-infrared fluorescence dye, ICG, was used to monitor the targeting of tumors in human bladders. The absorption spectrum of ICG-Var3 is shown in FIG. 1A. The fluorescence of ICG-Var3 increases about 25-fold in the presence of POPC liposomes (FIG. 1B). Thus, binding of ICG-Var3 to the lipid bilayers of cancerous cell membranes significantly enhances the emission of ICG.

Twenty two radical cystectomy patients were included in the study. Patient ages ranged from 51 to 84 (mean age 67.7 years), and the gender ratio: M/F was 19/3. Table 8 contains patient demographics, preoperative diagnosis, clinical stage of the disease and the results of imaging studies. The specimens did not show any adverse morphological findings after incubation with ICG-Var3, and there was no evidence of damage or degenerative effect in the non-tumoral tissue. The use of ICG-Var3 did not alter the pathological assessment of the radical cystectomy tissues. Overall, 29 malignant lesions were identified by pathology assessment of the 22 bladder specimens stained with ICG-Var3 (3 radical cystectomy cases were incubated ex vivo with ICG-Cys as negative controls). The frequencies of different pathologies in 29 lesions were as follows (FIG. 2A-L): high grade muscle invasive urothelial carcinoma (HGI) in 12; high grade non-muscle invasive urothelial carcinoma (HGN) in 5; carcinoma in situ (CIS) in 11, and high grade dysplasia in 1. In 7 cases near-infrared fluorescence imaging guided the pathologist to CIS not observed by white light inspection. In case #2 necrotic tissue inside a diverticulum was near-infrared fluorescence positive. For the negative control cases (cases #13, 19 and 20) only the ICG-Cys dye alone was used for instillation (at concentrations from 8 to 40 μM in an 80 ml volume), and no specific tumor targeting was observed.

The tabular results of the sensitivity/specificity tests are shown in Tables 9-10. The test was performed for cancerous versus normal tissue excluding targeting of necrotic and previously treated tissue (Tables 9A and 9B). The sensitivity and specificity of targeting of cancerous tissue versus normal were found to be 97% and 100%, respectively. If targeting of necrotic tissue from prior post trans-urethral removal of bladder tumors and previously treated (chemotherapy) necrotic tumors by ICG-Var3 is considered as a false positive, the specificity is reduced from 100% to 80% (Tables 10a and 10b).

ICG-Var3 Constructs Distinguish Cancer Cells from Normal Cells with High Sensitivity and Specificity An ICG-Var3 construct was used to target urothelial carcinoma in human bladder specimens immediately after surgical removal. ICG is an FDA approved near-infrared fluorescence dye that does not show any independent propensity for targeting neoplastic tissue as seen in renal cell carcinoma, mostly by perfusion and diffusion differences or neoplastic and normal tissue (washout). ICG is in clinical use to visualize vasculature or lymphatics (Tobis et al. (2012) J Endourol 26(7):797-802; Alander et al. (2012) Int J Biomed Imaging 2012:940585; Desmettre et al. (2000) Surv Ophthalmol 45(1):15-27). ICG has a low level of fluorescence in aqueous solution, while its emission increases upon binding to hydrophobic pockets of proteins (such as albumin) or cellular membranes. Targeting by the pHLIP® peptide is based on low pH-triggered insertion into the lipid bilayers of cancer cell membranes. Thus, the pHLIPO peptide tethers the ICG to the membrane, enhancing ICG fluorescence by about 25 fold.

To avoid/minimize targeting of normal cells by the ICG-Var3 peptide, the construct was instilled in pH 7.4 PBS supplemented with 10 mM of D-glucose to promote the uptake of the ICG-Var3 peptide by cancer cells. Glycolytic cancer cells exhibit high glucose uptake, which enhances acidification of the extracellular space in vitro and in vivo (Kozin et al. (2001) Cancer Res 61(12):4740-4743). Thus, our goal was to selectively promote increased acidity at cancer cell surfaces to enhance pHLIPO peptide insertion and targeting, while not affecting normal cells with normal metabolism.

A mixture of different subtypes of urothelial carcinoma was used, given that the disease had advanced to the point where the bladder had to be removed. These cases included typical high grade urothelial carcinoma but also had different variants with prominent squamous cell differentiation, micropapillary urothelial carcinoma, adenocarcinoma and plasmacytoid morphology. The sensitivity (97%) and specificity (100%) of tumor targeting by ICG-Var3 peptide was found to be irrelevant to the subtype of tumor. Half of the cystectomy specimens examined revealed evidence of necrosis and effects from prior treatments, and all revealed evidence of residual tumor (invasive or in-situ) adjacent and associated with necrosis, which was targeted by ICG-Var3 peptide, possibly from entrapment or uptake of ICG by necrotic areas. Previous studies did not show targeting of necrotic tissue by pHLIPO peptides in animal tumor models (Adochite et al. (2014) Mol Pharm 11(8):2896-2905). If targeting of necrotic and previously treated tissues are considered as false positives, the specificity is decreased to 80%, but no false positives were seen for unperturbed lesions.

One lesion gave a positive near-infrared fluorescence imaging signal in the presence of dysplasia, revealed by subsequent pathology analysis. Urothelial dysplasia is an incidental microscopic finding where urothelial cells show mild atypical features short of the diagnosis of carcinoma in situ. It is considered a pre-cancerous process and studies have shown that up to 19% of urothelial dysplasia cases develop urothelial carcinoma (Althausen et al. (1976) J Urol 116(5):575-580; Smith et al. (1983) Br J Urol 55(6):665-669; Zuk et al. (1988) J Clin Pathol 41(12):1277-1280). Although precancerous, it is recommended that patients with dysplasia receive proper clinical follow up for early detection of an imminent carcinoma. Dysplasia has not been clinically detectable, so the ICG-Var3 peptide may be a useful marker for detection of high grade dysplasia in urothelium, allowing early detection of precancerous lesions.

Bladder tissues are prone to inflammation and infection. Long standing inflammation and severe infections can cause transformations in the mucosa like cystitis cystica and cystitis glandularis that, due to high frequency, are considered normal findings in the urothelium. In one case, an area with marked uptake of ICG-Var3 peptide showed cystitis cystica et glandularis with chronic inflammation without any evidence of dysplasia or malignancy. It is noteworthy that almost all 22 cystectomy specimens revealed some degree of cystitis cystica et glandularis somewhere in the specimen. Only two lesions revealed cystitis cystica without any other pathology: one lesion (case #9) showed positive signal with ICG-Var3 peptide. When the instilled concentration of ICG-Var3 peptide was reduced to 4 the cystitis cystica in the second case (case #18) was not stained. Reducing the concentration of ICG-Var3 peptide did not affect targeting of high grade invasive carcinoma and CIS (case #17). Optimizing the concentration and shortening the time of the ICG-Var3 instillation allows a clear signal differentiation among inflamed, necrotic and cancerous tissue.

The ICG-Var3 peptide is a useful tool for the early detection of urothelial carcinoma, regardless of subtype, with high sensitivity and specificity. In various embodiments, the detection is used for monitoring the state of disease and/or for marking lesions for surgical removal. In some embodiments, the ICG-Var3 imaging agent improves diagnosis and resection of cancerous lesions in the bladder. In certain embodiments, the recurrence rate is reduced, patient outcomes are improved, and the cost of medical care for bladder cancer is lowered. In various embodiments, success with targeted imaging facilitates pHLIP® delivery of therapeutic molecules to bladder tumor cells, enabling the targeted treatment (e.g., the specific delivery of chemotherapeutic agents) of bladder cancers.

Without being bound by any theory, the ICG-Var3 construct is a generally applicable imaging agent, because it targets a general property of the tumor microenvironment, tumor acidity. Fluorescent pHLIP®s have been shown to target primary tumors and metastatic lesions by in more than 15 varieties of human, murine, and rat tumors, including lymphoma, melanoma, pancreatic, breast, and prostate transgenic mouse models and human tissue (bladder, kidney, upper urinary tract, breast, liver, oral and head/neck stained ex vivo).

TABLE 8

Demographic information, pathological stage and diagnosis, lesions seen by white light and fluorescence imaging.

| Case # | Sex Age | Pathological stage | Pathological diagnosis | Grade | Lesion number | White light diagnosis | Fluor. |
|---|---|---|---|---|---|---|---|
| 1 | M/63 | pT3aN1 | Infiltrating high grade urothelial carcinoma, CIS & necrosis | HGI | 1 | + | + |
| 2 | M/61 | pT0N0 | Diverticulum with urothelial atypia & treatment effects | — | — | + | + |
| 3 | F/84 | ypT3bN0 | Invasive high grade urothelial carcinoma | HGI | 2 | + | + |
|   |   |   | Invasive high grade urothelial carcinoma & necrosis | HGI | 3 | + | + |
| 4 | M/51 | pT2aN1 | Residual infiltrative high grade urothelial carcinoma micropapillary features, dysplasia & necrosis | HGI | 4 | + | + |
| 5 | M/69 | pTaN0 | Non-invasive high grade papillary carcinoma | HGN | 5 | + | + |
| 6 | M/65 | pT1N0 | Residual invasive high grade urothelial carcinoma, CIS & necrosis | HGI | 6 | + | + |
|   |   |   | CIS | CIS | 7 | + | + |
|   |   |   | CIS | CIS | 8 | + | + |
| 7 | M/61 | pT1N0 | Focally invasive high grade urothelial carcinoma, necrosis | HGI | 9 | + | + |
| 8 | M/79 | pT1N0 | Dysplasia | DIS | 10 | − | + |
|   |   |   | Treatment effect & CCCG | — | — | − | + |
| 9 | M/74 | pT0N0 | CCCG | — | — | − | + |
| 10 | F/82 | pT1N0 | Non-invasive high grade urothelial carcinoma | HGN | 11 | + | + |
|   |   |   | Invasive high grade urothelial carcinoma | HGI | 12 | + | − |
|   |   |   | CIS | CIS | 13 | − | + |
|   |   |   | CIS & CCCG | CIS | 14 | − | + |
| 11 | M/68 | pTisN0 | CIS & CCCG | CIS | 15 | + | + |
|   |   |   | CIS | CIS | 16 | − | + |
| 12 | M/71 | pTisN0 | Non-invasive high grade urothelial carcinoma | HGN | 17 | + | + |
|   |   |   | Non-invasive high grade urothelial carcinoma | HGN | 18 | + | + |
|   |   |   | CIS | CIS | 19 | − | + |
|   |   |   | CIS | CIS | 20 | − | + |
| 13* | M/66 | pT3N1 | Invasive high grade urothelial carcinoma |   |   | + | ICG-Cys |
|   |   |   | Ulceration, necrosis, CCCG |   |   | + |   |
| 14 | M/66 | pT1N0 | Non-invasive high grade urothelial carcinoma | HGN | 21 | + | + |
| 15 | M/57 | pT1N0 | Invasive high grade urothelial carcinoma | HGI | 22 | + | + |
| 16 | F/77 | pTisN0 | CIS with early invasion | CIS | 23 | + | + |
|   |   |   | CIS with early invasion | CIS | 24 | − | + |
| 17** | M/57 | pT1bN0 | Invasive high grade urothelial carcinoma | HGI | 25 | + | + |
|   |   |   | CIS with early invasion | CIS | 26 | + | + |
|   |   |   | Necrosis & treatment effect | — | — | + | + |

TABLE 8-continued

Demographic information, pathological stage and diagnosis, lesions seen by white light and fluorescence imaging.

| Case # | Sex Age | Pathological stage | Pathological diagnosis | Grade | Lesion number | White light diagnosis | Fluor. |
|---|---|---|---|---|---|---|---|
| 18** | M/72 | pT3aN0 | Invasive high grade urothelial carcinoma, CIS | HGI | 27 | + | + |
|  |  |  | Necrosis & treatment effect in diverticulum | — | — | + | − |
| 19 | M/64 | pT2aN0 | Invasive high grade urothelial carcinoma, CIS, Necrosis & treatment effect |  |  | + | ICG-Cys |
| 20 | M/63 | ypT0N0 | CCCG and reactive changes in scar |  |  | + | ICG-Cys |
| 21 | M/74 | pT3aN0 | Invasive high grade urothelial carcinoma in scar | HGI | 28 | + | + |
|  |  |  | Necrosis | — | — | + | + |
| 22** | M/66 | ypT3aN0 | Invasive high grade urothelial carcinoma with neuroendocrine features | HGI | 29 | + | + |

*40 μM of 80 mL of the construct was used for instillation
**4 μM of 80 mL of the construct was used for instillation

TABLE 9A

Tabular results of the sensitivity/specificity test of ICG-Var3 peptide targeting of cancerous lesions in the human bladder specimens: Carcinoma versus Normal excluding necrotic tissue and treatment effects.

| Receiver operator characteristics carcinoma vs normal | TP + FN | FP + TN | Sum |
|---|---|---|---|
| TP + FP | TP, 28 | FP, 0 | 28 |
| FN + TN | FN, 1 | TN, 19 | 20 |
| Sum | 29 | 19 |  |

TP is the true positive; TN is the true negative; FP is the false positive; FN is the false negative

TABLE 9B

Descriptive parameters

| Measure | Results |
|---|---|
| Sensitivity, TRP | 0.966 |
| Specificity, SPC | 1.000 |
| Positive predictive value, PPV | 1.000 |
| Negative predictive values, NPV | 0.950 |
| False positive rate, FPR | 0.000 |
| False negative rate, FNR | 0.034 |
| False discovery rate, FDR | 0.000 |
| False omission rate, FOR | 0.053 |

TABLE 10A

Tabular results of the sensitivity/specificity test of ICG-Var3 peptide targeting of cancerous lesions in the human bladder specimens: Carcinoma versus Normal including necrotic tissue and treatment effects.

| Receiver operator characteristics carcinoma vs normal + necrosis | TP + FN | FP + TN | Sum |
|---|---|---|---|
| TP + FP | TP, 28 | FP, 5 | 33 |
| FN + TN | FN, 1 | TN, 20 | 21 |
| Sum | 29 | 25 |  |

TP is the true positive; TN is the true negative; FP is the false positive; FN is the false negative

TABLE 10B

Descriptive parameters

| Measure | Results |
|---|---|
| Sensitivity, TRP | 0.966 |
| Specificity, SPC | 0.800 |
| Positive predictive value, PPV | 0.848 |
| Negative predictive values, NPV | 0.952 |
| False positive rate, FPR | 0.020 |
| False negative rate, FNR | 0.034 |
| False discovery rate, FDR | 0.152 |
| False omission rate, FOR | 0.040 |

Materials and Methods

Conjugation of ICG with the pHLIP® Peptide

A pHLIP® variant 3 (Var3) peptide with a single Cys residue at the N-terminus, ACDDQNPWRAYLDLL-FPTDTLLLDLLWA (SEQ ID NO: 4), was synthesized and purified by reversed phase chromatography by CS Bio, Inc (Menlo Park, California, USA). The near infrared fluorescent dye, indocyanine green (ICG) maleimide (Intrace Medical, Lausanne, Switzerland), was conjugated to the pHLIP® peptide at a ratio of 1:1 in DMF (dimethylformamide). The reaction progress was monitored by the reversed phase (Zorbax SB-C18 columns, 9.4×250 mm 5 Agilent Technology) high-performance liquid chromatography (HPLC) using a gradient from 5-70% acetonitrile in water containing 0.05% trifluoroacetic acid. Also, for the negative control, ICG-maleimide was conjugated with the free amino acid, L-cysteine (Sigma). The concentration of labeled peptide in buffer was determined by ICG absorption at 800 nm, $\varepsilon_{800}=137,000$ $M^{-1}$ $cm^{-1}$. The purity of the constructs was performed by analytical HPLC and SELDI-TOF mass spectrometry, the amount of free dye in the solution was less than 1%.

Liposome Preparation

Large unilamellar vesicles were prepared by extrusion. 2.5 mg POPC (Avanti Polar Lipids, Inc.; Alabaster, Alabama) lipids were dissolved in 0.5 ml chloroform, desolvated on a rotary evaporator and dried under high vacuum for 3 hours. The phospholipid film was then rehydrated in pH 7.4 PBS containing 10 mM D-glucose, vortexed for 5 minutes, and repeatedly extruded at least 15 times through a membrane with a 100 nm pore size.

Absorption and Fluorescence Measurements

Absorbance and fluorescence measurements were carried out on a Genesys 10S UV-Vis spectrophotometer (Thermo Scientific) and a SpectraMax M2 spectrofluorometer (Molecular Devices), respectively. The absorption spectra were measured in PBS pH 7.4 containing 10 mM D-glucose from 600 to 850 nm. The fluorescence spectra of 10 µM of ICG-Var3 peptide were measured from 810 to 850 nm at 790 nm excitation wavelength in PBS pH 7.4 containing 10 mM D-glucose, with or without 2 mM of POPC liposomes.

Ex Vivo Imaging of Bladder Specimens 22 urothelial carcinoma patients that were scheduled for radical cystectomy were selected over a twelve month period. After radical cystectomy, bladder specimens were immediately removed and irrigated 3 times for 5 min via catheter with non-buffered saline and instilled and incubated with 80 ml of 8 µM or 32.8 µg/ml (unless otherwise is stated, see notes to Table 8) of ICG-Var3 construct or ICG-Cys in PBS pH 7.4 containing 10 mM D-glucose for 60 minutes. Then, the unbound constructs were removed by rinsing with 80 ml of saline solution 3-5 times, the bladder was irrigated thoroughly with buffered saline and opened using a Y incision on the anterior wall. Using a da Vinci Si near-infrared fluorescence imaging system (Firefly®), ex vivo fluorescent and white light imaging of the entire bladder and its parts was performed. The fluorescent spots were marked and standard pathological analysis was carried out to explore the correlation between appearance of fluorescent signal and cancer lesions.

Pathological Analysis

The specimen was sectioned and submitted after 24 hour fixation in 10% phosphate-buffered formalin according to the standard institutional grossing manual, with emphasis on the marked areas of the bladder. The sections were processed for routine histology into paraffin-embedded blocks. Five micrometer thick tissue sections were obtained and stained for hematoxylin and eosin (H&E). Evaluation of pathology was performed by a genitourinary (GU) pathologist, and a standard report was prepared based on the American Joint Committee on Cancer (AJCC) Cancer Staging Manual, 7th edition, 2010.

Statistical Analysis

Statistical parameters were calculated according to the following equations:

$$TRP = \frac{TP}{TP+FN}; SPC = \frac{TN}{TN+FP}$$
$$PPV = \frac{TP}{TP+FP}; NPV = \frac{TN}{FN+TN};$$
$$FPR = \frac{FP}{FP+TN}; FNR = \frac{FN}{TP+FN};$$
$$FDR = \frac{FP}{TP*FP}; FOR = \frac{FN}{FP+TN}$$

Where TP is the true positive; TN is the true negative; FP is the false positive; FN is the false negative; TRP is the true positive rate or sensitivity; SPC is the true negative rate or specificity; PPV is the positive predictive value or precision; NPV is the negative predictive values; FPR is the false positive rate; FNR is the false negative rate; FDR is the false discovery rate; FOR is the false omission rate.

Example 2: Visualization and Detection of Cancerous Lesions

Visualization and detection of cancerous lesions in human body by systemic administration of a fluorescent or an optoacoustic imaging agents is very important and could be used to guide resection of tumors and detection/resection of lymph nodes with metastasized cancer cells. The main goal of the following study was investigation of ability of fluorescent ICG-Var3 and IR800-Var3 constructs to target various tumors in mice model after intravenous or intraperitoneal administration of fluorescent constructs.

A Var3 peptide (ACDDQNPWRAYLDLLFPTDTLLLD-LLWA; SEQ ID NO: 4) was purchased from CS Bio Co. Peptide was characterized by reversed phase high-performance liquid chromatography (RP-HPLC) using Zorbax SB-C18 and Zorbax SB-C8, 4.6×250 mm 5 µm columns (Agilent Technology). Peptide concentration was calculated by absorbance at 280 nm. Maleimide derivatives of ICG (indocyanine green, Intrace Medical) and IRDye® 800CW (IR800, Li-Cor Biosciences) were conjugated with a single Cys residue at the N-terminal end of the Var3 peptide. The conjugation reactions were performed in DMF (dimethylformamide) at a ratio of about 1:1 dye:peptide and incubated at room temperature for about 8 hours and then at 4° C. until the conjugation was completed. The reaction progress and purity was monitored by reverse phase RT-HPLC to ensure absence of free dyes in the final solution. The products were lyophilized and characterized by SELDI-TOF mass spectrometry. The concentration of conjugates was determined in methanol by absorbance using the following molar extinction coefficients: $e778=300,000$ $M^{-1} \cdot cm^{-1}$ (for IR800-pH-LIP®) and $61300=137,000$ $M^{-1} \cdot cm^{-1}$ (for ICG-pHLIP®).

Adult female nude mice and female BALB/cAnNHsd mice (Envigo), 20-25 g in body mass were used in the study. Mouse mammary cancer 4T1 cells were subcutaneously implanted in the right flank ($8 \times 10^5$ cells/0.1 mL/flank) of adult female BALB/cAnNHsd mice. Rat bladder cancer AY27 cells were subcutaneously implanted in the right flank ($8 \times 10^5$ cells/0.1 mL/flank) of adult female nude mice. When tumors reached approximately 5-6 mm in diameter, single tail vein injection or single intraperitoneal injection of fluorophore-pHLIP® solutions in PBS were performed. Fluorescent constructs were used in amounts of 100 µL of 40 µM or 100 µL of 20 µM, or 100 µL of 10 µM, or 100 µL of 5 µM. Imaging of mouse was performed at 16 hours after constructs administration. Skin was removed from the tumor site just before imaging while animal was under gas anesthesia, and mice were euthanized immediately after imaging. Tumor, kidney and liver were harvested, imaged and used for histopathological analysis. Imaging was performed using Stryker clinical imaging instrument. Autofluorescence was established by imaging mouse with no injection of fluorescent constructs (the level of autofluorescence signal was insignificant compared to the signal after the constructs administration).

The murine 4T1 xenograft model closely mimics stage IV of human breast cancer (Yang et al. (2004) Cell 117(7): 927-939; Eckhardt et al. (2005) Mol Cancer Res 3(1): 1-13; Tao et al. (2008) BMC Cancer 8: 228). It is also known that 4T1 mammary tumor generate significant level of lactate and serve as a good model of an aggressive, acidic tumor (Serganova et al. (2011) Cancer Res 17(19): 6250-6261). 4T1 is triple negative breast tumor, which is difficult to target. An excellent targeting of 4T1 tumor by ICG-Var3 (FIG. 11). In FIG. 12 it is shown targeting of rat bladder tumor in nude mice. The fluorescent signal of ICG-Var3 in tumors (as well as kidney and liver) showed concentration dependence (FIGS. 13 and 14). It is important to note that signal in tumor was higher than in kidney and similar or slightly less than in liver (FIG. 14). Both intravenous and intraperitoneal administration of ICG-Var3 led to the excellent tumor targeting and visualization of tumors at 16 hours after construct administration (FIG. 15). Tumor visualization by NIR signal after intravenous administration of ICG-Var3 and IR800-Var3 was compared (FIG. 16). Despite on the fact that both fluorescent constructs target tumor with high precision visualization of tumors using ICG-Var3 was much better compared to the visualization of tumors using IR800-Var3. Without being bound by any theory, better tumor visualization using ICG-Var3 might be due to the amplification (enhancement) of ICG fluorescence near the surface of cancer cells membrane and/or use of clinical imaging instrument (e.g., using a Stryker endoscope or many other clinical instruments), which are much better optimized for excitation and imaging of ICG dye rather than IR800 dye. The quantification of tumor uptake is provided in FIG. 17. The fluorescent signal in liver and kidney was also different for ICG-Var3 and IR800-Var3.

In embodiments, the fluorescent compound allows for visualization of tumor mass to establish clearly margin for tumor resection during fluorescent-guided surgical applications.

In FIG. 18 it is shown 2 different tumor masses with surrounding muscle tissue removed from the mice. The obtained images demonstrate that fluorescent signal is useful for identifying tumor margins, which was confirmed by standard hemolysin and eosin (H&E) histopathological analysis.

Example 3: Fluorescence Imaging of Blood Flow in Mice by ICG-Var3 and IR800-pHLIP®

Fluorescence angiography (FA) is widely used in various procedures to visualize blood vessels and monitor blood flow. ICG is employed in FA, however due to the fast blood clearance (half lifetime is just few minutes), the useful imaging window is restricted to few min after administration of ICG. In a course of some clinical procedures ICG is injected up to 10 times during a single procedure. There is obvious need to extend imaging window by using longer circulating imaging agents. Previous data clearly indicate that pHLIP®s have long circulation in blood compared to the peptides of similar sizes (Reshetnyak et al. (2011) Mol Imaging Biol 13(6): 1146-1156; Daumar et al. (2012) Bioconjug Chem 23(8): 1557-1566; Macholl et al. (2012) Mol Imaging Biol 14(6): 725-734; Adochite et al. (2014) Mol Pharm 11(8): 2896-2905; Cruz-Monserrate et al. (2014) Sci Rep 4: 4410; Viola-Villegas et al. (2014) Proc Natl Acad Sci USA 111(20): 7254-7259; Adochite et al. (2016) Mol Imaging Biol 18(5): 686-696; Demoin et al. (2016) Bioconjug Chem 27(9): 2014-2023). Therefore the possibility of imaging blood in mice was explored using near infrared ICG and IR800 conjugated pHLIP® peptides in comparison with ICG and IR800 dyes alone.

All peptides were purchased from CS Bio Co. A list of peptides used in the study is given in Table 11. Peptides were characterized by reversed phase high-performance liquid chromatography (RP-HPLC) using Zorbax SB-C18 and Zorbax SB-C8, 4.6×250 mm 5 µm columns (Agilent Technology). Peptide concentration was calculated by absorbance at 280 nm.

TABLE 11

List of pHLIP ® sequences used in the study.

| Peptide | Sequence |
|---|---|
| WT pHLIP ® | ACEQNPIYWARYADWLFTTPLLLLDLALLVDADEGT (SEQ ID NO: 444) |

TABLE 11-continued

List of pHLIP ® sequences used in the study.

| Peptide | Sequence |
|---|---|
| Var3 pHLIP ® | ACDDQNPWRAYLDLLFPTDTLLLDLLWA (SEQ ID NO: 4) |
| NpHLIP ® | ACEQNPIYWARYANWLFTTPLLLLNLALLVDADEGT (SEQ ID NO: 445) |
| Hum pHLIP ® | GCDNNEGFFATLGGEIPLWSDVVLAIEG (SEQ ID NO: 446) |

Maleimide derivatives of ICG (indocyanine green, Intrace Medical) and IRDye® 800CW (IR800, Li-COR Biosciences) were conjugated with free Cys residue or pHLIP® peptides with a single Cys residue at the N-terminal end of the peptides. The conjugation reactions were performed in DMF (dimethylformamide) at a ratio of about 1:1 dye: peptide and incubated at room temperature for about 8 hours and then at 4° C. until the conjugation was completed. The reaction progress and purity was monitored by reverse phase RT-HPLC to ensure absence of free dyes in the final solution. The products were lyophilized and characterized by SELDI-TOF mass spectrometry. The concentration of conjugates was determined in methanol by absorbance using the following molar extinction coefficients: $\varepsilon_{778}$=300,000 $M^{-1} \cdot cm^{-1}$ (for IR800-conjugates) and $\varepsilon_{800}$=137,000 $M^{-1} \cdot cm^{-1}$ (for ICG-conjugates).

Adult female nude mice (Envigo), 20 g in body mass were used in the study. Fluorescent constructs were given as a single tail vein injection in amounts of 100 µL of 40 µM in PBS. Imaging of mouse ear and leg was performed at 5, 30, 60, 90 and 120 min after construct administration. At 5, 30, 60, 90 and 120 min after construct administration 5 µL of blood was withdrawn from tail (and mixed with 5 µL of anticoagulating solution to preserve blood) while animal was under anesthesia. Mice were euthanized immediately after last imaging point (120 min). Blood collected from all animals was deposited on the glass slide, dried and imaged. Imaging was performed using Novadaq clinical imaging instrument. Autofluorescence was established by imaging mouse with no injection of fluorescent constructs (the level of autofluorescence signal was insignificant compared to the signal after the constructs administration).

NIR fluorescence images of animal's ears and legs obtained at different time points after the constructs administration are shown in FIGS. 20-37. All images are presented with adjusted contrast/brightness ratios to best present imaging of blood vessels. The first set of images was obtained with ICG conjugated with pHLIP®s and ICG-Cys. The imaging of dye alone (ICG-Cys) clearly demonstrates fast blood clearance of the dye. At 5 min after ICG-Cys injection it was already problematic to observe blood vessels. At the same time ICG-WT pHLIP® and ICG-Var3 pHLIP® exhibited an excellent persistent imaging of blood vessels within 2 hours. ICG-Hum pHLIP® was slow in reaching the best imagibility condition and was fast in decaying. ICG-NpHLIP® did not show good performance: the overall signal was low and imaging of blood flow was not well evident. The analysis of blood samples confirmed persistence of strong fluorescent signal within 2 hours for ICG-WT pHLIP® and ICG-Var3 pHLIP®, and significantly reduced signal of ICG-NpHLIP® in blood samples. The best performed peptides, WT and Var3 pHLIP®s, were tested also with another NIR fluorescent dye, IR800, to establish role of fluorescent dye. First, IR800-Cys alone did not allow to record good signal from the blood vessels. IR800-WT and IR800-Var3 pHLIP®s were better in imaging of blood vessels, however not nearly as good as ICG-WT and ICG-Var3 pHLIP®s. It was evident from images of ears and legs, as well as blood samples, that IR800 versions of pHLIP® constructs were leaking from blood and start to be distributed in tissue within 2 hours time period. It is clear that property of dye affects biodistribution and blood clearance.

The results indicate that the use of ICG-Var3 pHLIP® and ICG-WT pHLIP® leads to a significant improvement of imagibility of blood vessels and blood flow in numerous clinical procedures, since it can prolong time of imaging from 2-5 min to 2-3 hours.

Other Embodiments

While the invention has been described in conjunction with the description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

```
                            SEQUENCE LISTING

Sequence total quantity: 535
SEQ ID NO: 1            moltype = AA  length = 8
FEATURE                 Location/Qualifiers
REGION                  1..8
                        note = Description of Artificial Sequence: Synthetic peptide
MOD_RES                 5
                        note = Any protonatable amino acid
source                  1..8
                        mol_type = protein
                        organism = synthetic construct
SEQUENCE: 1
LFPTXTLL                                                                         8

SEQ ID NO: 2            moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 2
ADDQNPWRAY LDLLFPTDTL LLDLLWG                                                   27

SEQ ID NO: 3            moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 3
AKDDQNPWRA YLDLLFPTDT LLLDLLWG                                                  28

SEQ ID NO: 4            moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 4
ACDDQNPWRA YLDLLFPTDT LLLDLLWA                                                  28

SEQ ID NO: 5            moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 5
ADDQNPWRAY LDLLFPTDTL LLDLLWA                                                   27
```

```
SEQ ID NO: 6              moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 6
ADDQNPWRAY LDLLFPTDTL LLDLLWCA                                              28

SEQ ID NO: 7              moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 7
ADDQNPWRAY LDLLFPTDTL LLDLLWKA                                              28

SEQ ID NO: 8              moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 8
AKDDQNPWRA YLDLLFPTDT LLLDLLWA                                              28

SEQ ID NO: 9              moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 9
ACDDQNPWRA YLDLLFPTDT LLLDLLWG                                              28

SEQ ID NO: 10             moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 10
ADDQNPWRAY LDLLFPTDTL LLDLLWCG                                              28

SEQ ID NO: 11             moltype = AA  length = 28
FEATURE                   Location/Qualifiers
REGION                    1..28
                          note = Description of Artificial Sequence: Synthetic peptide
source                    1..28
                          mol_type = protein
                          organism = synthetic construct
SEQUENCE: 11
ADDQNPWRAY LDLLFPTDTL LLDLLWKG                                              28

SEQ ID NO: 12             moltype = AA  length = 29
FEATURE                   Location/Qualifiers
REGION                    1..29
                          note = Description of Artificial Sequence: Synthetic peptide
source                    1..29
                          mol_type = protein
                          organism = synthetic construct
SEQUENCE: 12
ACDDQNPWRA YLDLLFPTDT LLLDLLWKG                                             29

SEQ ID NO: 13             moltype = AA  length = 29
FEATURE                   Location/Qualifiers
REGION                    1..29
                          note = Description of Artificial Sequence: Synthetic peptide
source                    1..29
                          mol_type = protein
                          organism = synthetic construct
SEQUENCE: 13
```

```
AKDDQNPWRA YLDLLFPTDT LLLDLLWCG                                          29

SEQ ID NO: 14           moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 14
ACKDDQNPWR AYLDLLFPTD TLLLDLLWG                                          29

SEQ ID NO: 15           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 15
ACDDQNPWRA YLDLLFPTDT LLLDLLW                                            27

SEQ ID NO: 16           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 16
AKDDQNPWRA YLDLLFPTDT LLLDLLWC                                           28

SEQ ID NO: 17           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 17
ACDDQNPWAR YLDWLFPTDT LLLDL                                              25

SEQ ID NO: 18           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 18
CDNNNPWRAY LDLLFPTDTL LLDW                                               24

SEQ ID NO: 19           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 19
ACEEQNPWAR YLEWLFPTET LLLEL                                              25

SEQ ID NO: 20           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 20
ACEEQNPWRA YLELLFPTET LLLELLW                                            27

SEQ ID NO: 21           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
```

```
SEQUENCE: 21
CEEQQPWAQY LELLFPTETL LLEW                                              24

SEQ ID NO: 22           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 22
CEEQQPWRAY LELLFPTETL LLEW                                              24

SEQ ID NO: 23           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 23
AAEEQNPWAR YLEWLFPTET LLLEL                                             25

SEQ ID NO: 24           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 24
AKEEQNPWAR YLEWLFPTET LLLEL                                             25

SEQ ID NO: 25           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 25
LLFPTDTLLL                                                              10

SEQ ID NO: 26           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 26
LDLLFPTDTL LLD                                                          13

SEQ ID NO: 27           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 27
AYLDLLFPTD TLLLDLL                                                      17

SEQ ID NO: 28           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 28
DDQNPWRAYL DLLFPTDTLL LDLLW                                             25

SEQ ID NO: 29           moltype = AA  length = 21
FEATURE                 Location/Qualifiers
REGION                  1..21
                        note = Description of Artificial Sequence: Synthetic peptide
source                  1..21
                        mol_type = protein
```

|  |  |  |
|---|---|---|
| SEQUENCE: 29 | organism = synthetic construct | |
| WRAYLDLLFP TDTLLLDLLW G | | 21 |

SEQ ID NO: 30    moltype = AA  length = 20
FEATURE            Location/Qualifiers
REGION             1..20
                    note = Description of Artificial Sequence: Synthetic peptide
source             1..20
                    mol_type = protein
                    organism = synthetic construct
SEQUENCE: 30
WRAYLDLLFP TDTLLLDLLW                                          20

SEQ ID NO: 31    moltype = DNA  length = 6706
FEATURE            Location/Qualifiers
source             1..6706
                    mol_type = other DNA
                    organism = Homo sapiens
SEQUENCE: 31

```
agagtcatcc agctggagcc ctgagtggct gagctcaggc cttcgcagca ttcttgggtg    60
ggagcagcca cgggtcagcc acaagggcca cagccatgaa tggcacagaa ggccctaact   120
tctacgtgcc cttctccaat gcgacgggtg tggtacgcag cccccttcgag tacccacagt  180
actacctggc tgagccatgg cagttctcca tgctggccgc ctacatgttt ctgctgatcg   240
tgctgggctt cccccatcaac ttcctcacgc tctacgtcac cgtccagcac aagaagctgc  300
gcacgcctct caactacatc ctgctcaacc tagccgttgc tgacctcttc atggtcatgg   360
gtggcttcac cagcacccctc tacacctctc tgcatggata cttcgtcttc gggcccacag  420
gatgcaattt ggagggcttc tttgccaccc tgggcggtat gagccgggtg tgggtggggt  480
gtgcaggagc ccgggagcat ggaggggtct gggagagtcc cgggcttggc ggtggtggct  540
gagaggcctt ctcccttctc ctgtcctgtc aatgttatcc aaagccctca tatattcagt  600
caacaaacac cattcatggt gatagccggg ctgctgtttg tgcagggctg gcactgaaca  660
ctgccttgat cttatttgga gcaatatgcg cttgtctaat ttcacagcaa gaaaactgag  720
ctgaggctca aagaagtcaa gcgccctgct ggggcgtcac acagggacgg tgcagagtt   780
gagttggaag cccgcatcta tctcgggcca tgtttgcagc accaagcctc tgtttccctt  840
ggagcagctg tgctgagtca gacccaggct gggcactgag ggagagctgg gcaagccaga  900
cccctcctct ctgggggccc aagctcaggg tgggaagtgg attttccatt ctccagtcat  960
tgggtcttcc ctgtgctggg caatgggctc ggtcccctct ggcatcctct gcctcccctc 1020
tcagcccctg tcctcaggtg ccccctccagc ctccctgccg cgttccaagt ctcctggtgt 1080
tgagaaccgc aagcagccgc tctgaagcag ttccttttg ctttagaata atgtcttgca 1140
tttaacagga aaacagatgg ggtgctgcag ggataacaga tcccacttaa cagagaggaa 1200
aactgaggca gggagagggg aagagactca tttagggatg tggccaggca gcaacaagag 1260
cctaggtctc ctggctgtga tccaggaata tctctgctga gatgcaggag gagacgctag 1320
aagcagccat tgcaaagctg ggtgacgggg agagcttacc gccagccaca agcgtctctc 1380
tgccagcctt gccctgtctc cccatgtcc aggctgctgc ctcggtccca ttctcaggga 1440
atctctggcc attgttgggt gttgttgca ttcaataatc acagatcact cagttctggc 1500
cagaaggtgg gtgtgccact tacgggtggt tgttctctgc agggtcagtc ccagtttaca 1560
aatattgtcc ctttcactgt taggaatgtc ccagtttggt tgattaacta tatggccact 1620
ctccctatgg aacttcatgg ggtggtgagc aggacagatg tctgaattcc atcatttcct 1680
tcttcttcct ctgggcaaaa cattgcacat tgcttcatgg ctcctaggag aggccccac  1740
atgtccgggt tatttcattt cccgagaagg gagagggagg aaggactgcc aattctggtt 1800
ttccacacc tctgcattcc ttcccaacaa ggaacttctgc cccacattag gatgcattct 1860
tctgctaaac acacacacac acacacacac acacaacaca cacacacaca cacacacaca 1920
cacacacaca aaactcccta ccgggttccc agttcaatcc tgaccccctg atctgattcg 1980
tgtccccttat gggcccagag cgctaagcaa ataacttccc ccattccctg gaatttcttt 2040
gcccagctct cctcagcgtg tggtccctct gcccctcca cctcctccca gcaccaagct 2100
ctctccttcc ccaaggcctc ctcaaatccc tctcccactc ctggttgcct tcctagctac 2160
cctctcctg tctaggggg agtgcaccct ccttaggcag tggggtctgt gctgaccgcc 2220
tgctgactgc cttgcaggtg aaattgccct gtggtccttg tggtcctgg ccatcgagcg 2280
gtacgtggtg gtgtgtaagc ccatgagcaa cttccgcttc ggggagaacc atgccatcat 2340
gggcgttgcc ttcacctggg tcatgcgct ggcctgcgcc gcaccccac tcgccgctg   2400
gtccaggtaa tggcactgag cagaagggaa gaagctccgg gggctcttg tagggtcctc 2460
cagtcaggac tcaaacccag tagtgtctgg ttccaggcac tgaccttgta tgtctcctgg 2520
cccaaatgcc cactcagggt aggggtgtag ggcagaagaa gaaacagact ctaatgttgc 2580
tacaagggct ggtcccatct cctgagcccc atgtcaaaca gaatccaaga catcccaacc 2640
cttcaccttg gctgtgcccc taatcctcaa ctaagctagg cgcaaattcc aatcctcttt 2700
ggtctagtac cccgggggca gccccctcta accttgggcc tcagcagcag ggaggccac  2760
accttcctag tgcaggtggc catattgtgg cccccttggaa ctgggtccca ctcagcctct 2820
aggcgattgt ctcctaatgg ggctgagatg agacacagtg gggacagtgg tttggacaat 2880
aggactggtg actcggttgc cagaggcct catgtccctc tgtctccaga aaattcccaa  2940
tctcacttcc ctttcctcct cagtcttgct agggtccatt tcttacccct tgctgaattt 3000
gagcccaccc cctggacttt ttcccatct tctccaatct ggctagttc tatcctctgg  3060
aagcagagcc gctggacgct ctgggttccc tgaggccgt ccactgtcac caatatcagg  3120
aaccattgcc acgtcctaat gacgtgcgct ggaagctct agtttccaga agctgcacaa  3180
agatcccta gatactctgt gtgtcatct tggcgtgga aatactctc accctgggc   3240
taggaagacc tcggttttgta caaacttcct caaatgcaga gcctgagggc tctcccac   3300
tcctcaccaa cctctgcgt ggcatagccc tagcctcagc gggcagtgga tgctggggct 3360
gggcatgcag ggagaggctg ggtgggtgtca tctggtaacg cagccaccaa acaatgaagc 3420
gacactgatt ccacaaggtg catctgcatc cccatctgat ccattccatc ctgtcaccca 3480
gccatgcaga cgtttatgat ccccttttcc agggaggaaa tgtgaagccc cagaaagggc 3540
```

```
cagcgctcgg cagccacctt ggctgttccc aagtccctca caggcagggt ctccctacct    3600
gcctgtcctc aggtacatcc ccgagggcct gcagtgctcg tgtggaatcg actactacac    3660
gctcaagccg gaggtcaaca acgagtcttt tgtcatctac atgttcgtgg tccacttcac    3720
catccccatg attatcatct ttttctgcta tgggcagctc gtcttcaccg tcaaggaggt    3780
acgggccggg gggtgggcgg cctcacggct ctgagggtcc agcccccagc atgcatctgc    3840
ggctcctgct ccctggagga gccatggtct ggacccgggt cccgtgtcct gcaggccgct    3900
gcccagcagc aggagtcagc caccacacag aaggcagaga aggaggtcac ccgcatggtc    3960
atcatcatgg tcatcgcttt cctgatctgc tgggtgccct acgccagcgt ggcattctac    4020
atcttcaccc accagggctc caacttcggt cccatcttca tgaccatccc agcgttcttt    4080
gccaagagcg ccgccatcta caaccctgtc atctatatca tgatgaacaa gcaggtgcct    4140
actgcgggtg ggagggcccc agtgcccag gccacaggcg ctgcctgcca aggacaagct    4200
acttcccagg gcaggggagg gggctccatc agggttactg gcagcagtct tgggtcagca    4260
gtcccaatgg ggagtgtgtg agaaatgcag attcctggcc ccactcagaa ctgctgaatc    4320
tcagggtggg cccaggaacc tgcatttcca gcaagccctc cacaggtggc tcagatgctc    4380
actcaggtgg gagaagctcc agtcagctag ttctggaagc ccaatgtcaa agtcagaagg    4440
acccaagtcg ggaatgggat gggccagtct ccataaagct gaataaggag ctaaaaagtc    4500
ttattctgag gggtaaaggg gtaaagggtt cctcggagag gtacctccga ggggtaaaca    4560
gttgggtaaa cagtctctga agtcagctct gccattttct agctgtatgg ccctgggcaa    4620
gtcaattttcc ttctctgtgc tttgtttcc tcatccatag aaaggtagaa agggcaaaac    4680
accaaactct tggattacaa gagataattt acagaacacc cttggcacac agagggcacc    4740
atgaaatgtc acgggtgaca cagccccctt gtgctcagtc cctggcatct ctaggggtga    4800
ggagcgtctg cctagcaggt tccctccagg aagctggatt tgagtggatg ggcgctgga    4860
atcgtgaggg gcagaagcag gcaaaggtgc gggcgaacc tcactaacgt gccagttcca    4920
agcacactgt gggcagccct ggccctgact caagcctctt gccttccagt tccggaactg    4980
catgctcacc accatctgct gcggcaagaa cccactgggt gacgatgagg cctctgctac    5040
cgtgtccaag acggagacga gccaggtggc cccggcctaa gacctgccta ggactcttgg    5100
gccgactata ggcgtctccc atcccctaca ccttccccca gccacagcca tcccaccagg    5160
agcagcgcct gtgcagaatg aacgaagtca cataggctcc ttaattttt tttttttttt    5220
aagaaataat taatgaggct cctcactcac ctgggacagc ctgagaaggg acatccacca    5280
agacctactg atctggagtc ccacgttccc caaggccagg ggatgtgtg ccctcctcc    5340
tcccaactca tctttcagga acacgaggat tcttgctttc tggaaaagtg tcccagctta    5400
gggataagtg tctagcacag aatggggcac acagtaggtg cttaataaat gctggatgga    5460
tgcaggaagg aatggaggaa tgaatgggaa gggagaacat atctatcctc tcagaccctc    5520
gcagcagcag caactcatac ttggctaatg atatggagca gttgttttc cctccctggg    5580
cctcacttc ttctcctata aaatggaaat cccagatccc tggtcctgcc gacacgcagc    5640
tactgagaag accaaaagag gtgtgtgtgt gtctatgtgt gtgtttcagc actttgtaaa    5700
tagcaagaag ctgtacagat tctagttaat gttgtgaata acatcaatta atgtaactag    5760
ttaattacta tgattatcac ctcctgatag tgaacatttt gagattgggc attcagatga    5820
tggggtttca cccaaccttg gggcaggttt ttaaaaatta gctaggcatc aaggccagac    5880
cagggctggg ggttgggctg taggcaggga cagtcacagg aatgcagaat gcagtcatca    5940
gacctgaaaa aacaacactg ggggagggg acggtgaagg ccaagttccc aatgagggtg    6000
agattgggcc tggggtctca cccctagtgt ggggccccag gtcccgtgcc tcccttccc    6060
aatgtggcct atggagagac aggccttttc ctcagcctct ctgaagccac tgctctttg    6120
ctctagcacc tgggtcccag catctagagc atggagcctc tagaagccat gctcaccgc    6180
ccacatttaa ttaacagctg agtccctgat gtcatcctta tctcgaagag cttagaaaca    6240
aagagtggga aattccactg ggcctacctt ccttgggggat gttcatggc cccagtttcc    6300
agtttccctt gccagacaag cccatcttca gcagttgctc agttcctc cattctggag    6360
aatctgctcc aaaaagctgg ccacatctct gaggtgtcag aattaagctg cctcagtaac    6420
tgctcccct tctccatata agcaaagcca gaagctctag ctttacccag ctctgcctgg    6480
agactaaggc aaattgggcc attaaaagct cagctcctat gttggtatta acggtggtgg    6540
gttttgttgc tttcacactc tatccacagg atagattgaa actgccagct tccacctgat    6600
ccctgaccct gggatggctg gattgagcaa tgagcagagc caagcagcag agagtcccct    6660
ggggctagag gtggaggagg cagtcctggg aatgggaaaa acccca                   6706
```

```
SEQ ID NO: 32        moltype = AA  length = 348
FEATURE              Location/Qualifiers
source               1..348
                     mol_type = protein
                     organism = Homo sapiens
SEQUENCE: 32
MNGTEGPNFY VPFSNATGVV RSPFEYPQYY LAEPWQFSML AAYMFLLIVL GFPINFLTLY     60
VTVQHKKLRT PLNYILLNLA VADLFMVLGG FTSTLYTSLH GYFVFGPTGC NLEGFFATLG    120
GEIALWSLVV LAIERYVVVC KPMSNFRFGE NHAIMGVAFT WVMALACAAP PLAGWSRYIP    180
EGLQCSCGID YYTLKPEVNN ESFVIYMFVV HFTIPMIIIF FCYGQLVFTV KEAAAQQQES    240
ATTQKAEKEV TRMVIIMVIA FLICWVPYAS VAFYIFTHQG SNFGPIFMTI PAFFAKSAAI    300
YNPVIYIMMN KQFRNCMLTT ICCGKNPLGD DEASATVSKT ETSQVAPA                348

SEQ ID NO: 33        moltype = DNA  length = 2768
FEATURE              Location/Qualifiers
source               1..2768
                     mol_type = unassigned DNA
                     organism = Homo sapiens
SEQUENCE: 33
agagtcatcc agctggagcc ctgagtggct gagctcaggc cttcgcagca ttcttgggtg     60
ggagcagcca cgggtcagcc acaagggcca cagccatgaa tggcacagaa ggccctaact    120
tctacgtgcc cttctccaat gcgacgggtg tggtacgcag ccccttcgag tacccacagt    180
actacctggc tgagccatgg cagttctcca tgctggccgc ctacatgttt ctgctgatcg    240
tgctgggctt ccccatcaac ttcctcacgc tctacgtcac cgtccagcac aagaagctgc    300
gcacgccctc caactacatc ctgctcaacc tagccgtggc tgacctcttc atggtcctag    360
```

```
gtggcttcac cagcaccctc tacacctctc tgcatggata cttcgtcttc gggcccacag    420
gatgcaattt ggagggcttc tttgccaccc tgggcggtga aattgccctg tggtccttgg    480
tggtcctggc catcgagcgg tacgtggtgg tgtgtaagcc catgagcaac ttccgcttcg    540
gggagaacca tgccatcatg ggcgttgcct tcacctgggt catggcgctg gcctgcgccc    600
caccccact cgccggctgg tccaggtaca tccccgaggg cctgcagtgc tcgtgtggaa     660
tcgactacta cacgctcaag ccggaggtca acaacgagtc ttttgtcatc tacatgttca    720
tggtccactt caccatcccc atgattatca tctttttctg ctatgggcag ctcgtcttca    780
ccgtcaagga ggccgctgcc cagcagcagg agtcagccac cacacagaag gcagagaagg    840
aggtcacccg catggtcatc atcatggtca tcgctttcct gatctgctgg gtgccctacg    900
ccagcgtggc attctacatc ttcacccacc agggctccaa cttcggtccc atcttcatga    960
ccatcccagc gttctttgcc aagagcgccg ccatctacaa ccctgtcatc tatatcatga   1020
tgaacaagca gttccggaac tgcatgctca ccaccatctg ctgcggcaag aacccactgg   1080
gtgacgatga ggcctctgct accgtgtcca agacggagac gagccaggtg gccccggcct   1140
aagacctgcc taggactctg tggccgacta taggcgtcct ccatccccta cacctccc     1200
cagccacagc catcccacca ggagcagcgc ctgtgcagaa tgaacgaagt cacatagct    1260
ccttaatttt tttttttttt ttaagaaata attaatgagg ctcctcactc acctgggaca   1320
gcctgagaag ggacatccac caagacctac tgatctggag tcccacgttc cccaaggcca   1380
gcgggatgtg tgcccctcct cctcccaact catctttcag gaacacgagg attcttgctt   1440
tctggaaaag tgtcccagct tagggataag tgtctagcac agaatggggc acacagtagg   1500
tgcttaataa atgctggatg gatgcaggaa ggaatggagg aatgaatggg aagggagaac   1560
atatctatcc tctcagaccc tcgcagcagc agcaactcat acttggctaa tgatatggag   1620
cagttgtttt tccctccctg ggcctcactt tcttctccta taaaatggaa atcccagatc   1680
cctggtcctg ccgacacgca gctactgaga agaccaaaag aggtgtgtgt gtgtctatgt   1740
gtgtgtttca gcactttgta aatagcaaga agctgtacag attctagtta atgttgtgaa   1800
taacatcaat taatgtaact agttaattac tatgattatc acctcctgat agtgaacatt   1860
ttgagattgg gcattcagat gatggggttt cacccaacct tggggcaggt ttttaaaaat   1920
tagctaggca tcaaggccag accagggctg ggggttgggc tgtaggcagg gacagtcaca   1980
ggaatgcaga atgcagtcat cagacctgaa aaaacaacac tggggagggg ggacggtgaa   2040
ggccaagttc ccaatgaggg tgagattggg cctggggtct caccctagt gtggggcccc    2100
aggtcccgtg cctccccttc ccaatgtggc ctatggagga acaggccttt ctctcagcct   2160
ctggaagcca cctgctcttt tgctctagca cctgggtccc agcatctaga gcatgagcc    2220
tctagaagcc atgctcaccc gcccacattt aattaacagc tgagtccctg atgtcatcct   2280
tatctcgaag agcttagaaa caaagagtgg gaaattccac tgggcctacc ttccttgggg   2340
atgttcatgg gccccagttt ccagtttccc ttgccagaca agcccatctt cagcagttgc   2400
tagtccattc tccattctgg agaatctgct ccaaaaagct ggccacatct ctgaggtgtc   2460
agaattaagc tgcctcagta actgctcccc cttctccata taagcaaagc cagaagctct   2520
agctttaccc agctctgcct ggagactaag gcaaattggg ccattaaaag ctcagctcct   2580
atgttggtat taacggtggt gggttttgtt gctttcacac tctatccaca ggatagattg   2640
aaactgccag cttccacctg atccctgacc ctgggatggc tggattgagc aatgagcaga   2700
gccaagcagc acagagtccc ctgggctag aggtggagga ggcagtcctg ggaatgggaa    2760
aaaccca                                                             2768

SEQ ID NO: 34          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 34
WARYADWL                                                                   8

SEQ ID NO: 35          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 35
LWDAYRAW                                                                   8

SEQ ID NO: 36          moltype = AA   length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 36
WARYADWLFT TPLLLLDLAL L                                                   21

SEQ ID NO: 37          moltype = AA   length = 21
FEATURE                Location/Qualifiers
REGION                 1..21
                       note = Description of Artificial Sequence: Synthetic peptide
source                 1..21
                       mol_type = protein
                       organism = synthetic construct
```

```
SEQUENCE: 37
YARYADWLFT TPLLLLDLAL L                                                    21

SEQ ID NO: 38          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 38
WARYSDWLFT TPLLLYDLGL L                                                    21

SEQ ID NO: 39          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 39
WARYTDWFTT PLLLYDLALL A                                                    21

SEQ ID NO: 40          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 40
WARYTDWLFT TPLLLYDLGL L                                                    21

SEQ ID NO: 41          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 41
WARYADWLFT TPLLLLDLSL L                                                    21

SEQ ID NO: 42          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 42
LLALDLLLLP TTFLWDAYRA W                                                    21

SEQ ID NO: 43          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 43
LLALDLLLLP TTFLWDAYRA Y                                                    21

SEQ ID NO: 44          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 44
LLGLDYLLLP TTFLWDSYRA W                                                    21

SEQ ID NO: 45          moltype = AA  length = 21
FEATURE                Location/Qualifiers
REGION                 1..21
                       note = Description of Artificial Sequence: Synthetic peptide
source                 1..21
                       mol_type = protein
```

```
                        organism = synthetic construct
SEQUENCE: 45
ALLALDYLLL PTTFWDTYRA W                                                 21

SEQ ID NO: 46           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 46
LLGLDYLLLP TTFLWDTYRA W                                                 21

SEQ ID NO: 47           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 47
LLSLDLLLLP TTFLWDAYRA W                                                 21

SEQ ID NO: 48           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 48
GLAGLLGLEG LLGLPLGLLE GLWLGL                                            26

SEQ ID NO: 49           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 49
LGLWLGELLG LPLGLLGELG LLGALG                                            26

SEQ ID NO: 50           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 50
WRAYLDLLFP TDTLLLDLLW                                                   20

SEQ ID NO: 51           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 51
WLLDLLLTDT PFLLDLYARW                                                   20

SEQ ID NO: 52           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 52
WARYLEWLFP TETLLLEL                                                     18

SEQ ID NO: 53           moltype = AA  length = 18
FEATURE                 Location/Qualifiers
REGION                  1..18
                        note = Description of Artificial Sequence: Synthetic peptide
source                  1..18
```

```
                        mol_type = protein
                        organism = synthetic construct
SEQUENCE: 53
WAQYLELLFP TETLLLEW                                                        18

SEQ ID NO: 54           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 54
LELLLTETPF LWELYRAW                                                        18

SEQ ID NO: 55           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 55
WELLLTETPF LLELYQAW                                                        18

SEQ ID NO: 56           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 56
WLFTTPLLLL NGALLVE                                                         17

SEQ ID NO: 57           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 57
WLFTTPLLLL PGALLVE                                                         17

SEQ ID NO: 58           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 58
WARYADLLFP TTLAW                                                           15

SEQ ID NO: 59           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 59
EVLLAGNLLL LPTTFLW                                                         17

SEQ ID NO: 60           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 60
EVLLAGPLLL LPTTFLW                                                         17

SEQ ID NO: 61           moltype = AA  length = 15
FEATURE                 Location/Qualifiers
REGION                  1..15
                        note = Description of Artificial Sequence: Synthetic peptide
```

```
source                   1..15
                         mol_type = protein
                         organism = synthetic construct
SEQUENCE: 61
WALTTPFLLD AYRAW                                                         15

SEQ ID NO: 62            moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 62
NLEGFFATLG GEIALWSLVV LAIE                                               24

SEQ ID NO: 63            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 63
EGFFATLGGE IALWSDVVLA IE                                                 22

SEQ ID NO: 64            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 64
EGFFATLGGE IPLWSDVVLA IE                                                 22

SEQ ID NO: 65            moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 65
EIALVVLSWL AIEGGLTAFF GELN                                               24

SEQ ID NO: 66            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 66
EIALVVDSWL AIEGGLTAFF GE                                                 22

SEQ ID NO: 67            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 67
EIALVVDSWL PIEGGLTAFF GE                                                 22

SEQ ID NO: 68            moltype = AA  length = 21
FEATURE                  Location/Qualifiers
REGION                   1..21
                         note = Description of Artificial Sequence: Synthetic peptide
source                   1..21
                         mol_type = protein
                         organism = synthetic construct
SEQUENCE: 68
ILDLVFGLLF AVTSVDFLVQ W                                                  21

SEQ ID NO: 69            moltype = AA  length = 21
FEATURE                  Location/Qualifiers
REGION                   1..21
```

```
                        note = Description of Artificial Sequence: Synthetic peptide
source                  1..21
                        mol_type = protein
                        organism = synthetic construct
SEQUENCE: 69
WQVLFDVSTV AFLLGFVLDL I                                                   21

SEQ ID NO: 70           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 70
WARYADWLFT TPLLLLDLAL L                                                   21

SEQ ID NO: 71           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 71
YARYADWLFT TPLLLLDLAL L                                                   21

SEQ ID NO: 72           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 72
WARYSDWLFT TPLLLYDLGL L                                                   21

SEQ ID NO: 73           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 73
WARYTDWFTT PLLLYDLALL A                                                   21

SEQ ID NO: 74           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 74
WARYTDWLFT TPLLLYDLGL L                                                   21

SEQ ID NO: 75           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 75
WARYADWLFT TPLLLLDLSL L                                                   21

SEQ ID NO: 76           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 76
LLALDLLLLP TTFLWDAYRA W                                                   21

SEQ ID NO: 77           moltype = AA  length = 21
FEATURE                 Location/Qualifiers
```

```
REGION                  1..21
                        note = Description of Artificial Sequence: Synthetic peptide
source                  1..21
                        mol_type = protein
                        organism = synthetic construct
SEQUENCE: 77
LLALDLLLLP TTFLWDAYRA Y                                                 21

SEQ ID NO: 78           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 78
LLGLDYLLLP TTFLWDSYRA W                                                 21

SEQ ID NO: 79           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 79
ALLALDYLLL PTTFWDTYRA W                                                 21

SEQ ID NO: 80           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 80
LLGLDYLLLP TTFLWDTYRA W                                                 21

SEQ ID NO: 81           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 81
LLSLDLLLLP TTFLWDAYRA W                                                 21

SEQ ID NO: 82           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 82
GLAGLLGLEG LLGLPLGLLE GLWLGL                                            26

SEQ ID NO: 83           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 83
LGLWLGELLG LPLGLLGELG LLGALG                                            26

SEQ ID NO: 84           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 84
WRAYLDLLFP TDTLLLDLLW                                                   20

SEQ ID NO: 85           moltype = AA  length = 20
```

```
FEATURE              Location/Qualifiers
REGION               1..20
                     note = Description of Artificial Sequence: Synthetic peptide
source               1..20
                     mol_type = protein
                     organism = synthetic construct
SEQUENCE: 85
WLLDLLLTDT PFLLDLYARW                                                    20

SEQ ID NO: 86        moltype = AA  length = 18
FEATURE              Location/Qualifiers
REGION               1..18
                     note = Description of Artificial Sequence: Synthetic peptide
source               1..18
                     mol_type = protein
                     organism = synthetic construct
SEQUENCE: 86
WARYLEWLFP TETLLLEL                                                      18

SEQ ID NO: 87        moltype = AA  length = 18
FEATURE              Location/Qualifiers
REGION               1..18
                     note = Description of Artificial Sequence: Synthetic peptide
source               1..18
                     mol_type = protein
                     organism = synthetic construct
SEQUENCE: 87
WAQYLELLFP TETLLLEW                                                      18

SEQ ID NO: 88        moltype = AA  length = 18
FEATURE              Location/Qualifiers
REGION               1..18
                     note = Description of Artificial Sequence: Synthetic peptide
source               1..18
                     mol_type = protein
                     organism = synthetic construct
SEQUENCE: 88
LELLLTETPF LWELYRAW                                                      18

SEQ ID NO: 89        moltype = AA  length = 18
FEATURE              Location/Qualifiers
REGION               1..18
                     note = Description of Artificial Sequence: Synthetic peptide
source               1..18
                     mol_type = protein
                     organism = synthetic construct
SEQUENCE: 89
WELLLTETPF LLELYQAW                                                      18

SEQ ID NO: 90        moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 90
WLFTTPLLLL NGALLVE                                                       17

SEQ ID NO: 91        moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 91
WLFTTPLLLL PGALLVE                                                       17

SEQ ID NO: 92        moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 92
WARYADLLFP TTLAW                                                         15
```

```
SEQ ID NO: 93            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 93
EVLLAGNLLL LPTTFLW                                                   17

SEQ ID NO: 94            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 94
EVLLAGPLLL LPTTFLW                                                   17

SEQ ID NO: 95            moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 95
WALTTPFLLD AYRAW                                                     15

SEQ ID NO: 96            moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 96
NLEGFFATLG GEIALWSLVV LAIE                                           24

SEQ ID NO: 97            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 97
EGFFATLGGE IALWSDVVLA IE                                             22

SEQ ID NO: 98            moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 98
EGFFATLGGE IPLWSDVVLA IE                                             22

SEQ ID NO: 99            moltype = AA  length = 24
FEATURE                  Location/Qualifiers
REGION                   1..24
                         note = Description of Artificial Sequence: Synthetic peptide
source                   1..24
                         mol_type = protein
                         organism = synthetic construct
SEQUENCE: 99
EIALVVLSWL AIEGGLTAFF GELN                                           24

SEQ ID NO: 100           moltype = AA  length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 100
EIALVVDSWL AIEGGLTAFF GE                                             22
```

```
SEQ ID NO: 101        moltype = AA  length = 22
FEATURE               Location/Qualifiers
REGION                1..22
                      note = Description of Artificial Sequence: Synthetic peptide
source                1..22
                      mol_type = protein
                      organism = synthetic construct
SEQUENCE: 101
EIALVVDSWL PIEGGLTAFF GE                                                  22

SEQ ID NO: 102        moltype = AA  length = 21
FEATURE               Location/Qualifiers
REGION                1..21
                      note = Description of Artificial Sequence: Synthetic peptide
source                1..21
                      mol_type = protein
                      organism = synthetic construct
SEQUENCE: 102
ILDLVFGLLF AVTSVDFLVQ W                                                   21

SEQ ID NO: 103        moltype = AA  length = 21
FEATURE               Location/Qualifiers
REGION                1..21
                      note = Description of Artificial Sequence: Synthetic peptide
source                1..21
                      mol_type = protein
                      organism = synthetic construct
SEQUENCE: 103
WQVLFDVSTV AFLLGFVLDL I                                                   21

SEQ ID NO: 104        moltype = AA  length = 21
FEATURE               Location/Qualifiers
REGION                1..21
                      note = Description of Artificial Sequence: Synthetic peptide
MOD_RES               6
                      note = Asp, Glu, gamma-carboxyglutamic acid or
                       alpha-aminoadipic acid
MOD_RES               17
                      note = Asp, Glu, gamma-carboxyglutamic acid or
                       alpha-aminoadipic acid
source                1..21
                      mol_type = protein
                      organism = synthetic construct
SEQUENCE: 104
WARYAXWLFT TPLLLLXLAL L                                                   21

SEQ ID NO: 105        moltype = AA  length = 21
FEATURE               Location/Qualifiers
REGION                1..21
                      note = Description of Artificial Sequence: Synthetic peptide
MOD_RES               6
                      note = Asp, Glu, gamma-carboxyglutamic acid or
                       alpha-aminoadipic acid
MOD_RES               17
                      note = Asp, Glu, gamma-carboxyglutamic acid or
                       alpha-aminoadipic acid
source                1..21
                      mol_type = protein
                      organism = synthetic construct
SEQUENCE: 105
YARYAXWLFT TPLLLLXLAL L                                                   21

SEQ ID NO: 106        moltype = AA  length = 21
FEATURE               Location/Qualifiers
REGION                1..21
                      note = Description of Artificial Sequence: Synthetic peptide
MOD_RES               6
                      note = Asp, Glu, gamma-carboxyglutamic acid or
                       alpha-aminoadipic acid
MOD_RES               17
                      note = Asp, Glu, gamma-carboxyglutamic acid or
                       alpha-aminoadipic acid
source                1..21
                      mol_type = protein
                      organism = synthetic construct
SEQUENCE: 106
WARYSXWLFT TPLLLYXLGL L                                                   21
```

```
SEQ ID NO: 107          moltype = AA   length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 107
WARYTXWFTT PLLLYXLALL A                                                    21

SEQ ID NO: 108          moltype = AA   length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 108
WARYTXWLFT TPLLLYXLGL L                                                    21

SEQ ID NO: 109          moltype = AA   length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 109
WARYAXWLFT TPLLLLXLSL L                                                    21

SEQ ID NO: 110          moltype = AA   length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 110
LLALXLLLLP TTFLWXAYRA W                                                    21

SEQ ID NO: 111          moltype = AA   length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 111
LLALXLLLLP TTFLWXAYRA Y                                                    21
```

```
SEQ ID NO: 112          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 112
LLGLXYLLLP TTFLWXSYRA W                                                     21

SEQ ID NO: 113          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 113
ALLALXYLLL PTTFWXTYRA W                                                     21

SEQ ID NO: 114          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 114
LLGLXYLLLP TTFLWXTYRA W                                                     21

SEQ ID NO: 115          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 115
LLSLXLLLLP TTFLWXAYRA W                                                     21

SEQ ID NO: 116          moltype = AA  length = 26
FEATURE                 Location/Qualifiers
REGION                  1..26
                        note = Description of Artificial Sequence: Synthetic peptide
MOD_RES                 9
                        note = Asp, Glu, gamma-carboxyglutamic acid or
                         alpha-aminoadipic acid
MOD_RES                 20
                        note = Asp, Glu, gamma-carboxyglutamic acid or
                         alpha-aminoadipic acid
source                  1..26
                        mol_type = protein
                        organism = synthetic construct
SEQUENCE: 116
```

```
GLAGLLGLXG LLGLPLGLLX GLWLGL                                             26

SEQ ID NO: 117          moltype = AA  length = 26
FEATURE                 Location/Qualifiers
REGION                  1..26
                        note = Description of Artificial Sequence: Synthetic peptide
MOD_RES                 7
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
source                  1..26
                        mol_type = protein
                        organism = synthetic construct
SEQUENCE: 117
LGLWLGXLLG LPLGLLGXLG LLGALG                                             26

SEQ ID NO: 118          moltype = AA  length = 20
FEATURE                 Location/Qualifiers
REGION                  1..20
                        note = Description of Artificial Sequence: Synthetic peptide
MOD_RES                 6
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..20
                        mol_type = protein
                        organism = synthetic construct
SEQUENCE: 118
WRAYLXLLFP TXTLLLXLLW                                                    20

SEQ ID NO: 119          moltype = AA  length = 20
FEATURE                 Location/Qualifiers
REGION                  1..20
                        note = Description of Artificial Sequence: Synthetic peptide
MOD_RES                 4
                        note = Asp, Glu, gamma-carboxyglutamic acid or
                         alpha-aminoadipic acid
MOD_RES                 9
                        note = Asp, Glu, gamma-carboxyglutamic acid or
                         alpha-aminoadipic acid
MOD_RES                 15
                        note = Asp, Glu, gamma-carboxyglutamic acid or
                         alpha-aminoadipic acid
source                  1..20
                        mol_type = protein
                        organism = synthetic construct
SEQUENCE: 119
WLLXLLLTXT PFLLXLYARW                                                    20

SEQ ID NO: 120          moltype = AA  length = 18
FEATURE                 Location/Qualifiers
REGION                  1..18
                        note = Description of Artificial Sequence: Synthetic peptide
MOD_RES                 6
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..18
                        mol_type = protein
                        organism = synthetic construct
SEQUENCE: 120
WARYLXWLFP TXTLLLXL                                                      18

SEQ ID NO: 121          moltype = AA  length = 18
FEATURE                 Location/Qualifiers
REGION                  1..18
                        note = Description of Artificial Sequence: Synthetic peptide
```

```
MOD_RES              6
                     note = Asp, Glu, gamma-carboxyglutamic acid or
                      alpha-aminoadipic acid
MOD_RES              12
                     note = Asp, Glu, gamma-carboxyglutamic acid or
                      alpha-aminoadipic acid
MOD_RES              17
                     note = Asp, Glu, gamma-carboxyglutamic acid or
                      alpha-aminoadipic acid
source               1..18
                     mol_type = protein
                     organism = synthetic construct
SEQUENCE: 121
WAQYLXLLFP TXTLLLXW                                                       18

SEQ ID NO: 122       moltype = AA  length = 18
FEATURE              Location/Qualifiers
REGION               1..18
                     note = Description of Artificial Sequence: Synthetic peptide
MOD_RES              2
                     note = Asp, Glu, gamma-carboxyglutamic acid or
                      alpha-aminoadipic acid
MOD_RES              7
                     note = Asp, Glu, gamma-carboxyglutamic acid or
                      alpha-aminoadipic acid
MOD_RES              13
                     note = Asp, Glu, gamma-carboxyglutamic acid or
                      alpha-aminoadipic acid
source               1..18
                     mol_type = protein
                     organism = synthetic construct
SEQUENCE: 122
LXLLLTXTPF LWXLYRAW                                                       18

SEQ ID NO: 123       moltype = AA  length = 18
FEATURE              Location/Qualifiers
REGION               1..18
                     note = Description of Artificial Sequence: Synthetic peptide
MOD_RES              2
                     note = Asp, Glu, gamma-carboxyglutamic acid or
                      alpha-aminoadipic acid
MOD_RES              7
                     note = Asp, Glu, gamma-carboxyglutamic acid or
                      alpha-aminoadipic acid
MOD_RES              13
                     note = Asp, Glu, gamma-carboxyglutamic acid or
                      alpha-aminoadipic acid
source               1..18
                     mol_type = protein
                     organism = synthetic construct
SEQUENCE: 123
WXLLLTXTPF LLXLYQAW                                                       18

SEQ ID NO: 124       moltype = AA  length = 17
FEATURE              Location/Qualifiers
REGION               1..17
                     note = Description of Artificial Sequence: Synthetic peptide
MOD_RES              17
                     note = Asp, Glu, gamma-carboxyglutamic acid or
                      alpha-aminoadipic acid
source               1..17
                     mol_type = protein
                     organism = synthetic construct
SEQUENCE: 124
WLFTTPLLLL NGALLVX                                                        17

SEQ ID NO: 125       moltype = AA  length = 17
FEATURE              Location/Qualifiers
REGION               1..17
                     note = Description of Artificial Sequence: Synthetic peptide
MOD_RES              17
                     note = Asp, Glu, gamma-carboxyglutamic acid or
                      alpha-aminoadipic acid
source               1..17
                     mol_type = protein
                     organism = synthetic construct
SEQUENCE: 125
WLFTTPLLLL PGALLVX                                                        17
```

```
SEQ ID NO: 126          moltype = AA  length = 15
FEATURE                 Location/Qualifiers
REGION                  1..15
                        note = Description of Artificial Sequence: Synthetic peptide
MOD_RES                 6
                        note = Asp, Glu, gamma-carboxyglutamic acid or
                         alpha-aminoadipic acid
source                  1..15
                        mol_type = protein
                        organism = synthetic construct
SEQUENCE: 126
WARYAXLLFP TTLAW                                                                 15

SEQ ID NO: 127          moltype = AA  length = 17
FEATURE                 Location/Qualifiers
REGION                  1..17
                        note = Description of Artificial Sequence: Synthetic peptide
MOD_RES                 1
                        note = Asp, Glu, gamma-carboxyglutamic acid or
                         alpha-aminoadipic acid
source                  1..17
                        mol_type = protein
                        organism = synthetic construct
SEQUENCE: 127
XVLLAGNLLL LPTTFLW                                                               17

SEQ ID NO: 128          moltype = AA  length = 17
FEATURE                 Location/Qualifiers
REGION                  1..17
                        note = Description of Artificial Sequence: Synthetic peptide
MOD_RES                 1
                        note = Asp, Glu, gamma-carboxyglutamic acid or
                         alpha-aminoadipic acid
source                  1..17
                        mol_type = protein
                        organism = synthetic construct
SEQUENCE: 128
XVLLAGPLLL LPTTFLW                                                               17

SEQ ID NO: 129          moltype = AA  length = 15
FEATURE                 Location/Qualifiers
REGION                  1..15
                        note = Description of Artificial Sequence: Synthetic peptide
MOD_RES                 10
                        note = Asp, Glu, gamma-carboxyglutamic acid or
                         alpha-aminoadipic acid
source                  1..15
                        mol_type = protein
                        organism = synthetic construct
SEQUENCE: 129
WALTTPFLLX AYRAW                                                                 15

SEQ ID NO: 130          moltype = AA  length = 24
FEATURE                 Location/Qualifiers
REGION                  1..24
                        note = Description of Artificial Sequence: Synthetic peptide
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 24
                        note = Asp, Glu, gamma-carboxyglutamic acid or
                         alpha-aminoadipic acid
source                  1..24
                        mol_type = protein
                        organism = synthetic construct
SEQUENCE: 130
NLXGFFATLG GXIALWSLVV LAIX                                                       24

SEQ ID NO: 131          moltype = AA  length = 22
FEATURE                 Location/Qualifiers
REGION                  1..22
                        note = Description of Artificial Sequence: Synthetic peptide
MOD_RES                 1
                        note = Asp, Glu, gamma-carboxyglutamic acid or
                         alpha-aminoadipic acid
MOD_RES                 10
```

```
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
MOD_RES                 22
                        note = Asp, Glu, gamma-carboxyglutamic acid or
                         alpha-aminoadipic acid
source                  1..22
                        mol_type = protein
                        organism = synthetic construct
SEQUENCE: 131
XGFFATLGGX IALWSXVVLA IX                                                  22

SEQ ID NO: 132          moltype = AA  length = 22
FEATURE                 Location/Qualifiers
REGION                  1..22
                        note = Description of Artificial Sequence: Synthetic peptide
MOD_RES                 1
                        note = Asp, Glu, gamma-carboxyglutamic acid or
                         alpha-aminoadipic acid
MOD_RES                 10
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
MOD_RES                 22
                        note = Asp, Glu, gamma-carboxyglutamic acid or
                         alpha-aminoadipic acid
source                  1..22
                        mol_type = protein
                        organism = synthetic construct
SEQUENCE: 132
XGFFATLGGX IPLWSXVVLA IX                                                  22

SEQ ID NO: 133          moltype = AA  length = 24
FEATURE                 Location/Qualifiers
REGION                  1..24
                        note = Description of Artificial Sequence: Synthetic peptide
MOD_RES                 1
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
MOD_RES                 22
                        note = Asp, Glu, gamma-carboxyglutamic acid or
                         alpha-aminoadipic acid
source                  1..24
                        mol_type = protein
                        organism = synthetic construct
SEQUENCE: 133
XIALVVLSWL AIXGGLTAFF GXLN                                                24

SEQ ID NO: 134          moltype = AA  length = 22
FEATURE                 Location/Qualifiers
REGION                  1..22
                        note = Description of Artificial Sequence: Synthetic peptide
MOD_RES                 1
                        note = Asp, Glu, gamma-carboxyglutamic acid or
                         alpha-aminoadipic acid
MOD_RES                 7
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
MOD_RES                 22
                        note = Asp, Glu, gamma-carboxyglutamic acid or
                         alpha-aminoadipic acid
source                  1..22
                        mol_type = protein
                        organism = synthetic construct
SEQUENCE: 134
XIALVVXSWL AIXGGLTAFF GX                                                  22

SEQ ID NO: 135          moltype = AA  length = 22
FEATURE                 Location/Qualifiers
```

```
                                    -continued

REGION                  1..22
                        note = Description of Artificial Sequence: Synthetic peptide
MOD_RES                 1
                        note = Asp, Glu, gamma-carboxyglutamic acid or
                         alpha-aminoadipic acid
MOD_RES                 7
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
MOD_RES                 22
                        note = Asp, Glu, gamma-carboxyglutamic acid or
                         alpha-aminoadipic acid
source                  1..22
                        mol_type = protein
                        organism = synthetic construct
SEQUENCE: 135
XIALVVXSWL PIXGGLTAFF GX                                                    22

SEQ ID NO: 136          moltype = AA  length = 21
FEATURE                 Location/Qualifiers
REGION                  1..21
                        note = Description of Artificial Sequence: Synthetic peptide
MOD_RES                 3
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 136
ILXLVFGLLF AVTSVXFLVQ W                                                     21

SEQ ID NO: 137          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 19
                        note = Asp, Glu, gamma-carboxyglutamic acid or
                         alpha-aminoadipic acid
source                  1..21
                        mol_type = protein
                        organism = synthetic construct
SEQUENCE: 137
WQVLFXVSTV AFLLGFVLXL I                                                     21

SEQ ID NO: 138          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 138
WARYAXWLFT TPLLLLXLAL L                                                     21

SEQ ID NO: 139          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
```

```
                                  mol_type = protein
                                  organism = synthetic construct
SEQUENCE: 139
YARYAXWLFT TPLLLLXLAL L                                             21

SEQ ID NO: 140          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 140
WARYSXWLFT TPLLLYXLGL L                                             21

SEQ ID NO: 141          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 141
WARYTXWFTT PLLLYXLALL A                                             21

SEQ ID NO: 142          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 142
WARYTXWLFT TPLLLYXLGL L                                             21

SEQ ID NO: 143          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..21
                        mol_type = protein
                        organism = synthetic construct
SEQUENCE: 143
WARYAXWLFT TPLLLLXLSL L                                             21

SEQ ID NO: 144          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
```

```
source                  1..21
                        mol_type = protein
                        organism = synthetic construct
SEQUENCE: 144
LLALXLLLLP TTFLWXAYRA W                                              21

SEQ ID NO: 145          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 145
LLALXLLLLP TTFLWXAYRA Y                                              21

SEQ ID NO: 146          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 146
LLGLXYLLLP TTFLWXSYRA W                                              21

SEQ ID NO: 147          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 147
ALLALXYLLL PTTFWXTYRA W                                              21

SEQ ID NO: 148          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
                         alpha-aminoadipic acid
source                  1..21
                        mol_type = protein
                        organism = synthetic construct
SEQUENCE: 148
LLGLXYLLLP TTFLWXTYRA W                                              21

SEQ ID NO: 149          moltype = AA  length = 21
FEATURE                 Location/Qualifiers
REGION                  1..21
                        note = Description of Artificial Sequence: Synthetic peptide
MOD_RES                 5
                        note = Asp, Glu, gamma-carboxyglutamic acid or
                         alpha-aminoadipic acid
MOD_RES                 16
                        note = Asp, Glu, gamma-carboxyglutamic acid or
```

```
                            alpha-aminoadipic acid
source                      1..21
                            mol_type = protein
                            organism = synthetic construct
SEQUENCE: 149
LLSLXLLLLP TTFLWXAYRA W                                             21

SEQ ID NO: 150              moltype = AA  length = 26
FEATURE                     Location/Qualifiers
REGION                      1..26
                            note = Description of Artificial Sequence: Synthetic peptide
MOD_RES                     9
                            note = Asp, Glu, gamma-carboxyglutamic acid or
                            alpha-aminoadipic acid
MOD_RES                     20
                            note = Asp, Glu, gamma-carboxyglutamic acid or
                            alpha-aminoadipic acid
source                      1..26
                            mol_type = protein
                            organism = synthetic construct
SEQUENCE: 150
GLAGLLGLXG LLGLPLGLLX GLWLGL                                        26

SEQ ID NO: 151              moltype = AA  length = 26
FEATURE                     Location/Qualifiers
REGION                      1..26
                            note = Description of Artificial Sequence: Synthetic peptide
MOD_RES                     7
                            note = Asp, Glu, gamma-carboxyglutamic acid or
                            alpha-aminoadipic acid
MOD_RES                     18
                            note = Asp, Glu, gamma-carboxyglutamic acid or
                            alpha-aminoadipic acid
source                      1..26
                            mol_type = protein
                            organism = synthetic construct
SEQUENCE: 151
LGLWLGXLLG LPLGLLGXLG LLGALG                                        26

SEQ ID NO: 152              moltype = AA  length = 20
FEATURE                     Location/Qualifiers
REGION                      1..20
                            note = Description of Artificial Sequence: Synthetic peptide
MOD_RES                     6
                            note = Asp, Glu, gamma-carboxyglutamic acid or
                            alpha-aminoadipic acid
MOD_RES                     12
                            note = Asp, Glu, gamma-carboxyglutamic acid or
                            alpha-aminoadipic acid
MOD_RES                     17
                            note = Asp, Glu, gamma-carboxyglutamic acid or
                            alpha-aminoadipic acid
source                      1..20
                            mol_type = protein
                            organism = synthetic construct
SEQUENCE: 152
WRAYLXLLFP TXTLLLXLLW                                               20

SEQ ID NO: 153              moltype = AA  length = 20
FEATURE                     Location/Qualifiers
REGION                      1..20
                            note = Description of Artificial Sequence: Synthetic peptide
MOD_RES                     4
                            note = Asp, Glu, gamma-carboxyglutamic acid or
                            alpha-aminoadipic acid
MOD_RES                     9
                            note = Asp, Glu, gamma-carboxyglutamic acid or
                            alpha-aminoadipic acid
MOD_RES                     15
                            note = Asp, Glu, gamma-carboxyglutamic acid or
                            alpha-aminoadipic acid
source                      1..20
                            mol_type = protein
                            organism = synthetic construct
SEQUENCE: 153
WLLXLLLTXT PFLLXLYARW                                               20

SEQ ID NO: 154              moltype = AA  length = 18
FEATURE                     Location/Qualifiers
```

```
REGION                  1..18
                        note = Description of Artificial Sequence: Synthetic peptide
MOD_RES                 6
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..18
                        mol_type = protein
                        organism = synthetic construct
SEQUENCE: 154
WARYLXWLFP TXTLLLXL                                                              18

SEQ ID NO: 155          moltype = AA  length = 18
FEATURE                 Location/Qualifiers
REGION                  1..18
                        note = Description of Artificial Sequence: Synthetic peptide
MOD_RES                 6
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 17
                        note = Asp, Glu, gamma-carboxyglutamic acid or
                         alpha-aminoadipic acid
source                  1..18
                        mol_type = protein
                        organism = synthetic construct
SEQUENCE: 155
WAQYLXLLFP TXTLLLXW                                                              18

SEQ ID NO: 156          moltype = AA  length = 18
FEATURE                 Location/Qualifiers
REGION                  1..18
                        note = Description of Artificial Sequence: Synthetic peptide
MOD_RES                 2
                        note = Asp, Glu, gamma-carboxyglutamic acid or
                         alpha-aminoadipic acid
MOD_RES                 7
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
source                  1..18
                        mol_type = protein
                        organism = synthetic construct
SEQUENCE: 156
LXLLLTXTPF LWXLYRAW                                                              18

SEQ ID NO: 157          moltype = AA  length = 18
FEATURE                 Location/Qualifiers
REGION                  1..18
                        note = Description of Artificial Sequence: Synthetic peptide
MOD_RES                 2
                        note = Asp, Glu, gamma-carboxyglutamic acid or
                         alpha-aminoadipic acid
MOD_RES                 7
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
source                  1..18
                        mol_type = protein
                        organism = synthetic construct
SEQUENCE: 157
WXLLLTXTPF LLXLYQAW                                                              18

SEQ ID NO: 158          moltype = AA  length = 17
FEATURE                 Location/Qualifiers
REGION                  1..17
                        note = Description of Artificial Sequence: Synthetic peptide
MOD_RES                 17
```

```
                        note = Asp, Glu, gamma-carboxyglutamic acid or
                         alpha-aminoadipic acid
source                  1..17
                        mol_type = protein
                        organism = synthetic construct SEQUENCE: 158
WLFTTPLLLL NGALLVX                                                        17

SEQ ID NO: 159          moltype = AA  length = 17
FEATURE                 Location/Qualifiers
REGION                  1..17
                        note = Description of Artificial Sequence: Synthetic peptide
MOD_RES                 17
                        note = Asp, Glu, gamma-carboxyglutamic acid or
                         alpha-aminoadipic acid
source                  1..17
                        mol_type = protein
                        organism = synthetic construct SEQUENCE: 159
WLFTTPLLLL PGALLVX                                                        17

SEQ ID NO: 160          moltype = AA  length = 15
FEATURE                 Location/Qualifiers
REGION                  1..15
                        note = Description of Artificial Sequence: Synthetic peptide
MOD_RES                 6
                        note = Asp, Glu, gamma-carboxyglutamic acid or
                         alpha-aminoadipic acid
source                  1..15
                        mol_type = protein
                        organism = synthetic construct SEQUENCE: 160
WARYAXLLFP TTLAW                                                          15

SEQ ID NO: 161          moltype = AA  length = 17
FEATURE                 Location/Qualifiers
REGION                  1..17
                        note = Description of Artificial Sequence: Synthetic peptide
MOD_RES                 1
                        note = Asp, Glu, gamma-carboxyglutamic acid or
                         alpha-aminoadipic acid
source                  1..17
                        mol_type = protein
                        organism = synthetic construct SEQUENCE: 161
XVLLAGNLLL LPTTFLW                                                        17

SEQ ID NO: 162          moltype = AA  length = 17
FEATURE                 Location/Qualifiers
REGION                  1..17
                        note = Description of Artificial Sequence: Synthetic peptide
MOD_RES                 1
                        note = Asp, Glu, gamma-carboxyglutamic acid or
                         alpha-aminoadipic acid
source                  1..17
                        mol_type = protein
                        organism = synthetic construct SEQUENCE: 162
XVLLAGPLLL LPTTFLW                                                        17

SEQ ID NO: 163          moltype = AA  length = 15
FEATURE                 Location/Qualifiers
REGION                  1..15
                        note = Description of Artificial Sequence: Synthetic peptide
MOD_RES                 10
                        note = Asp, Glu, gamma-carboxyglutamic acid or
                         alpha-aminoadipic acid
source                  1..15
                        mol_type = protein
                        organism = synthetic construct SEQUENCE: 163
WALTTPFLLX AYRAW                                                          15

SEQ ID NO: 164          moltype = AA  length = 24
FEATURE                 Location/Qualifiers
REGION                  1..24
                        note = Description of Artificial Sequence: Synthetic peptide
MOD_RES                 3
                        note = Asp, Glu, gamma-carboxyglutamic acid or
```

```
                         alpha-aminoadipic acid
MOD_RES                  12
                         note = Asp, Glu, gamma-carboxyglutamic acid or
                         alpha-aminoadipic acid
MOD_RES                  24
                         note = Asp, Glu, gamma-carboxyglutamic acid or
                         alpha-aminoadipic acid
source                   1..24
                         mol_type = protein
                         organism = synthetic construct
SEQUENCE: 164
NLXGFFATLG GXIALWSLVV LAIX                                               24

SEQ ID NO: 165           moltype = AA  length = 22
FEATURE                  Location/Qualifiers
REGION                   1..22
                         note = Description of Artificial Sequence: Synthetic peptide
MOD_RES                  1
                         note = Asp, Glu, gamma-carboxyglutamic acid or
                         alpha-aminoadipic acid
MOD_RES                  10
                         note = Asp, Glu, gamma-carboxyglutamic acid or
                         alpha-aminoadipic acid
MOD_RES                  16
                         note = Asp, Glu, gamma-carboxyglutamic acid or
                         alpha-aminoadipic acid
MOD_RES                  22
                         note = Asp, Glu, gamma-carboxyglutamic acid or
                         alpha-aminoadipic acid
source                   1..22
                         mol_type = protein
                         organism = synthetic construct
SEQUENCE: 165
XGFFATLGGX IALWSXVVLA IX                                                 22

SEQ ID NO: 166           moltype = AA  length = 22
FEATURE                  Location/Qualifiers
REGION                   1..22
                         note = Description of Artificial Sequence: Synthetic peptide
MOD_RES                  1
                         note = Asp, Glu, gamma-carboxyglutamic acid or
                         alpha-aminoadipic acid
MOD_RES                  10
                         note = Asp, Glu, gamma-carboxyglutamic acid or
                         alpha-aminoadipic acid
MOD_RES                  16
                         note = Asp, Glu, gamma-carboxyglutamic acid or
                         alpha-aminoadipic acid
MOD_RES                  22
                         note = Asp, Glu, gamma-carboxyglutamic acid or
                         alpha-aminoadipic acid
source                   1..22
                         mol_type = protein
                         organism = synthetic construct
SEQUENCE: 166
XGFFATLGGX IPLWSXVVLA IX                                                 22

SEQ ID NO: 167           moltype = AA  length = 24
FEATURE                  Location/Qualifiers
REGION                   1..24
                         note = Description of Artificial Sequence: Synthetic peptide
MOD_RES                  1
                         note = Asp, Glu, gamma-carboxyglutamic acid or
                         alpha-aminoadipic acid
MOD_RES                  13
                         note = Asp, Glu, gamma-carboxyglutamic acid or
                         alpha-aminoadipic acid
MOD_RES                  22
                         note = Asp, Glu, gamma-carboxyglutamic acid or
                         alpha-aminoadipic acid
source                   1..24
                         mol_type = protein
                         organism = synthetic construct
SEQUENCE: 167
XIALVVLSWL AIXGGLTAFF GXLN                                               24

SEQ ID NO: 168           moltype = AA  length = 22
FEATURE                  Location/Qualifiers
REGION                   1..22
```

```
                        note = Description of Artificial Sequence: Synthetic peptide
MOD_RES                 1
                        note = Asp, Glu, gamma-carboxyglutamic acid or
                          alpha-aminoadipic acid
MOD_RES                 7
                        note = Asp, Glu, gamma-carboxyglutamic acid or
                          alpha-aminoadipic acid
MOD_RES                 13
                        note = Asp, Glu, gamma-carboxyglutamic acid or
                          alpha-aminoadipic acid
MOD_RES                 22
                        note = Asp, Glu, gamma-carboxyglutamic acid or
                          alpha-aminoadipic acid
source                  1..22
                        mol_type = protein
                        organism = synthetic construct
SEQUENCE: 168
XIALVVXSWL AIXGGLTAFF GX                                                    22

SEQ ID NO: 169          moltype = AA  length = 22
FEATURE                 Location/Qualifiers
REGION                  1..22
                        note = Description of Artificial Sequence: Synthetic peptide
MOD_RES                 1
                        note = Asp, Glu, gamma-carboxyglutamic acid or
                          alpha-aminoadipic acid
MOD_RES                 7
                        note = Asp, Glu, gamma-carboxyglutamic acid or
                          alpha-aminoadipic acid
MOD_RES                 13
                        note = Asp, Glu, gamma-carboxyglutamic acid or
                          alpha-aminoadipic acid
MOD_RES                 22
                        note = Asp, Glu, gamma-carboxyglutamic acid or
                          alpha-aminoadipic acid
source                  1..22
                        mol_type = protein
                        organism = synthetic construct
SEQUENCE: 169
XIALVVXSWL PIXGGLTAFF GX                                                    22

SEQ ID NO: 170          moltype = AA  length = 21
FEATURE                 Location/Qualifiers
REGION                  1..21
                        note = Description of Artificial Sequence: Synthetic peptide
MOD_RES                 3
                        note = Asp, Glu, gamma-carboxyglutamic acid or
                          alpha-aminoadipic acid
MOD_RES                 16
                        note = Asp, Glu, gamma-carboxyglutamic acid or
                          alpha-aminoadipic acid
source                  1..21
                        mol_type = protein
                        organism = synthetic construct
SEQUENCE: 170
ILXLVFGLLF AVTSVXFLVQ W                                                     21

SEQ ID NO: 171          moltype = AA  length = 21
FEATURE                 Location/Qualifiers
REGION                  1..21
                        note = Description of Artificial Sequence: Synthetic peptide
MOD_RES                 6
                        note = Asp, Glu, gamma-carboxyglutamic acid or
                          alpha-aminoadipic acid
MOD_RES                 19
                        note = Asp, Glu, gamma-carboxyglutamic acid or
                          alpha-aminoadipic acid
source                  1..21
                        mol_type = protein
                        organism = synthetic construct
SEQUENCE: 171
WQVLFXVSTV AFLLGFVLXL I                                                     21

SEQ ID NO: 172          moltype = AA  length = 34
FEATURE                 Location/Qualifiers
REGION                  1..34
                        note = Description of Artificial Sequence: Synthetic
                          polypeptide
source                  1..34
```

```
                              mol_type = protein
                              organism = synthetic construct
SEQUENCE: 172
AEQNPIYWAR YAEWLFTTPL LLLELALLVE AEET                              34

SEQ ID NO: 173           moltype = AA  length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 173
ADDQNPWRAY LDLLFPDTTD LLLLDLLWDA DET                               33

SEQ ID NO: 174           moltype = AA  length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 174
AEEQNPWRAY LELLFPETTE LLLLELLWEA EET                               33

SEQ ID NO: 175           moltype = AA  length = 34
FEATURE                  Location/Qualifiers
REGION                   1..34
                         note = Description of Artificial Sequence: Synthetic
                          polypeptide
MOD_RES                  13
                         note = Gamma-carboxyglutamic acid
MOD_RES                  24
                         note = Gamma-carboxyglutamic acid
source                   1..34
                         mol_type = protein
                         organism = synthetic construct
SEQUENCE: 175
AEQNPIYWAR YAXWLFTTPL LLLXLALLVD ADET                              34

SEQ ID NO: 176           moltype = AA  length = 34
FEATURE                  Location/Qualifiers
REGION                   1..34
                         note = Description of Artificial Sequence: Synthetic
                          polypeptide
MOD_RES                  13
                         note = Alpha-aminoadipic acid
MOD_RES                  24
                         note = Alpha-aminoadipic acid
source                   1..34
                         mol_type = protein
                         organism = synthetic construct
SEQUENCE: 176
AEQNPIYWAR YAXWLFTTPL LLLXLALLVD ADET                              34

SEQ ID NO: 177           moltype = AA  length = 34
FEATURE                  Location/Qualifiers
REGION                   1..34
                         note = Description of Artificial Sequence: Synthetic
                          polypeptide
MOD_RES                  13
                         note = Alpha-aminoadipic acid
MOD_RES                  24
                         note = Gamma-carboxyglutamic acid
source                   1..34
                         mol_type = protein
                         organism = synthetic construct
SEQUENCE: 177
AEQNPIYWAR YAXWLFTTPL LLLXLALLVD ADET                              34

SEQ ID NO: 178           moltype = AA  length = 33
FEATURE                  Location/Qualifiers
REGION                   1..33
                         note = Description of Artificial Sequence: Synthetic
                          polypeptide
source                   1..33
                         mol_type = protein
```

```
                        organism = synthetic construct
SEQUENCE: 178
CEQNPIYWAR YADWHFTTPL LLLDLALLVD ADE                               33

SEQ ID NO: 179          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 179
ADNNPWIYAR YADLTTFPLL LLDLALLVDF DD                                32

SEQ ID NO: 180          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 180
ADNNPFIYAR YADLTTWPLL LLDLALLVDF DD                                32

SEQ ID NO: 181          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 181
ADNNPFIYAR YADLTTFPLL LLDLALLVDW DD                                32

SEQ ID NO: 182          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 182
ADNNPFPYAR YADLTTWILL LLDLALLVDF DD                                32

SEQ ID NO: 183          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 183
ADNNPFIYAY RADLTTFPLL LLDLALLVDW DD                                32

SEQ ID NO: 184          moltype = AA  length = 32
FEATURE                 Location/Qualifiers
REGION                  1..32
                        note = Description of Artificial Sequence: Synthetic
                        polypeptide
source                  1..32
                        mol_type = protein
                        organism = synthetic construct
SEQUENCE: 184
ADNNPFIYAT YADLRTFPLL LLDLALLVDW DD                                32

SEQ ID NO: 185          moltype = AA  length = 30
FEATURE                 Location/Qualifiers
REGION                  1..30
                        note = Description of Artificial Sequence: Synthetic
                        polypeptide
source                  1..30
                        mol_type = protein
                        organism = synthetic construct
SEQUENCE: 185
```

ADDQNPWRAY LDLLFPTDTL LLDLLWDADE                                              30

SEQ ID NO: 186          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
source                  1..26
                        mol_type = protein
                        organism = synthetic construct
SEQUENCE: 186
ADDQNPWRAY LXLLFPTDTL LLDLLW                                                  26

SEQ ID NO: 187          moltype = AA  length = 26
FEATURE                 Location/Qualifiers
REGION                  1..26
                        note = Description of Artificial Sequence: Synthetic peptide
MOD_RES                 18
                        note = Gamma-carboxyglutamic acid
source                  1..26
                        mol_type = protein
                        organism = synthetic construct
SEQUENCE: 187
ADDQNPWRAY LDLLFPTXTL LLDLLW                                                  26

SEQ ID NO: 188          moltype = AA  length = 26
FEATURE                 Location/Qualifiers
REGION                  1..26
                        note = Description of Artificial Sequence: Synthetic peptide
MOD_RES                 23
                        note = Gamma-carboxyglutamic acid
source                  1..26
                        mol_type = protein
                        organism = synthetic construct
SEQUENCE: 188
ADDQNPWRAY LDLLFPTDTL LLXLLW                                                  26

SEQ ID NO: 189          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Gamma-carboxyglutamic acid
source                  1..26
                        mol_type = protein
                        organism = synthetic construct
SEQUENCE: 189
ADDQNPWRAY LXLLFPTXTL LLDLLW                                                  26

SEQ ID NO: 190          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 23
                        note = Gamma-carboxyglutamic acid
source                  1..26
                        mol_type = protein
                        organism = synthetic construct
SEQUENCE: 190
ADDQNPWRAY LXLLFPTDTL LLXLLW                                                  26

SEQ ID NO: 191          moltype = AA  length = 26
FEATURE                 Location/Qualifiers
REGION                  1..26
                        note = Description of Artificial Sequence: Synthetic peptide
MOD_RES                 18
                        note = Gamma-carboxyglutamic acid
MOD_RES                 23
                        note = Gamma-carboxyglutamic acid
source                  1..26
                        mol_type = protein
                        organism = synthetic construct
SEQUENCE: 191
ADDQNPWRAY LDLLFPTXTL LLXLLW                                                  26

```
SEQ ID NO: 192          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Gamma-carboxyglutamic acid
MOD_RES                 23
                        note = Gamma-carboxyglutamic acid
source                  1..26
                        mol_type = protein
                        organism = synthetic construct
SEQUENCE: 192
ADDQNPWRAY LXLLFPTXTL LLXLLW                                              26

SEQ ID NO: 193          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
source                  1..26
                        mol_type = protein
                        organism = synthetic construct
SEQUENCE: 193
ADDQNPWRAY LXLLFPTDTL LLDLLW                                              26

SEQ ID NO: 194          moltype = AA  length = 26
FEATURE                 Location/Qualifiers
REGION                  1..26
                        note = Description of Artificial Sequence: Synthetic peptide
MOD_RES                 18
                        note = Alpha-aminoadipic acid
source                  1..26
                        mol_type = protein
                        organism = synthetic construct
SEQUENCE: 194
ADDQNPWRAY LDLLFPTXTL LLDLLW                                              26

SEQ ID NO: 195          moltype = AA  length = 26
FEATURE                 Location/Qualifiers
REGION                  1..26
                        note = Description of Artificial Sequence: Synthetic peptide
MOD_RES                 23
                        note = Alpha-aminoadipic acid
source                  1..26
                        mol_type = protein
                        organism = synthetic construct
SEQUENCE: 195
ADDQNPWRAY LDLLFPTDTL LLXLLW                                              26

SEQ ID NO: 196          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 18
                        note = Alpha-aminoadipic acid
source                  1..26
                        mol_type = protein
                        organism = synthetic construct
SEQUENCE: 196
ADDQNPWRAY LXLLFPTXTL LLDLLW                                              26

SEQ ID NO: 197          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 23
                        note = Alpha-aminoadipic acid
source                  1..26
                        mol_type = protein
                        organism = synthetic construct
SEQUENCE: 197
```

```
ADDQNPWRAY LXLLFPTDTL LLXLLW                                        26

SEQ ID NO: 198          moltype = AA  length = 26
FEATURE                 Location/Qualifiers
REGION                  1..26
                        note = Description of Artificial Sequence: Synthetic peptide
MOD_RES                 18
                        note = Alpha-aminoadipic acid
MOD_RES                 23
                        note = Alpha-aminoadipic acid
source                  1..26
                        mol_type = protein
                        organism = synthetic construct
SEQUENCE: 198
ADDQNPWRAY LDLLFPTXTL LLXLLW                                        26

SEQ ID NO: 199          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 18
                        note = Alpha-aminoadipic acid
MOD_RES                 23
                        note = Alpha-aminoadipic acid
source                  1..26
                        mol_type = protein
                        organism = synthetic construct
SEQUENCE: 199
ADDQNPWRAY LXLLFPTXTL LLXLLW                                        26

SEQ ID NO: 200          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Alpha-aminoadipic acid
source                  1..26
                        mol_type = protein
                        organism = synthetic construct
SEQUENCE: 200
ADDQNPWRAY LXLLFPTXTL LLDLLW                                        26

SEQ ID NO: 201          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 23
                        note = Alpha-aminoadipic acid
source                  1..26
                        mol_type = protein
                        organism = synthetic construct
SEQUENCE: 201
ADDQNPWRAY LXLLFPTDTL LLXLLW                                        26

SEQ ID NO: 202          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Gamma-carboxyglutamic acid
MOD_RES                 23
                        note = Alpha-aminoadipic acid
source                  1..26
                        mol_type = protein
                        organism = synthetic construct
SEQUENCE: 202
ADDQNPWRAY LXLLFPTXTL LLXLLW                                        26

SEQ ID NO: 203          moltype = AA  length = 26
FEATURE                 Location/Qualifiers
REGION                  1..26
```

```
                        note = Description of Artificial Sequence: Synthetic peptide
MOD_RES                 12
                        note = Alpha-aminoadipic acid
MOD_RES                 18
                        note = Gamma-carboxyglutamic acid
source                  1..26
                        mol_type = protein
                        organism = synthetic construct
SEQUENCE: 203
ADDQNPWRAY LXLLFPTXTL LLDLLW                                               26

SEQ ID NO: 204          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 23
                        note = Gamma-carboxyglutamic acid
source                  1..26
                        mol_type = protein
                        organism = synthetic construct
SEQUENCE: 204
ADDQNPWRAY LXLLFPTDTL LLXLLW                                               26

SEQ ID NO: 205          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Alpha-aminoadipic acid
MOD_RES                 23
                        note = Gamma-carboxyglutamic acid
source                  1..26
                        mol_type = protein
                        organism = synthetic construct
SEQUENCE: 205
ADDQNPWRAY LXLLFPTXTL LLXLLW                                               26

SEQ ID NO: 206          moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 206
GEEQNPWLGA YLDLLFPLEL LGLLELGLW                                            29

SEQ ID NO: 207          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 207
EQNPIYILDL VFGLLFAVTS VDFLVQWDDA GD                                        32

SEQ ID NO: 208          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 208
NNEGFFATLG GEIALWSDVV LAIE                                                 24

SEQ ID NO: 209          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
```

```
SEQUENCE: 209
DNNEGFFATL GGEIPLWSDV VLAIE                                              25

SEQ ID NO: 210          moltype = AA  length = 34
FEATURE                 Location/Qualifiers
REGION                  1..34
                        note = Description of Artificial Sequence: Synthetic
                        polypeptide
source                  1..34
                        mol_type = protein
                        organism = synthetic construct
SEQUENCE: 210
AEQNPIYWAR YAEWLFTTPL LLLELALLVE AEET                                    34

SEQ ID NO: 211          moltype = AA  length = 33
FEATURE                 Location/Qualifiers
REGION                  1..33
                        note = Description of Artificial Sequence: Synthetic
                        polypeptide
source                  1..33
                        mol_type = protein
                        organism = synthetic construct
SEQUENCE: 211
ADDQNPWRAY LDLLFPDTTD LLLLDLLWDA DET                                     33

SEQ ID NO: 212          moltype = AA  length = 33
FEATURE                 Location/Qualifiers
REGION                  1..33
                        note = Description of Artificial Sequence: Synthetic
                        polypeptide
source                  1..33
                        mol_type = protein
                        organism = synthetic construct
SEQUENCE: 212
AEEQNPWRAY LELLFPETTE LLLLELLWEA EET                                     33

SEQ ID NO: 213          moltype = AA  length = 34
FEATURE                 Location/Qualifiers
REGION                  1..34
                        note = Description of Artificial Sequence: Synthetic
                        polypeptide
MOD_RES                 13
                        note = Gamma-carboxyglutamic acid
MOD_RES                 24
                        note = Gamma-carboxyglutamic acid
source                  1..34
                        mol_type = protein
                        organism = synthetic construct
SEQUENCE: 213
AEQNPIYWAR YAXWLFTTPL LLLXLALLVD ADET                                    34

SEQ ID NO: 214          moltype = AA  length = 34
FEATURE                 Location/Qualifiers
REGION                  1..34
                        note = Description of Artificial Sequence: Synthetic
                        polypeptide
MOD_RES                 13
                        note = Alpha-aminoadipic acid
MOD_RES                 24
                        note = Alpha-aminoadipic acid
source                  1..34
                        mol_type = protein
                        organism = synthetic construct
SEQUENCE: 214
AEQNPIYWAR YAXWLFTTPL LLLXLALLVD ADET                                    34

SEQ ID NO: 215          moltype = AA  length = 34
FEATURE                 Location/Qualifiers
REGION                  1..34
                        note = Description of Artificial Sequence: Synthetic
                        polypeptide
MOD_RES                 13
                        note = Alpha-aminoadipic acid
MOD_RES                 24
                        note = Gamma-carboxyglutamic acid
source                  1..34
                        mol_type = protein
                        organism = synthetic construct
SEQUENCE: 215
```

```
AEQNPIYWAR YAXWLFTTPL LLLXLALLVD ADET                                34

SEQ ID NO: 216          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 216
CEQNPIYWAR YADWHFTTPL LLLDLALLVD ADE                                 33

SEQ ID NO: 217          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 217
ADNNPWIYAR YADLTTFPLL LLDLALLVDF DD                                  32

SEQ ID NO: 218          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 218
ADNNPFIYAR YADLTTWPLL LLDLALLVDF DD                                  32

SEQ ID NO: 219          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 219
ADNNPFIYAR YADLTTFPLL LLDLALLVDW DD                                  32

SEQ ID NO: 220          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 220
ADNNPFPYAR YADLTTWILL LLDLALLVDF DD                                  32

SEQ ID NO: 221          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 221
ADNNPFIYAY RADLTTFPLL LLDLALLVDW DD                                  32

SEQ ID NO: 222          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 222
ADNNPFIYAT YADLRTFPLL LLDLALLVDW DD                                  32
```

```
SEQ ID NO: 223          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 223
ADDQNPWRAY LDLLFPTDTL LLDLLWDADE                                            30

SEQ ID NO: 224          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
source                  1..26
                        mol_type = protein
                        organism = synthetic construct
SEQUENCE: 224
ADDQNPWRAY LXLLFPTDTL LLDLLW                                                26

SEQ ID NO: 225          moltype = AA  length = 26
FEATURE                 Location/Qualifiers
REGION                  1..26
                        note = Description of Artificial Sequence: Synthetic peptide
MOD_RES                 18
                        note = Gamma-carboxyglutamic acid
source                  1..26
                        mol_type = protein
                        organism = synthetic construct
SEQUENCE: 225
ADDQNPWRAY LDLLFPTXTL LLDLLW                                                26

SEQ ID NO: 226          moltype = AA  length = 26
FEATURE                 Location/Qualifiers
REGION                  1..26
                        note = Description of Artificial Sequence: Synthetic peptide
MOD_RES                 23
                        note = Gamma-carboxyglutamic acid
source                  1..26
                        mol_type = protein
                        organism = synthetic construct
SEQUENCE: 226
ADDQNPWRAY LDLLFPTDTL LLXLLW                                                26

SEQ ID NO: 227          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Gamma-carboxyglutamic acid
source                  1..26
                        mol_type = protein
                        organism = synthetic construct
SEQUENCE: 227
ADDQNPWRAY LXLLFPTXTL LLDLLW                                                26

SEQ ID NO: 228          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 23
                        note = Gamma-carboxyglutamic acid
source                  1..26
                        mol_type = protein
                        organism = synthetic construct
SEQUENCE: 228
ADDQNPWRAY LXLLFPTDTL LLXLLW                                                26

SEQ ID NO: 229          moltype = AA  length = 26
FEATURE                 Location/Qualifiers
REGION                  1..26
                        note = Description of Artificial Sequence: Synthetic peptide
```

```
MOD_RES            18
                   note = Gamma-carboxyglutamic acid
MOD_RES            23
                   note = Gamma-carboxyglutamic acid
source             1..26
                   mol_type = protein
                   organism = synthetic construct
SEQUENCE: 229
ADDQNPWRAY LDLLFPTXTL LLXLLW                                           26

SEQ ID NO: 230     moltype = AA  length = 26
FEATURE            Location/Qualifiers
REGION             1..26
                   note = Description of Artificial Sequence: Synthetic peptide
MOD_RES            12
                   note = Gamma-carboxyglutamic acid
MOD_RES            18
                   note = Gamma-carboxyglutamic acid
MOD_RES            23
                   note = Gamma-carboxyglutamic acid
source             1..26
                   mol_type = protein
                   organism = synthetic construct
SEQUENCE: 230
ADDQNPWRAY LXLLFPTXTL LLXLLW                                           26

SEQ ID NO: 231     moltype = AA  length = 26
FEATURE            Location/Qualifiers
REGION             1..26
                   note = Description of Artificial Sequence: Synthetic peptide
MOD_RES            12
                   note = Alpha-aminoadipic acid
source             1..26
                   mol_type = protein
                   organism = synthetic construct
SEQUENCE: 231
ADDQNPWRAY LXLLFPTDTL LLDLLW                                           26

SEQ ID NO: 232     moltype = AA  length = 26
FEATURE            Location/Qualifiers
REGION             1..26
                   note = Description of Artificial Sequence: Synthetic peptide
MOD_RES            18
                   note = Alpha-aminoadipic acid
source             1..26
                   mol_type = protein
                   organism = synthetic construct
SEQUENCE: 232
ADDQNPWRAY LDLLFPTXTL LLDLLW                                           26

SEQ ID NO: 233     moltype = AA  length = 26
FEATURE            Location/Qualifiers
REGION             1..26
                   note = Description of Artificial Sequence: Synthetic peptide
MOD_RES            23
                   note = Alpha-aminoadipic acid
source             1..26
                   mol_type = protein
                   organism = synthetic construct
SEQUENCE: 233
ADDQNPWRAY LDLLFPTDTL LLXLLW                                           26

SEQ ID NO: 234     moltype = AA  length = 26
FEATURE            Location/Qualifiers
REGION             1..26
                   note = Description of Artificial Sequence: Synthetic peptide
MOD_RES            12
                   note = Alpha-aminoadipic acid
MOD_RES            18
                   note = Alpha-aminoadipic acid
source             1..26
                   mol_type = protein
                   organism = synthetic construct
SEQUENCE: 234
ADDQNPWRAY LXLLFPTXTL LLDLLW                                           26

SEQ ID NO: 235     moltype = AA  length = 26
FEATURE            Location/Qualifiers
REGION             1..26
```

```
                              note = Description of Artificial Sequence: Synthetic peptide
MOD_RES                       12
                              note = Alpha-aminoadipic acid
MOD_RES                       23
                              note = Alpha-aminoadipic acid
source                        1..26
                              mol_type = protein
                              organism = synthetic construct
SEQUENCE: 235
ADDQNPWRAY LXLLFPTDTL LLXLLW                                                      26

SEQ ID NO: 236                moltype = AA   length = 26
FEATURE                       Location/Qualifiers
REGION                        1..26
                              note = Description of Artificial Sequence: Synthetic peptide
MOD_RES                       18
                              note = Alpha-aminoadipic acid
MOD_RES                       23
                              note = Alpha-aminoadipic acid
source                        1..26
                              mol_type = protein
                              organism = synthetic construct
SEQUENCE: 236
ADDQNPWRAY LDLLFPTXTL LLXLLW                                                      26

SEQ ID NO: 237                moltype = AA   length = 26
FEATURE                       Location/Qualifiers
REGION                        1..26
                              note = Description of Artificial Sequence: Synthetic peptide
MOD_RES                       12
                              note = Alpha-aminoadipic acid
MOD_RES                       18
                              note = Alpha-aminoadipic acid
MOD_RES                       23
                              note = Alpha-aminoadipic acid
source                        1..26
                              mol_type = protein
                              organism = synthetic construct
SEQUENCE: 237
ADDQNPWRAY LXLLFPTXTL LLXLLW                                                      26

SEQ ID NO: 238                moltype = AA   length = 26
FEATURE                       Location/Qualifiers
REGION                        1..26
                              note = Description of Artificial Sequence: Synthetic peptide
MOD_RES                       12
                              note = Gamma-carboxyglutamic acid
MOD_RES                       18
                              note = Alpha-aminoadipic acid
source                        1..26
                              mol_type = protein
                              organism = synthetic construct
SEQUENCE: 238
ADDQNPWRAY LXLLFPTXTL LLDLLW                                                      26

SEQ ID NO: 239                moltype = AA   length = 26
FEATURE                       Location/Qualifiers
REGION                        1..26
                              note = Description of Artificial Sequence: Synthetic peptide
MOD_RES                       12
                              note = Gamma-carboxyglutamic acid
MOD_RES                       23
                              note = Alpha-aminoadipic acid
source                        1..26
                              mol_type = protein
                              organism = synthetic construct
SEQUENCE: 239
ADDQNPWRAY LXLLFPTDTL LLXLLW                                                      26

SEQ ID NO: 240                moltype = AA   length = 26
FEATURE                       Location/Qualifiers
REGION                        1..26
                              note = Description of Artificial Sequence: Synthetic peptide
MOD_RES                       12
                              note = Gamma-carboxyglutamic acid
MOD_RES                       18
                              note = Gamma-carboxyglutamic acid
MOD_RES                       23
                              note = Alpha-aminoadipic acid
```

```
                        -continued
source                  1..26
                        mol_type = protein
                        organism = synthetic construct
SEQUENCE: 240
ADDQNPWRAY LXLLFPTXTL LLXLLW                                          26

SEQ ID NO: 241          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 18
                        note = Gamma-carboxyglutamic acid
source                  1..26
                        mol_type = protein
                        organism = synthetic construct
SEQUENCE: 241
ADDQNPWRAY LXLLFPTXTL LLDLLW                                          26

SEQ ID NO: 242          moltype = AA  length = 26
FEATURE                 Location/Qualifiers
REGION                  1..26
                        note = Description of Artificial Sequence: Synthetic peptide
MOD_RES                 12
                        note = Alpha-aminoadipic acid
MOD_RES                 23
                        note = Gamma-carboxyglutamic acid
source                  1..26
                        mol_type = protein
                        organism = synthetic construct
SEQUENCE: 242
ADDQNPWRAY LXLLFPTDTL LLXLLW                                          26

SEQ ID NO: 243          moltype = AA  length = 26
FEATURE                 Location/Qualifiers
REGION                  1..26
                        note = Description of Artificial Sequence: Synthetic peptide
MOD_RES                 12
                        note = Gamma-carboxyglutamic acid
MOD_RES                 18
                        note = Alpha-aminoadipic acid
MOD_RES                 23
                        note = Gamma-carboxyglutamic acid
source                  1..26
                        mol_type = protein
                        organism = synthetic construct
SEQUENCE: 243
ADDQNPWRAY LXLLFPTXTL LLXLLW                                          26

SEQ ID NO: 244          moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 244
GEEQNPWLGA YLDLLFPLEL LGLLELGLW                                       29

SEQ ID NO: 245          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 245
EQNPIYILDL VFGLLFAVTS VDFLVQWDDA GD                                   32

SEQ ID NO: 246          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 246
```

NNEGFFATLG GEIALWSDVV LAIE                                              24

SEQ ID NO: 247           moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 247
DNNEGFFATL GGEIPLWSDV VLAIE                                             25

SEQ ID NO: 248           moltype = AA  length = 34
FEATURE                  Location/Qualifiers
REGION                   1..34
                         note = Description of Artificial Sequence: Synthetic
                         polypeptide
MOD_RES                  2
                         note = Asp, Glu, gamma-carboxyglutamic acid or
                         alpha-aminoadipic acid
MOD_RES                  13
                         note = Asp, Glu, gamma-carboxyglutamic acid or
                         alpha-aminoadipic acid
MOD_RES                  24
                         note = Asp, Glu, gamma-carboxyglutamic acid or
                         alpha-aminoadipic acid
MOD_RES                  30
                         note = Asp, Glu, gamma-carboxyglutamic acid or
                         alpha-aminoadipic acid
MOD_RES                  32
                         note = Asp, Glu, gamma-carboxyglutamic acid or
                         alpha-aminoadipic acid
MOD_RES                  33
                         note = Asp, Glu, gamma-carboxyglutamic acid or
                         alpha-aminoadipic acid
source                   1..34
                         mol_type = protein
                         organism = synthetic construct
SEQUENCE: 248
AXQNPIYWAR YAXWLFTTPL LLLXLALLVX AXXT                                   34

SEQ ID NO: 249           moltype = AA  length = 33
FEATURE                  Location/Qualifiers
REGION                   1..33
                         note = Description of Artificial Sequence: Synthetic
                         polypeptide
MOD_RES                  2
                         note = Asp, Glu, gamma-carboxyglutamic acid or
                         alpha-aminoadipic acid
MOD_RES                  3
                         note = Asp, Glu, gamma-carboxyglutamic acid or
                         alpha-aminoadipic acid
MOD_RES                  12
                         note = Asp, Glu, gamma-carboxyglutamic acid or
                         alpha-aminoadipic acid
MOD_RES                  17
                         note = Asp, Glu, gamma-carboxyglutamic acid or
                         alpha-aminoadipic acid
MOD_RES                  20
                         note = Asp, Glu, gamma-carboxyglutamic acid or
                         alpha-aminoadipic acid
MOD_RES                  25
                         note = Asp, Glu, gamma-carboxyglutamic acid or
                         alpha-aminoadipic acid
MOD_RES                  29
                         note = Asp, Glu, gamma-carboxyglutamic acid or
                         alpha-aminoadipic acid
MOD_RES                  31
                         note = Asp, Glu, gamma-carboxyglutamic acid or
                         alpha-aminoadipic acid
MOD_RES                  32
                         note = Asp, Glu, gamma-carboxyglutamic acid or
                         alpha-aminoadipic acid
source                   1..33
                         mol_type = protein
                         organism = synthetic construct
SEQUENCE: 249
AXXQNPWRAY LXLLFPXTTX LLLLXLLWXA XXT                                    33

-continued

| | |
|---|---|
| SEQ ID NO: 250 | moltype = AA   length = 33 |
| FEATURE | Location/Qualifiers |
| REGION | 1..33 |
| | note = Description of Artificial Sequence: Synthetic polypeptide |
| MOD_RES | 2 |
| | note = Asp, Glu, gamma-carboxyglutamic acid or alpha-aminoadipic acid |
| MOD_RES | 3 |
| | note = Asp, Glu, gamma-carboxyglutamic acid or alpha-aminoadipic acid |
| MOD_RES | 12 |
| | note = Asp, Glu, gamma-carboxyglutamic acid or alpha-aminoadipic acid |
| MOD_RES | 17 |
| | note = Asp, Glu, gamma-carboxyglutamic acid or alpha-aminoadipic acid |
| MOD_RES | 20 |
| | note = Asp, Glu, gamma-carboxyglutamic acid or alpha-aminoadipic acid |
| MOD_RES | 25 |
| | note = Asp, Glu, gamma-carboxyglutamic acid or alpha-aminoadipic acid |
| MOD_RES | 29 |
| | note = Asp, Glu, gamma-carboxyglutamic acid or alpha-aminoadipic acid |
| MOD_RES | 31 |
| | note = Asp, Glu, gamma-carboxyglutamic acid or alpha-aminoadipic acid |
| MOD_RES | 32 |
| | note = Asp, Glu, gamma-carboxyglutamic acid or alpha-aminoadipic acid |
| source | 1..33 |
| | mol_type = protein |
| | organism = synthetic construct |
| SEQUENCE: 250 | |
| AXXQNPWRAY LXLLFPXTTX LLLLXLLWXA XXT | 33 |

| | |
|---|---|
| SEQ ID NO: 251 | moltype = AA   length = 34 |
| FEATURE | Location/Qualifiers |
| REGION | 1..34 |
| | note = Description of Artificial Sequence: Synthetic polypeptide |
| MOD_RES | 2 |
| | note = Asp, Glu, gamma-carboxyglutamic acid or alpha-aminoadipic acid |
| MOD_RES | 13 |
| | note = Asp, Glu, gamma-carboxyglutamic acid or alpha-aminoadipic acid |
| MOD_RES | 24 |
| | note = Asp, Glu, gamma-carboxyglutamic acid or alpha-aminoadipic acid |
| MOD_RES | 30 |
| | note = Asp, Glu, gamma-carboxyglutamic acid or alpha-aminoadipic acid |
| MOD_RES | 32 |
| | note = Asp, Glu, gamma-carboxyglutamic acid or alpha-aminoadipic acid |
| MOD_RES | 33 |
| | note = Asp, Glu, gamma-carboxyglutamic acid or alpha-aminoadipic acid |
| source | 1..34 |
| | mol_type = protein |
| | organism = synthetic construct |
| SEQUENCE: 251 | |
| AXQNPIYWAR YAXWLFTTPL LLLXLALLVX AXXT | 34 |

| | |
|---|---|
| SEQ ID NO: 252 | moltype = AA   length = 34 |
| FEATURE | Location/Qualifiers |
| REGION | 1..34 |
| | note = Description of Artificial Sequence: Synthetic polypeptide |
| MOD_RES | 2 |
| | note = Asp, Glu, gamma-carboxyglutamic acid or alpha-aminoadipic acid |
| MOD_RES | 13 |
| | note = Asp, Glu, gamma-carboxyglutamic acid or alpha-aminoadipic acid |
| MOD_RES | 24 |

```
                           note = Asp, Glu, gamma-carboxyglutamic acid or
                              alpha-aminoadipic acid
MOD_RES                    30
                           note = Asp, Glu, gamma-carboxyglutamic acid or
                              alpha-aminoadipic acid
MOD_RES                    32
                           note = Asp, Glu, gamma-carboxyglutamic acid or
                              alpha-aminoadipic acid
MOD_RES                    33
                           note = Asp, Glu, gamma-carboxyglutamic acid or
                              alpha-aminoadipic acid
source                     1..34
                           mol_type = protein
                           organism = synthetic construct
SEQUENCE: 252
AXQNPIYWAR YAXWLFTTPL LLLXLALLVX AXXT                                        34

SEQ ID NO: 253             moltype = AA   length = 34
FEATURE                    Location/Qualifiers
REGION                     1..34
                           note = Description of Artificial Sequence: Synthetic
                              polypeptide
MOD_RES                    2
                           note = Asp, Glu, gamma-carboxyglutamic acid or
                              alpha-aminoadipic acid
MOD_RES                    13
                           note = Asp, Glu, gamma-carboxyglutamic acid or
                              alpha-aminoadipic acid
MOD_RES                    24
                           note = Asp, Glu, gamma-carboxyglutamic acid or
                              alpha-aminoadipic acid
MOD_RES                    30
                           note = Asp, Glu, gamma-carboxyglutamic acid or
                              alpha-aminoadipic acid
MOD_RES                    32
                           note = Asp, Glu, gamma-carboxyglutamic acid or
                              alpha-aminoadipic acid
MOD_RES                    33
                           note = Asp, Glu, gamma-carboxyglutamic acid or
                              alpha-aminoadipic acid
source                     1..34
                           mol_type = protein
                           organism = synthetic construct
SEQUENCE: 253
AXQNPIYWAR YAXWLFTTPL LLLXLALLVX AXXT                                        34

SEQ ID NO: 254             moltype = AA   length = 33
FEATURE                    Location/Qualifiers
REGION                     1..33
                           note = Description of Artificial Sequence: Synthetic
                              polypeptide
MOD_RES                    2
                           note = Asp, Glu, gamma-carboxyglutamic acid or
                              alpha-aminoadipic acid
MOD_RES                    13
                           note = Asp, Glu, gamma-carboxyglutamic acid or
                              alpha-aminoadipic acid
MOD_RES                    24
                           note = Asp, Glu, gamma-carboxyglutamic acid or
                              alpha-aminoadipic acid
MOD_RES                    30
                           note = Asp, Glu, gamma-carboxyglutamic acid or
                              alpha-aminoadipic acid
MOD_RES                    32
                           note = Asp, Glu, gamma-carboxyglutamic acid or
                              alpha-aminoadipic acid
MOD_RES                    33
                           note = Asp, Glu, gamma-carboxyglutamic acid or
                              alpha-aminoadipic acid
source                     1..33
                           mol_type = protein
                           organism = synthetic construct
SEQUENCE: 254
CXQNPIYWAR YAXWHFTTPL LLLXLALLVX AXX                                         33

SEQ ID NO: 255             moltype = AA   length = 32
FEATURE                    Location/Qualifiers
REGION                     1..32
                           note = Description of Artificial Sequence: Synthetic
```

```
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
                        organism = synthetic construct
SEQUENCE: 255
AXNNPWIYAR YAXLTTFPLL LLXLALLVXF XX                                32

SEQ ID NO: 256          moltype = AA  length = 32
FEATURE                 Location/Qualifiers
REGION                  1..32
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
                        organism = synthetic construct
SEQUENCE: 256
AXNNPFIYAR YAXLTTWPLL LLXLALLVXF XX                                32

SEQ ID NO: 257          moltype = AA  length = 32
FEATURE                 Location/Qualifiers
REGION                  1..32
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
```

-continued

```
                            organism = synthetic construct
SEQUENCE: 257
AXNNPFIYAR YAXLTTFPLL LLXLALLVXW XX                                32

SEQ ID NO: 258          moltype = AA  length = 32
FEATURE                 Location/Qualifiers
REGION                  1..32
                        note = Description of Artificial Sequence: Synthetic
                          polypeptide
MOD_RES                 2
                        note = Asp, Glu, gamma-carboxyglutamic acid or
                          alpha-aminoadipic acid
MOD_RES                 13
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
MOD_RES                 29
                        note = Asp, Glu, gamma-carboxyglutamic acid or
                          alpha-aminoadipic acid
MOD_RES                 31
                        note = Asp, Glu, gamma-carboxyglutamic acid or
                          alpha-aminoadipic acid
MOD_RES                 32
                        note = Asp, Glu, gamma-carboxyglutamic acid or
                          alpha-aminoadipic acid
source                  1..32
                        mol_type = protein
                        organism = synthetic construct
SEQUENCE: 258
AXNNPFPYAR YAXLTTWILL LLXLALLVXF XX                                32

SEQ ID NO: 259          moltype = AA  length = 32
FEATURE                 Location/Qualifiers
REGION                  1..32
                        note = Description of Artificial Sequence: Synthetic
                          polypeptide
MOD_RES                 2
                        note = Asp, Glu, gamma-carboxyglutamic acid or
                          alpha-aminoadipic acid
MOD_RES                 13
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
MOD_RES                 29
                        note = Asp, Glu, gamma-carboxyglutamic acid or
                          alpha-aminoadipic acid
MOD_RES                 31
                        note = Asp, Glu, gamma-carboxyglutamic acid or
                          alpha-aminoadipic acid
MOD_RES                 32
                        note = Asp, Glu, gamma-carboxyglutamic acid or
                          alpha-aminoadipic acid
source                  1..32
                        mol_type = protein
                        organism = synthetic construct
SEQUENCE: 259
AXNNPFIYAY RAXLTTFPLL LLXLALLVXW XX                                32

SEQ ID NO: 260          moltype = AA  length = 32
FEATURE                 Location/Qualifiers
REGION                  1..32
                        note = Description of Artificial Sequence: Synthetic
                          polypeptide
MOD_RES                 2
                        note = Asp, Glu, gamma-carboxyglutamic acid or
                          alpha-aminoadipic acid
MOD_RES                 13
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
MOD_RES                 29
                        note = Asp, Glu, gamma-carboxyglutamic acid or
                          alpha-aminoadipic acid
```

```
MOD_RES                31
                       note = Asp, Glu, gamma-carboxyglutamic acid or
                       alpha-aminoadipic acid
MOD_RES                32
                       note = Asp, Glu, gamma-carboxyglutamic acid or
                       alpha-aminoadipic acid
source                 1..32
                       mol_type = protein
                       organism = synthetic construct
SEQUENCE: 260
AXNNPFIYAT YAXLRTFPLL LLXLALLVXW XX                                          32

SEQ ID NO: 261         moltype = AA  length = 30
FEATURE                Location/Qualifiers
REGION                 1..30
                       note = Description of Artificial Sequence: Synthetic
                       polypeptide
MOD_RES                2
                       note = Asp, Glu, gamma-carboxyglutamic acid or
                       alpha-aminoadipic acid
MOD_RES                3
                       note = Asp, Glu, gamma-carboxyglutamic acid or
                       alpha-aminoadipic acid
MOD_RES                12
                       note = Asp, Glu, gamma-carboxyglutamic acid or
                       alpha-aminoadipic acid
MOD_RES                18
                       note = Asp, Glu, gamma-carboxyglutamic acid or
                       alpha-aminoadipic acid
MOD_RES                23
                       note = Asp, Glu, gamma-carboxyglutamic acid or
                       alpha-aminoadipic acid
MOD_RES                27
                       note = Asp, Glu, gamma-carboxyglutamic acid or
                       alpha-aminoadipic acid
MOD_RES                29
                       note = Asp, Glu, gamma-carboxyglutamic acid or
                       alpha-aminoadipic acid
MOD_RES                30
                       note = Asp, Glu, gamma-carboxyglutamic acid or
                       alpha-aminoadipic acid
source                 1..30
                       mol_type = protein
                       organism = synthetic construct
SEQUENCE: 261
AXXQNPWRAY LXLLFPTXTL LLXLLWXAXX                                             30

SEQ ID NO: 262         moltype = AA  length = 26
FEATURE                Location/Qualifiers
REGION                 1..26
                       note = Description of Artificial Sequence: Synthetic peptide
MOD_RES                2
                       note = Asp, Glu, gamma-carboxyglutamic acid or
                       alpha-aminoadipic acid
MOD_RES                3
                       note = Asp, Glu, gamma-carboxyglutamic acid or
                       alpha-aminoadipic acid
MOD_RES                12
                       note = Asp, Glu, gamma-carboxyglutamic acid or
                       alpha-aminoadipic acid
MOD_RES                18
                       note = Asp, Glu, gamma-carboxyglutamic acid or
                       alpha-aminoadipic acid
MOD_RES                23
                       note = Asp, Glu, gamma-carboxyglutamic acid or
                       alpha-aminoadipic acid
source                 1..26
                       mol_type = protein
                       organism = synthetic construct
SEQUENCE: 262
AXXQNPWRAY LXLLFPTXTL LLXLLW                                                 26

SEQ ID NO: 263         moltype = AA  length = 26
FEATURE                Location/Qualifiers
REGION                 1..26
                       note = Description of Artificial Sequence: Synthetic peptide
MOD_RES                2
                       note = Asp, Glu, gamma-carboxyglutamic acid or
                       alpha-aminoadipic acid
```

```
MOD_RES              3
                     note = Asp, Glu, gamma-carboxyglutamic acid or
                      alpha-aminoadipic acid
MOD_RES              12
                     note = Asp, Glu, gamma-carboxyglutamic acid or
                      alpha-aminoadipic acid
MOD_RES              18
                     note = Asp, Glu, gamma-carboxyglutamic acid or
                      alpha-aminoadipic acid
MOD_RES              23
                     note = Asp, Glu, gamma-carboxyglutamic acid or
                      alpha-aminoadipic acid
source               1..26
                     mol_type = protein
                     organism = synthetic construct
SEQUENCE: 263
AXXQNPWRAY LXLLFPTXTL LLXLLW                                              26

SEQ ID NO: 264       moltype = AA  length = 26
FEATURE              Location/Qualifiers
REGION               1..26
                     note = Description of Artificial Sequence: Synthetic peptide
MOD_RES              2
                     note = Asp, Glu, gamma-carboxyglutamic acid or
                      alpha-aminoadipic acid
MOD_RES              3
                     note = Asp, Glu, gamma-carboxyglutamic acid or
                      alpha-aminoadipic acid
MOD_RES              12
                     note = Asp, Glu, gamma-carboxyglutamic acid or
                      alpha-aminoadipic acid
MOD_RES              18
                     note = Asp, Glu, gamma-carboxyglutamic acid or
                      alpha-aminoadipic acid
MOD_RES              23
                     note = Asp, Glu, gamma-carboxyglutamic acid or
                      alpha-aminoadipic acid
source               1..26
                     mol_type = protein
                     organism = synthetic construct
SEQUENCE: 264
AXXQNPWRAY LXLLFPTXTL LLXLLW                                              26

SEQ ID NO: 265       moltype = AA  length = 26
FEATURE              Location/Qualifiers
REGION               1..26
                     note = Description of Artificial Sequence: Synthetic peptide
MOD_RES              2
                     note = Asp, Glu, gamma-carboxyglutamic acid or
                      alpha-aminoadipic acid
MOD_RES              3
                     note = Asp, Glu, gamma-carboxyglutamic acid or
                      alpha-aminoadipic acid
MOD_RES              12
                     note = Asp, Glu, gamma-carboxyglutamic acid or
                      alpha-aminoadipic acid
MOD_RES              18
                     note = Asp, Glu, gamma-carboxyglutamic acid or
                      alpha-aminoadipic acid
MOD_RES              23
                     note = Asp, Glu, gamma-carboxyglutamic acid or
                      alpha-aminoadipic acid
source               1..26
                     mol_type = protein
                     organism = synthetic construct
SEQUENCE: 265
AXXQNPWRAY LXLLFPTXTL LLXLLW                                              26

SEQ ID NO: 266       moltype = AA  length = 26
FEATURE              Location/Qualifiers
REGION               1..26
                     note = Description of Artificial Sequence: Synthetic peptide
MOD_RES              2
                     note = Asp, Glu, gamma-carboxyglutamic acid or
                      alpha-aminoadipic acid
MOD_RES              3
                     note = Asp, Glu, gamma-carboxyglutamic acid or
                      alpha-aminoadipic acid
MOD_RES              12
```

```
                        note = Asp, Glu, gamma-carboxyglutamic acid or
                          alpha-aminoadipic acid
MOD_RES                 18
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
source                  1..26
                        mol_type = protein
                        organism = synthetic construct
SEQUENCE: 266
AXXQNPWRAY LXLLFPTXTL LLXLLW                                              26

SEQ ID NO: 267          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                          alpha-aminoadipic acid
MOD_RES                 3
                        note = Asp, Glu, gamma-carboxyglutamic acid or
                          alpha-aminoadipic acid
MOD_RES                 12
                        note = Asp, Glu, gamma-carboxyglutamic acid or
                          alpha-aminoadipic acid
MOD_RES                 18
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
source                  1..26
                        mol_type = protein
                        organism = synthetic construct
SEQUENCE: 267
AXXQNPWRAY LXLLFPTXTL LLXLLW                                              26

SEQ ID NO: 268          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                          alpha-aminoadipic acid
MOD_RES                 3
                        note = Asp, Glu, gamma-carboxyglutamic acid or
                          alpha-aminoadipic acid
MOD_RES                 12
                        note = Asp, Glu, gamma-carboxyglutamic acid or
                          alpha-aminoadipic acid
MOD_RES                 18
                        note = Asp, Glu, gamma-carboxyglutamic acid or
                          alpha-aminoadipic acid
MOD_RES                 23
                        note = Asp, Glu, gamma-carboxyglutamic acid or
                          alpha-aminoadipic acid
source                  1..26
                        mol_type = protein
                        organism = synthetic construct
SEQUENCE: 268
AXXQNPWRAY LXLLFPTXTL LLXLLW                                              26

SEQ ID NO: 269          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                          alpha-aminoadipic acid
MOD_RES                 3
                        note = Asp, Glu, gamma-carboxyglutamic acid or
                          alpha-aminoadipic acid
MOD_RES                 12
                        note = Asp, Glu, gamma-carboxyglutamic acid or
                          alpha-aminoadipic acid
MOD_RES                 18
                        note = Asp, Glu, gamma-carboxyglutamic acid or
```

```
                              alpha-aminoadipic acid
MOD_RES             23
                    note = Asp, Glu, gamma-carboxyglutamic acid or
                    alpha-aminoadipic acid
source              1..26
                    mol_type = protein
                    organism = synthetic construct
SEQUENCE: 269
AXXQNPWRAY LXLLFPTXTL LLXLLW                                              26

SEQ ID NO: 270      moltype = AA   length = 26
FEATURE             Location/Qualifiers
REGION              1..26
                    note = Description of Artificial Sequence: Synthetic peptide
MOD_RES             2
                    note = Asp, Glu, gamma-carboxyglutamic acid or
                    alpha-aminoadipic acid
MOD_RES             3
                    note = Asp, Glu, gamma-carboxyglutamic acid or
                    alpha-aminoadipic acid
MOD_RES             12
                    note = Asp, Glu, gamma-carboxyglutamic acid or
                    alpha-aminoadipic acid
MOD_RES             18
                    note = Asp, Glu, gamma-carboxyglutamic acid or
                    alpha-aminoadipic acid
MOD_RES             23
                    note = Asp, Glu, gamma-carboxyglutamic acid or
                    alpha-aminoadipic acid
source              1..26
                    mol_type = protein
                    organism = synthetic construct
SEQUENCE: 270
AXXQNPWRAY LXLLFPTXTL LLXLLW                                              26

SEQ ID NO: 271      moltype = AA   length = 26
FEATURE             Location/Qualifiers
REGION              1..26
                    note = Description of Artificial Sequence: Synthetic peptide
MOD_RES             2
                    note = Asp, Glu, gamma-carboxyglutamic acid or
                    alpha-aminoadipic acid
MOD_RES             3
                    note = Asp, Glu, gamma-carboxyglutamic acid or
                    alpha-aminoadipic acid
MOD_RES             12
                    note = Asp, Glu, gamma-carboxyglutamic acid or
                    alpha-aminoadipic acid
MOD_RES             18
                    note = Asp, Glu, gamma-carboxyglutamic acid or
                    alpha-aminoadipic acid
MOD_RES             23
                    note = Asp, Glu, gamma-carboxyglutamic acid or
                    alpha-aminoadipic acid
source              1..26
                    mol_type = protein
                    organism = synthetic construct
SEQUENCE: 271
AXXQNPWRAY LXLLFPTXTL LLXLLW                                              26

SEQ ID NO: 272      moltype = AA   length = 26
FEATURE             Location/Qualifiers
REGION              1..26
                    note = Description of Artificial Sequence: Synthetic peptide
MOD_RES             2
                    note = Asp, Glu, gamma-carboxyglutamic acid or
                    alpha-aminoadipic acid
MOD_RES             3
                    note = Asp, Glu, gamma-carboxyglutamic acid or
                    alpha-aminoadipic acid
MOD_RES             12
                    note = Asp, Glu, gamma-carboxyglutamic acid or
                    alpha-aminoadipic acid
MOD_RES             18
                    note = Asp, Glu, gamma-carboxyglutamic acid or
                    alpha-aminoadipic acid
MOD_RES             23
                    note = Asp, Glu, gamma-carboxyglutamic acid or
                    alpha-aminoadipic acid
```

```
                              235                              236
                                   -continued source                    1..26
                          mol_type = protein
                          organism = synthetic construct
SEQUENCE: 272
AXXQNPWRAY LXLLFPTXTL LLXLLW                                        26

SEQ ID NO: 273            moltype = AA  length = 26
FEATURE                   Location/Qualifiers
REGION                    1..26
                          note = Description of Artificial Sequence: Synthetic peptide
MOD_RES                   2
                          note = Asp, Glu, gamma-carboxyglutamic acid or
                           alpha-aminoadipic acid
MOD_RES                   3
                          note = Asp, Glu, gamma-carboxyglutamic acid or
                           alpha-aminoadipic acid
MOD_RES                   12
                          note = Asp, Glu, gamma-carboxyglutamic acid or
                           alpha-aminoadipic acid
MOD_RES                   18
                          note = Asp, Glu, gamma-carboxyglutamic acid or
                           alpha-aminoadipic acid
MOD_RES                   23
                          note = Asp, Glu, gamma-carboxyglutamic acid or
                           alpha-aminoadipic acid
source                    1..26
                          mol_type = protein
                          organism = synthetic construct
SEQUENCE: 273
AXXQNPWRAY LXLLFPTXTL LLXLLW                                        26

SEQ ID NO: 274            moltype = AA  length = 26
FEATURE                   Location/Qualifiers
REGION                    1..26
                          note = Description of Artificial Sequence: Synthetic peptide
MOD_RES                   2
                          note = Asp, Glu, gamma-carboxyglutamic acid or
                           alpha-aminoadipic acid
MOD_RES                   3
                          note = Asp, Glu, gamma-carboxyglutamic acid or
                           alpha-aminoadipic acid
MOD_RES                   12
                          note = Asp, Glu, gamma-carboxyglutamic acid or
                           alpha-aminoadipic acid
MOD_RES                   18
                          note = Asp, Glu, gamma-carboxyglutamic acid or
                           alpha-aminoadipic acid
MOD_RES                   23
                          note = Asp, Glu, gamma-carboxyglutamic acid or
                           alpha-aminoadipic acid
source                    1..26
                          mol_type = protein
                          organism = synthetic construct
SEQUENCE: 274
AXXQNPWRAY LXLLFPTXTL LLXLLW                                        26

SEQ ID NO: 275            moltype = AA  length = 26
FEATURE                   Location/Qualifiers
REGION                    1..26
                          note = Description of Artificial Sequence: Synthetic peptide
MOD_RES                   2
                          note = Asp, Glu, gamma-carboxyglutamic acid or
                           alpha-aminoadipic acid
MOD_RES                   3
                          note = Asp, Glu, gamma-carboxyglutamic acid or
                           alpha-aminoadipic acid
MOD_RES                   12
                          note = Asp, Glu, gamma-carboxyglutamic acid or
                           alpha-aminoadipic acid
MOD_RES                   18
                          note = Asp, Glu, gamma-carboxyglutamic acid or
                           alpha-aminoadipic acid
MOD_RES                   23
                          note = Asp, Glu, gamma-carboxyglutamic acid or
                           alpha-aminoadipic acid
source                    1..26
                          mol_type = protein
                          organism = synthetic construct
SEQUENCE: 275
```

AXXQNPWRAY LXLLFPTXTL LLXLLW                                                26

SEQ ID NO: 276          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 276
AXXQNPWRAY LXLLFPTXTL LLXLLW                                                26

SEQ ID NO: 277          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 277
AXXQNPWRAY LXLLFPTXTL LLXLLW                                                26

SEQ ID NO: 278          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 278
AXXQNPWRAY LXLLFPTXTL LLXLLW                                                26

SEQ ID NO: 279          moltype = AA  length = 26
FEATURE                 Location/Qualifiers

```
REGION              1..26
                    note = Description of Artificial Sequence: Synthetic peptide
MOD_RES             2
                    note = Asp, Glu, gamma-carboxyglutamic acid or
                     alpha-aminoadipic acid
MOD_RES             3
                    note = Asp, Glu, gamma-carboxyglutamic acid or
                     alpha-aminoadipic acid
MOD_RES             12
                    note = Asp, Glu, gamma-carboxyglutamic acid or
                     alpha-aminoadipic acid
MOD_RES             18
                    note = Asp, Glu, gamma-carboxyglutamic acid or
                     alpha-aminoadipic acid
MOD_RES             23
                    note = Asp, Glu, gamma-carboxyglutamic acid or
                     alpha-aminoadipic acid
source              1..26
                    mol_type = protein
                    organism = synthetic construct
SEQUENCE: 279
AXXQNPWRAY LXLLFPTXTL LLXLLW                                              26

SEQ ID NO: 280      moltype = AA   length = 26
FEATURE             Location/Qualifiers
REGION              1..26
                    note = Description of Artificial Sequence: Synthetic peptide
MOD_RES             2
                    note = Asp, Glu, gamma-carboxyglutamic acid or
                     alpha-aminoadipic acid
MOD_RES             3
                    note = Asp, Glu, gamma-carboxyglutamic acid or
                     alpha-aminoadipic acid
MOD_RES             12
                    note = Asp, Glu, gamma-carboxyglutamic acid or
                     alpha-aminoadipic acid
MOD_RES             18
                    note = Asp, Glu, gamma-carboxyglutamic acid or
                     alpha-aminoadipic acid
MOD_RES             23
                    note = Asp, Glu, gamma-carboxyglutamic acid or
                     alpha-aminoadipic acid
source              1..26
                    mol_type = protein
                    organism = synthetic construct
SEQUENCE: 280
AXXQNPWRAY LXLLFPTXTL LLXLLW                                              26

SEQ ID NO: 281      moltype = AA   length = 26
FEATURE             Location/Qualifiers
REGION              1..26
                    note = Description of Artificial Sequence: Synthetic peptide
MOD_RES             2
                    note = Asp, Glu, gamma-carboxyglutamic acid or
                     alpha-aminoadipic acid
MOD_RES             3
                    note = Asp, Glu, gamma-carboxyglutamic acid or
                     alpha-aminoadipic acid
MOD_RES             12
                    note = Asp, Glu, gamma-carboxyglutamic acid or
                     alpha-aminoadipic acid
MOD_RES             18
                    note = Asp, Glu, gamma-carboxyglutamic acid or
                     alpha-aminoadipic acid
MOD_RES             23
                    note = Asp, Glu, gamma-carboxyglutamic acid or
                     alpha-aminoadipic acid
source              1..26
                    mol_type = protein
                    organism = synthetic construct
SEQUENCE: 281
AXXQNPWRAY LXLLFPTXTL LLXLLW                                              26

SEQ ID NO: 282      moltype = AA   length = 29
FEATURE             Location/Qualifiers
REGION              1..29
                    note = Description of Artificial Sequence: Synthetic peptide
MOD_RES             2
                    note = Asp, Glu, gamma-carboxyglutamic acid or
```

```
                                alpha-aminoadipic acid
MOD_RES                         3
                                note = Asp, Glu, gamma-carboxyglutamic acid or
                                alpha-aminoadipic acid
MOD_RES                         13
                                note = Asp, Glu, gamma-carboxyglutamic acid or
                                alpha-aminoadipic acid
MOD_RES                         19
                                note = Asp, Glu, gamma-carboxyglutamic acid or
                                alpha-aminoadipic acid
MOD_RES                         25
                                note = Asp, Glu, gamma-carboxyglutamic acid or
                                alpha-aminoadipic acid
source                          1..29
                                mol_type = protein
                                organism = synthetic construct
SEQUENCE: 282
GXXQNPWLGA YLXLLFPLXL LGLLXLGLW                                              29

SEQ ID NO: 283                  moltype = AA  length = 32
FEATURE                         Location/Qualifiers
REGION                          1..32
                                note = Description of Artificial Sequence: Synthetic
                                polypeptide
MOD_RES                         1
                                note = Asp, Glu, gamma-carboxyglutamic acid or
                                alpha-aminoadipic acid
MOD_RES                         9
                                note = Asp, Glu, gamma-carboxyglutamic acid or
                                alpha-aminoadipic acid
MOD_RES                         22
                                note = Asp, Glu, gamma-carboxyglutamic acid or
                                alpha-aminoadipic acid
MOD_RES                         28
                                note = Asp, Glu, gamma-carboxyglutamic acid or
                                alpha-aminoadipic acid
MOD_RES                         29
                                note = Asp, Glu, gamma-carboxyglutamic acid or
                                alpha-aminoadipic acid
MOD_RES                         32
                                note = Asp, Glu, gamma-carboxyglutamic acid or
                                alpha-aminoadipic acid
source                          1..32
                                mol_type = protein
                                organism = synthetic construct
SEQUENCE: 283
XQNPIYILXL VFGLLFAVTS VXFLVQWXXA GX                                          32

SEQ ID NO: 284                  moltype = AA  length = 24
FEATURE                         Location/Qualifiers
REGION                          1..24
                                note = Description of Artificial Sequence: Synthetic peptide
MOD_RES                         3
                                note = Asp, Glu, gamma-carboxyglutamic acid or
                                alpha-aminoadipic acid
MOD_RES                         12
                                note = Asp, Glu, gamma-carboxyglutamic acid or
                                alpha-aminoadipic acid
MOD_RES                         18
                                note = Asp, Glu, gamma-carboxyglutamic acid or
                                alpha-aminoadipic acid
MOD_RES                         24
                                note = Asp, Glu, gamma-carboxyglutamic acid or
                                alpha-aminoadipic acid
source                          1..24
                                mol_type = protein
                                organism = synthetic construct
SEQUENCE: 284
NNXGFFATLG GXIALWSXVV LAIX                                                   24

SEQ ID NO: 285                  moltype = AA  length = 25
FEATURE                         Location/Qualifiers
REGION                          1..25
                                note = Description of Artificial Sequence: Synthetic peptide
MOD_RES                         1
                                note = Asp, Glu, gamma-carboxyglutamic acid or
                                alpha-aminoadipic acid
MOD_RES                         4
                                note = Asp, Glu, gamma-carboxyglutamic acid or
```

```
                            alpha-aminoadipic acid
MOD_RES                     13
                            note = Asp, Glu, gamma-carboxyglutamic acid or
                            alpha-aminoadipic acid
MOD_RES                     19
                            note = Asp, Glu, gamma-carboxyglutamic acid or
                            alpha-aminoadipic acid
MOD_RES                     25
                            note = Asp, Glu, gamma-carboxyglutamic acid or
                            alpha-aminoadipic acid
source                      1..25
                            mol_type = protein
                            organism = synthetic construct
SEQUENCE: 285
XNNXGFFATL GGXIPLWSXV VLAIX                                                    25

SEQ ID NO: 286              moltype = AA  length = 34
FEATURE                     Location/Qualifiers
REGION                      1..34
                            note = Description of Artificial Sequence: Synthetic
                            polypeptide
MOD_RES                     2
                            note = Asp, Glu, gamma-carboxyglutamic acid or
                            alpha-aminoadipic acid
MOD_RES                     13
                            note = Asp, Glu, gamma-carboxyglutamic acid or
                            alpha-aminoadipic acid
MOD_RES                     24
                            note = Asp, Glu, gamma-carboxyglutamic acid or
                            alpha-aminoadipic acid
MOD_RES                     30
                            note = Asp, Glu, gamma-carboxyglutamic acid or
                            alpha-aminoadipic acid
MOD_RES                     32
                            note = Asp, Glu, gamma-carboxyglutamic acid or
                            alpha-aminoadipic acid
MOD_RES                     33
                            note = Asp, Glu, gamma-carboxyglutamic acid or
                            alpha-aminoadipic acid
source                      1..34
                            mol_type = protein
                            organism = synthetic construct
SEQUENCE: 286
AXQNPIYWAR YAXWLFTTPL LLLXLALLVX AXXT                                          34

SEQ ID NO: 287              moltype = AA  length = 33
FEATURE                     Location/Qualifiers
REGION                      1..33
                            note = Description of Artificial Sequence: Synthetic
                            polypeptide
MOD_RES                     2
                            note = Asp, Glu, gamma-carboxyglutamic acid or
                            alpha-aminoadipic acid
MOD_RES                     3
                            note = Asp, Glu, gamma-carboxyglutamic acid or
                            alpha-aminoadipic acid
MOD_RES                     12
                            note = Asp, Glu, gamma-carboxyglutamic acid or
                            alpha-aminoadipic acid
MOD_RES                     17
                            note = Asp, Glu, gamma-carboxyglutamic acid or
                            alpha-aminoadipic acid
MOD_RES                     20
                            note = Asp, Glu, gamma-carboxyglutamic acid or
                            alpha-aminoadipic acid
MOD_RES                     25
                            note = Asp, Glu, gamma-carboxyglutamic acid or
                            alpha-aminoadipic acid
MOD_RES                     29
                            note = Asp, Glu, gamma-carboxyglutamic acid or
                            alpha-aminoadipic acid
MOD_RES                     31
                            note = Asp, Glu, gamma-carboxyglutamic acid or
                            alpha-aminoadipic acid
MOD_RES                     32
                            note = Asp, Glu, gamma-carboxyglutamic acid or
                            alpha-aminoadipic acid
source                      1..33
                            mol_type = protein
```

```
                        organism = synthetic construct
SEQUENCE: 287
AXXQNPWRAY LXLLFPXTTX LLLLXLLWXA XXT                              33

SEQ ID NO: 288          moltype = AA  length = 33
FEATURE                 Location/Qualifiers
REGION                  1..33
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 17
                        note = Asp, Glu, gamma-carboxyglutamic acid or
                        alpha-aminoadipic acid
MOD_RES                 20
                        note = Asp, Glu, gamma-carboxyglutamic acid or
                        alpha-aminoadipic acid
MOD_RES                 25
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..33
                        mol_type = protein
                        organism = synthetic construct
SEQUENCE: 288
AXXQNPWRAY LXLLFPXTTX LLLLXLLWXA XXT                              33

SEQ ID NO: 289          moltype = AA  length = 34
FEATURE                 Location/Qualifiers
REGION                  1..34
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 24
                        note = Asp, Glu, gamma-carboxyglutamic acid or
                        alpha-aminoadipic acid
MOD_RES                 30
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
MOD_RES                 33
                        note = Asp, Glu, gamma-carboxyglutamic acid or
                        alpha-aminoadipic acid
source                  1..34
                        mol_type = protein
                        organism = synthetic construct
SEQUENCE: 289
AXQNPIYWAR YAXWLFTTPL LLLXLALLVX AXXT                             34

SEQ ID NO: 290          moltype = AA  length = 34
FEATURE                 Location/Qualifiers
REGION                  1..34
                        note = Description of Artificial Sequence: Synthetic
                        polypeptide
MOD_RES                 2
                        note = Asp, Glu, gamma-carboxyglutamic acid or
                        alpha-aminoadipic acid
```

```
MOD_RES                 13
                        note = Asp, Glu, gamma-carboxyglutamic acid or
                        alpha-aminoadipic acid
MOD_RES                 24
                        note = Asp, Glu, gamma-carboxyglutamic acid or
                        alpha-aminoadipic acid
MOD_RES                 30
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
MOD_RES                 33
                        note = Asp, Glu, gamma-carboxyglutamic acid or
                        alpha-aminoadipic acid
source                  1..34
                        mol_type = protein
                        organism = synthetic construct
SEQUENCE: 290
AXQNPIYWAR YAXWLFTTPL LLLXLALLVX AXXT                                           34

SEQ ID NO: 291

```
SEQ ID NO: 293          moltype = AA   length = 32
FEATURE                 Location/Qualifiers
REGION                  1..32
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
                        organism = synthetic construct
SEQUENCE: 293
AXNNPWIYAR YAXLTTFPLL LLXLALLVXF XX                                  32

SEQ ID NO: 294          moltype = AA   length = 32
FEATURE                 Location/Qualifiers
REGION                  1..32
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
                        organism = synthetic construct
SEQUENCE: 294
AXNNPFIYAR YAXLTTWPLL LLXLALLVXF XX                                  32

SEQ ID NO: 295          moltype = AA   length = 32
FEATURE                 Location/Qualifiers
REGION                  1..32
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 13
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
```

```
                           note = Asp, Glu, gamma-carboxyglutamic acid or
                              alpha-aminoadipic acid
source                     1..32
                           mol_type = protein
                           organism = synthetic construct
SEQUENCE: 295
AXNNPFIYAR YAXLTTFPLL LLXLALLVXW XX                                    32

SEQ ID NO: 296             moltype = AA  length = 32
FEATURE                    Location/Qualifiers
REGION                     1..32
                           note = Description of Artificial Sequence: Synthetic
                              polypeptide
MOD_RES                    2
                           note = Asp, Glu, gamma-carboxyglutamic acid or
                              alpha-aminoadipic acid
MOD_RES                    13
                           note = Asp, Glu, gamma-carboxyglutamic acid or
                              alpha-aminoadipic acid
MOD_RES                    23
                           note = Asp, Glu, gamma-carboxyglutamic acid or
                              alpha-aminoadipic acid
MOD_RES                    29
                           note = Asp, Glu, gamma-carboxyglutamic acid or
                              alpha-aminoadipic acid
MOD_RES                    31
                           note = Asp, Glu, gamma-carboxyglutamic acid or
                              alpha-aminoadipic acid
MOD_RES                    32
                           note = Asp, Glu, gamma-carboxyglutamic acid or
                              alpha-aminoadipic acid
source                     1..32
                           mol_type = protein
                           organism = synthetic construct
SEQUENCE: 296
AXNNPFPYAR YAXLTTWILL LLXLALLVXF XX                                    32

SEQ ID NO: 297             moltype = AA  length = 32
FEATURE                    Location/Qualifiers
REGION                     1..32
                           note = Description of Artificial Sequence: Synthetic
                              polypeptide
MOD_RES                    2
                           note = Asp, Glu, gamma-carboxyglutamic acid or
                              alpha-aminoadipic acid
MOD_RES                    13
                           note = Asp, Glu, gamma-carboxyglutamic acid or
                              alpha-aminoadipic acid
MOD_RES                    23
                           note = Asp, Glu, gamma-carboxyglutamic acid or
                              alpha-aminoadipic acid
MOD_RES                    29
                           note = Asp, Glu, gamma-carboxyglutamic acid or
                              alpha-aminoadipic acid
MOD_RES                    31
                           note = Asp, Glu, gamma-carboxyglutamic acid or
                              alpha-aminoadipic acid
MOD_RES                    32
                           note = Asp, Glu, gamma-carboxyglutamic acid or
                              alpha-aminoadipic acid
source                     1..32
                           mol_type = protein
                           organism = synthetic construct
SEQUENCE: 297
AXNNPFIYAY RAXLTTFPLL LLXLALLVXW XX                                    32

SEQ ID NO: 298             moltype = AA  length = 32
FEATURE                    Location/Qualifiers
REGION                     1..32
                           note = Description of Artificial Sequence: Synthetic
                              polypeptide
MOD_RES                    2
                           note = Asp, Glu, gamma-carboxyglutamic acid or
                              alpha-aminoadipic acid
MOD_RES                    13
                           note = Asp, Glu, gamma-carboxyglutamic acid or
                              alpha-aminoadipic acid
MOD_RES                    23
                           note = Asp, Glu, gamma-carboxyglutamic acid or
```

```
                        alpha-aminoadipic acid
MOD_RES                 29
                        note = Asp, Glu, gamma-carboxyglutamic acid or
                        alpha-aminoadipic acid
MOD_RES                 31
                        note = Asp, Glu, gamma-carboxyglutamic acid or
                        alpha-aminoadipic acid
MOD_RES                 32
                        note = Asp, Glu, gamma-carboxyglutamic acid or
                        alpha-aminoadipic acid
source                  1..32
                        mol_type = protein
                        organism = synthetic construct
SEQUENCE: 298
AXNNPFIYAT YAXLRTFPLL LLXLALLVXW XX                                      32

SEQ ID NO: 299          moltype = AA  length = 30
FEATURE                 Location/Qualifiers
REGION                  1..30
                        note = Description of Artificial Sequence: Synthetic
                        polypeptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 18
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
MOD_RES                 27
                        note = Asp, Glu, gamma-carboxyglutamic acid or
                        alpha-aminoadipic acid
MOD_RES                 29
                        note = Asp, Glu, gamma-carboxyglutamic acid or
                        alpha-aminoadipic acid
MOD_RES                 30
                        note = Asp, Glu, gamma-carboxyglutamic acid or
                        alpha-aminoadipic acid
source                  1..30
                        mol_type = protein
                        organism = synthetic construct
SEQUENCE: 299
AXXQNPWRAY LXLLFPTXTL LLXLLWXAXX                                         30

SEQ ID NO: 300          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 18
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
source                  1..26
                        mol_type = protein
                        organism = synthetic construct
SEQUENCE: 300
AXXQNPWRAY LXLLFPTXTL LLXLLW                                             26

SEQ ID NO: 301          moltype = AA  length = 26
FEATURE                 Location/Qualifiers
REGION                  1..26
```

```
                        note = Description of Artificial Sequence: Synthetic peptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 18
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
source                  1..26
                        mol_type = protein
                        organism = synthetic construct
SEQUENCE: 301
AXXQNPWRAY LXLLFPTXTL LLXLLW                                              26

SEQ ID NO: 302          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 18
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
source                  1..26
                        mol_type = protein
                        organism = synthetic construct
SEQUENCE: 302
AXXQNPWRAY LXLLFPTXTL LLXLLW                                              26

SEQ ID NO: 303          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                        alpha-aminoadipic acid
MOD_RES                 3
                        note = Asp, Glu, gamma-carboxyglutamic acid or
                        alpha-aminoadipic acid
MOD_RES                 12
                        note = Asp, Glu, gamma-carboxyglutamic acid or
                        alpha-aminoadipic acid
MOD_RES                 18
                        note = Asp, Glu, gamma-carboxyglutamic acid or
                        alpha-aminoadipic acid
MOD_RES                 23
                        note = Asp, Glu, gamma-carboxyglutamic acid or
                        alpha-aminoadipic acid
source                  1..26
                        mol_type = protein
                        organism = synthetic construct
SEQUENCE: 303
AXXQNPWRAY LXLLFPTXTL LLXLLW                                              26

SEQ ID NO: 304          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                        alpha-aminoadipic acid
```

```
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 304
AXXQNPWRAY LXLLFPTXTL LLXLLW                                              26

SEQ ID NO: 305          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 305
AXXQNPWRAY LXLLFPTXTL LLXLLW                                              26

SEQ ID NO: 306          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
                        note = Asp, Glu, gamma-carboxyglutamic acid or
                         alpha-aminoadipic acid
MOD_RES                 18
                        note = Asp, Glu, gamma-carboxyglutamic acid or
                         alpha-aminoadipic acid
MOD_RES                 23
                        note = Asp, Glu, gamma-carboxyglutamic acid or
                         alpha-aminoadipic acid
source                  1..26
                        mol_type = protein
                        organism = synthetic construct
SEQUENCE: 306
AXXQNPWRAY LXLLFPTXTL LLXLLW                                              26

SEQ ID NO: 307          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                         alpha-aminoadipic acid
MOD_RES                 3
                        note = Asp, Glu, gamma-carboxyglutamic acid or
                         alpha-aminoadipic acid
MOD_RES                 12
```

```
                        note = Asp, Glu, gamma-carboxyglutamic acid or
                           alpha-aminoadipic acid
MOD_RES                 18
                        note = Asp, Glu, gamma-carboxyglutamic acid or
                           alpha-aminoadipic acid
MOD_RES                 23
                        note = Asp, Glu, gamma-carboxyglutamic acid or
                           alpha-aminoadipic acid
source                  1..26
                        mol_type = protein
                        organism = synthetic construct
SEQUENCE: 307
AXXQNPWRAY LXLLFPTXTL LLXLLW                                              26

SEQ ID NO: 308          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                           alpha-aminoadipic acid
MOD_RES                 3
                        note = Asp, Glu, gamma-carboxyglutamic acid or
                           alpha-aminoadipic acid
MOD_RES                 12
                        note = Asp, Glu, gamma-carboxyglutamic acid or
                           alpha-aminoadipic acid
MOD_RES                 18
                        note = Asp, Glu, gamma-carboxyglutamic acid or
                           alpha-aminoadipic acid
MOD_RES                 23
                        note = Asp, Glu, gamma-carboxyglutamic acid or
                           alpha-aminoadipic acid
source                  1..26
                        mol_type = protein
                        organism = synthetic construct
SEQUENCE: 308
AXXQNPWRAY LXLLFPTXTL LLXLLW                                              26

SEQ ID NO: 309          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                           alpha-aminoadipic acid
MOD_RES                 3
                        note = Asp, Glu, gamma-carboxyglutamic acid or
                           alpha-aminoadipic acid
MOD_RES                 12
                        note = Asp, Glu, gamma-carboxyglutamic acid or
                           alpha-aminoadipic acid
MOD_RES                 18
                        note = Asp, Glu, gamma-carboxyglutamic acid or
                           alpha-aminoadipic acid
MOD_RES                 23
                        note = Asp, Glu, gamma-carboxyglutamic acid or
                           alpha-aminoadipic acid
source                  1..26
                        mol_type = protein
                        organism = synthetic construct
SEQUENCE: 309
AXXQNPWRAY LXLLFPTXTL LLXLLW                                              26

SEQ ID NO: 310          moltype = AA  length = 26
FEATURE                 Location/Qualifiers
REGION                  1..26
                        note = Description of Artificial Sequence: Synthetic peptide
MOD_RES                 2
                        note = Asp, Glu, gamma-carboxyglutamic acid or
                           alpha-aminoadipic acid
MOD_RES                 3
                        note = Asp, Glu, gamma-carboxyglutamic acid or
                           alpha-aminoadipic acid
MOD_RES                 12
                        note = Asp, Glu, gamma-carboxyglutamic acid or
                           alpha-aminoadipic acid
MOD_RES                 18
                        note = Asp, Glu, gamma-carboxyglutamic acid or
```

| | | |
|---|---|---|
| MOD_RES | 23 | |
| | note = Asp, Glu, gamma-carboxyglutamic acid or alpha-aminoadipic acid | |
| source | 1..26 | |
| | mol_type = protein | |
| | organism = synthetic construct | |

SEQUENCE: 310

AXXQNPWRAY LXLLFPTXTL LLXLLW  26

| | | |
|---|---|---|
| SEQ ID NO: 311 | moltype = AA  length = 26 | |
| FEATURE | Location/Qualifiers | |
| REGION | 1..26 | |
| | note = Description of Artificial Sequence: Synthetic peptide | |
| MOD_RES | 2 | |
| | note = Asp, Glu, gamma-carboxyglutamic acid or alpha-aminoadipic acid | |
| MOD_RES | 3 | |
| | note = Asp, Glu, gamma-carboxyglutamic acid or alpha-aminoadipic acid | |
| MOD_RES | 12 | |
| | note = Asp, Glu, gamma-carboxyglutamic acid or alpha-aminoadipic acid | |
| MOD_RES | 18 | |
| | note = Asp, Glu, gamma-carboxyglutamic acid or alpha-aminoadipic acid | |
| MOD_RES | 23 | |
| | note = Asp, Glu, gamma-carboxyglutamic acid or alpha-aminoadipic acid | |
| source | 1..26 | |
| | mol_type = protein | |
| | organism = synthetic construct | |

SEQUENCE: 311

AXXQNPWRAY LXLLFPTXTL LLXLLW  26

| | | |
|---|---|---|
| SEQ ID NO: 312 | moltype = AA  length = 26 | |
| FEATURE | Location/Qualifiers | |
| REGION | 1..26 | |
| | note = Description of Artificial Sequence: Synthetic peptide | |
| MOD_RES | 2 | |
| | note = Asp, Glu, gamma-carboxyglutamic acid or alpha-aminoadipic acid | |
| MOD_RES | 3 | |
| | note = Asp, Glu, gamma-carboxyglutamic acid or alpha-aminoadipic acid | |
| MOD_RES | 12 | |
| | note = Asp, Glu, gamma-carboxyglutamic acid or alpha-aminoadipic acid | |
| MOD_RES | 18 | |
| | note = Asp, Glu, gamma-carboxyglutamic acid or alpha-aminoadipic acid | |
| MOD_RES | 23 | |
| | note = Asp, Glu, gamma-carboxyglutamic acid or alpha-aminoadipic acid | |
| source | 1..26 | |
| | mol_type = protein | |
| | organism = synthetic construct | |

SEQUENCE: 312

AXXQNPWRAY LXLLFPTXTL LLXLLW  26

| | | |
|---|---|---|
| SEQ ID NO: 313 | moltype = AA  length = 26 | |
| FEATURE | Location/Qualifiers | |
| REGION | 1..26 | |
| | note = Description of Artificial Sequence: Synthetic peptide | |
| MOD_RES | 2 | |
| | note = Asp, Glu, gamma-carboxyglutamic acid or alpha-aminoadipic acid | |
| MOD_RES | 3 | |
| | note = Asp, Glu, gamma-carboxyglutamic acid or alpha-aminoadipic acid | |
| MOD_RES | 12 | |
| | note = Asp, Glu, gamma-carboxyglutamic acid or alpha-aminoadipic acid | |
| MOD_RES | 18 | |
| | note = Asp, Glu, gamma-carboxyglutamic acid or alpha-aminoadipic acid | |
| MOD_RES | 23 | |
| | note = Asp, Glu, gamma-carboxyglutamic acid or alpha-aminoadipic acid | |

```
                           SEQ ID NO: 314        moltype = AA  length = 26
                           FEATURE              Location/Qualifiers
                           REGION               1..26
                                                note = Description of Artificial Sequence: Synthetic peptide
                           MOD_RES              2
                                                note = Asp, Glu, gamma-carboxyglutamic acid or
                                                  alpha-aminoadipic acid
                           MOD_RES              3
                                                note = Asp, Glu, gamma-carboxyglutamic acid or
                                                  alpha-aminoadipic acid
                           MOD_RES              12
                                                note = Asp, Glu, gamma-carboxyglutamic acid or
                                                  alpha-aminoadipic acid
                           MOD_RES              18
                                                note = Asp, Glu, gamma-carboxyglutamic acid or
                                                  alpha-aminoadipic acid
                           MOD_RES              23
                                                note = Asp, Glu, gamma-carboxyglutamic acid or
                                                  alpha-aminoadipic acid
                           source               1..26
                                                mol_type = protein
                                                organism = synthetic construct
SEQUENCE: 313
AXXQNPWRAY LXLLFPTXTL LLXLLW                                                 26

SEQ ID NO: 314        moltype = AA  length = 26
                           FEATURE              Location/Qualifiers
                           REGION               1..26
                                                note = Description of Artificial Sequence: Synthetic peptide
                           MOD_RES              2
                                                note = Asp, Glu, gamma-carboxyglutamic acid or
                                                  alpha-aminoadipic acid
                           MOD_RES              3
                                                note = Asp, Glu, gamma-carboxyglutamic acid or
                                                  alpha-aminoadipic acid
                           MOD_RES              12
                                                note = Asp, Glu, gamma-carboxyglutamic acid or
                                                  alpha-aminoadipic acid
                           MOD_RES              18
                                                note = Asp, Glu, gamma-carboxyglutamic acid or
                                                  alpha-aminoadipic acid
                           MOD_RES              23
                                                note = Asp, Glu, gamma-carboxyglutamic acid or
                                                  alpha-aminoadipic acid
                           source               1..26
                                                mol_type = protein
                                                organism = synthetic construct
SEQUENCE: 314
AXXQNPWRAY LXLLFPTXTL LLXLLW                                                 26

SEQ ID NO: 315        moltype = AA  length = 26
                           FEATURE              Location/Qualifiers
                           REGION               1..26
                                                note = Description of Artificial Sequence: Synthetic peptide
                           MOD_RES              2
                                                note = Asp, Glu, gamma-carboxyglutamic acid or
                                                  alpha-aminoadipic acid
                           MOD_RES              3
                                                note = Asp, Glu, gamma-carboxyglutamic acid or
                                                  alpha-aminoadipic acid
                           MOD_RES              12
                                                note = Asp, Glu, gamma-carboxyglutamic acid or
                                                  alpha-aminoadipic acid
                           MOD_RES              18
                                                note = Asp, Glu, gamma-carboxyglutamic acid or
                                                  alpha-aminoadipic acid
                           MOD_RES              23
                                                note = Asp, Glu, gamma-carboxyglutamic acid or
                                                  alpha-aminoadipic acid
                           source               1..26
                                                mol_type = protein
                                                organism = synthetic construct
SEQUENCE: 315
AXXQNPWRAY LXLLFPTXTL LLXLLW                                                 26

SEQ ID NO: 316        moltype = AA  length = 26
                           FEATURE              Location/Qualifiers
                           REGION               1..26
                                                note = Description of Artificial Sequence: Synthetic peptide
                           MOD_RES              2
                                                note = Asp, Glu, gamma-carboxyglutamic acid or
                                                  alpha-aminoadipic acid
                           MOD_RES              3
                                                note = Asp, Glu, gamma-carboxyglutamic acid or
                                                  alpha-aminoadipic acid
                           MOD_RES              12
                                                note = Asp, Glu, gamma-carboxyglutamic acid or
                                                  alpha-aminoadipic acid
                           MOD_RES              18
                                                note = Asp, Glu, gamma-carboxyglutamic acid or
                                                  alpha-aminoadipic acid
                           MOD_RES              23
                                                note = Asp, Glu, gamma-carboxyglutamic acid or
                                                  alpha-aminoadipic acid
                           source               1..26
                                                mol_type = protein
                                                organism = synthetic construct
SEQUENCE: 316
```

```
AXXQNPWRAY LXLLFPTXTL LLXLLW

```
REGION                    1..29
                          note = Description of Artificial Sequence: Synthetic peptide
MOD_RES                   2
                          note = Asp, Glu, gamma-carboxyglutamic acid or
                           alpha-aminoadipic acid
MOD_RES                   3
                          note = Asp, Glu, gamma-carboxyglutamic acid or
                           alpha-aminoadipic acid
MOD_RES                   13
                          note = Asp, Glu, gamma-carboxyglutamic acid or
                           alpha-aminoadipic acid
MOD_RES                   19
                          note = Asp, Glu, gamma-carboxyglutamic acid or
                           alpha-aminoadipic acid
MOD_RES                   25
                          note = Asp, Glu, gamma-carboxyglutamic acid or
                           alpha-aminoadipic acid
source                    1..29
                          mol_type = protein
                          organism = synthetic construct
SEQUENCE: 320
GXXQNPWLGA YLXLLFPLXL LGLLXLGLW                                              29

SEQ ID NO: 321            moltype = AA  length = 32
FEATURE                   Location/Qualifiers
REGION                    1..32
                          note = Description of Artificial Sequence: Synthetic
                           polypeptide
MOD_RES                   1
                          note = Asp, Glu, gamma-carboxyglutamic acid or
                           alpha-aminoadipic acid
MOD_RES                   9
                          note = Asp, Glu, gamma-carboxyglutamic acid or
                           alpha-aminoadipic acid
MOD_RES                   22
                          note = Asp, Glu, gamma-carboxyglutamic acid or
                           alpha-aminoadipic acid
MOD_RES                   28
                          note = Asp, Glu, gamma-carboxyglutamic acid or
                           alpha-aminoadipic acid
MOD_RES                   29
                          note = Asp, Glu, gamma-carboxyglutamic acid or
                           alpha-aminoadipic acid
MOD_RES                   32
                          note = Asp, Glu, gamma-carboxyglutamic acid or
                           alpha-aminoadipic acid
source                    1..32
                          mol_type = protein
                          organism = synthetic construct
SEQUENCE: 321
XQNPIYILXL VFGLLFAVTS VXFLVQWXXA GX                                          32

SEQ ID NO: 322            moltype = AA  length = 24
FEATURE                   Location/Qualifiers
REGION                    1..24
                          note = Description of Artificial Sequence: Synthetic peptide
MOD_RES                   3
                          note = Asp, Glu, gamma-carboxyglutamic acid or
                           alpha-aminoadipic acid
MOD_RES                   12
                          note = Asp, Glu, gamma-carboxyglutamic acid or
                           alpha-aminoadipic acid
MOD_RES                   18
                          note = Asp, Glu, gamma-carboxyglutamic acid or
                           alpha-aminoadipic acid
MOD_RES                   24
                          note = Asp, Glu, gamma-carboxyglutamic acid or
                           alpha-aminoadipic acid
source                    1..24
                          mol_type = protein
                          organism = synthetic construct
SEQUENCE: 322
NNXGFFATLG GXIALWSXVV LAIX                                                   24

SEQ ID NO: 323            moltype = AA  length = 25
FEATURE                   Location/Qualifiers
REGION                    1..25
                          note = Description of Artificial Sequence: Synthetic peptide
MOD_RES                   1
```

```
                        note = Asp, Glu, gamma-carboxyglutamic acid or
                         alpha-aminoadipic acid
MOD_RES                 4
                        note = Asp, Glu, gamma-carboxyglutamic acid or
                         alpha-aminoadipic acid
MOD_RES                 13
                        note = Asp, Glu, gamma-carboxyglutamic acid or
                         alpha-aminoadipic acid
MOD_RES                 19
                        note = Asp, Glu, gamma-carboxyglutamic acid or
                         alpha-aminoadipic acid
MOD_RES                 25
                        note = Asp, Glu, gamma-carboxyglutamic acid or
                         alpha-aminoadipic acid
source                  1..25
                        mol_type = protein
                        organism = synthetic construct
SEQUENCE: 323
XNNXGFFATL GGXIPLWSXV VLAIX                                                 25

SEQ ID NO: 324          moltype =     length =
SEQUENCE: 324
000

SEQ ID NO: 325          moltype = AA   length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 325
WRAYLDLLFP TDTLLLDLLW                                                       20

SEQ ID NO: 326          moltype = AA   length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 326
WLLDLLLTDT PFLLDLYARW                                                       20

SEQ ID NO: 327          moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 327
WARYADWLFT TPLLLLDLAL LVDADE                                                26

SEQ ID NO: 328          moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 328
EDADVLLALD LLLLPTTFLW DAYRAW                                                26

SEQ ID NO: 329          moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 329
GLAGLLGLEG LLGLPLGLLE GLWLGL                                                26

SEQ ID NO: 330          moltype = AA   length = 18
FEATURE                 Location/Qualifiers
REGION                  1..18
                        note = Description of Artificial Sequence: Synthetic peptide
source                  1..18
```

```
                                -continued mol_type = protein
                         organism = synthetic construct
SEQUENCE: 330
WARYLEWLFP TETLLLEL                                                  18

SEQ ID NO: 331          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 331
WAQYLELLFP TETLLLEW                                                  18

SEQ ID NO: 332          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 332
WLFTTPLLLL NGALLVE                                                   17

SEQ ID NO: 333          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 333
WLFTTPLLLL PGALLVE                                                   17

SEQ ID NO: 334          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 334
WARYADLLFP TTLAW                                                     15

SEQ ID NO: 335          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 335
GNLEGFFATL GGEIALWSLV VLAIE                                          25

SEQ ID NO: 336          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 336
EGFFATLGGE IALWSDVVLA IE                                             22

SEQ ID NO: 337          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 337
EGFFATLGGE IPLWSDVVLA IE                                             22

SEQ ID NO: 338          moltype = AA  length = 25
FEATURE                 Location/Qualifiers
REGION                  1..25
                        note = Description of Artificial Sequence: Synthetic peptide
```

```
source                  1..25
                        mol_type = protein
                        organism = synthetic construct
SEQUENCE: 338
EIALVVLSWL AIEGGLTAFF GELNG                                          25

SEQ ID NO: 339          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 339
EIALVVDSWL AIEGGLTAFF GE                                             22

SEQ ID NO: 340          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 340
EIALVVDSWL PIEGGLTAFF GE                                             22

SEQ ID NO: 341          moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 341
ILDLVFGLLF AVTSVDFLVQ W                                              21

SEQ ID NO: 342          moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 342
WQVLFDVSTV AFLLGFVLDL I                                              21

SEQ ID NO: 343          moltype = AA  length = 34
FEATURE                 Location/Qualifiers
REGION                  1..34
                        note = Description of Artificial Sequence: Synthetic
                        polypeptide
source                  1..34
                        mol_type = protein
                        organism = synthetic construct
SEQUENCE: 343
AEQNPIYWAR YADWLFTTPL LLLDLALLVD ADET                                34

SEQ ID NO: 344          moltype = AA  length = 34
FEATURE                 Location/Qualifiers
REGION                  1..34
                        note = Description of Artificial Sequence: Synthetic
                        polypeptide
source                  1..34
                        mol_type = protein
                        organism = synthetic construct
SEQUENCE: 344
AEQNPIYWAR YAEWLFTTPL LLLELALLVE AEET                                34

SEQ ID NO: 345          moltype = AA  length = 33
FEATURE                 Location/Qualifiers
REGION                  1..33
                        note = Description of Artificial Sequence: Synthetic
                        polypeptide
source                  1..33
                        mol_type = protein
                        organism = synthetic construct
SEQUENCE: 345
ADDQNPWRAY LDLLFPDTTD LLLLDLLWDA DET                                 33
```

```
SEQ ID NO: 346            moltype = AA   length = 33
FEATURE                   Location/Qualifiers
REGION                    1..33
                          note = Description of Artificial Sequence: Synthetic
                          polypeptide
source                    1..33
                          mol_type = protein
                          organism = synthetic construct
SEQUENCE: 346
AEEQNPWRAY LELLFPETTE LLLLELLWEA EET                                    33

SEQ ID NO: 347            moltype = AA   length = 34
FEATURE                   Location/Qualifiers
REGION                    1..34
                          note = Description of Artificial Sequence: Synthetic
                          polypeptide
MOD_RES                   13
                          note = Gamma-carboxyglutamic acid
source                    1..34
                          mol_type = protein
                          organism = synthetic construct
SEQUENCE: 347
AEQNPIYWAR YAXWLFTTPL LLLDLALLVD ADET                                   34

SEQ ID NO: 348            moltype = AA   length = 34
FEATURE                   Location/Qualifiers
REGION                    1..34
                          note = Description of Artificial Sequence: Synthetic
                          polypeptide
MOD_RES                   24
                          note = Gamma-carboxyglutamic acid
source                    1..34
                          mol_type = protein
                          organism = synthetic construct
SEQUENCE: 348
AEQNPIYWAR YADWLFTTPL LLLXLALLVD ADET                                   34

SEQ ID NO: 349            moltype = AA   length = 34
FEATURE                   Location/Qualifiers
REGION                    1..34
                          note = Description of Artificial Sequence: Synthetic
                          polypeptide
MOD_RES                   13
                          note = Gamma-carboxyglutamic acid
MOD_RES                   24
                          note = Gamma-carboxyglutamic acid
source                    1..34
                          mol_type = protein
                          organism = synthetic construct
SEQUENCE: 349
AEQNPIYWAR YAXWLFTTPL LLLXLALLVD ADET                                   34

SEQ ID NO: 350            moltype = AA   length = 34
FEATURE                   Location/Qualifiers
REGION                    1..34
                          note = Description of Artificial Sequence: Synthetic
                          polypeptide
MOD_RES                   13
                          note = Alpha-aminoadipic acid
source                    1..34
                          mol_type = protein
                          organism = synthetic construct
SEQUENCE: 350
AEQNPIYWAR YAXWLFTTPL LLLDLALLVD ADET                                   34

SEQ ID NO: 351            moltype = AA   length = 34
FEATURE                   Location/Qualifiers
REGION                    1..34
                          note = Description of Artificial Sequence: Synthetic
                          polypeptide
MOD_RES                   24
                          note = Alpha-aminoadipic acid
source                    1..34
                          mol_type = protein
                          organism = synthetic construct
SEQUENCE: 351
AEQNPIYWAR YADWLFTTPL LLLXLALLVD ADET                                   34

SEQ ID NO: 352            moltype = AA   length = 34
```

```
FEATURE              Location/Qualifiers
REGION               1..34
                     note = Description of Artificial Sequence: Synthetic
                     polypeptide
MOD_RES              13
                     note = Alpha-aminoadipic acid
MOD_RES              24
                     note = Alpha-aminoadipic acid
source               1..34
                     mol_type = protein
                     organism = synthetic construct
SEQUENCE: 352
AEQNPIYWAR YAXWLFTTPL LLLXLALLVD ADET                                    34

SEQ ID NO: 353       moltype = AA  length = 34
FEATURE              Location/Qualifiers
REGION               1..34
                     note = Description of Artificial Sequence: Synthetic
                     polypeptide
MOD_RES              13
                     note = Gamma-carboxyglutamic acid
MOD_RES              24
                     note = Alpha-aminoadipic acid
source               1..34
                     mol_type = protein
                     organism = synthetic construct
SEQUENCE: 353
AEQNPIYWAR YAXWLFTTPL LLLXLALLVD ADET                                    34

SEQ ID NO: 354       moltype = AA  length = 34
FEATURE              Location/Qualifiers
REGION               1..34
                     note = Description of Artificial Sequence: Synthetic
                     polypeptide
MOD_RES              13
                     note = Alpha-aminoadipic acid
MOD_RES              24
                     note = Gamma-carboxyglutamic acid
source               1..34
                     mol_type = protein
                     organism = synthetic construct
SEQUENCE: 354
AEQNPIYWAR YAXWLFTTPL LLLXLALLVD ADET                                    34

SEQ ID NO: 355       moltype = AA  length = 37
FEATURE              Location/Qualifiers
REGION               1..37
                     note = Description of Artificial Sequence: Synthetic
                     polypeptide
source               1..37
                     mol_type = protein
                     organism = synthetic construct
SEQUENCE: 355
GGEQNPIYWA RYADWLFTTP LLLLDLALLV DADEGTG                                 37

SEQ ID NO: 356       moltype = AA  length = 36
FEATURE              Location/Qualifiers
REGION               1..36
                     note = Description of Artificial Sequence: Synthetic
                     polypeptide
source               1..36
                     mol_type = protein
                     organism = synthetic construct
SEQUENCE: 356
GGEQNPIYWA RYADWLFTTP LLLLDLALLV DADEGT                                  36

SEQ ID NO: 357       moltype = AA  length = 37
FEATURE              Location/Qualifiers
REGION               1..37
                     note = Description of Artificial Sequence: Synthetic
                     polypeptide
source               1..37
                     mol_type = protein
                     organism = synthetic construct
SEQUENCE: 357
AAEQNPIYWA RYADWLFTTP LLLLDLALLV DADEGTG                                 37

SEQ ID NO: 358       moltype = AA  length = 35
FEATURE              Location/Qualifiers
```

```
REGION                      1..35
                            note = Description of Artificial Sequence: Synthetic
                             polypeptide
source                      1..35
                            mol_type = protein
                            organism = synthetic construct
SEQUENCE: 358
AEQNPIYWAR YADWLFTTPL LLLDLALLVD ADEGT                                      35

SEQ ID NO: 359              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 359
AEQNPIYWAR YANWLFTTPL LLLNLALLVD ADEGTG                                     36

SEQ ID NO: 360              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 360
AEQNPIYWAR YAKWLFTTPL LLLKLALLVD ADEGTG                                     36

SEQ ID NO: 361              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 361
GGEQNPIYWA RYADWLFTTP LLLLDLALLV NANQGT                                     36

SEQ ID NO: 362              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 362
AAEQNPIYWA RYADWLFTTP LLLLALALLV DADEGT                                     36

SEQ ID NO: 363              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 363
AAEQNPIYWA RYAAWLFTTP LLLLDLALLV DADEGT                                     36

SEQ ID NO: 364              moltype = AA   length = 36
FEATURE                     Location/Qualifiers
REGION                      1..36
                            note = Description of Artificial Sequence: Synthetic
                             polypeptide
source                      1..36
                            mol_type = protein
                            organism = synthetic construct
SEQUENCE: 364
AAEQNPIYWA RYADWLFTTA LLLLDLALLV DADEGT                                     36

SEQ ID NO: 365              moltype = AA   length = 36
FEATURE                     Location/Qualifiers
REGION                      1..36
                            note = Description of Artificial Sequence: Synthetic
```

```
                           polypeptide
source                     1..36
                           mol_type = protein
                           organism = synthetic construct
SEQUENCE: 365
AAEQNPIYWA RYADWLFTTP LLLLELALLV DADEGT                                   36

SEQ ID NO: 366             moltype = AA  length = 36
FEATURE                    Location/Qualifiers
REGION                     1..36
                           note = Description of Artificial Sequence: Synthetic
                           polypeptide
source                     1..36
                           mol_type = protein
                           organism = synthetic construct
SEQUENCE: 366
AAEQNPIYWA RYAEWLFTTP LLLLDLALLV DADEGT                                   36

SEQ ID NO: 367             moltype = AA  length = 39
FEATURE                    Location/Qualifiers
REGION                     1..39
                           note = Description of Artificial Sequence: Synthetic
                           polypeptide
source                     1..39
                           mol_type = protein
                           organism = synthetic construct
SEQUENCE: 367
AAEQNPIIYW ARYADWLFTD LPLLLLDLLA LLVDADEGT                                39

SEQ ID NO: 368             moltype = AA  length = 36
FEATURE                    Location/Qualifiers
REGION                     1..36
                           note = Description of Artificial Sequence: Synthetic
                           polypeptide
source                     1..36
                           mol_type = protein
                           organism = synthetic construct
SEQUENCE: 368
GEQNPIYWAQ YADWLFTTPL LLLDLALLVD ADEGCG                                   36

SEQ ID NO: 369             moltype = AA  length = 37
FEATURE                    Location/Qualifiers
REGION                     1..37
                           note = Description of Artificial Sequence: Synthetic
                           polypeptide
source                     1..37
                           mol_type = protein
                           organism = synthetic construct
SEQUENCE: 369
GGEQNPIYWA RYADWLFTTP LLLDLLALLV DADEGCG                                  37

SEQ ID NO: 370             moltype = AA  length = 37
FEATURE                    Location/Qualifiers
REGION                     1..37
                           note = Description of Artificial Sequence: Synthetic
                           polypeptide
source                     1..37
                           mol_type = protein
                           organism = synthetic construct
SEQUENCE: 370
GGEQNPIYWA RYADWLFTTP LLLLLDALLV DADEGCG                                  37

SEQ ID NO: 371             moltype = AA  length = 37
FEATURE                    Location/Qualifiers
REGION                     1..37
                           note = Description of Artificial Sequence: Synthetic
                           polypeptide
source                     1..37
                           mol_type = protein
                           organism = synthetic construct
SEQUENCE: 371
GGEQNPIYWA RYDAWLFTTP LLLLDLALLV DADEGTG                                  37

SEQ ID NO: 372             moltype = AA  length = 37
FEATURE                    Location/Qualifiers
REGION                     1..37
                           note = Description of Artificial Sequence: Synthetic
                           polypeptide
source                     1..37
```

```
                        mol_type = protein
                        organism = synthetic construct
SEQUENCE: 372
GGEQNPIYWA RYAWDLFTTP LLLLDLALLV DADEGCG                                37

SEQ ID NO: 373          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 373
AAEQNPIYWA RYADWLFTTG LLLLDLALLV DADEGT                                 36

SEQ ID NO: 374          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 374
DDDEDNPIYW ARYADWLFTT PLLLLHGALL VDADCT                                 36

SEQ ID NO: 375          moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 375
DDDEDNPIYW ARYAHWLFTT PLLLLHGALL VDADECT                                37

SEQ ID NO: 376          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 376
CEQNPIYWAR YADWHFTTPL LLLDLALLVD ADEGT                                  35

SEQ ID NO: 377          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 377
AEQNPIYWAR YADFLFTTPL LLLDLALLVD ADET                                   34

SEQ ID NO: 378          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 378
AEQNPIYFAR YADWLFTTPL LLLDLALLVD ADEGT                                  35

SEQ ID NO: 379          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
```

```
SEQUENCE: 379
AEQNPIYFAR YADFLFTTPL LLLDLALLWD ADET                                34

SEQ ID NO: 380          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 380
ADNNPWIYAR YADLTTFPLL LLDLALLVDF DD                                  32

SEQ ID NO: 381          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 381
ADNNPFIYAR YADLTTWPLL LLDLALLVDF DD                                  32

SEQ ID NO: 382          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 382
ADNNPFIYAR YADLTTFPLL LLDLALLVDW DD                                  32

SEQ ID NO: 383          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 383
ADNNPFPYAR YADLTTWILL LLDLALLVDF DD                                  32

SEQ ID NO: 384          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 384
ADNNPFIYAY RADLTTFPLL LLDLALLVDW DD                                  32

SEQ ID NO: 385          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 385
ADNNPFIYAT YADLRTFPLL LLDLALLVDW DD                                  32

SEQ ID NO: 386          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 386
TEDADVLLAL DLLLLPTTFL WDAYRAWYPN QEA                                 33
```

```
SEQ ID NO: 387          moltype = AA   length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 387
AEDQNPYWAR YADWLFTTPL LLLDLALLVD G                                      31

SEQ ID NO: 388          moltype = AA   length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 388
AEDQNPYWAR YADWLFTTPL LLLELALLVE G                                      31

SEQ ID NO: 389          moltype = AA   length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 389
AEDQNPYWRA YADLFTPLTL LDLLALWDG                                         29

SEQ ID NO: 390          moltype = AA   length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 390
ADDQNPWRAY LDLLFPTDTL LLDLLWG                                           27

SEQ ID NO: 391          moltype = AA   length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 391
ADDQNPWRAY LDLLFPTDTL LLDLLWDADE G                                      31

SEQ ID NO: 392          moltype = AA   length = 27
FEATURE                 Location/Qualifiers
REGION                  1..27
                        note = Description of Artificial Sequence: Synthetic peptide
MOD_RES                 12
                        note = Gamma-carboxyglutamic acid
source                  1..27
                        mol_type = protein
                        organism = synthetic construct
SEQUENCE: 392
ADDQNPWRAY LXLLFPTDTL LLDLLWG                                           27

SEQ ID NO: 393          moltype = AA   length = 27
FEATURE                 Location/Qualifiers
REGION                  1..27
                        note = Description of Artificial Sequence: Synthetic peptide
MOD_RES                 18
                        note = Gamma-carboxyglutamic acid
source                  1..27
                        mol_type = protein
                        organism = synthetic construct
SEQUENCE: 393
ADDQNPWRAY LDLLFPTXTL LLDLLWG                                           27

SEQ ID NO: 394          moltype = AA   length = 27
```

```
FEATURE              Location/Qualifiers
REGION               1..27
                     note = Description of Artificial Sequence: Synthetic peptide
MOD_RES              23
                     note = Gamma-carboxyglutamic acid
source               1..27
                     mol_type = protein
                     organism = synthetic construct
SEQUENCE: 394
ADDQNPWRAY LDLLFPTDTL LLXLLWG                                                    27

SEQ ID NO: 395       moltype = AA  length = 27
FEATURE              Location/Qualifiers
REGION               1..27
                     note = Description of Artificial Sequence: Synthetic peptide
MOD_RES              12
                     note = Gamma-carboxyglutamic acid
MOD_RES              18
                     note = Gamma-carboxyglutamic acid
source               1..27
                     mol_type = protein
                     organism = synthetic construct
SEQUENCE: 395
ADDQNPWRAY LXLLFPTXTL LLDLLWG                                                    27

SEQ ID NO: 396       moltype = AA  length = 27
FEATURE              Location/Qualifiers
REGION               1..27
                     note = Description of Artificial Sequence: Synthetic peptide
MOD_RES              12
                     note = Gamma-carboxyglutamic acid
MOD_RES              23
                     note = Gamma-carboxyglutamic acid
source               1..27
                     mol_type = protein
                     organism = synthetic construct
SEQUENCE: 396
ADDQNPWRAY LXLLFPTDTL LLXLLWG                                                    27

SEQ ID NO: 397       moltype = AA  length = 27
FEATURE              Location/Qualifiers
REGION               1..27
                     note = Description of Artificial Sequence: Synthetic peptide
MOD_RES              18
                     note = Gamma-carboxyglutamic acid
MOD_RES              23
                     note = Gamma-carboxyglutamic acid
source               1..27
                     mol_type = protein
                     organism = synthetic construct
SEQUENCE: 397
ADDQNPWRAY LDLLFPTXTL LLXLLWG                                                    27

SEQ ID NO: 398       moltype = AA  length = 27
FEATURE              Location/Qualifiers
REGION               1..27
                     note = Description of Artificial Sequence: Synthetic peptide
MOD_RES              12
                     note = Gamma-carboxyglutamic acid
MOD_RES              18
                     note = Gamma-carboxyglutamic acid
MOD_RES              23
                     note = Gamma-carboxyglutamic acid
source               1..27
                     mol_type = protein
                     organism = synthetic construct
SEQUENCE: 398
ADDQNPWRAY LXLLFPTXTL LLXLLWG                                                    27

SEQ ID NO: 399       moltype = AA  length = 27
FEATURE              Location/Qualifiers
REGION               1..27
                     note = Description of Artificial Sequence: Synthetic peptide
MOD_RES              12
                     note = Alpha-aminoadipic acid
source               1..27
                     mol_type = protein
                     organism = synthetic construct
SEQUENCE: 399
```

```
ADDQNPWRAY LXLLFPTDTL LLDLLWG                                            27

SEQ ID NO: 400          moltype = AA  length = 27
FEATURE                 Location/Qualifiers
REGION                  1..27
                        note = Description of Artificial Sequence: Synthetic peptide
MOD_RES                 18
                        note = Alpha-aminoadipic acid
source                  1..27
                        mol_type = protein
                        organism = synthetic construct
SEQUENCE: 400
ADDQNPWRAY LDLLFPTXTL LLDLLWG                                            27

SEQ ID NO: 401          moltype = AA  length = 27
FEATURE                 Location/Qualifiers
REGION                  1..27
                        note = Description of Artificial Sequence: Synthetic peptide
MOD_RES                 23
                        note = Alpha-aminoadipic acid
source                  1..27
                        mol_type = protein
                        organism = synthetic construct
SEQUENCE: 401
ADDQNPWRAY LDLLFPTDTL LLXLLWG                                            27

SEQ ID NO: 402          moltype = AA  length = 27
FEATURE                 Location/Qualifiers
REGION                  1..27
                        note = Description of Artificial Sequence: Synthetic peptide
MOD_RES                 12
                        note = Alpha-aminoadipic acid
MOD_RES                 18
                        note = Alpha-aminoadipic acid
source                  1..27
                        mol_type = protein
                        organism = synthetic construct
SEQUENCE: 402
ADDQNPWRAY LXLLFPTXTL LLDLLWG                                            27

SEQ ID NO: 403          moltype = AA  length = 27
FEATURE                 Location/Qualifiers
REGION                  1..27
                        note = Description of Artificial Sequence: Synthetic peptide
MOD_RES                 12
                        note = Alpha-aminoadipic acid
MOD_RES                 23
                        note = Alpha-aminoadipic acid
source                  1..27
                        mol_type = protein
                        organism = synthetic construct
SEQUENCE: 403
ADDQNPWRAY LXLLFPTDTL LLXLLWG                                            27

SEQ ID NO: 404          moltype =     length =
SEQUENCE: 404
000

SEQ ID NO: 405          moltype =     length =
SEQUENCE: 405
000

SEQ ID NO: 406          moltype =     length =
SEQUENCE: 406
000

SEQ ID NO: 407          moltype =     length =
SEQUENCE: 407
000

SEQ ID NO: 408          moltype = AA  length = 27
FEATURE                 Location/Qualifiers
REGION                  1..27
                        note = Description of Artificial Sequence: Synthetic peptide
MOD_RES                 18
                        note = Alpha-aminoadipic acid
MOD_RES                 23
                        note = Alpha-aminoadipic acid
source                  1..27
```

```
                            mol_type = protein
                            organism = synthetic construct
SEQUENCE: 408
ADDQNPWRAY LDLLFPTXTL LLXLLWG                                              27

SEQ ID NO: 409             moltype = AA  length = 27
FEATURE                    Location/Qualifiers
REGION                     1..27
                           note = Description of Artificial Sequence: Synthetic peptide
MOD_RES                    12
                           note = Alpha-aminoadipic acid
MOD_RES                    18
                           note = Alpha-aminoadipic acid
MOD_RES                    23
                           note = Alpha-aminoadipic acid
source                     1..27
                           mol_type = protein
                           organism = synthetic construct
SEQUENCE: 409
ADDQNPWRAY LXLLFPTXTL LLXLLWG                                              27

SEQ ID NO: 410             moltype = AA  length = 27
FEATURE                    Location/Qualifiers
REGION                     1..27
                           note = Description of Artificial Sequence: Synthetic peptide
MOD_RES                    12
                           note = Gamma-carboxyglutamic acid
MOD_RES                    18
                           note = Alpha-aminoadipic acid
source                     1..27
                           mol_type = protein
                           organism = synthetic construct
SEQUENCE: 410
ADDQNPWRAY LXLLFPTXTL LLDLLWG                                              27

SEQ ID NO: 411             moltype = AA  length = 27
FEATURE                    Location/Qualifiers
REGION                     1..27
                           note = Description of Artificial Sequence: Synthetic peptide
MOD_RES                    12
                           note = Gamma-carboxyglutamic acid
MOD_RES                    23
                           note = Alpha-aminoadipic acid
source                     1..27
                           mol_type = protein
                           organism = synthetic construct
SEQUENCE: 411
ADDQNPWRAY LXLLFPTDTL LLXLLWG                                              27

SEQ ID NO: 412             moltype = AA  length = 27
FEATURE                    Location/Qualifiers
REGION                     1..27
                           note = Description of Artificial Sequence: Synthetic peptide
MOD_RES                    12
                           note = Gamma-carboxyglutamic acid
MOD_RES                    18
                           note = Gamma-carboxyglutamic acid
MOD_RES                    23
                           note = Alpha-aminoadipic acid
source                     1..27
                           mol_type = protein
                           organism = synthetic construct
SEQUENCE: 412
ADDQNPWRAY LXLLFPTXTL LLXLLWG                                              27

SEQ ID NO: 413             moltype = AA  length = 27
FEATURE                    Location/Qualifiers
REGION                     1..27
                           note = Description of Artificial Sequence: Synthetic peptide
MOD_RES                    12
                           note = Alpha-aminoadipic acid
MOD_RES                    18
                           note = Gamma-carboxyglutamic acid
source                     1..27
                           mol_type = protein
                           organism = synthetic construct
SEQUENCE: 413
ADDQNPWRAY LXLLFPTXTL LLDLLWG                                              27
```

| | | |
|---|---|---|
| SEQ ID NO: 414 | moltype = AA length = 27 | |
| FEATURE | Location/Qualifiers | |
| REGION | 1..27 | |
| | note = Description of Artificial Sequence: Synthetic peptide | |
| MOD_RES | 12 | |
| | note = Alpha-aminoadipic acid | |
| MOD_RES | 23 | |
| | note = Gamma-carboxyglutamic acid | |
| source | 1..27 | |
| | mol_type = protein | |
| | organism = synthetic construct | |
| SEQUENCE: 414 | | |
| ADDQNPWRAY LXLLFPTDTL LLXLLWG | | 27 |
| | | |
| SEQ ID NO: 415 | moltype = AA length = 27 | |
| FEATURE | Location/Qualifiers | |
| REGION | 1..27 | |
| | note = Description of Artificial Sequence: Synthetic peptide | |
| MOD_RES | 12 | |
| | note = Gamma-carboxyglutamic acid | |
| MOD_RES | 18 | |
| | note = Alpha-aminoadipic acid | |
| MOD_RES | 23 | |
| | note = Gamma-carboxyglutamic acid | |
| source | 1..27 | |
| | mol_type = protein | |
| | organism = synthetic construct | |
| SEQUENCE: 415 | | |
| ADDQNPWRAY LXLLFPTXTL LLXLLWG | | 27 |
| | | |
| SEQ ID NO: 416 | moltype = AA length = 30 | |
| FEATURE | Location/Qualifiers | |
| REGION | 1..30 | |
| | note = Description of Artificial Sequence: Synthetic polypeptide | |
| source | 1..30 | |
| | mol_type = protein | |
| | organism = synthetic construct | |
| SEQUENCE: 416 | | |
| GEEQNPWLGA YLDLLFPLEL LGLLELGLWG | | 30 |
| | | |
| SEQ ID NO: 417 | moltype = AA length = 28 | |
| FEATURE | Location/Qualifiers | |
| REGION | 1..28 | |
| | note = Description of Artificial Sequence: Synthetic peptide | |
| source | 1..28 | |
| | mol_type = protein | |
| | organism = synthetic construct | |
| SEQUENCE: 417 | | |
| ADDDDDDPWQ AYLDLLFPTD TLLLDLLW | | 28 |
| | | |
| SEQ ID NO: 418 | moltype = AA length = 26 | |
| FEATURE | Location/Qualifiers | |
| REGION | 1..26 | |
| | note = Description of Artificial Sequence: Synthetic peptide | |
| source | 1..26 | |
| | mol_type = protein | |
| | organism = synthetic construct | |
| SEQUENCE: 418 | | |
| AEEQNPWRAY LELLFPTETL LLELLW | | 26 |
| | | |
| SEQ ID NO: 419 | moltype = AA length = 24 | |
| FEATURE | Location/Qualifiers | |
| REGION | 1..24 | |
| | note = Description of Artificial Sequence: Synthetic peptide | |
| source | 1..24 | |
| | mol_type = protein | |
| | organism = synthetic construct | |
| SEQUENCE: 419 | | |
| ADDQNPWARY LDWLFPTDTL LLDL | | 24 |
| | | |
| SEQ ID NO: 420 | moltype = AA length = 23 | |
| FEATURE | Location/Qualifiers | |
| REGION | 1..23 | |
| | note = Description of Artificial Sequence: Synthetic peptide | |
| source | 1..23 | |
| | mol_type = protein | |
| | organism = synthetic construct | |
| SEQUENCE: 420 | | |

DNNNPWRAYL DLLFPTDTLL LDW                                     23

SEQ ID NO: 421         moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 421
AEEQNPWARY LEWLFPTETL LLEL                                    24

SEQ ID NO: 422         moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 422
DDDDDDPWQA YLDLFPTDTL ALDLW                                   25

SEQ ID NO: 423         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 423
EEQQPWAQYL ELLFPTETLL LEW                                     23

SEQ ID NO: 424         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 424
EEQQPWRAYL ELLFPTETLL LEW                                     23

SEQ ID NO: 425         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 425
AEDQNPWARY ADWLFPTTLL LLD                                     23

SEQ ID NO: 426         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 426
AEEQNPWARY AEWLFPTTLL LLE                                     23

SEQ ID NO: 427         moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 427
AEDQNPWARY ADLLFPTTLA W                                       21

SEQ ID NO: 428         moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct

```
SEQUENCE: 428
AEEQNPWARY AELLFPTTLA W                                                     21

SEQ ID NO: 429          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 429
DDDDDNPNYW ARYANWLFTT PLLLLNGALL VEAEET                                     36

SEQ ID NO: 430          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 430
DDDDDNPNYW ARYAPWLFTT PLLLLPGALL VEAEET                                     36

SEQ ID NO: 431          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 431
AEQNPIYFAR YADFLFTTPL LLLDLALLWD ADET                                       34

SEQ ID NO: 432          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 432
AEQNPIYWAR YADFLFTTPL LLLDLALLVD ADET                                       34

SEQ ID NO: 433          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 433
AEQNPIYWAR YADWLFTTPL                                                       20

SEQ ID NO: 434          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 434
AEQNPIYFAR YADLLFPTTL AW                                                    22

SEQ ID NO: 435          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 435
AEQNPIYWAR YADLLFPTTL AF                                                    22

SEQ ID NO: 436          moltype = AA  length = 22
FEATURE                 Location/Qualifiers
```

```
REGION                  1..22
                        note = Description of Artificial Sequence: Synthetic peptide
source                  1..22
                        mol_type = protein
                        organism = synthetic construct
SEQUENCE: 436
AEQNPIYWAR YADLLFPTTL AW                                                  22

SEQ ID NO: 437          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 437
AEQNPIYFAR YADWLFTTPL                                                     20

SEQ ID NO: 438          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 438
EDQNPWARYA DLLFPTTLAW                                                     20

SEQ ID NO: 439          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 439
GLAGLAGLLG LEGLLGLPLG LLEGLWLGLE LEGNA                                    35

SEQ ID NO: 440          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 440
EQNPIYILDL VFGLLFAVTS VDFLVQWDDA GD                                       32

SEQ ID NO: 441          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 441
GNLEGFFATL GGEIALWSLV VLAIE                                               25

SEQ ID NO: 442          moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 442
GNNEGFFATL GGEIALWSDV VLAIEG                                              26

SEQ ID NO: 443          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 443
GDNNEGFFAT LGGEIPLWSD VVLAIEG                                             27
```

```
SEQ ID NO: 444          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 444
ACEQNPIYWA RYADWLFTTP LLLLDLALLV DADEGT                                 36

SEQ ID NO: 445          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 445
ACEQNPIYWA RYANWLFTTP LLLLNLALLV DADEGT                                 36

SEQ ID NO: 446          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 446
GCDNNEGFFA TLGGEIPLWS DVVLAIEG                                          28

SEQ ID NO: 447          moltype =     length =
SEQUENCE: 447
000

SEQ ID NO: 448          moltype =     length =
SEQUENCE: 448
000

SEQ ID NO: 449          moltype =     length =
SEQUENCE: 449
000

SEQ ID NO: 450          moltype =     length =
SEQUENCE: 450
000

SEQ ID NO: 451          moltype =     length =
SEQUENCE: 451
000

SEQ ID NO: 452          moltype =     length =
SEQUENCE: 452
000

SEQ ID NO: 453          moltype =     length =
SEQUENCE: 453
000

SEQ ID NO: 454          moltype =     length =
SEQUENCE: 454
000

SEQ ID NO: 455          moltype = AA  length = 26
FEATURE                 Location/Qualifiers
REGION                  1..26
                        note = Description of Artificial Sequence: Synthetic peptide
MOD_RES                 2
                        note = Ala, Ile, Leu, Met, Phe, Pro, Trp, Tyr, Val or Gly
MOD_RES                 3
                        note = Ala, Ile, Leu, Met, Phe, Pro, Trp, Tyr, Val or Gly
MOD_RES                 5
                        note = Ala, Ile, Leu, Met, Phe, Pro, Trp, Tyr, Val or Gly
MOD_RES                 6
                        note = Ala, Ile, Leu, Met, Phe, Pro, Trp, Tyr, Val or Gly
MOD_RES                 8
                        note = Ala, Ile, Leu, Met, Phe, Pro, Trp, Tyr, Val or Gly
```

| | |
|---|---|
| MOD_RES | 9 |
| | note = Asp, Glu, gamma-carboxyglutamic acid or alpha-aminoadipic acid |
| MOD_RES | 11 |
| | note = Ala, Ile, Leu, Met, Phe, Pro, Trp, Tyr, Val or Gly |
| MOD_RES | 12 |
| | note = Ala, Ile, Leu, Met, Phe, Pro, Trp, Tyr, Val or Gly |
| MOD_RES | 14 |
| | note = Ala, Ile, Leu, Met, Phe, Pro, Trp, Tyr, Val or Gly |
| MOD_RES | 15 |
| | note = Ala, Ile, Leu, Met, Phe, Pro, Trp, Tyr, Val or Gly |
| MOD_RES | 16 |
| | note = Ala, Ile, Leu, Met, Phe, Pro, Trp, Tyr, Val or Gly |
| MOD_RES | 18 |
| | note = Ala, Ile, Leu, Met, Phe, Pro, Trp, Tyr, Val or Gly |
| MOD_RES | 19 |
| | note = Ala, Ile, Leu, Met, Phe, Pro, Trp, Tyr, Val or Gly |
| MOD_RES | 20 |
| | note = Asp, Glu, gamma-carboxyglutamic acid or alpha-aminoadipic acid |
| MOD_RES | 22 |
| | note = Ala, Ile, Leu, Met, Phe, Pro, Trp, Tyr, Val or Gly |
| MOD_RES | 23 |
| | note = Ala, Ile, Leu, Met, Phe, Pro, Trp, Tyr, Val or Gly |
| MOD_RES | 24 |
| | note = Ala, Ile, Leu, Met, Phe, Pro, Trp, Tyr, Val or Gly |
| MOD_RES | 26 |
| | note = Ala, Ile, Leu, Met, Phe, Pro, Trp, Tyr, Val or Gly |
| source | 1..26 |
| | mol_type = protein |
| | organism = synthetic construct |
| SEQUENCE: 455 | |
| GXXGXXGXXG XXGXXXGXXX GXXXGX | 26 |
| | |
| SEQ ID NO: 456 | moltype = AA  length = 26 |
| FEATURE | Location/Qualifiers |
| REGION | 1..26 |
| | note = Description of Artificial Sequence: Synthetic peptide |
| MOD_RES | 1 |
| | note = Ala, Ile, Leu, Met, Phe, Pro, Trp, Tyr, Val or Gly |
| MOD_RES | 3 |
| | note = Ala, Ile, Leu, Met, Phe, Pro, Trp, Tyr, Val or Gly |
| MOD_RES | 4 |
| | note = Ala, Ile, Leu, Met, Phe, Pro, Trp, Tyr, Val or Gly |
| MOD_RES | 5 |
| | note = Ala, Ile, Leu, Met, Phe, Pro, Trp, Tyr, Val or Gly |
| MOD_RES | 7 |
| | note = Asp, Glu, gamma-carboxyglutamic acid or alpha-aminoadipic acid |
| MOD_RES | 8 |
| | note = Ala, Ile, Leu, Met, Phe, Pro, Trp, Tyr, Val or Gly |
| MOD_RES | 9 |
| | note = Ala, Ile, Leu, Met, Phe, Pro, Trp, Tyr, Val or Gly |
| MOD_RES | 11 |
| | note = Ala, Ile, Leu, Met, Phe, Pro, Trp, Tyr, Val or Gly |
| MOD_RES | 12 |
| | note = Ala, Ile, Leu, Met, Phe, Pro, Trp, Tyr, Val or Gly |
| MOD_RES | 13 |
| | note = Ala, Ile, Leu, Met, Phe, Pro, Trp, Tyr, Val or Gly |
| MOD_RES | 15 |
| | note = Ala, Ile, Leu, Met, Phe, Pro, Trp, Tyr, Val or Gly |
| MOD_RES | 16 |
| | note = Ala, Ile, Leu, Met, Phe, Pro, Trp, Tyr, Val or Gly |
| MOD_RES | 18 |
| | note = Asp, Glu, gamma-carboxyglutamic acid or alpha-aminoadipic acid |
| MOD_RES | 19 |
| | note = Ala, Ile, Leu, Met, Phe, Pro, Trp, Tyr, Val or Gly |
| MOD_RES | 21 |
| | note = Ala, Ile, Leu, Met, Phe, Pro, Trp, Tyr, Val or Gly |
| MOD_RES | 22 |
| | note = Ala, Ile, Leu, Met, Phe, Pro, Trp, Tyr, Val or Gly |
| MOD_RES | 24 |
| | note = Ala, Ile, Leu, Met, Phe, Pro, Trp, Tyr, Val or Gly |
| MOD_RES | 25 |
| | note = Ala, Ile, Leu, Met, Phe, Pro, Trp, Tyr, Val or Gly |
| source | 1..26 |
| | mol_type = protein |
| | organism = synthetic construct |

```
SEQUENCE: 456
XGXXXGXXXG XXXGXXGXXG XXGXXG                                              26

SEQ ID NO: 457           moltype =    length =
SEQUENCE: 457
000

SEQ ID NO: 458           moltype =    length =
SEQUENCE: 458
000

SEQ ID NO: 459           moltype =    length =
SEQUENCE: 459
000

SEQ ID NO: 460           moltype =    length =
SEQUENCE: 460
000

SEQ ID NO: 461           moltype =    length =
SEQUENCE: 461
000

SEQ ID NO: 462           moltype =    length =
SEQUENCE: 462
000

SEQ ID NO: 463           moltype =    length =
SEQUENCE: 463
000

SEQ ID NO: 464           moltype =    length =
SEQUENCE: 464
000

SEQ ID NO: 465           moltype =    length =
SEQUENCE: 465
000

SEQ ID NO: 466           moltype =    length =
SEQUENCE: 466
000

SEQ ID NO: 467           moltype =    length =
SEQUENCE: 467
000

SEQ ID NO: 468           moltype =    length =
SEQUENCE: 468
000

SEQ ID NO: 469           moltype = AA  length = 25
FEATURE                  Location/Qualifiers
REGION                   1..25
                         note = Description of Artificial Sequence: Synthetic peptide
MOD_RES                  3
                         note = Ala, Ile, Leu, Met, Phe, Pro, Trp, Tyr, Val or Gly
MOD_RES                  4
                         note = Asp, Glu, gamma-carboxyglutamic acid or
                          alpha-aminoadipic acid
MOD_RES                  6
                         note = Ala, Ile, Leu, Met, Phe, Pro, Trp, Tyr, Val or Gly
MOD_RES                  7
                         note = Ala, Ile, Leu, Met, Phe, Pro, Trp, Tyr, Val or Gly
MOD_RES                  8
                         note = Ala, Ile, Leu, Met, Phe, Pro, Trp, Tyr, Val or Gly
MOD_RES                  9
                         note = Ser, Thr or Gly
MOD_RES                  10
                         note = Ala, Ile, Leu, Met, Phe, Pro, Trp, Tyr, Val or Gly
MOD_RES                  13
                         note = Asp, Glu, gamma-carboxyglutamic acid or
                          alpha-aminoadipic acid
MOD_RES                  14
                         note = Ala, Ile, Leu, Met, Phe, Pro, Trp, Tyr, Val or Gly
MOD_RES                  15
                         note = Ala, Ile, Leu, Met, Phe, Pro, Trp, Tyr, Val or Gly
MOD_RES                  16
                         note = Ala, Ile, Leu, Met, Phe, Pro, Trp, Tyr, Val or Gly
```

```
                          -continued

MOD_RES         17
                note = Ala, Ile, Leu, Met, Phe, Pro, Trp, Tyr, Val or Gly
MOD_RES         18
                note = Ser, Thr or Gly
MOD_RES         19
                note = Ala, Ile, Leu, Met, Phe, Pro, Trp, Tyr, Val or Gly
MOD_RES         20
                note = Ala, Ile, Leu, Met, Phe, Pro, Trp, Tyr, Val or Gly
MOD_RES         21
                note = Ala, Ile, Leu, Met, Phe, Pro, Trp, Tyr, Val or Gly
MOD_RES         22
                note = Ala, Ile, Leu, Met, Phe, Pro, Trp, Tyr, Val or Gly
MOD_RES         23
                note = Ala, Ile, Leu, Met, Phe, Pro, Trp, Tyr, Val or Gly
MOD_RES         24
                note = Ala, Ile, Leu, Met, Phe, Pro, Trp, Tyr, Val or Gly
MOD_RES         25
                note = Asp, Glu, gamma-carboxyglutamic acid or
                 alpha-aminoadipic acid
source          1..25
                mol_type = protein
                organism = synthetic construct
SEQUENCE: 469
GNXXGXXXXX GGXXXXXXXX XXXXX                                         25

SEQ ID NO: 470          moltype =   length =
SEQUENCE: 470
000

SEQ ID NO: 471          moltype =   length =
SEQUENCE: 471
000

SEQ ID NO: 472          moltype = AA  length = 25
FEATURE                 Location/Qualifiers
REGION                  1..25
                note = Description of Artificial Sequence: Synthetic peptide
MOD_RES         1
                note = Asp, Glu, gamma-carboxyglutamic acid or
                 alpha-aminoadipic acid
MOD_RES         2
                note = Ala, Ile, Leu, Met, Phe, Pro, Trp, Tyr, Val or Gly
MOD_RES         3
                note = Ala, Ile, Leu, Met, Phe, Pro, Trp, Tyr, Val or Gly
MOD_RES         4
                note = Ala, Ile, Leu, Met, Phe, Pro, Trp, Tyr, Val or Gly
MOD_RES         5
                note = Ala, Ile, Leu, Met, Phe, Pro, Trp, Tyr, Val or Gly
MOD_RES         6
                note = Ala, Ile, Leu, Met, Phe, Pro, Trp, Tyr, Val or Gly
MOD_RES         7
                note = Ala, Ile, Leu, Met, Phe, Pro, Trp, Tyr, Val or Gly
MOD_RES         8
                note = Ser, Thr or Gly
MOD_RES         9
                note = Ala, Ile, Leu, Met, Phe, Pro, Trp, Tyr, Val or Gly
MOD_RES         10
                note = Ala, Ile, Leu, Met, Phe, Pro, Trp, Tyr, Val or Gly
MOD_RES         11
                note = Ala, Ile, Leu, Met, Phe, Pro, Trp, Tyr, Val or Gly
MOD_RES         12
                note = Ala, Ile, Leu, Met, Phe, Pro, Trp, Tyr, Val or Gly
MOD_RES         13
                note = Asp, Glu, gamma-carboxyglutamic acid or
                 alpha-aminoadipic acid
MOD_RES         16
                note = Ala, Ile, Leu, Met, Phe, Pro, Trp, Tyr, Val or Gly
MOD_RES         17
                note = Ser, Thr or Gly
MOD_RES         18
                note = Ala, Ile, Leu, Met, Phe, Pro, Trp, Tyr, Val or Gly
MOD_RES         19
                note = Ala, Ile, Leu, Met, Phe, Pro, Trp, Tyr, Val or Gly
MOD_RES         20
                note = Ala, Ile, Leu, Met, Phe, Pro, Trp, Tyr, Val or Gly
MOD_RES         22
                note = Asp, Glu, gamma-carboxyglutamic acid or
                 alpha-aminoadipic acid
MOD_RES         23
```

```
                        note = Ala, Ile, Leu, Met, Phe, Pro, Trp, Tyr, Val or Gly
source                  1..25
                        mol_type = protein
                        organism = synthetic construct
SEQUENCE: 472
XXXXXXXXXX XXXGGXXXXX GXXNG                                               25

SEQ ID NO: 473          moltype =    length =
SEQUENCE: 473
000

SEQ ID NO: 474          moltype =    length =
SEQUENCE: 474
000

SEQ ID NO: 475          moltype =    length =
SEQUENCE: 475
000

SEQ ID NO: 476          moltype =    length =
SEQUENCE: 476
000

SEQ ID NO: 477          moltype =    length =
SEQUENCE: 477
000

SEQ ID NO: 478          moltype =    length =
SEQUENCE: 478
000

SEQ ID NO: 479          moltype =    length =
SEQUENCE: 479
000

SEQ ID NO: 480          moltype =    length =
SEQUENCE: 480
000

SEQ ID NO: 481          moltype =    length =
SEQUENCE: 481
000

SEQ ID NO: 482          moltype =    length =
SEQUENCE: 482
000

SEQ ID NO: 483          moltype =    length =
SEQUENCE: 483
000

SEQ ID NO: 484          moltype =    length =
SEQUENCE: 484
000

SEQ ID NO: 485          moltype = AA   length = 26
FEATURE                 Location/Qualifiers
REGION                  1..26
                        note = Description of Artificial Sequence: Synthetic peptide
MOD_RES                 2
                        note = Ala, Ile, Leu, Met, Phe, Pro, Trp, Tyr, Val or Gly
MOD_RES                 3
                        note = Ala, Ile, Leu, Met, Phe, Pro, Trp, Tyr, Val or Gly
MOD_RES                 5
                        note = Ala, Ile, Leu, Met, Phe, Pro, Trp, Tyr, Val or Gly
MOD_RES                 6
                        note = Ala, Ile, Leu, Met, Phe, Pro, Trp, Tyr, Val or Gly
MOD_RES                 8
                        note = Ala, Ile, Leu, Met, Phe, Pro, Trp, Tyr, Val or Gly
MOD_RES                 9
                        note = Asp, Glu, gamma-carboxyglutamic acid or
                        alpha-aminoadipic acid
MOD_RES                 11
                        note = Ala, Ile, Leu, Met, Phe, Pro, Trp, Tyr, Val or Gly
MOD_RES                 12
                        note = Ala, Ile, Leu, Met, Phe, Pro, Trp, Tyr, Val or Gly
MOD_RES                 14
                        note = Ala, Ile, Leu, Met, Phe, Pro, Trp, Tyr, Val or Gly
MOD_RES                 15
```

|  |  |
|---|---|
| MOD_RES | 16 |
|  | note = Ala, Ile, Leu, Met, Phe, Pro, Trp, Tyr, Val or Gly |
| MOD_RES | 18 |
|  | note = Ala, Ile, Leu, Met, Phe, Pro, Trp, Tyr, Val or Gly |
| MOD_RES | 19 |
|  | note = Ala, Ile, Leu, Met, Phe, Pro, Trp, Tyr, Val or Gly |
| MOD_RES | 20 |
|  | note = Asp, Glu, gamma-carboxyglutamic acid or alpha-aminoadipic acid |
| MOD_RES | 22 |
|  | note = Ala, Ile, Leu, Met, Phe, Pro, Trp, Tyr, Val or Gly |
| MOD_RES | 23 |
|  | note = Ala, Ile, Leu, Met, Phe, Pro, Trp, Tyr, Val or Gly |
| MOD_RES | 24 |
|  | note = Ala, Ile, Leu, Met, Phe, Pro, Trp, Tyr, Val or Gly |
| MOD_RES | 26 |
|  | note = Ala, Ile, Leu, Met, Phe, Pro, Trp, Tyr, Val or Gly |
| source | 1..26 |
|  | mol_type = protein |
|  | organism = synthetic construct |
| SEQUENCE: 485 | |
| GXXGXXGXXG XXGXXXGXXX GXXXGX | 26 |

|  |  |
|---|---|
| SEQ ID NO: 486 | moltype = AA  length = 26 |
| FEATURE | Location/Qualifiers |
| REGION | 1..26 |
|  | note = Description of Artificial Sequence: Synthetic peptide |
| MOD_RES | 1 |
|  | note = Ala, Ile, Leu, Met, Phe, Pro, Trp, Tyr, Val or Gly |
| MOD_RES | 3 |
|  | note = Ala, Ile, Leu, Met, Phe, Pro, Trp, Tyr, Val or Gly |
| MOD_RES | 4 |
|  | note = Ala, Ile, Leu, Met, Phe, Pro, Trp, Tyr, Val or Gly |
| MOD_RES | 5 |
|  | note = Ala, Ile, Leu, Met, Phe, Pro, Trp, Tyr, Val or Gly |
| MOD_RES | 7 |
|  | note = Asp, Glu, gamma-carboxyglutamic acid or alpha-aminoadipic acid |
| MOD_RES | 8 |
|  | note = Ala, Ile, Leu, Met, Phe, Pro, Trp, Tyr, Val or Gly |
| MOD_RES | 9 |
|  | note = Ala, Ile, Leu, Met, Phe, Pro, Trp, Tyr, Val or Gly |
| MOD_RES | 11 |
|  | note = Ala, Ile, Leu, Met, Phe, Pro, Trp, Tyr, Val or Gly |
| MOD_RES | 12 |
|  | note = Ala, Ile, Leu, Met, Phe, Pro, Trp, Tyr, Val or Gly |
| MOD_RES | 13 |
|  | note = Ala, Ile, Leu, Met, Phe, Pro, Trp, Tyr, Val or Gly |
| MOD_RES | 15 |
|  | note = Ala, Ile, Leu, Met, Phe, Pro, Trp, Tyr, Val or Gly |
| MOD_RES | 16 |
|  | note = Ala, Ile, Leu, Met, Phe, Pro, Trp, Tyr, Val or Gly |
| MOD_RES | 18 |
|  | note = Asp, Glu, gamma-carboxyglutamic acid or alpha-aminoadipic acid |
| MOD_RES | 19 |
|  | note = Ala, Ile, Leu, Met, Phe, Pro, Trp, Tyr, Val or Gly |
| MOD_RES | 21 |
|  | note = Ala, Ile, Leu, Met, Phe, Pro, Trp, Tyr, Val or Gly |
| MOD_RES | 22 |
|  | note = Ala, Ile, Leu, Met, Phe, Pro, Trp, Tyr, Val or Gly |
| MOD_RES | 24 |
|  | note = Ala, Ile, Leu, Met, Phe, Pro, Trp, Tyr, Val or Gly |
| MOD_RES | 25 |
|  | note = Ala, Ile, Leu, Met, Phe, Pro, Trp, Tyr, Val or Gly |
| source | 1..26 |
|  | mol_type = protein |
|  | organism = synthetic construct |
| SEQUENCE: 486 | |
| XGXXXGXXXG XXXGXXGXXG XXGXXG | 26 |

|  |  |
|---|---|
| SEQ ID NO: 487 | moltype =   length = |
| SEQUENCE: 487 | |
| 000 | |

|  |  |
|---|---|
| SEQ ID NO: 488 | moltype =   length = |
| SEQUENCE: 488 | |
| 000 | |

| | | |
|---|---|---|
| SEQ ID NO: 489<br>SEQUENCE: 489<br>000 | moltype = | length = |
| SEQ ID NO: 490<br>SEQUENCE: 490<br>000 | moltype = | length = |
| SEQ ID NO: 491<br>SEQUENCE: 491<br>000 | moltype = | length = |
| SEQ ID NO: 492<br>SEQUENCE: 492<br>000 | moltype = | length = |
| SEQ ID NO: 493<br>SEQUENCE: 493<br>000 | moltype = | length = |
| SEQ ID NO: 494<br>SEQUENCE: 494<br>000 | moltype = | length = |
| SEQ ID NO: 495<br>SEQUENCE: 495<br>000 | moltype = | length = |
| SEQ ID NO: 496<br>SEQUENCE: 496<br>000 | moltype = | length = |
| SEQ ID NO: 497<br>SEQUENCE: 497<br>000 | moltype = | length = |
| SEQ ID NO: 498<br>SEQUENCE: 498<br>000 | moltype = | length = |

```
SEQ ID NO: 499           moltype = AA   length = 25
FEATURE                  Location/Qualifiers
REGION                   1..25
                         note = Description of Artificial Sequence: Synthetic peptide
MOD_RES                  3
                         note = Ala, Ile, Leu, Met, Phe, Pro, Trp, Tyr, Val or Gly
MOD_RES                  4
                         note = Asp, Glu, gamma-carboxyglutamic acid or
                          alpha-aminoadipic acid
MOD_RES                  6
                         note = Ala, Ile, Leu, Met, Phe, Pro, Trp, Tyr, Val or Gly
MOD_RES                  7
                         note = Ala, Ile, Leu, Met, Phe, Pro, Trp, Tyr, Val or Gly
MOD_RES                  8
                         note = Ala, Ile, Leu, Met, Phe, Pro, Trp, Tyr, Val or Gly
MOD_RES                  9
                         note = Ser, Thr or Gly
MOD_RES                  10
                         note = Ala, Ile, Leu, Met, Phe, Pro, Trp, Tyr, Val or Gly
MOD_RES                  13
                         note = Asp, Glu, gamma-carboxyglutamic acid or
                          alpha-aminoadipic acid
MOD_RES                  14
                         note = Ala, Ile, Leu, Met, Phe, Pro, Trp, Tyr, Val or Gly
MOD_RES                  15
                         note = Ala, Ile, Leu, Met, Phe, Pro, Trp, Tyr, Val or Gly
MOD_RES                  16
                         note = Ala, Ile, Leu, Met, Phe, Pro, Trp, Tyr, Val or Gly
MOD_RES                  17
                         note = Ala, Ile, Leu, Met, Phe, Pro, Trp, Tyr, Val or Gly
MOD_RES                  18
                         note = Ser, Thr or Gly
MOD_RES                  19
                         note = Ala, Ile, Leu, Met, Phe, Pro, Trp, Tyr, Val or Gly
MOD_RES                  20
                         note = Ala, Ile, Leu, Met, Phe, Pro, Trp, Tyr, Val or Gly
MOD_RES                  21
                         note = Ala, Ile, Leu, Met, Phe, Pro, Trp, Tyr, Val or Gly
```

```
MOD_RES         22
                note = Ala, Ile, Leu, Met, Phe, Pro, Trp, Tyr, Val or Gly
MOD_RES         23
                note = Ala, Ile, Leu, Met, Phe, Pro, Trp, Tyr, Val or Gly
MOD_RES         24
                note = Ala, Ile, Leu, Met, Phe, Pro, Trp, Tyr, Val or Gly
MOD_RES         25
                note = Asp, Glu, gamma-carboxyglutamic acid or
                 alpha-aminoadipic acid
source          1..25
                mol_type = protein
                organism = synthetic construct
SEQUENCE: 499
GNXXGXXXXX GGXXXXXXXX XXXXX                                              25

SEQ ID NO: 500          moltype =    length =
SEQUENCE: 500
000

SEQ ID NO: 501          moltype =    length =
SEQUENCE: 501
000

SEQ ID NO: 502          moltype = AA  length = 25
FEATURE                 Location/Qualifiers
REGION                  1..25
                        note = Description of Artificial Sequence: Synthetic peptide
MOD_RES         1
                note = Asp, Glu, gamma-carboxyglutamic acid or
                 alpha-aminoadipic acid
MOD_RES         2
                note = Ala, Ile, Leu, Met, Phe, Pro, Trp, Tyr, Val or Gly
MOD_RES         3
                note = Ala, Ile, Leu, Met, Phe, Pro, Trp, Tyr, Val or Gly
MOD_RES         4
                note = Ala, Ile, Leu, Met, Phe, Pro, Trp, Tyr, Val or Gly
MOD_RES         5
                note = Ala, Ile, Leu, Met, Phe, Pro, Trp, Tyr, Val or Gly
MOD_RES         6
                note = Ala, Ile, Leu, Met, Phe, Pro, Trp, Tyr, Val or Gly
MOD_RES         7
                note = Ala, Ile, Leu, Met, Phe, Pro, Trp, Tyr, Val or Gly
MOD_RES         8
                note = Ser, Thr or Gly
MOD_RES         9
                note = Ala, Ile, Leu, Met, Phe, Pro, Trp, Tyr, Val or Gly
MOD_RES         10
                note = Ala, Ile, Leu, Met, Phe, Pro, Trp, Tyr, Val or Gly
MOD_RES         11
                note = Ala, Ile, Leu, Met, Phe, Pro, Trp, Tyr, Val or Gly
MOD_RES         12
                note = Ala, Ile, Leu, Met, Phe, Pro, Trp, Tyr, Val or Gly
MOD_RES         13
                note = Asp, Glu, gamma-carboxyglutamic acid or
                 alpha-aminoadipic acid
MOD_RES         16
                note = Ala, Ile, Leu, Met, Phe, Pro, Trp, Tyr, Val or Gly
MOD_RES         17
                note = Ser, Thr or Gly
MOD_RES         18
                note = Ala, Ile, Leu, Met, Phe, Pro, Trp, Tyr, Val or Gly
MOD_RES         19
                note = Ala, Ile, Leu, Met, Phe, Pro, Trp, Tyr, Val or Gly
MOD_RES         20
                note = Ala, Ile, Leu, Met, Phe, Pro, Trp, Tyr, Val or Gly
MOD_RES         22
                note = Asp, Glu, gamma-carboxyglutamic acid or
                 alpha-aminoadipic acid
MOD_RES         23
                note = Ala, Ile, Leu, Met, Phe, Pro, Trp, Tyr, Val or Gly
source          1..25
                mol_type = protein
                organism = synthetic construct
SEQUENCE: 502
XXXXXXXXXX XXXGGXXXXX GXXNG                                              25

SEQ ID NO: 503          moltype =    length =
SEQUENCE: 503
000
```

| | | |
|---|---|---|
| SEQ ID NO: 504 SEQUENCE: 504 | moltype = length = | |
| 000 | | |
| SEQ ID NO: 505 SEQUENCE: 505 | moltype = length = | |
| 000 | | |
| SEQ ID NO: 506 SEQUENCE: 506 | moltype = length = | |
| 000 | | |
| SEQ ID NO: 507 SEQUENCE: 507 | moltype = length = | |
| 000 | | |
| SEQ ID NO: 508 SEQUENCE: 508 | moltype = length = | |
| 000 | | |
| SEQ ID NO: 509 FEATURE REGION | moltype = AA  length = 33 Location/Qualifiers 1..33 note = Description of Artificial Sequence: Synthetic polypeptide | |
| MOD_RES | 2 note = Asp, Glu, gamma-carboxyglutamic acid or alpha-aminoadipic acid | |
| MOD_RES | 5 note = Ala, Ile, Leu, Met, Phe, Pro, Trp, Tyr, Val or Gly | |
| MOD_RES | 6 note = Ala, Ile, Leu, Met, Phe, Pro, Trp, Tyr, Val or Gly | |
| MOD_RES | 7 note = Ala, Ile, Leu, Met, Phe, Pro, Trp, Tyr, Val or Gly | |
| MOD_RES | 8 note = Ala, Ile, Leu, Met, Phe, Pro, Trp, Tyr, Val or Gly | |
| MOD_RES | 9 note = Ala, Ile, Leu, Met, Phe, Pro, Trp, Tyr, Val or Gly | |
| MOD_RES | 11 note = Ala, Ile, Leu, Met, Phe, Pro, Trp, Tyr, Val or Gly | |
| MOD_RES | 12 note = Ala, Ile, Leu, Met, Phe, Pro, Trp, Tyr, Val or Gly | |
| MOD_RES | 13 note = Asp, Glu, gamma-carboxyglutamic acid or alpha-aminoadipic acid | |
| MOD_RES | 14 note = Ala, Ile, Leu, Met, Phe, Pro, Trp, Tyr, Val or Gly | |
| MOD_RES | 16 note = Ala, Ile, Leu, Met, Phe, Pro, Trp, Tyr, Val or Gly | |
| MOD_RES | 17 note = Ser, Thr or Gly | |
| MOD_RES | 18 note = Ser, Thr or Gly | |
| MOD_RES | 19 note = Ala, Ile, Leu, Met, Phe, Pro, Trp, Tyr, Val or Gly | |
| MOD_RES | 20 note = Ala, Ile, Leu, Met, Phe, Pro, Trp, Tyr, Val or Gly | |
| MOD_RES | 21 note = Ala, Ile, Leu, Met, Phe, Pro, Trp, Tyr, Val or Gly | |
| MOD_RES | 22 note = Ala, Ile, Leu, Met, Phe, Pro, Trp, Tyr, Val or Gly | |
| MOD_RES | 23 note = Ala, Ile, Leu, Met, Phe, Pro, Trp, Tyr, Val or Gly | |
| MOD_RES | 24 note = Asp, Glu, gamma-carboxyglutamic acid or alpha-aminoadipic acid | |
| MOD_RES | 25 note = Ala, Ile, Leu, Met, Phe, Pro, Trp, Tyr, Val or Gly | |
| MOD_RES | 26 note = Ala, Ile, Leu, Met, Phe, Pro, Trp, Tyr, Val or Gly | |
| MOD_RES | 27 note = Ala, Ile, Leu, Met, Phe, Pro, Trp, Tyr, Val or Gly | |
| MOD_RES | 28 note = Ala, Ile, Leu, Met, Phe, Pro, Trp, Tyr, Val or Gly | |
| MOD_RES | 29 note = Ala, Ile, Leu, Met, Phe, Pro, Trp, Tyr, Val or Gly | |
| MOD_RES | 30 note = Asp, Glu, gamma-carboxyglutamic acid or | |

```
                         -continued
                          alpha-aminoadipic acid
MOD_RES                  31
                          note = Ala, Ile, Leu, Met, Phe, Pro, Trp, Tyr, Val or Gly
MOD_RES                  32
                          note = Asp, Glu, gamma-carboxyglutamic acid or
                          alpha-aminoadipic acid
MOD_RES                  33
                          note = Asp, Glu, gamma-carboxyglutamic acid or
                          alpha-aminoadipic acid
source                   1..33
                          mol_type = protein
                          organism = synthetic construct
SEQUENCE: 509
CXQNXXXXXR XXXXHXXXXX XXXXXXXXXX XXX                              33

SEQ ID NO: 510           moltype =   length =
SEQUENCE: 510
000

SEQ ID NO: 511           moltype =   length =
SEQUENCE: 511
000

SEQ ID NO: 512           moltype =   length =
SEQUENCE: 512
000

SEQ ID NO: 513           moltype =   length =
SEQUENCE: 513
000

SEQ ID NO: 514           moltype =   length =
SEQUENCE: 514
000

SEQ ID NO: 515           moltype =   length =
SEQUENCE: 515
000

SEQ ID NO: 516           moltype =   length =
SEQUENCE: 516
000

SEQ ID NO: 517           moltype =   length =
SEQUENCE: 517
000

SEQ ID NO: 518           moltype =   length =
SEQUENCE: 518
000

SEQ ID NO: 519           moltype =   length =
SEQUENCE: 519
000

SEQ ID NO: 520           moltype =   length =
SEQUENCE: 520
000

SEQ ID NO: 521           moltype = AA  length = 33
FEATURE                  Location/Qualifiers
REGION                   1..33
                          note = Description of Artificial Sequence: Synthetic
                          polypeptide
MOD_RES                  2
                          note = Asp, Glu, gamma-carboxyglutamic acid or
                          alpha-aminoadipic acid
MOD_RES                  5
                          note = Ala, Ile, Leu, Met, Phe, Pro, Trp, Tyr, Val or Gly
MOD_RES                  6
                          note = Ala, Ile, Leu, Met, Phe, Pro, Trp, Tyr, Val or Gly
MOD_RES                  7
                          note = Ala, Ile, Leu, Met, Phe, Pro, Trp, Tyr, Val or Gly
MOD_RES                  8
                          note = Ala, Ile, Leu, Met, Phe, Pro, Trp, Tyr, Val or Gly
MOD_RES                  9
                          note = Ala, Ile, Leu, Met, Phe, Pro, Trp, Tyr, Val or Gly
MOD_RES                  11
                          note = Ala, Ile, Leu, Met, Phe, Pro, Trp, Tyr, Val or Gly
```

| | |
|---|---|
| MOD_RES | 12 |
| | note = Ala, Ile, Leu, Met, Phe, Pro, Trp, Tyr, Val or Gly |
| MOD_RES | 13 |
| | note = Asp, Glu, gamma-carboxyglutamic acid or alpha-aminoadipic acid |
| MOD_RES | 14 |
| | note = Ala, Ile, Leu, Met, Phe, Pro, Trp, Tyr, Val or Gly |
| MOD_RES | 16 |
| | note = Ala, Ile, Leu, Met, Phe, Pro, Trp, Tyr, Val or Gly |
| MOD_RES | 17 |
| | note = Ser, Thr or Gly |
| MOD_RES | 18 |
| | note = Ser, Thr or Gly |
| MOD_RES | 19 |
| | note = Ala, Ile, Leu, Met, Phe, Pro, Trp, Tyr, Val or Gly |
| MOD_RES | 20 |
| | note = Ala, Ile, Leu, Met, Phe, Pro, Trp, Tyr, Val or Gly |
| MOD_RES | 21 |
| | note = Ala, Ile, Leu, Met, Phe, Pro, Trp, Tyr, Val or Gly |
| MOD_RES | 22 |
| | note = Ala, Ile, Leu, Met, Phe, Pro, Trp, Tyr, Val or Gly |
| MOD_RES | 23 |
| | note = Ala, Ile, Leu, Met, Phe, Pro, Trp, Tyr, Val or Gly |
| MOD_RES | 24 |
| | note = Asp, Glu, gamma-carboxyglutamic acid or alpha-aminoadipic acid |
| MOD_RES | 25 |
| | note = Ala, Ile, Leu, Met, Phe, Pro, Trp, Tyr, Val or Gly |
| MOD_RES | 26 |
| | note = Ala, Ile, Leu, Met, Phe, Pro, Trp, Tyr, Val or Gly |
| MOD_RES | 27 |
| | note = Ala, Ile, Leu, Met, Phe, Pro, Trp, Tyr, Val or Gly |
| MOD_RES | 28 |
| | note = Ala, Ile, Leu, Met, Phe, Pro, Trp, Tyr, Val or Gly |
| MOD_RES | 29 |
| | note = Ala, Ile, Leu, Met, Phe, Pro, Trp, Tyr, Val or Gly |
| MOD_RES | 30 |
| | note = Asp, Glu, gamma-carboxyglutamic acid or alpha-aminoadipic acid |
| MOD_RES | 31 |
| | note = Ala, Ile, Leu, Met, Phe, Pro, Trp, Tyr, Val or Gly |
| MOD_RES | 32 |
| | note = Asp, Glu, gamma-carboxyglutamic acid or alpha-aminoadipic acid |
| MOD_RES | 33 |
| | note = Asp, Glu, gamma-carboxyglutamic acid or alpha-aminoadipic acid |
| source | 1..33 |
| | mol_type = protein |
| | organism = synthetic construct |

SEQUENCE: 521

CXQNXXXXXR XXXXHXXXXX XXXXXXXXXX XXX    33

SEQ ID NO: 522    moltype =    length =
SEQUENCE: 522
000

SEQ ID NO: 523    moltype =    length =
SEQUENCE: 523
000

SEQ ID NO: 524    moltype =    length =
SEQUENCE: 524
000

SEQ ID NO: 525    moltype =    length =
SEQUENCE: 525
000

SEQ ID NO: 526    moltype =    length =
SEQUENCE: 526
000

SEQ ID NO: 527    moltype =    length =
SEQUENCE: 527
000

SEQ ID NO: 528    moltype =    length =
SEQUENCE: 528

```
000

SEQ ID NO: 529          moltype =    length =
SEQUENCE: 529
000

SEQ ID NO: 530          moltype =    length =
SEQUENCE: 530
000

SEQ ID NO: 531          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 531
NLEGFFATLG GEIALWSLVV LAIE                                              24

SEQ ID NO: 532          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 532
EIALVVLSWL AIEGGLTAFF GELN                                              24

SEQ ID NO: 533          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 533
LFPTDTLL                                                                8

SEQ ID NO: 534          moltype = AA  length = 5
FEATURE                 Location/Qualifiers
REGION                  1..5
                        note = Description of Artificial Sequence: Synthetic peptide
MOD_RES                 3
                        note = Any amino acid
source                  1..5
                        mol_type = protein
                        organism = synthetic construct
SEQUENCE: 534
WLXLL                                                                   5

SEQ ID NO: 535          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 535
WLGLL                                                                   5
```

What is claimed is:

1. A method for removing diseased or damaged tissue in a subject, comprising:
   (a) administering a pH-triggered polypeptide fluorophore compound having the structure:

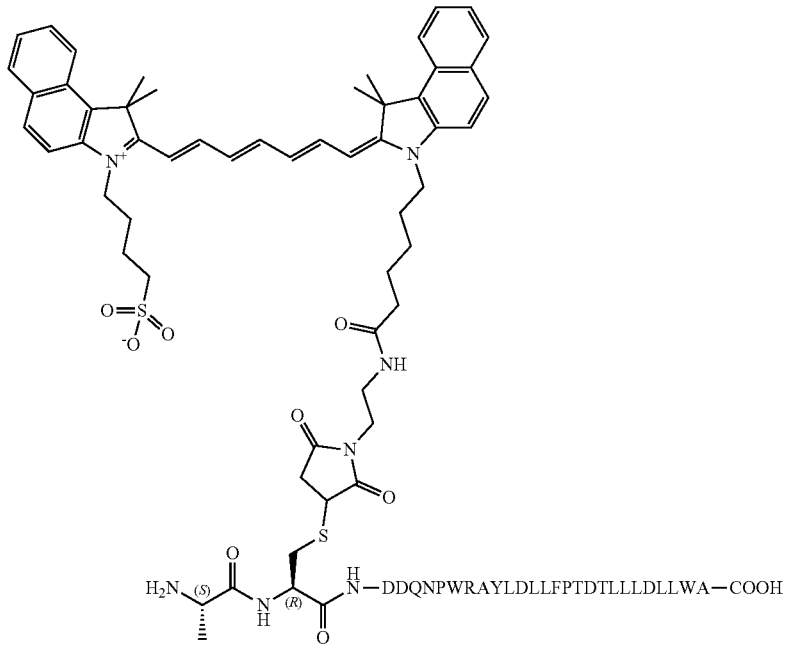

(SEQ ID NO: 4) to the subject;
   (b) contacting the subject with electromagnetic radiation comprising an excitation wavelength of the fluorophore;
   (c) detecting electromagnetic radiation emitted from the compound, wherein detection of the radiation indicates the presence of the diseased or damaged tissue; and
   (d) surgically removing the diseased or damaged tissue identified by step (c).

2. The method of claim 1, wherein the level of radiation emitted from the diseased or damaged tissue is at least 20% greater than a level of radiation emitted from a normal non-diseased or non-damaged tissue.

3. The method of claim 1, wherein the compound is administered to the subject via intravesical instillation, intravenous administration, intraperitoneal administration, topical administration, mucosal administration, or oral administration.

4. The method of claim 1, wherein the compound is administered by applying a liquid, powder, or a spray comprising the compound to a surface of the subject.

5. The method of claim 4, wherein the surface comprises a site within the body of the subject that is accessed via surgery.

6. The method of claim 1, wherein electromagnetic radiation emitted from the compound is detected in vivo.

7. The method of claim 1, wherein electromagnetic radiation emitted from the compound is detected ex vivo.

8. The method of claim 1, further comprising a washing step in which the subject that has been contacted with the compound is washed to remove excess compound before detecting.

9. The method of claim 1, wherein the pH-triggered polypeptide fluorophore compound further comprises a pharmaceutically acceptable carrier.

10. The method of claim 1, wherein the electromagnetic radiation emitted from the compound is used to guide surgery to determine the margins of the diseased tissue.

11. The method of claim 1, wherein the electromagnetic radiation emitted from the compound is used to determine whether the diseased or damaged tissue is present in the subject following surgical removal of a first amount of diseased or damaged tissue.

12. The method of claim 1, wherein the pH-triggered polypeptide fluorophore compound is used as an agent in preoperative, intraoperative and postoperative settings.

13. The method of claim 3, wherein the compound is administered to the subject via intravenous administration.

14. A method for removing diseased or damaged tissue in a subject, comprising:
   (a) contacting a biological sample from a subject ex vivo with a pH-triggered polypeptide fluorophore compound having the structure:

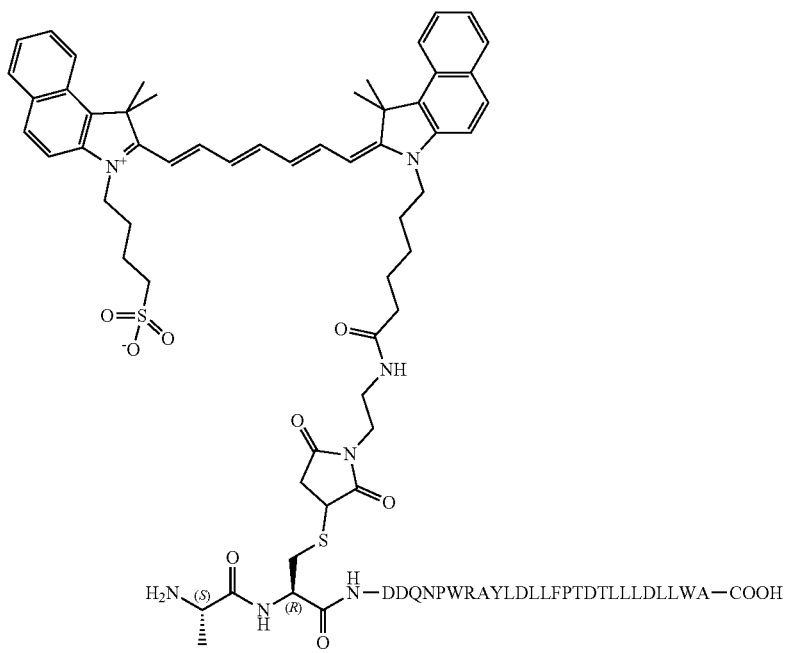

(SEQ ID NO: 4);

(b) contacting the biological sample with electromagnetic radiation comprising an excitation wavelength of the fluorophore; and (c) detecting electromagnetic radiation emitted from the fluorophore, wherein detection of the radiation indicates the presence of the diseased or damaged tissue; and (d) surgically removing the diseased or damaged tissue identified by step (c) from the subject.

15. The method of claim 14, wherein the biological sample comprises a tissue biopsy specimen, a liquid biopsy specimen, a surgically removed tissue, a surgically removed liquid, or blood.

16. The method of claim 14, further comprising a washing step in which the biological sample that has been contacted with the compound is washed to remove excess compound composition before detecting.

17. The method of claim 14, wherein the pH-triggered polypeptide fluorophore compound further comprises a pharmaceutically acceptable carrier.

* * * * *